US007851604B2

(12) United States Patent
Jones

(10) Patent No.: US 7,851,604 B2
(45) Date of Patent: Dec. 14, 2010

(54) TRANSCRIPTIONAL REGULATOR

(75) Inventor: Michael H. Jones, Ibaraki (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 475 days.

(21) Appl. No.: 11/709,624

(22) Filed: Feb. 22, 2007

(65) Prior Publication Data

US 2007/0148738 A1 Jun. 28, 2007

Related U.S. Application Data

(60) Division of application No. 10/702,148, filed on Nov. 5, 2003, now Pat. No. 7,189,818, which is a division of application No. 09/839,479, filed on Apr. 20, 2001, now Pat. No. 6,727,222, which is a division of application No. 09/418,710, filed on Oct. 15, 1999, now Pat. No. 6,596,482, which is a continuation-in-part of application No. PCT/JP98/01783, filed on Apr. 17, 1998.

(30) Foreign Application Priority Data

| Apr. 18, 1997 | (JP) | .................................. 9/116570 |
| Oct. 24, 1997 | (JP) | .................................. 9/310027 |

(51) Int. Cl.
*C07H 21/04* (2006.01)
*A61K 38/00* (2006.01)

(52) U.S. Cl. ..................... 536/23.1; 536/24.3; 536/23.5; 536/26.41

(58) Field of Classification Search ........................ None
See application file for complete search history.

(56) References Cited

U.S. PATENT DOCUMENTS

| 5,654,150 | A | * | 8/1997 | King et al. ...................... 435/6 |
| 6,531,447 | B1 | * | 3/2003 | Ruben et al. ..................... 514/2 |
| 6,596,482 | B1 | | 7/2003 | Jones |
| 6,727,222 | B2 | | 4/2004 | Jones |
| 7,189,818 | B2 | | 3/2007 | Jones |
| 2003/0224405 | A1 | | 12/2003 | Jones |

OTHER PUBLICATIONS

Zang et al. (1995) Effects of zinc finger mutations on the nucleic acid binding activities of Xenopus transcription factor IIIA, Biochemistry, vol. 324, No. 47, pp. 15545-15552.*
Zhou et al. (2005) The PHD finger/bromodomain of NoRC interacts with acetylated histone H4K16 and is sufficient for rDNA silencing, Curr. Biol., vol. 15, No. 15, pp. 1434-1438.*
Nagase et al. (1997) Prediction of the coding sequences of unidentified human genes. VII. The complete sequences of 100 new cDNA clones from brain which can code for large proteins in vitro, DNA Res., vol. 4, No. 2, pp. 141-150.*
Zhang et al. (1996) An analysis of base frequencies in the anti-sense strands corresponding to the 180 human protein coding sequences, Amino acids, vol. 10, pp. 253-262.*
Attwood, T.K., "The Babel of Bioinformatics", 2000, Science, vol. 290(5491);471-473.
Beck et al., "A homologue of the *Drosophila* female sterile hemeotic (fsh) gene in the class II region of the human MHC," *DNA Seq* 1992;2(4):203-10 (abstract).
Bochar et al., "A family of chromatin remodeling factors related to Williams syndrome transcription factor", Proc. Natl. Acad. Sci. USA, vol. 97(3), pp. 1038-1043 (2000).
Collins et al., "An ACF1-ISWI chromatin-remodeling complex is required for DNA replication through heterochromatin", Nature Genetics,vol. 32(4), pp. 627-632 (2002).
Colman, Research in Immunology, 145(1): 33-36, 1994.
Dhalluin et al., "Structure and ligand a histone acetyltransferase bromodomain," Nature, vol. 399, pp. 491-496, Jun. 3, 1999.
Fujiki et al., "Ligand-induced transrepression by VDR through association of WSTF with acetylated histories", EMBO J., 24:3881-3894 (2005).
Gems et al., "An abundantly expressed mucin-like protein . . . ", 1996, Proc Natl Acad Sci USA, vol. 93(4);1665-1670.
GenBank Accession No. M23221, *D. melanogaster* fsh membrane protein, 7.6 kb mRNA, complete cds., Apr. 26, 1993.
GenBank Accession No. M23222, *D. melanogaster* fsh membrane protein, 5.9 kb mRNA, complete cds., Apr. 26, 1993.
GenBank Accession No. M85049, *D. melanogaster* brahma protein mRNA, complete cds., Jul. 13, 1994.
GenBank Accession No. M87651, *S. cerevisiae* bromodomain of SPT7 gene, partial cds., Apr. 27, 1993.
GenBank Accession No. M61703 M55906, *S. cerevisiae* SNF2 protein gene, complete cds., Apr. 27, 1993.
GenBank Accession No. X07024, *H. sapiens* mRNA for CCG1 protein, Jul. 17, 2001.
GenBank Accession No. M80613, human homolog of *Drosophila* female sterile homeotic mRNA, complete cds., Jun. 22, 1995.
Haynes et al., "The bromodomain; a conserved sequence found in human, *Drosophila* and yeast proteins," Nucleic Acids Research, vol. 20, p. 2603, Apr. 2, 1992.
Haynes et al., "The *Drosophila* fsh locus, a maternal effect homeotic gene, encodes apparent membrane proteins," *Dev Biol* Jul. 1989;134(1):246-57 (abstract).
Hillier et al., "Generation and analysis of 280,000 human expressed sequence tags", Database EMBL *'Online!*, Database Accession No. H70181, XP002198410, Oct. 25, 1995.
Hillier et al., "The WashU-Merck EST Project", Database EMBL *'Online!*, Database Accession No. R66814, XP002198411, Jun. 4, 1995.
Hillier et al., "Generation and analysis of 280,000 human expressed sequence tags", Database EMBL *'Online!*, Database Accession No. AA112166, XP002193345, Nov. 9, 1996.
Hillier et al., "Generation and analysis of 280,000 human expressed sequence tags", Database EMBL *'Online!*, Database Accession No. AA102574, XP002193346, Oct. 30, 1996.

(Continued)

*Primary Examiner*—Anand U Desai
*Assistant Examiner*—Samuel Liu
(74) *Attorney, Agent, or Firm*—Fish & Richardson P.C.

(57) ABSTRACT

Genes each encoding a novel transcriptional regulator having a bromodomain have been successfully isolated from a human testis cDNA library using primers prepared based on an EST sequence found using the bromodomain sequence of the transcriptional regulator. These genes are structurally analogous to each other.

36 Claims, 20 Drawing Sheets

OTHER PUBLICATIONS

Ito et al., "ACF consists of two subunits, Acf1 and ISWI, that function cooperatively in the ATP-dependent catalysis of chromatin assembly," *Genes & Development*, vol. 13, pp. 1529-1539, 1999.

Jones et al., "A Novel Family of Bromodomain Genes", *Genomics*, 63 pp. 40-45, 2000.

Jones, M.H., "The bromodomain revisited," Letters, pp. 151-153, 1997.

LeRoy et al., "Purification and Characterization of a Human Factor That Assembles and Remodels Chromatin", The Journal of Biological Chemistry, vol. 275(20), pp. 14787-14790 (2000).

Lu et al., "A Novel Human Gene, WSTF, Is Deleted in Williams Syndrome," *Genomics*, vol. 54, pp. 241-249, 1998.

Nicolas et al., "Molecular cloning of polybromo, a nuclear protein containing multiple domains including five bromodomains, a truncated HMG-box, and two repeats of a novel domain", *Gene*, 175 pp. 233-240, 1996.

Nielson et al., "Cloning and sequencing of a human cDNA encoding a putative transcription factor containing a bromodomain", *Biochimica et Biophysica Acta*, 1306 pp. 14-16, 1996.

Robertson et al., 1994; Genomics 23;42-50.

Skolnick et al., "From genes to protein structure and function; novel applications . . . ", 2000, Trends Biotechnol, vol. 18(1);34-39.

Tamkun et al., "brhma: A Regulator of *Drosophila* Homeotic Genes Structurally Related to the Yeast Transcriptional Activator SNF2/SWI2," *Cell*, vol. 68, pp. 561-572, Feb. 7, 1992.

Yasui et al., "Identification of Target Genes Within an Amplicon at I4qI2-qI3 in Esophageal Squamous Cell Carcinoma", Genes Chromosomes Cancer, vol. 32(2), pp. 112-118 (2001).

Fish & Richardson P.C., Preliminary Amendment, in U.S. Appl. No. 10/702,148, filed Nov. 5, 2003 (8 pages).

Restriction Requirement, in U.S. Appl. No. 10/702,148, mailed Jun. 13, 2005 (4 pages).

Fish & Richardson P.C., Response to Restriction Requirement mailed Jun. 13, 2005, , in U.S. Appl. No. 10/702,148, filed Jul. 11, 2005 (1 page).

Office Action, in U.S. Appl. No. 10/702,148, mailed Aug. 3, 2005 (10 pages).

Fish & Richardson P.C., Response to Office Action mailed Aug. 3, 2005, , in U.S. Appl. No. 10/702,148, filed Feb. 2, 2006 (13 pages).

Final Office Action, in U.S. Appl. No. 10/702,148, mailed Apr. 17, 2006 (7 pages).

Fish & Richardson P.C., Response to Final Office Action mailed Apr. 17, 2006, , in U.S. Appl. No. 10/702,148, filed Sep. 15, 2006 (11 pages).

Notice of Allowance and Availability, including Examiner Interview, in U.S. Appl. No. 10/702,148, mailed Oct. 18, 2006 (9 pages).

Fish & Richardson P.C., Response to Notice of Allowance and Availability, in U.S. Appl. No. 10/702,148, filed Dec. 26, 2006 (2 pages).

Fish & Richardson P.C., Preliminary Amendment, in U.S. Appl. No. 10/376,537, filed Feb. 28, 2003 (54 pages).

Fish & Richardson P.C., Preliminary Amendment, in U.S. Appl. No. 10/376,537, filed Nov. 5, 2003 (3 pages).

Restriction Requirement, in U.S. Appl. No. 10/376,537, mailed Apr. 13, 2005 (7 pages).

Fish & Richardson P.C., Amendment in Reply to Office Action mailed Apr. 13, 2005, filed May 13, 2005 (12 pages).

Office Action, in U.S. Appl. No. 10/376,537, mailed Jul. 14, 2005 (8 pages).

Notice of Abandonment, in U.S. Appl. No. 10/376,537, mailed Mar. 13, 2006 (2 pages).

Fish & Richardson P.C., Preliminary Amendment, in U.S. Appl. No. 09/839,479, filed Apr. 20, 2001 (3 pages).

Restriction Requirement, in U.S. Appl. No. 09/839,479, mailed Sep. 17, 2002 (4 pages).

Fish & Richardson P.C., Response to Restriction Requirement, mailed Sep. 17, 2002, in U.S. Appl. No. 09/839,479, filed Oct. 17, 2002 (1 page).

Office Action, in U.S. Appl. No. 09/839,479, mailed Jan. 14, 2003 (15 pages).

Fish & Richardson P.C., Amendment in Reply dated Sep. 17, 2002, in U.S. Appl. No. 09/839,479, filed Jun. 12, 2003 (25 pages).

Notice of Allowance and Notice of Allowability, in U.S. Appl. No. 09/839,479, mailed Aug. 11, 2003 (10 pages).

Fish & Richardson P.C., Response to Notice of Allowance, in U.S. Appl. No. 09/839,479, mailed Nov. 6, 2003 (26 pages).

Response to Rule 312 Communication, in U.S. Appl. No. 09/839,479, mailed Jan. 5, 2004 (2 pages).

Fish & Richardson P.C., Request for Certificate of Correction, in U.S. Appl. No. 09/839,479, mailed Nov. 11, 2005 (6 pages).

Certificate of Correction, in U.S. Appl. No. 09/839,479, mailed Feb. 7, 2006 (2 pages).

Fish & Richardson P.C., Preliminary Amendment, in U.S. Appl. No. 09/418,710, filed Oct. 19, 2000 (3 pages).

Restriction Requirement, in U.S. Appl. No. 09/418,710, mailed Dec. 7, 2000 (7 pages).

Fish & Richardson P.C., Response to Restriction Requirement mailed Dec. 7, 2000, in U.S. Appl. No. 09/418,710, filed Mar. 7, 2001 (1 page).

Office Action, in U.S. Appl. No. 09/418,710, mailed May 16, 2001 (8 pages).

Fish & Richardson P.C., Response to Office Action mailed May 16, 2001, in U.S. Appl. No. 09/418,710, filed Nov. 15, 2001 (17 pages).

Fish & Richardson P.C., Supplemental Amendment, U.S. Appl. No. 09/418,710, filed Jan. 11, 2001 (7 pages).

Final Office Action, in U.S. Appl. No. 09/418,710, mailed Jun. 4, 2002 (6 pages).

Fish & Richardson P.C., Response to Final Office Action mailed Jun. 4, 2002, U.S. Appl. No. 09/418,710, filed Sep. 25, 2002 (16 pages).

Notice of Allowance and Notice of Allowability, in U.S. Appl. No. 09/418,710, mailed Oct. 16, 2002 (8 pages).

Fish & Richardson P.C., Response to Notice of Allowance and Amendment After Allowance, U.S. Appl. No. 09/418,710, filed Jan. 15, 2003 (16 pages).

Interview Summary, in U.S. Appl. No. 09/418,710, mailed Mar. 20, 2003 (3 pages).

Fish & Richardson P.C., Applicant's Statement of the Substance of the Interview, U.S. Appl. No. 09/418,710, filed Apr. 9, 2003 (1 page).

Response to Rule 312 Communication, in U.S. Appl. No. 09/418,710, mailed May 23, 2003 (2 pages).

Fish & Richardson P.C., Request for Certificate of Correction, U.S. Appl. No. 09/418,710, filed Dec. 11, 2003 (3 pages).

Certificate of Correction in U.S. Appl. No. 09/418,710, mailed Jun. 8, 2004 (2 pages).

Fish & Richardson P.C., Request for Second Certificate of Correction, U.S. Appl. No. 09/418,710, filed Nov. 22, 2004 (4 pages).

Certificate of Correction in U.S. Appl. No. 09/418,710, mailed Feb. 1, 2005 (1 page).

Fish & Richardson P.C., Request for Third Certificate of Correction, U.S. Appl. No. 09/418,710, filed Nov. 15, 2005 (3 pages).

Certificate of Correction in U.S. Appl. No. 09/418,710, mailed Feb. 1, 2005 (1 page).

Hillier et al., "The WashU-Merck EST Project", DDBJ/EMBL/GenBank Accession No. AA013017, Nov. 29, 1996. Downloaded from the Internet at URL: <www.ncbi.nlm.nih.gov/entrez/viewer.fcgi?1474044:EST:626923>.

Hillier et al., "The WashU-Merck EST Project", DDBJ/EMBL/GenBank Accession No. AA015589, Nov. 29, 1996. Downloaded from the Internet at URL: <www.ncbi.nlm.nih.gov/entrez/viewer.fcgi?1476728:EST:629607>.

Hillier et al., "Generation and analysis of 280,000 human expressed sequence tags", DDBJ/EMBL/GenBank Accession No. N76552, Jan. 28, 1997. Downloaded from the Internet at URL: <www.ncbi.nlm.nih.gov/entrez/viewer.fcgi?1239130:EST:482891>.

* cited by examiner

```
BAZ    SWPFLKLVSKIQ--VPDYYDIIKKPIALNIIREKVNKCEYKLASEFIDDIELMFSNCFEYN
TFIID  SWPFLKPVNKKQ--VKDYTVIKRPMDLETIGKNIEAHRYHSRAEYLADIELIATNCEQYN
CCG1   TYPFHTPVNAKV--VKDYYKIITRPMDLQTLRENVRKRLYPSREEFREHLELIVKNSATYN
PCAF   AWPFMEPVKRTE--APGYYEVIRSPMDLKTMSERLKNRYYVSKKLFMADLQRVFTNCKEYN
CBP    SLPFRQPVDPQLLGIPDYFDIVKNPMDLSTIKRKLDTGQYQEPWQYVDDVWLMFNNAWLYN
```

FIG. 1A

```
            *              *           *                    *  *
BAZ    CKIC-------------RKKGDAEN----MVLCDGCDRGHHTYCV--RPKLKTVPEGD-WFCPEC
U13646 CQIC-------------KSMDGDE-----MLVCDGCESGCHMECF--RPRMTKVPEGD-WFCQRC
RBBP2  CMFCG------------RGNNEDK-----LLLCDGCDDSYHTFCL--IPPLPDVPKGD-WRCPKC
MOZ.1  CSFCLG-----------TKEQNREKKPEELISCADCGNSGHPSCLKFSPELTVRVKALRWQCIEC
MOZ.2  CSSCRD-----------QGKNADN-----MLFCDSCDRGFHMECC--DPPLTRMPKGM-WICQIC
p300   CEKCFNEIQGESVSLGDDPSQPQTTINKEQFSKRKNDTLDPELFVECTECGRKMHQICV--LHHEIIWPAG--FVCDGC
CBP    CEKCFTEIQGENVTLGDDPSQPQTTISKDQFEKKKNDTLDPEPFVDCKECGRKMHQICV--LHYDIIWPSG--FVCDNC
```

FIG. 1B

Chr 14

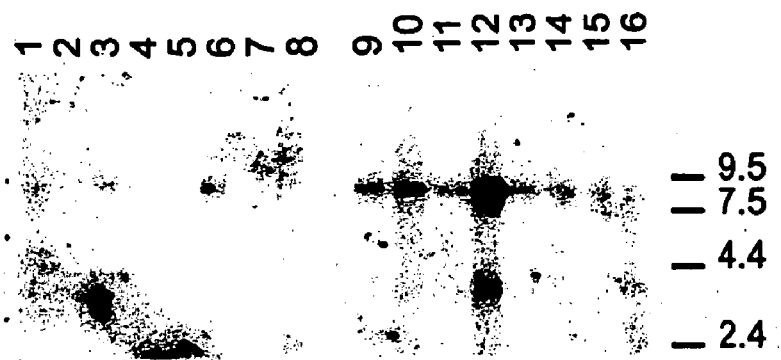
FIG. 3
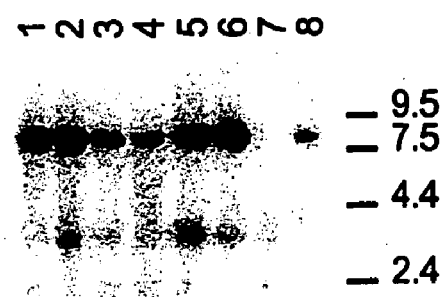
FIG. 4A
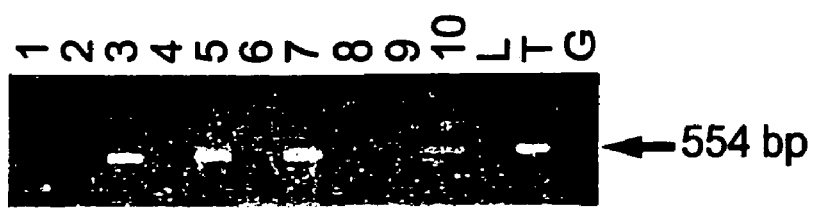
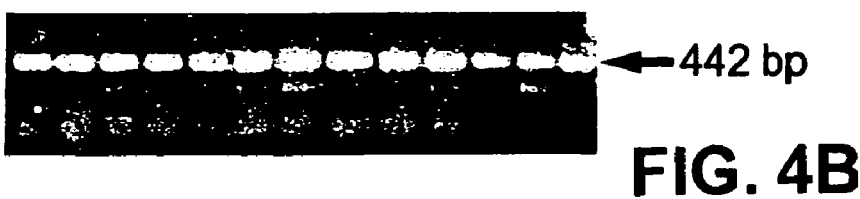
FIG. 4B

FIG. 6A bromodomains

```
BAZ     SWPFLKLIVSKIQV--PDYDIIKKPIALNIIREK------------------------------------VNKCEYKLASEFIDDIELMFSNCFEYN
CCG     SWPFHHPVNKKFV--PDYYKVIVNPMDLETIRKN------------------------------------ISKHKYQSRESFLDDVNLILANSVKYN
BAZ2    AWPFLEPVNPRLV--SGYRRIIKNPMDFSTMRER------------------------------------LLRGGYTSSEEFAADALLVFDNCQTFN
PCAF    AWPFMEPVKRTEA--PGYYEVIRSPMDLKTMSER------------------------------------LKNRYYVSKKLFMADLQRVFTNCKEYN
U13646  ALPFLEPVNPKLV--PGYKMIISKPMDLKTIROKNEKLIVSETYQFCFFAIFDLKLKMKITQYETPEDFAEDIELMFANCRQFN
CBP     SLPFRQPVDPQLLGIPDYFDIVKNPMDLSTIKRK------------------------------------LDTGQYQEPWQYVDDVWLMFNNAWLYN
```

FIG. 6B

C4HC3 Zn finger

```
           *    *                                *   *   *  *                *      *
BAZ     CKIC-------------------------------RKKGDAEN----MVLCDGCDRGHHTYCV--RPKLKTVPEGD-WFCPEC
U13646  CQIC-------------------------------KSMDGDE-----MLVCDGCESGCHMECF--RPRMTKVPEGD-WFCQRC
RBBP2   CMFCG------------------------------RGNNEDK-----LLLCDGCDDSYHTFCL--IPPLPDVPKGD-WRCPKC
MOZ.1   CSFCLG-----------------------TKEQNREKKPEE------LISCADCGNSGHPSCLKFSPELTVRVKALRWQCIEC
MOZ.2   CSSCRD--------------------------------QGKNADN--MLFCDSCDRGFHMECC--DPPLTRMPKGM-WICQIC
p300    CEKCFNEIQGESVSLGDDPSQPQTTINKEQFSKRKNDTLDPELFVECTECGRKMHQICVL--HHEIIWPAG--FVCDGC
BAZ2    CLVC-------------------------------RKGDNDE-----FLLLCDGCDRGCHIYCH--RPKMEAVPEGD-WFCTVC
```

```
baz1α    1   REEKRKYVEYLKQWSKPREDMEC..............DDLKELPEPTPVKTR.LPPEIFG
u13646   1   LNDEFTEELVHSQIMSNGVDE.CKIREREADDLLVNINDVRHLPDFSRIGNQCLSSQGFA
baz2α    1   LEERQKQQMILEEMKKPTEDM.C............LTDHQPLPDFSRVPGLTLPSGAFS
baz2β    1   LEQRRLELEMAKELKKPNEDM.C............LADQKPLPELPRIPGLVLSGSTFS baz1α   46   DALMVLEFLNAFGEL..FDLQDEFPDGVTLEVLEEALVGN.DSEGPLCELIFFFLTAIFQ
u13646  60   DALMVHEFVQNFGHVLGIDLEI.APK...LESLCAGLDGDANHAEQTLQITRQLLRLALE
baz2α   47   DCLTIVEFLHSFGKVLGFDPAKDVPS...LGVLQEGLLCQGDSLGEVQDLLVRLIKAALH
baz2β   47   DCLMVVQFLRNFGKVLGFDVNIDVPN..LSVLQEGLLNIGDSMGEVQDLLVRLLSAAVC baz1α  103   AIAEEEEVAKEQLTDADTKGCSLKSLDLDSCTLSEIILRLHILASGADVTSANAKYRYQK
u13646 116   FPGM...GNEKRF......GQGGGEMGLDRENFSEVMRLFLIDKGKR..............
baz2α  104   DPGFPSYCQSLKIL.......GEKVSEIPLTRDNVSEILRCFLMAYGVE..............
baz2β  104   DPGLITGYKAKTAL.......GEHLLNVGVNRDNVSEILQIFMEAHCGQ..............

baz1α  163   RGGFDATDDACMELRLSNPSLVKKLSSTSVYDLTPGEKMKILHALCGKL
u13646 154   .........................GEELSQPLLTCNFLSISPEQKASILAFLCDEL
baz2α  146   .........................PALCDRLRTQPFQAQPPQQKAAVLAFPVHEL
baz2β  146   .........................TELTESLKTKAFQAHTPAQKASVLAFLINEL
```

FIG. 10

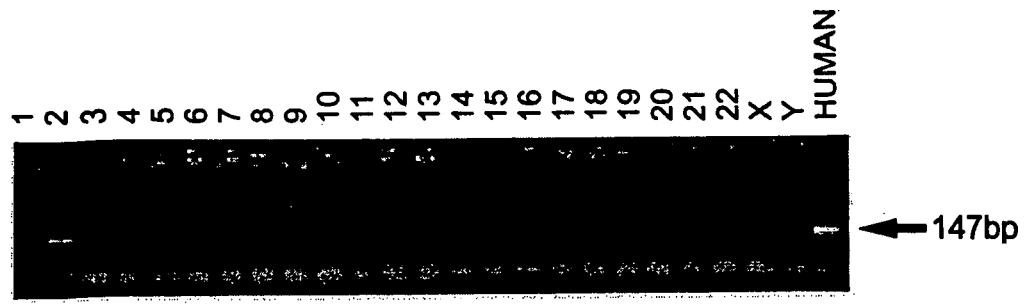
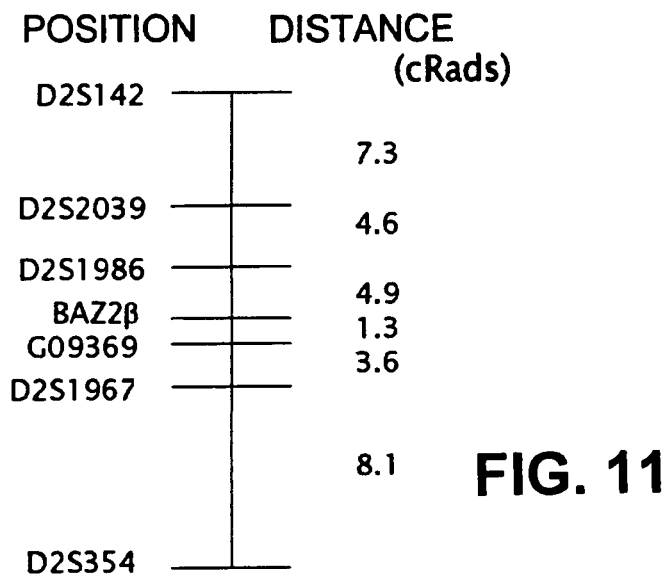
FIG. 11
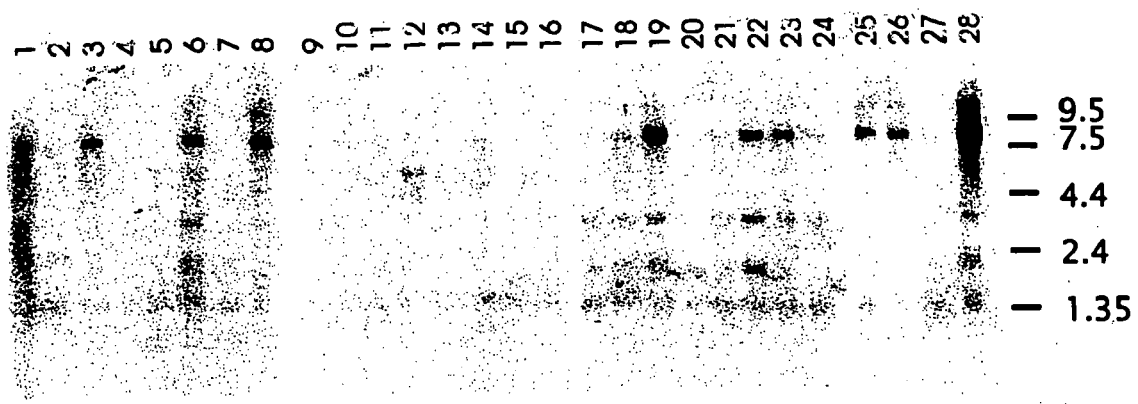
FIG. 12

```
BAZ1βS  YPITAVSLMEALSADKGGFLYLNRVLVIL----LQTLLQDEIAEDYGELGMKLSEIPLTHSVSE
        ::::::::::::::::::::::::::::::    ::::::::::::::::::::::::::::::
BAZ1βL  YPITAVSLMEALSADKGGFLYLNRVLVILLQTLLQTLLQDEIAEDYGELGMKLSEIPLTHSVSE
        630       640       650       660       670       680       690
```

```
BAZ1Bs    1  ..............................................................
BAZ1A     1  ..............................................................
BAZ2A     1  ..............................MEMEANEANDHFNFTGL
BAZ2B     1  ..............................................................

BAZ1Bs    1  ..............................................................
BAZ1A     1  ..............................................................
BAZ2A    18  PPAPAASGLKPSPSSGEG......LYTNGSPMNF.........PQQGKSLNGDVNVNGLS
BAZ2B     1  ......MGQTKSTSSGGGNRKCNQEQSKNQPLDARVDKIKDKKPRK.KAMESSSNSDSDS

BAZ1Bs    1  ..............................................................
BAZ1A     1  ..............................................................
BAZ2A    63  .TVSHTTTSGILNSAPHSSSTSHLHHPSVAYDCLWNYSQYPSANPGSNLKDPPLLSQFSG
BAZ2B    54  GTSSDTSSEGI.....SSSDSDDLEEDEEEEDQSIEESEDDDSDSESEAQHK......SN

BAZ1Bs    1  ..............................................................
BAZ1A     1  ..............................................................
BAZ2A   122  GQYPLNGILGGSRQPSSPSHNTNLRAGSQKFWANGTHSPMGLNFDSQELYDSFPDQNFE.
BAZ2B   103  NQVLLHGI....SDPKADGQKATEKAQEKRI.....HQPLPLAFESQT..HSFQSQQKQP

BAZ1Bs    1  ..............................................................
BAZ1A     1  MEDASESSRGVAPLINNVVLPGSPLSLPVSVTGCKSHRVANKKVEARSEKLLPTALPPSE
BAZ2A   181  EVCSGIHP........DEAAEKEMTSVVAENGTGLVCSLE....LEEEQPELKMCGYNGS
BAZ2B   152  QVLSQQLPFIFQSSQAKEESVNKHTSVI..QSTGLVSNVKPLSLVNQAKKETYM......

BAZ1Bs    1  ..............................................................
BAZ1A    61  PKVDQKLPRSSERRGSGGGTQFPARSRAVAAGEAAARGAAGPERGSPLGRRVSPRCLCSG
BAZ2A   229  VPSVESLHQEVSVLVPDPTVSCLDDPSHLPDQLEDTPILSED...SLEPFNSLAPEPVSG
BAZ2B   204  ............KLIVPSPDVLKAGNK....NTSEESSLLTSELRSKREQYKQAFP.....

BAZ1Bs    1  ........................MAPLLGRKPFPLVNPLPGEEPF...FTIPHT
BAZ1A   121  EGGQVAVGVIAGKRGRRGRDGSRRAPGGREMPLLHRKPFVRQKPPADLRPDEEVFYCKVT
BAZ2A   286  GLYGIDDTELMGAEDKLPLEDSPVISALDCPSLNNATAFSLLADDSQTSTSIFASP.TSP
BAZ2B   244  .......SQLKKQESSKSLK..KVIAALSNPKATSSSP....AHPKQTLENNHPNPFLTN

BAZ1Bs   29  QEAFRTREEYEARLERYSERIWTCKSTGSSQLTHKEAWEEEQEVAELLKEEFPAWYEKLV
BAZ1A   181  NEIFRHYDDFFERTILCNSLVWSCAVTGRPGLTYQEALESEKKARQNLQS.FP...EPLI
BAZ2A   345  PVLG........ESVLQDNSFDLNNGSDAEQEEMETQSSDFPPSLTQPAPDQSSTIQLHP
BAZ2B   291  ALLGNHQPNGVIQSVIQEAPLALTTKTKMQSKINENIAAASSTPFSSPV.NLSTSGRRTP

BAZ1Bs   89  LEMVHHNTAS....LEKLVDTAWLEIMTKYAVGEECDFEVGKEKMLKVKIVKIHPLEKVD
BAZ1A   237  IPVLYLTSLTHRSRLHEICDDIFAYVKDRYFVEETVEVIRNNGARLQCTILEVLP.....
BAZ2A   397  ATSPAVSPTTSPAVSLVVSPAASPEISPEVCPAASTVVSPAVFSVV..............
BAZ2B   350  GNQTPVMPSASPILH...SQGKEKAVSNNVNPVKTQHHSHPAKSLVEQFRGTDSDIPSSK
```

FIG. 14

```
BAZ1Bs  145  EEATEKKSDGACDSPSSDKENSSQIAQDHQKK...ETVVKEDEGRRESINDRARRSPRKL
BAZ1A   292  ..............PS....HQNGFANGHVNSVDGETIIISDSDDSETQS.........
BAZ2A   443  ..........................................................
BAZ2B   407  DSEDSNEDEEEDDEEEDEEDDEDDESDDSQSESDSNSESDTEGSEEEDDDDKDQDESDSD

BAZ1Bs  202  PTSLKKGERKWAPPKFLPHKYDVK.LQNEDKIISNVPADSLIRTERPPNKEIVRYFTRHN
BAZ1A   324  .CSFQNGKKKDAIDPLL.FKYKVQPTKKELHESAIVKATQISRRKHLFSRDKLKLFLKQH
BAZ2A   443  ..........SPASSAVLPAVSLEVPLTASVTSPKASPVTSPAAAFP.TASPANKDVSS
BAZ2B   467  TEGEKTSMKLNKTTSSVKSPSMSLTGHSTPRNLHIAKAPGSAPAALCSESQSPA......

BAZ1Bs  261  ALRAGTGENAPWVVEDELVKKYSLPS......KFSDFLLDPYKYMTLNPSTKRKNTGSPD
BAZ1A   382  C......EPQEGVIK...IKASSLSTYKIAEQDFSYFFPDDPPTFIFSPANRRR..GRPP
BAZ2A   491  FLETTADVEEITGEGLTASG.SGDVMRRRIATPEEVRLPLQHGWRREVRIKKGSHRWQGE
BAZ2B   521  FLGTSSST.......LTSSPHSGTSKRRRVTDERELRIPLEYGWQRETRIRNFGGRLQGE

BAZ1Bs  315  RKPSKKSKTDNSSLSSPLNPKLWCHVHLKKSLSGSPLKVKNSKNSKSPEEHLEEMMKMMS
BAZ1A   431  KRI.HISQEDN..............VANKQTLA........SYRSKATKER.........
BAZ2A   550  TWYYGPCGKRMKQFPEVIKYLSRNLVHSVRREHFSFSPRMPVGDFFEERDTPEGLQWVQL
BAZ2B   574  VAYYAPCGKKLRQYPEVIKYLSRNGIMDISRDNFSFSAKIRVGDFYEARDGPQEMQWCLL

BAZ1Bs  375  PNKLHTNFHIPKKGPPAKKPGKHSDKPLKAKGRSKGILNGQKSTGNSKSPKKGLKTPKTK
BAZ1A   459  .....................DKLLK.................QEEMKSLAFEKAK
BAZ2A   610  SAEEIPSRIQAITGKRGRPRNTEKAKTKEVPKVKRGRGRPPKVKITELLNKTDNRPLKKL
BAZ2B   634  KEEDVIPRIRAMEGRRGRPPNPDRQRAREESRMRRRKGRPPNVGNAEFLDNADAKLLRKL

BAZ1Bs  435  MKQMTLLDMAKGTQKMTRAPRNSGGTPRTSSKPHKHLPPAALHLIAYYKENKDREDKRSA
BAZ1A   477  LKR..........................EKADALEAKKKEKEDKEKKR..
BAZ2A   670  EAQET...........LNEEDKAKIAKSKKKMR......QKVQRGECLTTIQGQARNKR
BAZ2B   694  QAQEIARQAAQIKLLRKLQKQEQARVAKEAKKQQAIMAAEEKRKQKEQIKIMKQQEKIKR

BAZ1Bs  495  LSCVISKTARLLSSEDRARLPEELRSLVQKRYELLEHKKRWASM...............
BAZ1A   500  ....................EECKKIVEEER........L................
BAZ2A   712  KQETKSLKHK......EAKKKSKAEKEKGKT..KQEKLKEK........VKREKKEKVK
BAZ2B   754  IQQIRMEKELRAQQILEAKKKKKEEAANAKLLEAEKRIKEKEMRRQQAVLLKHQERERRR

L               L              L L            L
BAZ1Bs  539  ............SEEQRKEYLKKKREELKKKLKEKAKERREKEMLERLEKQKR.YEDQEL
BAZ1A   512  ............KKKEEKERLKVEREKEREKLREE.....KRKYVEYLKQWSKPREDMEC
BAZ2A   755  M...........KEKEEVTKAKPACKADK.TLATQRRLEERQKQQMILEEMKKPTEDMCL
BAZ2B   814  QHMMLMKAMEARKKAEEKERLKQEKRDEK.RLNKERKLEQRRLELEMAKELKKPNEDMCL

L          L L           L     L       LL         L  L   LL
BAZ1Bs  586  TG.KNLPAFRLVDTPEGLPNTLFGDVAMVVEFLSCYSGLLLPDAQYP...ITAVSLMEAL.
BAZ1A   555  DDLKELPEPTPVKT..RLPPEIFGDALMVLEFLNAFGELFDLQDEFPDGVTLEVLEEALV
BAZ2A   803  TDHQPLPDFSRVPGLT.LPSGAFSDCLTIVEFLHSFGKVLGFDPAK.DVPSLGVLQEGLL
BAZ2B   873  ADQKPLPELPRIPGLV.LSGSTFSDCLMVVQFLRNFGKVLGFDVNI.DVPNLSVLQEGLL
```

FIG. 15

```
                  LXXLL       L     LXXLLXXLL
BAZ1Bs  642  S.ADKGG......FLYLNRVLVILLQTLLQDEIAE....DYGELGMKLSEIPLTLHSVSE
BAZ1A   613  G.NDSEGPLCELLFFFLTAIFQAIAEE..EEEVAKEQLTDADTKGCSLKSLDLDSCTLSE
BAZ2A   861  CQGDSLGEVQDL........LVRLLKAALHDPGFPSYCQSLKILGEKVSEIPLTRDNVSE
BAZ2B   931  NIGDSMGEVQDL........LVRLLSAAVCDPGLITGYKAKTALGEHLLNVGVNRDNVSE

L L                                          L     L        L
BAZ1Bs  691  LVRLCLRRSDVQEESEGSDTD.......DNKDSAAFEDNEVQDEFLEKLETSEFFELTSE
BAZ1A   670  ILRLHILASGADVTSANAKYRYQKRGGFDATDDACMELRLSNPSLVKKLSSTSVYDLTPG
BAZ2A   913  ILRCFLMAYGVE............................PALCDRLRTQPFQAQPPQ
BAZ2B   983  ILQIFMEAHCGQ............................TELTESLKTKAFQAHTPA

L   L    LL
BAZ1Bs  744  EKLQILTALCHRILMTYSVQD....................HMETRQQMSAELWKER
BAZ1A   730  EKMKILHALCGKLLTLVSTRDFIEDYVDILRQAKQEFRELKAEQHRKEREEAAARIRKRK
BAZ2A   943  QKAAVLAFPVHELNGSTLIINEIDKTLESM...........SSYRKNKWIVEGRLRR..
BAZ2B  1013  QKASVLAFLINELACSKSVVSEIDKNIDYM...........SNLRRDKWVVEGKLRK..

BAZ1Bs  781  LAVLKEENDKKRAEKQKRKEMEAKNKENGKVENGLGKTDRKKRIVKFEPQVDTEA....E
BAZ1A   790  EEKLKEQEQKMKEKQEKLKEDEQRNS...TADISIGEEEREDFDTSIESK.DTEQKELDQ
BAZ2A   989  ...LKTVLAKRTGRSE....VEMGRPEECLG.......RRRSSRIM.E........ETS
BAZ2B  1059  ...LRIIHAKKTGKRDTSGGIDLGEEQHPLGTPTPGRKRRRKGGDS.DYDDDDDDDSDDQ

BAZ1Bs  837  DMI........SAVKSRRLLAIQAK.KEREIQEREMKV..KLERQAEEERIRKHKAAAEK
BAZ1A   846  DMFTEDEDDPGSHKRGRRGKRGQNGFKEFTRQEQINCVTRELLTADEEEALKQEHQRKEK
BAZ2A  1025  GMEEEEEEESIAAVPGRRGR..RDGE.....VDATASSIPELERQIEKLSKRQLF.....
BAZ2B  1115  GDEDDEDEEDKEDQKGKKTDICEDED.....EGDQAASVEELEKQIEKLSKQQSQ.....

BAZ1Bs  886  AFQEGIAKAKLVMRRTPIGTDRNHNRYWLFSDEVPGLFIEK...GWV.HDSIDYRFNHHC
BAZ1A   906  ELLEKIQSAIACTNIFPLGRDRMYRRYWIFPS.IPGLFIEEDYSGLT.EDMLLPRPSSF.
BAZ2A  1073  .FRKKLLHSSQMLRAVSLGQDRYRRRYWVLPY.LAGIFVEGTEGNLVPEEVIKKETDSLK
BAZ2B  1165  .YRRKLFDASHSLRSVMFGPDRYRRRYWILPR.CGGIFVEGMESGEGLEE.IAKEREKLK

LXXLL
BAZ1Bs  942  KDHTVSGDEDYCPRSKKANLGKNASMNTQHGTATE.........................
BAZ1A   963  QNNVQSQDPQVSTKTGEPLMSESTS.NIDQGPRDH.........................
BAZ2A  1131  VAAHASLNPALFSMKMELAGSNTTASSPARARSRP.LKTKPG...FMQ.PRHFKSPVRGQ
BAZ2B  1222  KAESVQIKEEMF....ETSGDSLNCSNTDHCEQKEDLKEKDNTNLFLQKPGSFSKLSKLL

BAZ1Bs  977  ............................................................
BAZ1A   997  ............................................................
BAZ2A  1186  DSEQPQAQLQPEAQLHVPAQPQPQLQLQLQSHKGFLEQEGSPLSLGQSQHDLSQSAFLSW
BAZ2B  1278  EV....AKMPPESEVMTP.KPNAGANGCTLSY.....QNSGKHSLGSVQSTATQSN....

BAZ1Bs  977  ............................................................
BAZ1A   997  ............................................................
BAZ2A  1246  LSQTQSHSSLLSSSVLTPDSSPGKL.DPAPSQPPEEPEPDEAESSPDLQAFWFNISAQMP
BAZ2B  1324  VEKADSNNLFNTGS.....SGPGKFYSPLPNDQLLKTLTEKNRQ.......WFSLLPRTP
```

FIG. 16

```
BAZ1Bs  977 ..............................................................
BAZ1A   997 ..............................................................
BAZ2A  1305 CNAAP.......TPPLAVSEDQP.....TPSPQQLASSKPMNRPSAANPC..SPVQFSS.
BAZ2B  1372 CDDTSLTHADMSTASLVTPQSQPPSKSPSPTPAPLGSS..AQNPVGLNPFALSPLQVKGG

BAZ1Bs  977 ..............................................................
BAZ1A   997 ..............................................................
BAZ2A  1350 TPLAGLAPKRRAGDPG............EMPQSPTGLGQPKRRGRPPSKFFKQMEQRYLTQ
BAZ2B  1430 VSMMGL...QFCGWPTGVVTSNIPFTLSVPSLGSGLGLSEGNG.............NSFLTS

LXXLL
BAZ1Bs  977 ...............................VAVETTTPKQGQNLWFLCDSQKELDELL
BAZ1A   997 ...............................SVQLPKPVHKPNRWCFYSSCEQLDQLI
BAZ2A  1399 LTA............................QPVPPEMCSGWWWIPDPEMLDAML
BAZ2B  1476 NVASSKSESPVPQNEKATSAQPAAVEVAKPVDFPSPKPIPEEMQFGWWRIIDPEDLKALL

BAZ1Bs 1005 NCLHPQGIRESQLKERLEKRYQDIIHSI........HLARKPNLGLKS...........
BAZ1A  1024 EALNSRGHRESALKETLLQEKSRICAQLARFSEEKFHFSDKPQPDSKPTYSRGRSSNAYD
BAZ2A  1426 KALHPRGIREKALHKHLNK..................HRDFLQEVCLRPS......ADPIF
BAZ2B  1536 KVLHLRGIREKALQKQIQK..................HLDYITQACLKNK......DVAII

BAZ1Bs 1045 ....CDGNQELLNFLRSDLIEVATRLQKGGLGYVEETSEFEARVISLEKLKDFGECVIAL
BAZ1A  1084 PSQMCAEKQLELR.LRDFLLDIEDRIYQGTLGAIKVTDRHIWR..................
BAZ2A  1463 EPRQLPAFQ...EGIMSW..SPKEKTYETDLAVLQWVEELEQRVIMSDLQIRGWTCPSPD
BAZ2B  1573 ELNENEENQVTRDIVENW..SVEEQAMEMDLSVLQQVEDLERRVASASLQVKGWMCPEPA

BAZ1Bs 1101 QASVIKKFLQGFMAPKQKRR...KLQSEDSAKTEEVDEEKKMVEEAKV............
BAZ1A  1126 ..SALESGRYELLSEENKENGIIKTVNED.VEEMEIDEQTKVIVKDRLLGIKTETPSTVS
BAZ2A  1518 ST.......REDLAYCEHLSDSQ....EDITWRGPGREGL.APQRKTTNPLDLAVMRLAA
BAZ2B  1631 SE.......REDLVYFEHKSFTKLCKEHDGEFTGEDESSAHALERKSDNPLDIAVTRLAD

BAZ1Bs 1146 ...............................ASALEKWKTAIREAQ
BAZ1A  1183 TNASTPQSVSSVVHYLAMALFQIEQGIERRFLKAPLDASPSGRSYKTVLDRWRESLLSSA
BAZ2A  1566 LEQNVKRRYLREPLWPTHEVVLEKALLSTPNGAPEGTTTEISYEITPRIRIWRQTLQRCR
BAZ2B  1684 LERNIERR...................IEEDIAPGLRVWRRALSEAR

C  C              C  C       H  C
BAZ1Bs 1161 TFSRMHVLLGMLDACIKWDMSAENARCKVCPKKGEDDKLILCDECNKAFHLFCLRPALYE
BAZ1A  1243 SLSQVFLHLSTLDRSVIWSKSILNARCKICRKKGDAENMVLCDGCDRGHHTYCVRPKLKT
BAZ2A  1626 SAAHVCLCLGHLERSIAWEKSVNKVTCLVCRKGDNDEFLLLCDGCDRGCHIYCHRPKMEA
BAZ2B  1712 SAAQVALCIQQLQKSIAWEKSIMKVYCQICRKGDNEELLLLCDGCDKGCHTYCHRPKITT

C  C
BAZ1Bs 1221 VPDGEWQCPACQPAT.ARRNS.RGRNYTE.ESASEDS...EDDESDEEEEEEEEEEE..
BAZ1A  1303 VPEGDWFCPECRPKQRCRRLSFRQRPSLESDEDVEDSMGGEDDEVDGDEEEGQSEEEEYE
BAZ2A  1686 VPEGDWFCTVC.................................
BAZ2B  1772 IPDGWFCPAC..................................
```

FIG. 17

```
BAZ1Bs1273  ........EDYEVAGLRLR.......PRKTIRGKHSVIPPAARSGRRPGKKPHSTRRSQP
BAZ1A  1363  VEQDEDDSQEEEEVSLPKRGRPQVRLPVKT.RGKLSSSFSSRGQQQEPGRYPSRSQQSTP
BAZ2A  1697  ...............LAQ...........QVEGEFT............QKPGFPKRGQK
BAZ2B  1783  ...............IAKASGQTLKIKKLHVKG...............KKTNESKKGKK

BAZ1Bs1318  K................APPVDDAEVDELVLQTK..........................
BAZ1A  1422  KTTVSSKTGRSLRKINSAPPT...ETKSLRIASRSTRHSHGPLQADVFVELLSPRRKRRG
BAZ2A  1718  ............RKSGYSLNFSEGDGRR................................
BAZ2B  1812  VTLTGDTEDEDSASTSSSLKRGNKDLQK................................

BAZ1Bs1336  ............................................................
BAZ1A  1479  RKSANNTPENSPNFPNFRVIATKSSEQSRSVNIASKLSLQESESKRRCRKRQSPEPSPVT
BAZ2A  1734  ................RRVLLKGRESPAAGPRYSEERLSPSKRRRLSMRNHHS.......
BAZ2B  1840  ................RKM.....EENTSINLSKQESFTSVKKPK...RDDSK......

Bromodomain motif
BAZ1Bs1336  ...RSSRRQS..LELQKCEEILHKIVKYRFSWPFREPVTRDEAEDYYDVITHPMDFQTVQ
BAZ1A  1539  LGRRSSGRQGGVHELSAFEQLVVELVRHDDSWPFLKLVSKIQVPDYYDIIKKPIALNIIR
BAZ2A  1771  ..............DLTFCEIILMEMESHDAAWPFLEPVNPRLVSGYRRIIKNPMDFSTMR
BAZ2B  1869  ..............DLALCSMILTEMETHEDAWPFLLPVNLKLVPGYKKVIKKPMDFSTIR LXXL
BAZ1Bs1391  NKCSCGSYRSVQEFLTDMKQVFTNAEVYNCRGSHVLSCMVKTE...........QCLVVL
BAZ1A  1599  EKVNKCEYKLASEFIDDIELMFSNCFEYNPRNTSEAKAGTRLQAFEH......IQAQKLG
BAZ2A  1818  ERLLRGGYTSSEEFAADALLVFDNCQTFNEDDSEVGKAGHIMRRFFESRWEEFYQGKQAN
BAZ2B  1916  EKLSSGQYPNLETFALDVRLVFDNCETFNEDDSDIGRAGHNMRKYFEKKWTDTFKVS...

L
BAZ1Bs1440  LH......KHLPGHPYVRRKRKKFPDRLAEDEGDSEPEAVGQSRDEDRRSREAEIQEWLQ
BAZ1A  1653  LHVTPSNVDQVSTPPAAKKSRI......................................
BAZ2A  1878  L...........................................................
BAZ2B  1973  ............................................................

BAZ1Bs1494  DTSLYSAKINSKDHNCFMMLVNTQFCMALTDTVT
BAZ1A  1675  .................................
BAZ2A  1879  .................................
BAZ2B  1973  .................................
```

FIG. 18

The numbers above refer to the amino acid residue position in SEQ ID NO: 21

US 7,851,604 B2

TRANSCRIPTIONAL REGULATOR

This application is a divisional application of U.S. application Ser. No. 10/702,148 (now U.S. Pat. No. 7,189,818), filed Nov. 5, 2003, which is a divisional application of U.S. application Ser. No. 09/839,479 (now U.S. Pat. No. 6,727,222) filed Apr. 20, 2001, which is a divisional application of U.S. application Ser. No. 09/418,710 (now U.S. Pat. No. 6,596,482), filed Oct. 15, 1999, which is a continuation-in-part application of PCT/JP98/01783, filed Apr. 17, 1998, and claims priority from Japanese Application Nos. 9/116570, filed Apr. 18, 1997, and 9/310027, filed Oct. 24, 1997. The contents of each of the foregoing applications are incorporated by reference herein.

TECHNICAL FIELD

The present invention relates to a novel transcriptional regulator containing a bromodomain and a gene encoding it.

BACKGROUND

The bromodomain is a characteristic motif of proteins found in transcriptional regulators. Proteins having a bromodomain usually contain one or two (Tamkun, J. W. et al., (1992), Nuc. Acids Res., 20:2603), but sometimes as many as five bromodomain motifs (Nicolas, R. H. and Goodwin, G. H. (1996), Gene, 175 (12):233-240). This motif is found in a wide variety of animals. For example, it is identified in yeast (Winston, F. et al., (1987), Genetics, 115:649-656; Laurent, B. C. et al., (1991), Proc. Natl. Acad. Sci. USA, 88:2687-2691), in Drosophila (Digan, M. E. et al., (1986), Dev. Biol., 114:161-169; Tamkun, J. W. et al., (1992), Cell, 68:561-572), and in the genes for transcriptional regulators in mammals (Denis, G. V. and Green, M. R. (1996), Genes and Devel., 10:261-271; Yang, X. J. et al., (1996), Nature, 382:319-324).

All transcriptional regulators containing a bromodomain serve to control signal-dependent transcription in actively proliferating cells (Tamkun, J. W. et al., (1992), Cell, 68:561-572; Haynes, S.R. et al., (1992), Nuc. Acids Res., 20:2603). Due to this feature of these transcriptional regulators, it is suggested that cancer may develop if the gene for the protein containing a bromodomain is not normally controlled. In fact, several studies have shown that human transcriptional regulators with a bromodomain RING3 (Really Interesting New Gene 3), p300/CBP (Creb Binding Protein), and PCAF (p300/CBP-Associated Factor) may be involved in oncogenesis.

RING3 is a transcriptional regulator highly homologous with the fsh protein that regulates development of Drosophila (Haynes, S. R. et al., (1989), Dev. Biol., 134:246-257). RING3 is a nuclear serine/threonine kinase having autophosphorylating activity. This activity of RING3 correlates with a proliferating state in chronic or acute lymphocytic leukemia. For instance, when Denis and Green collected lymphocytes of peripheral blood from 10 patients suffering from leukemia, kinase activity associated with RING3 was identified in all of the 10 patients but not in normal controls (Denis, G. V. and Green, M. R. (1996), Genes and Develop., 10:261-271). Furthermore, this activity was not detected in the blood cells from patients whose leukemia had remitted by virtue of chemotherapy.

p300 and CBP (CREB binding protein) encode highly similar proteins and are thus often called p300/CBP. p300/CBP is a co-activator for a transcriptional regulator CREB (cAMP responsive element binding protein) (Kwok, RPS et al., (1994), Nature, 370:223-226), and is considered as a key protein for growth regulation. Mutation in p300/CBP has been found in familial or sporadic cancers. Germline mutation of CBP results in Rubinstein-Taybi syndrome, which causes patients to develop various malignant tumors (Petrij, F. et al., (1995), Nature, 376:348-51), while mutation in p300 is found in sporadic colorectal and gastric cancers (Muraoka, M. et al., (1996), Oncogene, 12:1565-1569). Furthermore, CBP is fused with MOZ (Monocytic leukemia Zinc finger protein) in a t (8; 16) (p11; p13) translocation found in a certain kinds of acute myelocytic leukemia. The fusion protein has histone-acetyltransferase domains derived from both genes (Bannister, A. J. and Kouzarides, T. (1996), Nature, 384:641-643; Orgyzco, V. V. et al., (1996), Cell, 87:953-959; Brownwell, J. E. and Allis, C. D. (1996), Curr. Opin. Genet. Devel., 6:176-184). Since acetylated histone is known to be associated with transcriptionally active chromatin, the fusion protein may be involved in leukemogenesis by way of aberrant histone acetylation (Brownwell, J. E. and Allis, C. D. (1996), Curr. Opin. Genet. Devel., 6:176-184).

p300/CBP is also considered to be associated with cancer since it interacts with known oncogene products. For example, p300/CBP binds to E1A protein (Arany, Z. et al., (1995), Nature, 374:81-84), one of the early genes of adenovirus. p300 is also a co-activator for transcription factors, c-Myb (Dai, P. et al., (1996), Genes Dev., 10:528-540) and c-Fos (Bannister, A. J. and Kouzarides, T. (1996), Nature, 384:641-643).

PCAF, is considered to inhibit the interaction of E1A with p300/CBP by competing with E1A for binding to p300/CBP (Yang, X. J. et al., (1996), Nature, 382:319-324). PCAF also has histone-acetyltransferase activity.

Thus, it is thought that transcriptional regulators containing a bromodomain are involved in regulation of cell growth, and that their aberrant regulation may be closely related to various diseases, particularly to cancer. Transcriptional regulators containing a bromodomain have thus recently received much attention as novel targets for specifically treating cancer.

DISCLOSURE OF THE INVENTION

The objective of the present invention is to provide a novel transcriptional regulator containing a bromodomain and a gene encoding it, and a method of screening for a candidate compound as a medicament by using them.

As a result of research to achieve the above objective, the inventors successfully isolated several genes, each of which encodes a novel transcriptional regulator containing a bromodomain. The genes were isolated from a human testis cDNA library using primers designed based on EST sequences which had been identified using known bromodomain sequences as probes. In addition, the inventors have found that the structures of the isolated genes resemble one another, thus they constitute a family. The inventors have also found that the isolated genes or proteins encoded by them can be used to screen the candidate compounds for a medicament that controls the activity of the proteins or other factors interacting therewith.

Thus, the present invention relates to novel transcriptional regulators each having a bromodomain and the genes encoding them, and to a method of screening for a candidate compound as a medicament using said proteins or genes, and more specifically relates to:

(1) a transcriptional regulator having a bromodomain, which comprises the amino acid sequence shown in SEQ ID NO:1, 13, 21, 27, or 29, or said sequence wherein one or more amino acids are substituted, deleted, or added;

(2) a transcriptional regulator having a bromodomain, which is encoded by DNA hybridizing with DNA comprising the nucleotide sequence shown in SEQ ID NO:2, 14, 22, 28 or 30;

(3) DNA coding for the transcriptional regulator according to (1) or (2);

(4) a vector comprising the DNA according to (3);

(5) a transformant expressibly retaining the DNA according to (3);

(6) a method for producing the transcriptional regulator according to (1) or (2), which comprises culturing the transformant according to (5);

(7) an antibody binding to the transcriptional regulator according to (1) or (2);

(8) a method of screening a compound having binding activity to the transcriptional regulator according to (1) or (2), wherein the method comprises contacting a sample with the transcriptional regulator according to (1) or (2) and selecting a compound having binding activity to the transcriptional regulator according to (1) or (2);

(9) a compound having binding activity to the transcriptional regulator according to (1) or (2), which can be isolated according to the method of (8);

(10) the compound according to (9), which is naturally occurring; and

(11) DNA specifically hybridizing with DNA comprising the nucleotide sequence shown in SEQ ID NO:2, 14, 22, 28, or 30 and having at least 15 nucleotides.

Here, the term "transcriptional regulator(s)" means protein(s) that control gene expression, and "bromodomain" means an amino acid motif conserved among the transcriptional regulators associated with signal-dependent transcription, wherein said motif is involved in protein-protein interaction.

The present invention relates to novel transcriptional regulators having a bromodomain (BAZ (Bromodomain, Atypical Zinc Finger) family). The nucleotide sequences of cDNA isolated by the inventors, which belong to BAZ family, are shown in SEQ ID NO:2 (BAZ(BAZ1α)), SEQ ID NO:14 (BAZ2α), SEQ ID NO:22 (BAZ2β), and SEQ ID NO:28 and 30 (BAZ1β). The amino acid sequences of proteins encoded by the cDNA are also shown in SEQ ID NO:1 (BAZ (BAZ1α)), SEQ ID NO:13 (BAZ2α), SEQ ID NO:21 (BAZ2β), and SEQ ID NO:27 and 29 (BAZ1β).

The bromodomain is characteristic of a structural region that is conserved among a group of transcriptional regulators involved in signal-dependent transcription (Tamkun, J. W. et al., (1992), Cell, 68:561-572; Haynes, S. R. et al., (1992), Nuc. Acids Res., 20:2603), and it has been reported that the six mammalian genes, i.e., RING3, p300/CBP, PCAF, BRG1 (Brahma-Related Gene 1), HRX (Human Tri-Thorax)/ALL-1 (Acute Lymphocytic Leukemia-1), and TIF1(Transcriptional Intermediary Factor 1), which encode transcriptional regulators having a bromodomain, are associated with cancer. That the transcriptional regulators having a bromodomain are commonly associated with cancer suggests that the genes isolated by the inventors are also associated with cancer. Other than a bromodomain motif, the proteins encoded by the genes isolated by the inventors share the characteristic motifs of (1) C4HC3 zinc-finger, which is found in the proteins expressed in a wide range of organisms from yeast to human and is believed to be involved in a protein-protein interaction or nonspecific binding to DNA; (2) leucine zipper, which is present in many transcriptional regulators and is known to contribute to form a dimer with the protein itself or other proteins (Busch, S. J. and Sassone-Corsi, P. (1990), Trends in Genetics, 6:36-40); (3) LXXLL motif, a motif commonly found among many transcriptional co-activators, which is shown to be required for mediation of transcription induced by a nuclear receptor (Torchia, J. et al., (1997), Nature, 387: 677-684; Heery, D. M. et al., (1997), Nature, 387:733-736); and (4) nuclear transport signal, which confers the transporting activity into the nucleus on the proteins synthesized in the cytoplasm.

The combination of a bromodomain and C4HC3 zinc finger is known to be associated with several breakpoint genes of leukemia (Tkachuk, D. C. et al., (1992), Cell, 71:691-700; Gu, Y. et al., (1992), Cell, 71:701-798; Miki, T. et al., (1991), Proc. Nat. Acad. Sci., 88:5167-5171; Le Douarin B. et al., (1995), EMBO J., 14:2020-2033; Borrow, J. et al., (1996), Nature Genet., 14:33-41). Accordingly, the genes isolated by the inventors are important candidates for breakpoint genes of cancers.

The transcriptional regulators of the present invention can be prepared as recombinant proteins generated using a recombinant gene technique, or as naturally occurring proteins, according to a method known to one skilled in the art. The recombinant proteins can be prepared using a method such as incorporating DNA encoding a transcriptional regulator of the present invention (e.g., DNA having the nucleotide sequence shown in SEQ ID NO:2, 14, 22, 28, or 30) into a suitable expression vector, which is then introduced into host cells, and purifying the protein obtained from the transformant. The naturally occurring proteins can be prepared using a method such as preparing a column which utilizes an antibody obtained from a small animal immunized with the recombinant protein prepared as above, and subjecting the extract from a tissue or cells in which a transcriptional regulator of the present invention is overexpressed (e.g., testis and cancer cells) to affinity chromatography using said column.

The present invention also relates to transcriptional regulators functionally equivalent to the transcriptional regulators of the present invention having the amino acid sequence shown in SEQ ID NO: 1, 13, 21, 27, or 29. A method of introducing mutation into amino acids of a protein to isolate a protein functionally equivalent to a particular protein is well known to one skilled in the art. Thus, it is well within the art of an ordinarily skilled person to isolate a transcriptional regulator functionally equivalent to the transcriptional regulators of the present invention having the amino acid sequence shown in SEQ ID NO: 1, 13, 21, 27, or 29 by appropriately modifying, for example, substituting amino acids without affecting the function of the transcriptional regulator. Mutation in an amino acid of a protein can also occur spontaneously. The transcriptional regulators of the present invention include those having a bromodomain and the amino acid sequence of SEQ ID NO:1, 13, 21, 27, or 29 wherein one or more amino acids are substituted, deleted, or added. Examples of known methods for introducing amino acid mutation into the protein are a site-directed mutagenesis system using PCR (GIBCO-BRL, Gaithersburg, Maryland) and a site-directed mutagenesis using oligonucleotides (Kramer, W. and Fritz, H. J. (1987), Methods in Enzymol., 154:350-367). The number of mutagenized amino acids is usually 50 amino acids or less, preferably 30 amino acids or less, more preferably 10 amino acids or less, and most preferably three amino acids or less.

As another method of isolating a functionally equivalent protein utilizing a hybridization technique (Sambrook, J. et al., Molecular Cloning 2nd ed. 9.47-9.58, Cold Spring Harbor Lab. press, 1989) is well known to one skilled in the art. Based on the DNA sequence encoding the transcriptional regulator of the present invention shown in. SEQ ID NO:2, 14, 22, 28, or 30, or the fragment thereof, a person with ordinary skill in the art can isolate DNA highly homologous to said DNA sequences using a hybridization technique (Sambrook, J. et al., Molecular Cloning 2nd ed. 9.47-9.58, Cold Spring Harbor Lab. press, 1989) to obtain a transcriptional regulator functionally equivalent to the transcriptional regulators. The transcriptional regulators of the present invention include those encoded by DNA that hybridizes with DNA comprising the DNA sequence shown in SEQ ID NO:2, 14, 22, 28, or 30, and which contains a bromodomain. The hybridization and washing conditions for isolating DNA encoding a functionally equivalent protein are defined as low stringency: 42° C., 2×SSC, 0.1% SDS; moderate stringency: 50° C., 2×SSC, 0.1% SDS; and high stringency: 65° C., 2×SSC, 0.1% SDS. The transcriptional regulators obtained by the hybridization technique may have amino acid homology of preferably 40% or more, more preferably 60% or more, still more preferably 80% or more, or most preferably 95% or more, with the transcriptional regulators having the amino acid sequence shown in SEQ ID NO:1, 13, 21, 27, or 29. In particular, high homology in the bromodomain sequence is considered significant for the function associated with cancer. Functionally equivalent transcriptional regulators to be isolated may contain, other than a bromodomain, a sequence involved in interaction with another protein (e.g., leucine-zipper or LXXLL motif), a sequence involved in binding to DNA (e.g. zinc finger), or a nuclear transport signal. The presence of the bromodomain in the protein can be identified by searching the bromodomain motif PROSITE database on DNASIS (HITACHI Software engineering).

The present invention also relates to DNA that codes for a transcriptional regulator of the present invention. The DNA of the present invention includes cDNA, genomic DNA, and chemically synthesized DNA, but is not limited thereto as long as it codes for a transcriptional regulator of the present invention. cDNA can be prepared, for example, by designing a primer based on the nucleic acid sequence shown in SEQ ID NO:2, 14, 22, 28, or 30 and performing plaque PCR (see Affara, N. A. et al., (1994), Genomics, 22:205-210). The genomic DNA can be prepared according to a standard technique using, for example, Qiagen genomic DNA kits (Qiagen, Hilden, Germany). The DNA sequence thus obtained can be determined according to a standard technique using a commercially available dye terminator sequencing kit (Applied Biosystems) and the like. In addition to applying to the production of recombinant proteins as described below, the DNA of the present invention may be applied to gene therapy and the like.

The present invention also relates to a vector into which the DNA of the present invention is inserted. There is no particular limitations to the vector into which the DNA of the present invention is inserted, and various types of vectors, e.g. for expressing the transcriptional regulators of the present invention in vivo and for preparing recombinant proteins, may be used for each purpose. Vectors used for expressing the transcriptional regulators of the present invention in vivo (in particular, for gene therapy) include the adenovirus vector pAdexLcw and the retrovirus vector pZIPneo. A LacSwitch II expression system (Stratagene; La Jolla, Calif.) is advantageous when mammalian cells, such as CHO, COS, and NIH3T3 cells, are used. An expression vector is particularly useful for producing a transcriptional regulator of the present invention. Although there is no particular limitation to the expression vectors, the following vectors are preferred: pREP4 (Qiagen, Hilden, Germany) when E. coli is used; SP-Q01 (Stratagene, La Jolla, Calif.) when yeast is used; and BAC-to-BAC baculovirus expression system (GIBCO-BRL, Gaithersburg, Maryland) when insect cells are used. The DNA of the present invention can be inserted into vectors using a standard method.

The present invention also relates to a transformant expressibly retaining the DNA of the present invention. The transformants of the present invention include one harboring the above-described vector into which the DNA of the present invention is inserted and one having the DNA of the present invention integrated into its genome. The DNA of the present invention can be retained in the transformant in any form as long as the transformant expressibly retains the DNA of the present invention. There is no limitation to host cells into which a vector of the present invention is introduced. If the cells are used to express a transcriptional regulator of the present invention in vivo, desired cells may be used as target cells. Cells such as E. coli, yeast cells, animal cells, and insect cells can be used for producing the transcriptional regulators of the present invention. The vector can be introduced into the cells by methods such as electroporation and heat shock. Recombinant proteins can be isolated and purified from the transformants generated for producing the said proteins according to a standard method.

The present invention also relates to antibodies that bind to the transcriptional regulators of the present invention. The antibodies of the present invention include, but are not limited to, polyclonal and monoclonal antibodies. Also included are antisera obtained by immunizing an animal such as a rabbit with a transcriptional regulator of the present invention, any class of polyclonal or monoclonal antibodies, humanized antibodies generated by gene recombination, and human antibodies. The antibodies of the present invention can be prepared according to the following method. For polyclonal antibodies, antisera can be obtained by immunizing a small animal, such as a rabbit, with a transcriptional regulator of the present invention, then recovering the fractions that only recognize the transcriptional regulator of the present invention through an affinity column coupled with the transcriptional regulator of the present invention. Immunoglobulin G or M can be prepared by purifying the fractions through a Protein A or G column. For monoclonal antibodies, a small animal, such as a mouse, is immunized with a transcriptional regulator of the invention, the spleen is removed from the mouse and homogenized into cells, the cells are fused with myeloma cells from a mouse using a reagent such as polyethylene glycol, and clones that produce antibodies against the transcriptional regulator of the invention are selected from the resulting fused cells (hybridoma). The hybridoma obtained is then transplanted into the abdominal cavity of a mouse, and the ascites are recovered from the mouse. The obtained monoclonal antibodies can then be prepared by purifying, for example, by ammonium sulfate precipitation through a Protein A or G column, by DEAE ion exchanging chromatography, or through an affinity column coupled with the transcriptional regulator of the invention. Besides being used to purify or detect the transcriptional regulators of the present invention, the antibodies of the present invention can be applied to antibody therapy.

The present invention also relates to a screening method for a compound that binds to transcriptional regulators of the present invention. The screening method of the present invention includes steps of contacting a transcriptional regulator of the present invention with a test sample and selecting a compound that has binding activity for the transcriptional regulator of the present invention. Test samples used for the screening include, but are not limited to, a cell extract, a supernatant of the cell culture, a library of synthetic low molecular weight compounds, a purified protein, an expression product of a gene library, and a library of synthetic peptides.

Methods well known to one skilled in the art for isolating a compound binding to a transcriptional regulator of the present invention using the regulator are as follows. A protein that binds to a transcriptional regulator of the present invention can be screened by West-western blotting comprising steps of generating a cDNA library from the cells expected to express the protein that binds to a transcriptional regulator of the present invention (e.g., testis tissue cell and tumor cell lines HL-60, HeLa S3, Raji, and SW480) using a phage vector (λgt11, ZAP, etc.), allowing the cDNA library to express on the LB-agarose plate, fixing the expressed proteins on a filter, reacting them with the transcriptional regulator of the present invention purified as a biotin-labeled protein or a fusion protein with GST protein, and detecting plaques expressing the protein bound to the regulator on the filter with streptavidin or anti-GST antibody (Skolnik, E. Y., Margolis, B., Mohammadi, M., Lowenstein, E., Fisher, R., Drepps, A., Ullrich, A. and Schlessinger, J. (1991), Cloning of PI3 kinase-associated p85 utilizing a novel method for expression/cloning of target proteins for receptor tyrosine kinases, Cell, 65:83-90). Alternatively, the method comprises expressing in yeast cells a transcriptional regulator of the present invention which is fused with SFR or GAL4 binding region, constructing a cDNA library in which proteins are expressed in a fusion protein with the transcription activation site of VP16 or GAL4 from the cells expected to express a protein that binds to the transcriptional regulator of the present invention, introducing the cDNA library into the above-described yeast cells, isolating the cDNA derived from the library from the detected positive clones, and introducing and expressing it in *E. coli*. (If a protein that binds to the transcriptional regulator of the present invention is expressed, a reporter gene is activated by the binding of the two proteins. The positive clones can then be identified.) This method can be performed using Two-hybrid system (MATCHMAKER Two-Hybrid System, Mammalian MATCHMAKER Two-Hybrid Assay Kit, MATCHMAKER One-Hybrid System (all from Clontech); HybriZAP Two-Hybrid Vector System (Stratagene) or in accordance with Dalton, S. and Treisman R. (1992), Characterization of SAP-1, a protein recruited by serum response factor to the c-fos serum response element, Cell, 68:597-612). Another method is to apply a culture supernatant or a cell extract from the cells suspected to express a protein which binds to the transcriptional regulator of the present invention onto an affinity column coupled with the transcriptional regulator of the present invention, and purify the protein specifically bound to the column.

Also well known to one skilled in the art are a method of screening molecules that bind to a transcriptional regulator of the present invention by reacting the immobilized transcriptional regulator of present invention with a synthetic compound, natural substance bank, or a random phage peptide display library, and a method of screening low molecular weight compounds, proteins (or their genes), or peptides which bind to a transcriptional regulator of the present invention by utilizing the high-throughput technique of combinatorial chemistry (Wrighton, N. C., Farrell, F. X., Chang, R., Kashuyap, A. K., Barbone, F. P., Mulcahy, L. S., Johnson, D. L., Barrett, R. W., Jolliffe, L. K., Dower, W. J., Small peptides as potent mimetics of the protein hormone erythropoietin, Science (UNITED STATES) Jul. 26, 1996, 273:458-464; Verdine, G. L., The combinatorial chemistry of nature, Nature (ENGLAND), Nov. 7, 1996, 384:11-13; Hogan, J. C. Jr., Directed combinatorial chemistry, Nature (ENGLAND), Nov. 7, 1996, 384:17-19). The compounds thus isolated, which bind to a transcriptional regulator of the present invention, may be used to treat cancer or other proliferative diseases. When the compounds isolated by the screening method of the present invention are used as pharmaceuticals, they can be formulated by a known pharmacological process. For example, they can be administered to a patient with pharmaceutically acceptable carriers and vehicles (e.g., physiological saline, vegetable oil, a dispersant, a surfactant, and a stabilizer). The compounds may be percutaneously, intranasally, transbronchially, intramuscularly, intravenously, or orally administered, depending on their properties.

The present invention also relates to DNA specifically hybridizing with DNA coding a protein of the present invention and having at least 15 nucleotides. As used herein, "specifically hybridizing" means that no cross-hybridization occurs between DNA encoding other proteins under conditions of moderate stringency. Such DNA may be used as a probe for detecting and isolating the DNA encoding the protein of the present invention, and as a primer for amplifying the DNA encoding the protein of the present invention.

An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, and (iii) cell clones: e.g., as these occur in a DNA library such as a cDNA or genomic DNA library.

The term "substantially pure" as used herein in reference to a given polypeptide means that the polypeptide is substantially free from other biological compounds, such as those in cellular material, viral material, or culture medium, with which the polypeptide was associated (e.g., in the course of production by recombinant DNA techniques or before purification from a natural biological source). The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC (High Performance Liquid Chromatography) analysis.

A "conservative amino acid substitution" is one in which an amino acid residue is replaced with another residue having a chemically similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As used herein, "percent identity" of two amino acid sequences or of two nucleic acids is determined using the algorithm of Karlin and Altschul (Proc. Natl. Acad. Sci. USA 87:2264-2268, 1990), modified as in Karlin and Altschul (Proc. Natl. Acad. Sci. USA 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score=100, wordlength=12 to obtain nucleotide sequences homologous to a nucleic acid molecules of the invention. BLAST protein searches are performed with the XBLAST program, score=50, wordlength=3 to obtain amino acid sequences homologous to a reference polypeptide. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., XBLAST and NBLAST) are used. See www.ncbi.nlm.nih.gov.

Unless otherwise defined, all technical and scientific terms used herein have the same meaning as commonly understood by one of ordinary skill in the art to which this invention belongs. In case of conflict, the present application, including definitions, will control. All publications, patent applications, patents, and other references mentioned herein are incorporated by reference. The materials, methods, and examples are illustrative only and not intended to be limiting. Other features and advantages of the invention will be apparent from the detailed description, and from the claims.

BRIEF DESCRIPTION OF THE DRAWINGS

FIGS. 1A and 1B compare certain BAZ (BAZ1α) domains with those of other proteins. In FIG. 1A, the bromodomain of BAZ (BAZ1α; SEQ ID NO:37) is compared with that of TFIID from yeast (SEQ ID NO:38), CCG1 from human (SEQ ID NO:39), PCAF (SEQ ID NO:40), and CBP (SEQ ID NO:41). In FIG. 1B, C4HC3 Zn finger of BAZ (BAZ1α; SEQ ID NO:42) is compared with those of U13646 (SEQ ID NO:43), retinoblastoma binding protein RBP2 (SEQ ID NO:44), two species of MOZ SEQ ID NOs:45 and 46, respectively), p300 (SEQ ID NO:47), and CBP (SEQ ID NO:48). The conserved amino acids, cysteine and histidine, are indicated by "*." In both FIGS. 1A and B, identical amino acids are represented by bold letters, and similar amino acids are underlined.

FIG. 3 shows the expression of BAZ (BAZ1α) in normal tissues (Lane 1, heart; Lane 2, brain; Lane 3, placenta; Lane 4, lung; Lane 5, liver; Lane 6, skeletal muscle; Lane 7, kidney; Lane 8, pancreas; Lane 9, spleen; Lane 10, thymus; Lane 11, prostate; Lane 12, testis; Lane 13, ovary; Lane 14, small intestine; Lane 15, colon (mucous lining); and Lane 16, leukocytes in the peripheral blood). The bottom of the figure shows control bands using actin probes.

FIGS. 4A and 4B show the expression of BAZ (BAZ1α) in carcinoma. FIG. 4A depicts the Northern blot analysis in the carcinoma cell lines (Lane 1, promyelocytic leukemia HL 60; Lane 2, HeLa S3 cells; Lane 3, chronic myelocytic leukemia K-562; Lane 4, lymphoblastic leukemia MOLT-4; Lane 5, Burkitt's lymphoma Raji; Lane 6, large intestine adenocarcinoma SW480; Lane 7, lung carcinoma A549; and Lane 8, melanoma G361). FIG. 4B shows the RT-PCR analysis of primary lung carcinoma of Lane 10. The top panel shows the amplified product of 554 by from BAZ (BAZ1α) gene using primers U and N, and the bottom shows the amplified product of 442 by from G3PDH gene using primers G3U and G3L. In the figures, L refers to normal human lung; T, to normal human testis; and G, to normal human genomic DNA.

FIGS. 6A and 6B show alignments of certain domains of BAZ2α and domains of other proteins. In FIG. 6A, the bromodomain of BAZ2α (BAZ2 in the figure; SEQ ID NO:51) is aligned with BAZ (BAZ1α; SEQ ID NO:49), human CCG1 (SEQ ID NO:50), PCAF (SEQ ID NO:52), U13646 (SEQ ID NO:53) and CBP (SEQ ID NO:54). In FIG. 6B, C4HC3 Zn finger of BAZ2α (SEQ ID NO:61) is aligned with BAZ (BAZ1α; SEQ ID NO:55), U13646 (SEQ ID NO:56), retinoblastoma binding protein RBP2 (SEQ ID NO:57), 2 zinc fingers of MOZ (SEQ ID NO:58 and 60, respectively), and p300 (SEQ ID NO:60). The conserved cysteine and histidine are indicated by "*."

FIG. 10 compares the amino acid sequence of LH domain in BAZ2β (SEQ ID NO:65) with those of corresponding domains in other proteins (BAZ1α (SEQ ID NO:62), U13646 (SEQ ID NO:63), and BAZ2α (SEQ ID NO:64)). The positions of conserved leucine residues are indicated by arrows on the sequences. LXXLL motifs are boxed.

FIG. 11 shows a chromosome map of BAZ2β. The product of 147 bp was specifically amplified in the cell line as a monochromosome for human chromosome 2. This product was amplified by PCR using primers nb7n and nb7ee. The numbers 1 to Y in the figure indicate chromosome numbers. The location of BAZ2β on chromosome 2 was determined by Genebridge 4 radiation hybrid panel analysis.

FIG. 12 shows an analysis of the expression of BAZ2β in normal tissues, carcinoma cell lines, and fetal tissues (Lane 1, heart; Lane 2, brain; Lane 3, placenta; Lane 4, lung; Lane 5, liver; Lane 6, skeletal muscle; Lane 7, kidney; Lane 8, pancreas; Lane 9, spleen; Lane 10, thymus; Lane 11, prostate; Lane 12, testis; Lane 13, uterus; Lane 14, small intestine; Lane 15, colon (mucous lining); Lane 16, leukocytes in the peripheral blood; Lane 17, fetal brain; Lane 18, fetal lung; Lane 19, fetal liver; Lane 20, fetal kidney; Lane 21, acute leukemia HL-60; Lane 22, HeLa S3 cells; Lane 23, chronic myelocytic leukemia K-562; Lane 24, lymphoblastic leukemia MOLT-4; Lane 25, Burkitt's lymphoma Raji; Lane 26, large intestine adenocarcinoma SW480; Lane 27, lung carcinoma A549; and Lane 28, melanoma G361). The sizes of the transcripts are indicated on the right side of the figure.

FIG. 13 shows the alignments of variable portions of BAZ1βS (SEQ ID NO:66) and BAZ1βL (SEQ ID NO:67).

FIG. 14 shows the alignments of N terminal amino acid sequences from BAZ1βS (SEQ ID NO:68) and three other members of the BAZ family ("BAZ1A" (SEQ ID NO:69), "BAZ2A" (SEQ ID NO:70), and "BAZ2B" (SEQ ID NO:71)). The residues with 50% or more sequence homology are indicated by bold letters, and those with 50% or more sequence similarity by underlining. Conserved LXXLL motifs and C4HC3 zinc fingers are indicated on the alignments. Conserved leucine residues in the surrounding region of the LXXLL motif are indicated. The location of a bromodomain motif is indicated by a black line on the alignments.

FIG. 15 shows the alignments of the amino acid sequences from BAZ1βS (SEQ ID NO:68) and three other members of the BAZ family (continued from FIG. 14).

FIG. 16 shows the alignments of the amino acid sequences from BAZ1βS (SEQ ID NO:68) and three other members of the BAZ family (continued from FIG. 15).

FIG. 17 shows the alignments of the amino acid sequences from BAZ1βS (SEQ ID NO:68) and three other members of the BAZ family (continued from FIG. 16).

FIG. 18 shows the alignments of the amino acid sequences from BAZ1βS (SEQ ID NO:68) and three other members of the BAZ family (continued from FIG. 17).

In FIG. 20A, the BAZ1β probe is hybridized with two transcripts in a wide range of tissues (Lane 1, heart; Lane 2, brain; Lane 3, placenta; Lane 4, lung; Lane 5, liver; Lane 6, skeletal muscle; Lane 7, kidney; Lane 8, pancreas; Lane 9, spleen; Lane 10, thymus; Lane 11, prostate; Lane 12, testis; Lane 13, uterus; Lane 14, small intestine; Lane 15, colon (mucous lining); and Lane 16, leukocytes in the peripheral blood). FIG. 20B shows controls using an actin probe. In FIG. 20B, the blot in FIG. 20A was used to rehybridize with the actin probe.

BEST MODE FOR IMPLEMENTING THE INVENTION

Figure 2A:
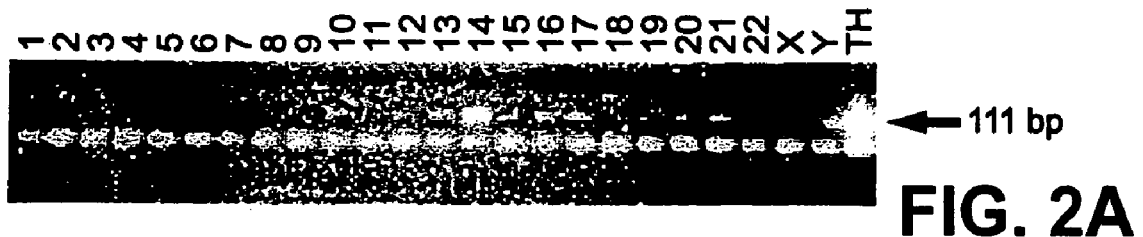
FIG. 2A shows assignments of chromosome 14 based on the analysis of a monochromosome hybrid cell panel using primers B (SEQ ID NO:6) and M (SEQ ID NO:7). The numbers 1 to Y in the figure refer to chromosome numbers, and TH refers to total human chromosomes. The 111 bp product was specifically amplified in the cell line GM10479, monochromosomel for a human chromosome 14.

The present invention is further illustrated with reference to the following examples, but is not to be construed to be limited thereto.

EXAMPLE 1

Isolation and Analysis of BAZ Gene (1) Identification of Novel Genes each Containing a Bromodomain The EST database was searched by means of BLAST using the DNA sequence that encodes the 5' bromodomain motif of the RING3 gene (SEQ ID NO:3) (Beck, S. et al., (1992), DNA Sequence, 2:203-210), and a number of ESTs identical to the probe sequence were retrieved. The following experiment was then performed for one of those EST, H70181. H70181 has the highest homology to transcription activator GCN5 of yeast (Georgakopoulos, T. and Thireos, G. (1992), EMBO J., 11 (11):4145-4152) or human (Candau, R. et al., (1996), Mol. Cell. Biol., 16 (2):593-602).

(2) Isolation of a Full-length Sequence

To clone a full-length sequence of EST H70181, PCR primers were designed; primer U, SEQ ID NO:4/ AGAAAAAGACAATCTCCAGAGCA, and primer L, SEQ ID NO:5/GCTGTCATCATGTCGTACCAATTC. The specific product of 129 bp obtained from testis cDNA was amplified by RT-PCR using said primers. The amplified product was directly purified through a QIA Quick (Qiagen) purification column. This PCR product was used as a probe for screening the testis cDNA library (Clontech; HL3023a). The probe was labeled with [α-$^{32}$P]dCTP by random priming, and purified using a Chromaspin 10 Column (Clontech); the cDNA clone obtained was used to re-screen the library. This process was repeated until a series of overlapped clones was obtained, and thus a full-length sequence was obtained. The isolated sequence was 5,934 bp in total. The isolated gene was designated "BAZ" (Bromodomain, Atypical Zinc finger). BAZ has an open reading frame (ORF) (SEQ ID NO:1) coding for 1,674 amino acids from the nucleotide positions 125-5147. The ORF is followed by 787bp of a 3' untranslated region and terminated with a poly-A tail. The polyadenylation signal (AATAAA) is located at 21 bp upstream from the poly-A tail. The nucleotide sequence together with the deduced amino acid sequence therefrom is shown in SEQ ID NO:2.

The filter screening of the library was performed in ExpressHyb hybridization solution (Clontech) at 65° C. for 1 hour. The filter was then washed until a final stringency of 1×SSC and 0.1% SDS at 65° C. was attained. All the sequencing was performed on automated sequencing apparatus ABI 377 (Perkin Elmer, Norwalk, Conn.), utilizing ABI dye terminator chemistry.

(3) Identification of the Homology and Motifs Characterizing the Transcription Factors A protein database search using the amino acid sequence of BAZ revealed that a protein encoded by a continuous 2.2 Mb gene sequence of the chromosome III of C. Eelegans (Wilson, R. et al., (1994), Nature, 368:32-38) is most similar (46% similarity and 23% identity). The same regions having similarity were found in various transcription factors such as the 250 KD subunit of TFIID (Ruppert, S., Wang, E., and Tjian, R. (1993),.Nature 362:175-179) and p300/CBP (Eckner, R. et al., (1994), Genes Dev., 8 (8):869-884; Chrivia, J. C. et al., (1993), Nature, 365:855-859). A motif search of amino acid sequences in the PROSITE database on DNASIS (HITACHI Software Engineering Co.) identified a single bromodomain (amino acid residues 1569-1627 of SEQ ID NO: 1). The sequence of this bromodomain, together with those of other bromodomains, is shown in FIG. 1A. A BLAST search using C4HC3 Zn finger (C4HC3ZF), which is the motif conserved among a great variety of proteins such as U13646, identified retinoblastoma binding protein RBP2 (Fattaey, A. R. et al., (1993), Oncogene, 8:3149-3156), MOZ (Borrow, J. et al., (1996), Nature Genet., 14:33-41), and p300/CBP(Koken, M. H. et al., (1995), CR Acad. Sci. III, 318:733-739), a motif of 45 amino acids (corresponding to amino acid residues 1269-1313 of SEQ ID NO:1). C4HC3ZFs present in these genes are shown in FIG. 1B. The function of BAZ as a transcriptional regulator is implied by the fact that it is similar to several transcriptional regulators, in particular, a bromodomain motif conserved together with C4HC3ZF and p300/CBP. The similarity of BAZ to p300/CBP is not limited to C4HC3 zinc finger and bromodomain regions; well conserved regions are also found adjacent to the bromodomain. Homology was not found between BAZ and histone-acetyltransferase domain, and between BAZ and other domains in which p300/CBP is present. However, BAZ potentially has HAT activity since the histone-acetyltransferase domain is not well conserved among proteins.

Several sorts of sequence motifs characterized by the nuclear proteins were identified at 11 sites by employing the PSORT program (psort.nibb.ac.jp) utilizing a wide variety of conserved nuclear localization sequences.

(4) Mapping of BAZ

Figure 2B:
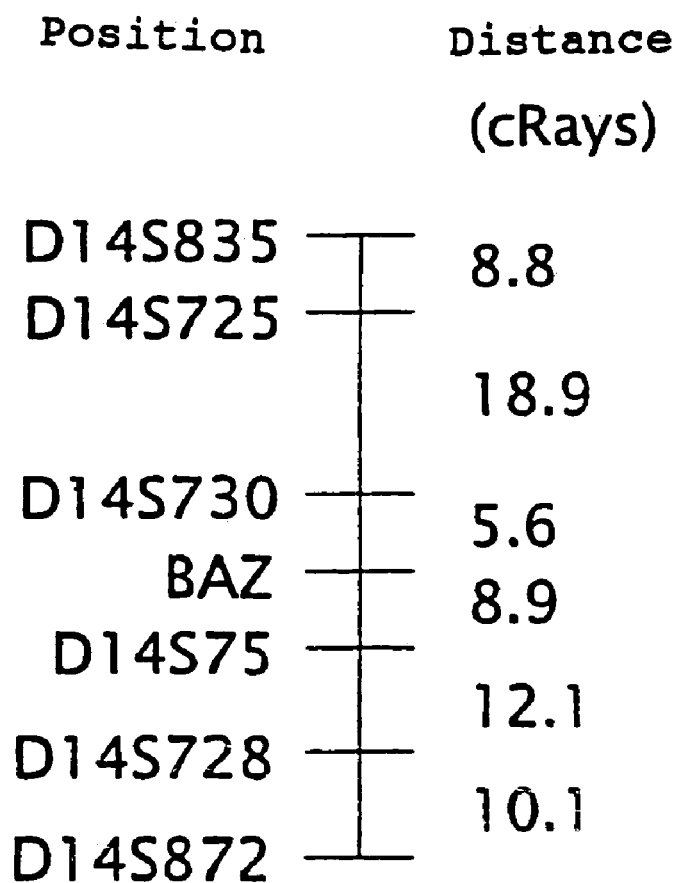
FIG. 2B depicts the location of BAZ (BAZ1α) on chromosome 14 as determined by Genebridge 4 radiation hybrid nanel analysis.

Primers B SEQ ID NO:6/AACACAAGTGAAG-CAAAAGCTGGA and M SEQ ID NO:7/GTGGTGT-GCTAACTTGGTCCACAT (obtained from the 3' end of the gene) were used to amplify DNA obtained from each of the 24 monochromosomes of human/rodent somatic cell lines available from Coriell Cell Respositories, New Jersey (Dubois, B. L. and Naylor, S. (1993), Genomics, 16:315-319). The expected product of 111 bp was amplified only from GM10479, a monochromosomal cell line for human chromosome 14 (see FIG. 2A). Primers B (SEQ ID NO:6) and M (SEQ ID NO:7) were subsequently used for PCR onto a GeneBridge 4 radiation hybrid panel (Research Genetics, Huntsville, Ala.). The binary codes generated by assessing whether each hybrid is positive or negative for amplification were compared with the analogous codes for the markers constituting a framework map, using the server located at www-genome.wi.mit.edu./cgi-bin/contig/rhmapper.pl. This step was repeated using primers W: SEQ ID NO:8/CCCATCGTGAGTCAAGAGTGTCTGT and X: SEQ ID NO:9/CTCGCTTCTACCTTTTTATTGGCT (from the 5' end of the gene). Based on the pattern obtained from this panel by identifying the amplification in the panel, BAZ was proved to be located on the 14q between the two markers D14S730 and D14S75 (see FIG. 2B).

(5) Analysis of BAZ Expression in the Normal Tissues

The probe as synthesized in Example 1 (2) by amplifying cDNAs from testis with PCR using the above-described primers U (SEQ ID NO:4) and L (SEQ ID NO:5) was used for Northern blot analysis of 16 panels of normal tissues. The probe hybridized with a single species of mRNA of 7.0 kb, which corresponds to the length of the ORF identified from the sequence of the gene. Though this transcript was expressed in almost all the tissues at very low levels, it was expressed in testis at a relatively high level (see FIG. 3). The transcript was not detectable in brain, lung, liver, kidney, and colon (it was possibly expressed at non-detectable levels). A slightly smaller transcript of 6.5 kb was also detected only in testis at a low level. Since the cells divide more vigorously in the testis than any other tissue examined, the expression pattern is thought to correspond to the role for BAZ during active proliferation. Hybridization for Northern blot analysis was performed in Express Hyb hybridization solution (Clontech) at 65° C. for 1 hour. The filters were washed until the final stringency reached 1×SSC and 0.1% SDS at 65° C. Imaging was performed using a Fuji BAS Image Analyzer (Fuji Photo Film).

(6) Analysis of BAZ Expression in Tumor

That BAZ is highly expressed in the testis suggests the possibility of its high level expression in vigorously proliferating tumors. Thus, Northern analysis of eight panels of tumor cell lines was carried out, using the same probe as used in Example 1 (5). As a result, the transcript of 7.0 kb alone was hybridized with the probe as when the normal tissue was used. Compared with most normal tissues, however, the transcriptional levels are remarkably higher in most of the tumor cell lines (see FIG. 4A). Specifically, the expression was higher in the tumor cell lines HL-60, HeLa S3, Raji, and SW480. In contrast, the expression levels in K-562, MOLT-4, A549, and G361 are almost the same as those in normal tissues.

RT-PCR was used to examine the expression of BAZ in the primary lung carcinomas as shown in Table 1.

TABLE 1

| Sample No. | Patients | | Carcinoma |
|---|---|---|---|
| | age | sex | |
| 1 | 49 | male | papillary adenocarcinoma |
| 2 | 63 | male | papillary adenocarcinoma (moderately differentiated) |
| 3 | 60 | male | papillary adenocarcinoma (poorly differentiated) |
| 4 | 70 | male | squamous cell carcinoma (fusiform cell variant) |
| 5 | 76 | male | papillary adenocarcinoma |
| 6 | 65 | male | large lung cell carcinoma (moderately differntiated) |
| 7 | 77 | male | squamous cell carcinoma (poorly differentiated) |
| 8 | 45 | male | acinic adenocarcinoma |
| 9 | 50 | male | carcinoid tumor |
| 10 | 66 | male | choriocarcinoma |

Each of the 10 samples was amplified using the primers G3U SEQ ID NO:10/TCATCATCTCTGCCCCCTCT-GTCTG and G3L SEQ ID NO: 11/GACGCCTGCTTCAC-CACCTTCTTG, which are the primers for amplifying 442 bp of a house-keeping gene G3PDH, and the primers U, SEQ ID NO:4 and N, SEQ ID NO:12/ TCATGTGGTCAATCAAT-TGTTTGT, which are primers for BAZ (see FIG. 4). G3PDH was used to determine that an equal amount of mRNA was present in each sample.

The primers for BAZ were selected to specifically amplify the cDNA but not genomic DNA. The amplified product was definitely detected in the sample from the testis and the two lung tumors, but not from the other eight samples from the lung tumor or the normal lungs.

RT-PCR was performed according to a standard technique in which total RNA was extracted according to the AGPC method (Chomczynski, P. and Sacchi, N. (1987), Analytical Biochem., 162:156-159), then single-stranded DNA was synthesised with an oligo (dT15) primer and MMLV reverse transcriptase, a part of which was used for the RT-PCR. The RT-PCR was performed using AmpliTaq gold (ABI), with 27 cycles of annealing at 60°C. to amplify G3PDH and 33 cycles of annealing at 55°C. to amplify BAZ. The conditions for hybridization and imaging were the same as in Example 1 (5).

EXAMPLE 2

Isolation and Analysis of BAZ2α gene (1) Identification of a Novel Gene Containing a Bromodomain and Isolation of its Full-length Sequence The DNA encoding the bromodomain of BAZ is highly homologous to that of GCN5. The DNA sequence encoding the bromodomain motif of human GCN5 gene (Candau, R. et al., (1996), Mol. Cell. Biol., 16 Q):593-602) was used to search the EST database using BLAST. The Motif search was performed using PROSITE. Proteins were compared using Bestfit in GCG. The nuclear transport signal was identified using PSORT. As a result, a number of ESTs were found to be identical to the probe sequence. Among them, an EST (Accession Number: N76552) obtained from a fetal liver/spleen cDNA library proved to be a novel gene.

To start cloning the full-length sequence of EST N76552, PCR primers were designed to amplify a particular product of 91 bp from the testis cDNA library; primer NB 16U (SEQ ID NO: 15/ TGACTCTGAAGTAGGCAAGGCTGG) and primer NB 16L (SEQ ID NO:16/ CTTGCCTCACAGATTG-GCCTGT). The PCR product was used as a probe to screen the testis cDNA library (Clontech; HL3023a). The amplified product was directly purified through a QIA Quick (Qiagen) purification column. The cDNA clone having sequences corresponding to EST was used to re-screen the library.

This process was repeated until a series of overlapped clones having a full-length sequence of the complete coding region was obtained. All the sequencing was performed with automated sequencing apparatus ABI 377 (Perkin Elmer, Norwalk, Conn.), utilizing ABI dye terminator chemistry. As a result, a continuous sequence consisting of 9,408 bp nucleotides in total size was generated. Theoretical translation of this sequence showed a presence of methionine codon at the nucleotide position of 740. An open reading frame (ORF) coding 1878 amino acids starts from this position and terminates at the nucleotide position 6373. The ORF is followed by a 3' untranslated region consisting of at least a 3 kb nucleotide sequence. The nucleotide sequence of the cDNA obtained is shown in SEQ ID NO:14, and the amino acid sequence deduced from the cDNA is shown in SEQ ID NO: 13. The isolated clone was designated BAZ2α.

Figure 5:
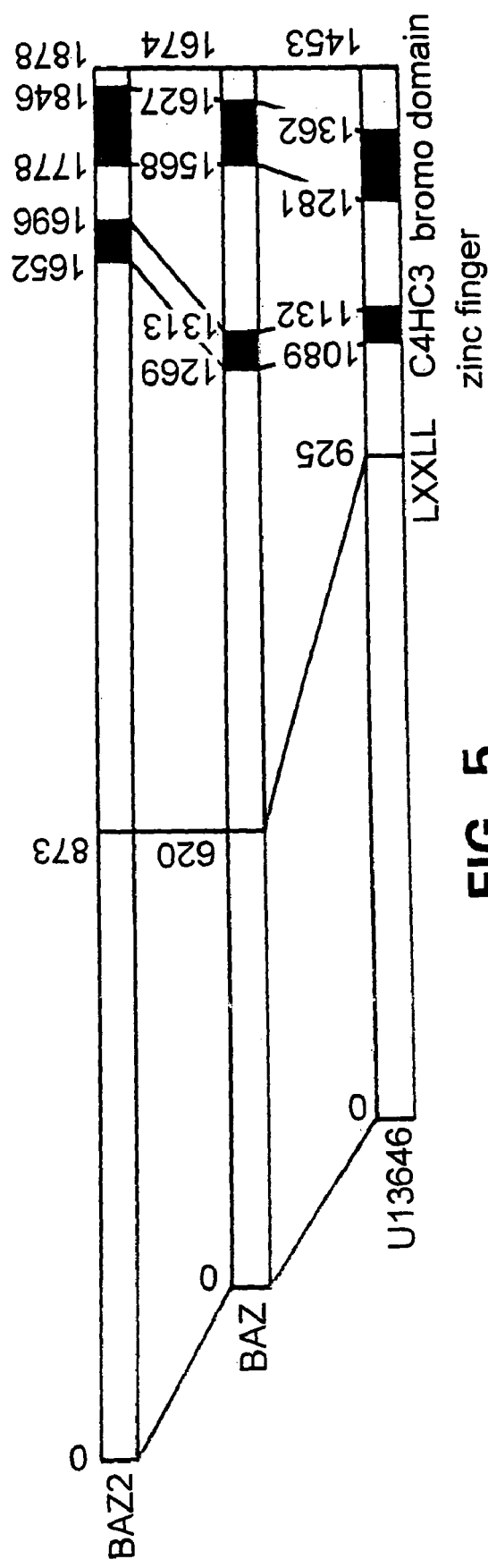
FIG. 5 compares the conserved domains among BAZ (BAZ1α), BAZ2α, and U13646.

(2) Identification of the Homology and Motifs Characteristic of Transcription Factors Like BAZ, BAZ2α was shown to have the highest homology with the protein encoded by a C. elegans bromodomain gene U13646, the gene forming a part of a continuous 2.2 Mb segment of chromosome III of C. elegans (Wilson, R. et al., (1994), Nature, 368:32-38) by searching the protein databases with the amino acid sequence of BAZ2α. The regions which showed similarity were identified using various transcription factors such as the 250 KD subunit of TFIID (Ruppert, S., Wang, E. and Tjian, R. (1993), Nature 362:175-179) and p300/CBP (Eckner, R. et al., (1994), Genes Dev., 8 (8): 869-884; Chrivia, J. C. et al., (1993), Nature, 365:855-859). The bromodomain was located between the amino acid residues 1788 and 1846. The alignments of BAZ2α, BAZ, and U13646 are shown in FIG. 5. The alignments of the sequence of the BAZ2α bromodomain and those of other bromodomains are shown in FIG. 6A. Moreover, a single motif consisting of 45 amino acids (amino acid residues 1652-1696) was identified. This motif codes C4HC3 Zinc finger (C4HC3ZF), a motif conserved among a large number of proteins such as BAZ, U13646, retinoblastoma binding protein RBP2 (Fattaey, A. R. et al., (1993), Oncogene, 8:3149-3156), MOZ (Borrow, J. et al., (1996) Nature Genet., 14:33-41), and p300/CBP (Koken, M. H. et al., (1995) CR, 4 cad. Sci. III, 318:733-739) by BLAST searching. The alignments of C4HC3ZF from these genes are shown in FIG. 6B. BAZ2α resembles BAZ, which suggests the possibility that the two proteins closely relate and form a part of a protein family having a similar function. Like BAZ, BAZ2α wholly resembles several transcription factors and has C4HC3ZF and bromodomain motifs conserved among p300/CBP and TIF1, especially indicating that BAZ is likely to function as a transcriptional regulator.

An LXXLL motif, which is believed to be required for mediating transcription induced by nuclear receptors (Torchia, J. et al., (1997), Nature, 387:677-684; Herry, D. M. et al., (1997), Nature 387:733-736), is located at amino acid residue 872. PROSITE motif searching revealed that this motif was located at the 3' end of the leucine zipper (amino acid residues 852-873). The relative locations of LXXLL, C4HC3, and bromodomain motifs in BAZ2α are remarkably similar to those of U13646 and BAZ (FIG. 5). Furthermore, in either case, the LXXLL motif is located behind the helix structure characterized by conserved lysine residues existing at regular intervals.

(3) Mapping of BAZ2α

Figure 7A:
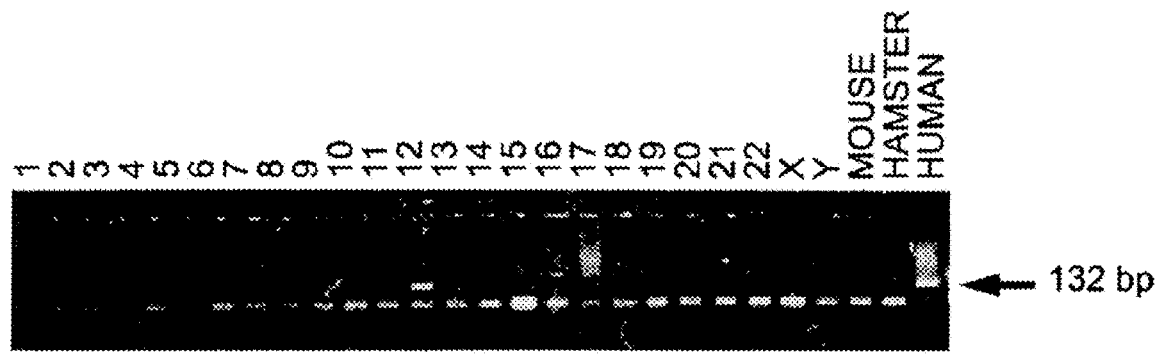
FIG. 7A shows assignments of chromosome 12 based on the analysis of a monochromosome hybrid cell panel using primers D (SEQ ID NO:16) and E (SEQ ID NO:17). The numbers 1 to Y in the figure refer to chromosome numbers. The product of 132 bp was specifically amplified in the cell line GM10868a, a monochromosome for human chromosome 12.
Figure 7B:
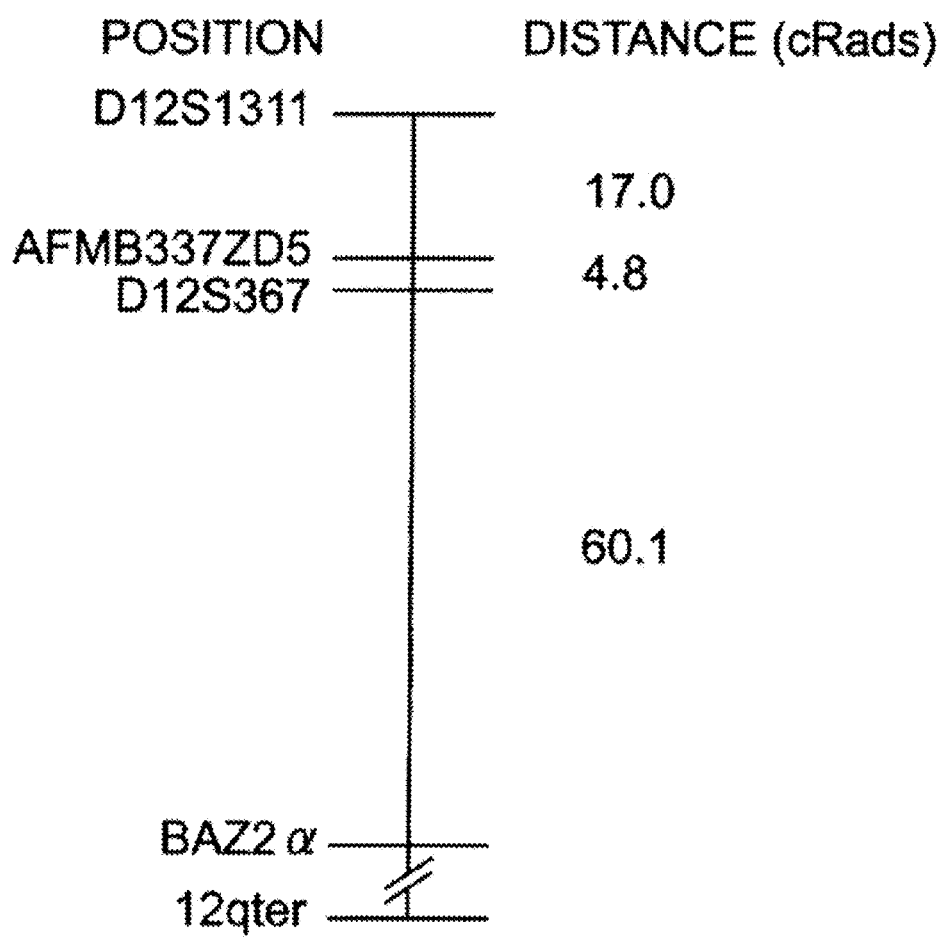
FIG. 7B depicts the location of BAZ2 (BAZ2α) on chromosome 12 as determined by Genebridge 4 radiation hybrid panel analysis.

To locate BAZ2α on the chromosome, PCR primers D (SEQ ID NO:17/TTGCCGTATTTGGCTGGTATC)and E (SEQ ID NO:18/CATAGAGAAGAGGGCAGGGTTGA), which amplify a fragment of 132 bp, were used to amplify the DNA from each of the 24 monochromosomes of human/ rodent somatic cell lines (Dubois, B. L. and Naylor, S. (1993), Genomics, 16:315-319) obtained from Coriell Cell Respositories (New Jersey). The BAZ2α-containing region was identified using 91 GeneBridge 4 radiation hybrid panels (Walter M. A. et al., (1994), Nature Genetics, 7:22-28). These panels were screened by PCR using primers D and E again. The binary codes generated by assessing whether each hybrid is positive or negative for amplification were compared with the analogous codes for the markers constituting a framework map, using the server located at www-genome.wi.mit.edu/ cgi-bin/contig/rhmapper.pl. BAZ2α was thus proved to be located 12q24.3-ter from D12S367 (see FIG. 7B).

(4) Analysis of the BAZ2α Expression

Figure 8A:
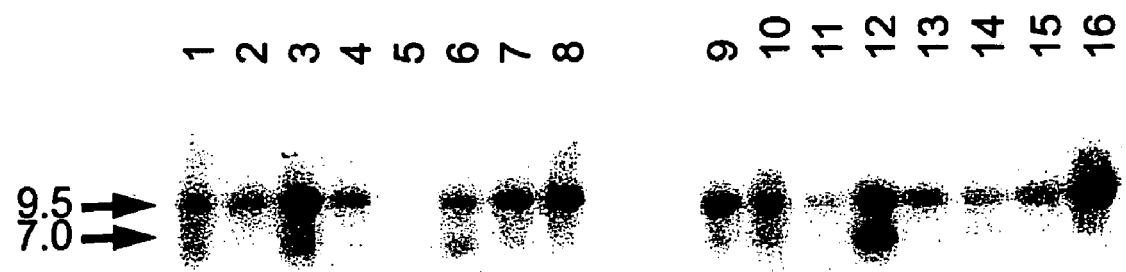
FIG. 8A shows the expression of BAZ2α in normal tissues (A: Lane 1, heart; Lane 2, brain; Lane 3, placenta; Lane 4, lung; Lane 5, liver; Lane 6, skeletal muscle; Lane 7, kidney; Lane 8, pancreas; Lane 9, spleen; Lane 10, thymus; Lane 11, prostate; Lane 12, testis; Lane 13, uterus; Lane 14, small intestine; Lane 15, colon (mucous lining); and Lane 16, leukocytes in the peripheral blood).
Figure 8B:
FIG. 8B shows controls using actin probe.

The probe (a 481 bp fragment of BAZ2α gene) prepared by amplifying the DNA from one of the clones obtained from the testis cDNA library (Clontech)in Example 2 (1) using primers gt10F (SEQ ID NO:19/ CTTTTGAGCAAGTTCAGCCT) and NB16N (SEQ ID NO:20/ GTCGGCTTCTTCATTTC-CTCCA) was used for Northern analysis of 16 panels of normal tissues (Clontech). The probe was labeled with [α-$^{32}$P]dCTP by random priming and purified using a Chromaspin 10 column (Clontech). Hybridization for Northern analysis and library filter screening were performed in the ExpressHyb hybridization solution (Clontech) at 65° C. for 1 hour. The filters were then washed until the final stringency reached 0.5×SSC and 0.1% SDS. Imaging was performed using a Fuji BAS Image Analyzer. The result showed that this probe was hybridized with a single species of mRNA of 10.5 kb in almost all the tissues; this length corresponds to that of ORF identified from the gene sequence (FIG. 8). The transcript was expressed in almost all the tissues at a low level. Another transcript of 9.0 kb was detected and was primarily expressed in the testis. This band survived the high-stringent wash. The second transcript is thought to be an alternatively spliced form of, or a different gene closely related to, BAZ2α.

EXAMPLE 3

Isolation and Analysis of BAZ2β Gene (1) Identification of a Novel Gene Containing a Bromodomain and Isolation of its Full-length Sequence A BLAST search was performed against the EST databases using the various nucleotide sequences containing a known bromodomain motif. Several ESTs which may encode the bromodomain gene were identified based on the result of the search using the nucleotide sequence of the SMAP gene (Nielsen, M. S. et al., (1996), Biochem. Biophys. Acta). Among them, an EST (Gnbank Accession Number: AA015589) obtained from a retinal cDNA library was proved to be a novel gene, the protein deduced from which has the highest homology with BAZ2α.

Its full-length sequence was isolated. The full-length gene for EST AA01307 was cloned as follows. First, PCR primers nb3U (SEQ ID NO:31/ TGGATGATGCTGAGGTGGATGA) and nb3L (SEQ ID NO:32/ GGGGTGCTGGATGACATCATAG) were designed to obtain a product of 184 bp specific to the primers from a testis cDNA library. The amplified product was directly purified using a QIA Quick (Qiagen) purification column. The PCR product was used as a probe to screen the testis cDNA library (Clontech HL3024a), and the cDNA clone containing the EST sequence was used to re-screen the library. This process was repeated after joining the clones. As a result, two types of nucleotide sequences were obtained and designated BAZ1β. The two sequences were further designated BAZ1βS for the shorter sequence and BAZ1βL for the longer one. The shorter sequence consisted of 5,561 nucleotides and encoded a protein of 1527 amino acids; the longer sequence consisted of 5,573 nucleotides and encoded a protein of 1531 amino acids, containing a tandem repeat of TACAGACCCTCC (SEQ ID NO:72) in one frame. This repeat gave rise to an insertion of four amino acids LLQT at position 658, which interestingly resulted in an additional LXXLL motif. BAZ1βS had four LXXLL motifs initiated at positions 655, 658, 1000, and 1436, while BAZ1βL had five LXXLL motifs initiated at positions 655, 658, 663, 1004, and 1440. FIG. 13 shows an alignment of the portions having multiple LXXLL motifs of BAZ1βS and BAZ1βL.

(2) Homology and the Characteristics of the Motifs of the Transcriptional Regulator The motifs of the protein encoded by the gene obtained were searched for in PROSITE. The proteins were compared using Bestfit from GCG. A nuclear transport signal was identified through PSORT (psort.nibb.ac.jp/form.html).

Figure 9:
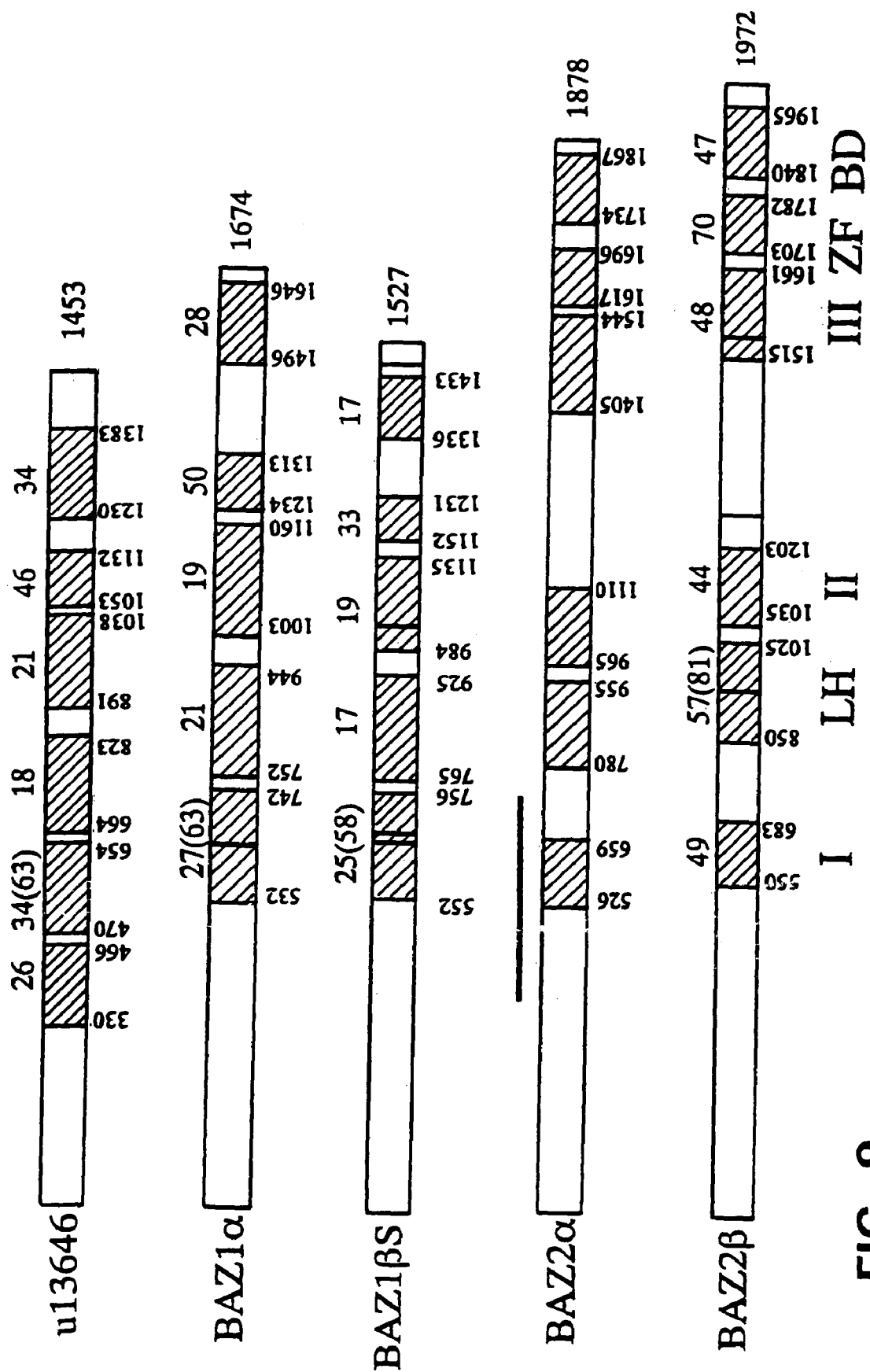
FIG. 9 compares the conserved domains of BAZ2β, BAZ1α, BAZ2α, U13646, and BAZ1βS. Each has at least five domains. BAZ1α lacks domain I. The figures on the bars of BAZ2β, BAZ1α, U13646, and BAZ1βS represent the percentage of the homology with BAZ2α. The values in the LH domain represent the percentage of the homology with leucine residues. Black bands in the LH domain indicate where the LXXLL motif is present in all three BAZ genes. LH, ZF, and BD represent leucine-rich helix domain, C4HC3 zinc finger, and bromodomain, respectively.

As for BAZ and BAZ2α, a database search based on the amino acid sequences predicted from the registered genes showed that this gene has the greatest similarity to the protein encoded by the bromodomain gene U13646 from the nematode (C. elegans). This nematode bromodomaingene corresponds to a portion of a 2.2 Mb segment derived from chromosome III of the nematode (C. elegans) (Wilson, R. et al., (1994), Nature, 368:32-38). The gene, however, shows homology to BAZ and BAZ2α to a larger extent. Actually, the similarity of the protein encoded by this gene to BAZ and BAZ2α suggests the possibility that these three proteins are closely related to one another, and, moreover, that they are a part of a broader family of proteins with similar functions. This gene was designated BAZ2β (for bromodomain, atypical zinc finger), since it has the greatest association with BAZ2α. BAZ was also renamed BAZ1β. The amino acid sequence of BAZ2β is shown in FIG. 9 together with those of BAZ1α, BAZ2α, U13646, and BAZ1βS described below. At least five regions or domains can be identified from the sequences. The first domain (I) is not present in BAZ1α, but is in the other three proteins. The existence of a leucine-rich helical structure (LH) was predicted from the analysis of the next domain. LXXLL motif is present at the central part of this domain on all BAZs except U13646. This motif potentially confers the interaction with the nuclear receptors on the protein (Torchia, J. et al., (1997), Nature, 387:677-684; Heery, D. M. et al., (1997), Nature, 387:733-736). Both domains II and III are highly conserved, suggesting their functional importance. Each protein has a highly conserved C4HC3 zinc finger (Aasland, R. et al., (1995), Trends Biochem. Sci., 20:56-59; Koken, M. H. et al., (1995), CR Acad. Sci. III, 318:733-739; Saha, V. et al., (1995), Proc. Natl. Acad. Sci., 92:9737-9741) and a bromodomain. In addition, a conserved region is found upstream from the zinc-finger motif, and the region can also be functionally important. Similarly, there are conserved sequences upstream from the bromodomain motif. Such conserved domains are aligned in FIG. 10. Like BAZ1α and BAZ2α, BAZ2β exhibits great similarity to several transcription factors and is thus expected to function as a transcription factor. Consistent with this function, estimation of the protein localization in the cell using the PSORT program revealed that BAZ2β has 19 consensus nuclear localization sequences (Robbins, J. et al., (1991), Cell, 64:615-23) in total.

(3) Chromosomal Mapping of BAZ2β

To create a chromosome map of BAZ2β, primers nb7n (SEQ ID NO:25/TGTTGCTGCATCACTTGTGTAGTT) and NB7ee (SEQ ID NO:26/GGCATGACAATAATGTCTGCAAA) were prepared and used to amplify the DNA obtained from each of the 24 human/rodent monochromosomal somatic cell lines (Dubois, B. L. and Naylor, S. (1993), Genomics, 16:315-319). The amplification of the 147 bp fragment as expected PCR product indicated that the gene was likely to be located on human monochromosome 2 (FIG. 11). The locus region of BAZ2β was determined by use of 91 radiation hybrid panels of GeneBridge 4 (Walter, M.A. et al., (1994), Nature Genetics, 7:22-28). The hybrid panels were screened by PCR using primers nb7n and nb7ee again. The binary codes generated by assessing whether each hybrid is positive or negative for the amplification were compared with the analogous codes for the markers constituting a framework map, using the server located at www-genome.wi.mit.edu/cgi-bin/contig/rhmapper.pl to identify the chromosomal locus of this gene. As a result, BAZ2β was confirmed to be located on chromosome 2q23-24 and between markers D2S1986 and G09369 (FIG. 11).

(4) Analysis of the BAZ2β Expression

The cDNA probe containing the sequence corresponding to nucleotide residues 1700-4000 was used for Northern analysis of 16 normal tissues, eight tumor cell lines, and four fetal tissues (FIG. 12). The probe was labeled with [$\alpha$-$^{32}$P] dCTP by random priming and purified on a Chromaspin 10 column (Clontech). Hybridization for Northern analysis was performed at 65° C. for 1 hour using ExpressHyb hybridization solution (Clontech). Subsequently, the filters were washed at 65° C. until the final stringency reached 0.5×SSC and 0.1% SDS. Autoradiography was then performed at −70° C. for 1 to 3 days to intensify the signals of the filters. This probe detected an mRNA of about 9.5 kb, a transcript whose size agreed with that of the ORF identified from the nucleotide sequence, in almost all the tissues examined. Besides this band, a transcript of about 6.5 kb was predominantly expressed in the testis. Since this band remained unchanged even after the high stringent wash (0.1×SSC, at 65° C.), it was considered to be specifically expressed. The second transcript could be an alternatively spliced product of BAZ2β, but no clone implying this event was found. It was also likely that expression of another gene closely related to BAZ2β was detected. In addition to these transcripts, several mRNAs were detected in most tissues. Such transcripts were considered to be derived from other genes each having an analogous sequence. Another analysis using another probe containing a bromodomain revealed the expression of the transcript of 6.5 kb only in the testis and of a 8.5 kb transcript in a wide range of tissues.

EXAMPLE 4

Isolation and Analysis of BAZ1β (BAZ1βS and BAZ1βL) Genes (1) Identification of Novel Genes Containing a Bromodomain and Isolation of their Full-length Nucleotide Sequences A BLAST search was performed against the EST database using the nucleotide sequence of the bromodomain motif from human GCN5 gene (Candau et al., (1996), Mol. Cell. Biol., 16:593-602). Several ESTs possibly coding a number of bromodomain genes were identified. Among them, an EST (Gnbank accession Number: AA01307) derived from a retinal cDNA library was found to be a novel gene.

Its full-length sequence was isolated. The full-length gene for EST AA01307 was cloned as follows. First, PCR primers nb3U (SEQ ID NO:31/ TGGATGATGCTGAGGTGGATGA) and nb3L (SEQ ID NO:32/ GGGGTGCTGGATGACATCATAG) were designed to obtain a product of 184 bp specific to the primers from a testis cDNA library. The amplified product was directly purified using a QIAQuick (Qiagen) purification column. The PCR product was used as a probe to screen the testis cDNA library (Clontech HL3024a), and the cDNA clone containing the EST sequence was used to re-screen the library. This process was repeated after joining the clones. As a result, two types of nucleotide sequences were obtained and designated BAZ1β. The two sequences were further designated BAZ1βS for the shorter sequence and BAZ1βL for the longer one. The shorter sequence consisted of 5,561 nucleotides and encoded a protein of 1527 amino acids; the longer sequence consisted of 5,573 nucleotides and encoded a protein of 1531 amino acids, containing a tandem repeat of TACAGACCCTCC (SEQ ID NO:72) in one frame. This repeat gave rise to an insertion of four amino acids LLQT at position 658, which interestingly resulted in an additional LXXLL motif. BAZ1βS had four LXXLL motifs initiated at positions 655, 658, 1000, and 1436, while BAZ1βL had five LXXLL motifs initiated at positions 655, 658, 663, 1004, and 1440. FIG. 13 shows an alignment of the portions having multiple LXXLL motifs of BAZ1βS and BAZ1βL.

To determine whether the variability of the LXXLL motif is attributed to alteration of splicing or polymorphism, a pair of primers consisting of NB3KK (SEQ ID NO:33/ GAGTG-CAGATAAGGGTGGCTTTTT) and NB3LL (SEQ ID NO:34/ CCAATTCACCATAGTCTTCGGCTA), which correspond to both sides of the variable region, was prepared and used to amplify genomic DNA and cDNA. As a result, these primers amplified a product of the same size from both of the templates. This implies the sequence variant is generated within an intron. Therefore, the variation of the sequence is probably caused by polymorphism. This may affect the interaction with the nuclear receptors. The nucleotide sequence of BAZ1βS cDNA thus obtained is shown in SEQ ID NO:28, and the deduced amino acid sequence of the protein encoded by the cDNA is shown in SEQ ID NO:27. The nucleotide sequence of BAZ1βL cDNA is also shown in SEQ ID NO:30, and the deduced amino acid sequence of the protein encoded by the cDNA is shown in SEQ ID NO:29. All the nucleotide sequences were determined with automated sequencing apparatus ABI 377, using ABI dye terminator chemistry. Hybridization for the filter screening of the library was performed in ExpressHyb hybridization solution (Clontech) at 65° C. for 1 hour. The filters were washed at 65° C. until the final stringency reached 0.5×SSC and 0.1% SDS. Subsequently, the filters were autoradiographed at −70° C. for 4 days to intensify the signals or autoradiographed for 4 hours with the Fuji BAS system.

(2) Homology and Characteristics of the Motifs of the Transcriptional Regulator

The motifs of the proteins encoded by BAZ1βS and BAZ1βL genes were searched in PROSITE. The proteins were compared using a MAP program of a BCM search launcher (dot.imgen.bcm.tmc.edu:9331/multi-align/multi-align.html) under the default setting conditions; the output results were edited using a box shade program (ulrec3.unil.ch/software/BOX_form.htmlat). A nuclear transport signal was identified through PSORT (psort.nib-b.ac.jp/form.html).

Several motifs characteristic of transcriptional regulators were found in both BAZ1βS and BAZ1βL. They were bromodomain, C4HC3 zinc finger (C4HC3ZF), and LXXLL motifs. LXXLL motifs were present in the leucine-rich domain conserved among other BAZ family member protein genes and U13646 (FIG. 9). Although the importance of this domain has not been clarified, it can form a leucine zipper responsible for forming a dimer of the protein. It has been reported that such motifs are commonly found in the transcriptional regulators of eukaryotes (Busch and Sassone-Corsi, 1990) and that LXXLL motifs also interact with the nuclear receptors (Torchia et al., (1997), Nature, 387:677-684; Heery et al., (1997), Nature 387:733-736). That the predicted amino acid sequences have extensive similarity to several kinds of transcription regulators indicates the possibility that their genes function as transcriptional regulators. This is further supported by the fact that 13 nuclear localized consensus sequences (Robbins et al., (1991), Cell, 64:615-23) were found in total based on the prediction of the cellular localization of the proteins using the PSORT program. The predicted amino acid sequences exhibited the highest similarity to BAZ1α. They also showed similarity to the proteins encoded by BAZ2α; BAZ2β, and C. elegans bromodomain gene U13646. Among the six domains, the first domain existed in BAZ2α, BAZ2β, and U13646, but not in BAZ1βS, BAZ1βL, or BAZ1α. Comparing the whole structures of these gene products, the region between domains II and III is the most similar to that of BAZ1α (FIGS. 14-18). Like other members of BAZ family, these gene products also have motifs that are present in the protein assumed to be encoded by nematode (C. elegans) bromodomain gene U13646 (Wilson et al., (1994) Nature, 368:32-38) that is identified by analyzing genome sequences of the genes. Alignment of the sequences of BAZ1βS, other members of the BAZ family, and U13646 reveals that the most highly conserved regions are located between the center and the C terminus of the sequences (FIGS. 14-18). For U13646, this region is not depicted in the figures, and only N terminal region is aligned with that of BAZ1βS and BAZ1α.

(3) Chromosomal Mapping of BAZ1β

Figures 19A, 19B:
FIG. 19A shows mapping of BAZ1β on chromosome seven by monochromosome hybrid cell line panel analysis. A product of 156 bp was observed to be amplified in the cell line GM10791 by PCR using primers nb3S and nb3T. The numbers 1 to Y in the figure indicate chromosome numbers.
FIG. 19B shows the location of BAZ1β on chromosome seven as determined by Genebridge 4 radiation hybrid panel analysis. BAZ1β is located between 7q11-21 markers D7S489 and D7S669.

To create a chromosome map of BAZ1β, primers nb3S (SEQ ID NO:35/GAAACGGGAGGAGCTGAAAAAG) and nb3T (SEQ ID NO:36/CCTTCAGGGGTATCCAC-CAATC) were prepared and used to amplify the DNA obtained from each of the 24 human/rodent monochromosomal somatic cell lines (Dubois, B. L. and Naylor, S. (1993), Genomics, 16:315-319). The expected PCR product of 156 bp was amplified from GM10791 from two distinct cell lines, suggesting that the BAZ1β gene is likely to be located on human chromosome 7 (FIG. 19A). The locus of BAZ1β was determined using 91 radiation hybrid panels of GeneBridge 4 (Walter, M. A. et al., (1994), Nature Genetics, 7:22-28). The hybrid panels were screened by performing PCR with primers nb3S and nb3T again. The locus of this gene was identified by comparing the binary codes generated by assessing each hybrid as positive or negative for the amplification with the analogous codes for the markers constituting a framework map using the server located at www-genome.wi.mit.edu/cgi-bin/contig/rhmapper.pl. As a result, BAZ1β was confirmed to be mapped on chromosome 7q11-22 and also located between the markers D7S489 and D7S669 (FIG. 19B).

(4) Analysis of the BAZ1β Expression

Figure 20A:
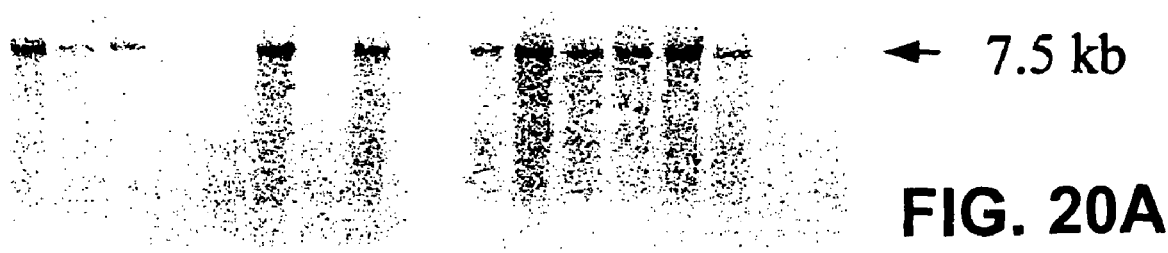
FIGS. 20A and 20B show the expression analysis of BAZ1β in normal tissues.
Figure 20B:

The cDNA probe of 156 bp prepared by PCR for the testis cDNA using primers nb3S and nb3T was used for Northern analysis of 16 panels of normal tissues (FIG. 20). The probe was labeled with [α-$^{32}$P]dCTP by random priming and purified with a Chromaspin 10 column (Clontech). Hybridization for Northern analysis was performed at 65° C. for 1 hour in ExpressHyb hybridization solution (Clontech). The filters were washed at 65° C. until the final stringency reached 0.5×SSC and 0.1% SDS. Subsequently, autoradiography was performed at −70° C. for 4 days to intensify the signals of the filters or for 4 hours with a Fuji BAS system. This probe detected an mRNA of 7.5 kb in almost all the tissues examined. The transcript was analogous to a 7.0 kb transcript of BAZ1α.

EXAMPLE 5

Expression and Purification of BAZ2β Fusion Protein

Figure 21:
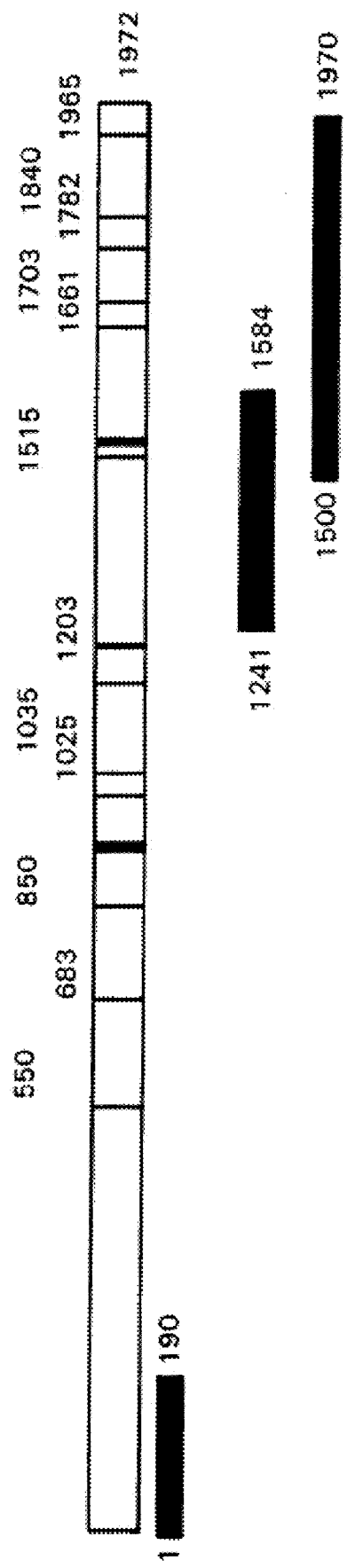
FIG. 21 shows the regions within BAZ2β which are covered by expression clones. Conserved domains (shadowed boxes) and LXXLL motifs (black lines) are indicated. Positions of the first and the last amino acids of each domain are indicated on the bar. Clone 1 covers amino acids 1-190; clone 9, amino acids 1241-1584; and clone 11, amino acids 1500-1970.

Three constructs for BAZ2β were prepared with pGEX vector (Pharmacia) used to express fusion proteins in bacteria. Each of the three constructs contained the sequence corresponding to the amino acid positions 1-190, 1241-1584, or 1500-1970 of BAZ2α (FIG. 21). The expression of the fusion protein was mediated by the IPTG-inducible promoter located upstream from the cloning site. The expressed proteins were purified through an affinity matrix containing glutathione-Sepharose beads since the expressed protein was fused to glutathione-S-transferase (GST). Specifically, the GST fusion proteins were expressed and purified according to the instructions appended to GST purification modules (Pharmacia). The cultured volume was 400 ml, and proteins were induced by 0.1 mM IPTG at 30° C. overnight. Western blotting was performed using BioRad reagents included in an Alkaline Phosphatase Conjugate Substrate kit, according to the manual appended to the kit.

Figure 22:
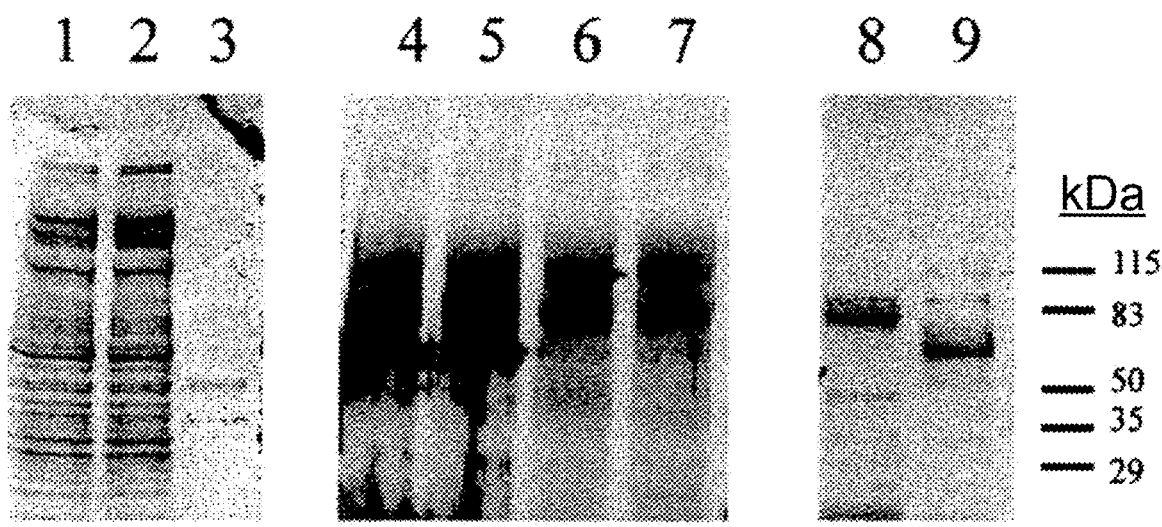
FIG. 22 is a photograph of electrophoretic patterns showing SDS-PAGE analysis of GST protein (Lane 1, cell lysate (BAZ2β.1); Lane 2, flow through fraction (BAZ2β.1); Lane 3, purified fusion protein (BAZ2β.1); Lane 4, cell lysate (BAZ2β.11); Lane 5, cell lysate (BAZ2β.9); Lane 6, flow through fraction (BAZ2β.11); Lane 7, flow through fraction (BAZ2β.9); Lane 8, purified protein (BAZ2β.11); and Lane 9, purified protein (BAZ2β.9). The positions of molecular weight markers are indicated on the right (kDa).
Figure 23:
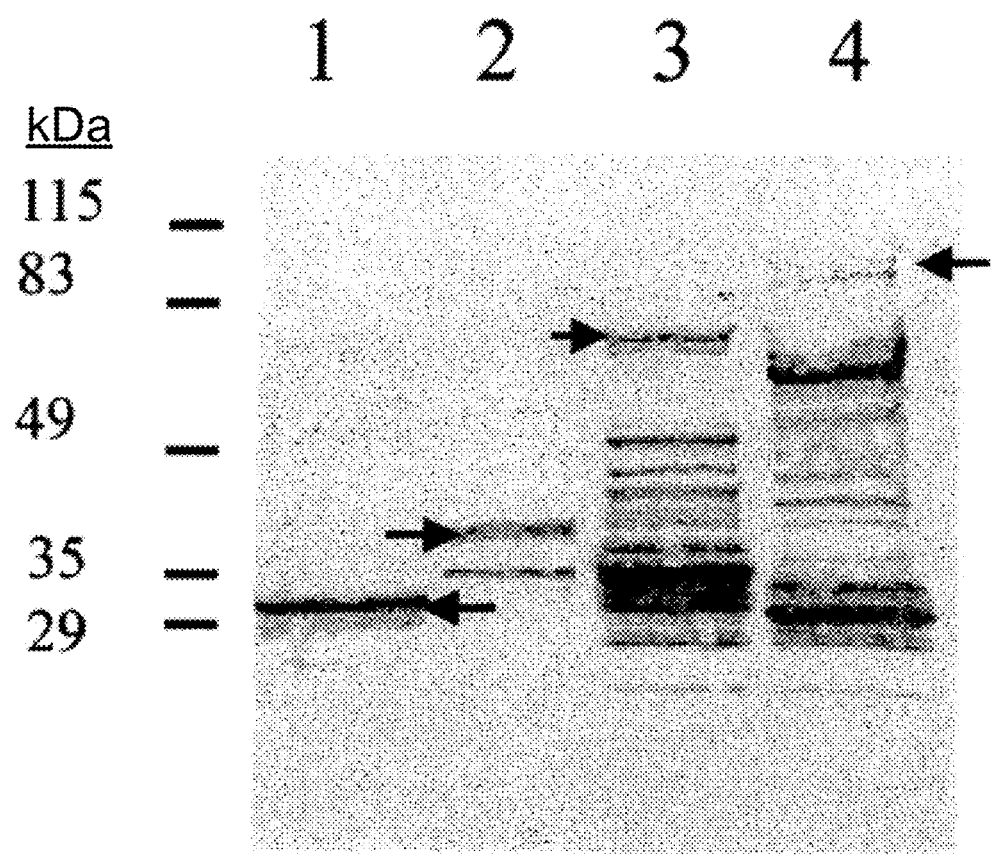
FIG. 23 is a photograph of electrophoresis showing Western analysis of purified GST-fusion protein (Lane 1, GST; Lane 2, GST-BAZ2β.1; Lane 3, GST-BAZ2β.9; and Lane 4, GST-BAZ2β.11).

The results of analyzing the expressed protein on the 4-20% gradient SDS-polyacrylamide gel showed that the induced proteins were not detected in the bacterial cell lysates before purification (FIG. 22, Lanes 1, 4, and 5), indicating that the induction through the promoter was not strong in any construct. In any case, however, distinctive proteins (Table 2) with molecular weights corresponding to those predicted were detected (FIG. 23, Lanes 3, 8, and 9). To prove that the purified proteins were the desired fusion proteins, western blot was carried out using the anti-GST antibody. As a result, purified protein with the corresponding size predicted for each protein was detected.

TABLE 2

| Construct | Amino acid region | Predicted MWT kDal | Detected MWT kDal |
|---|---|---|---|
| BAZ2β.1 | 1-190 | 51 | 50 |
| BAZ2β.9 | 1241-1584 | 67 | 65 |
| BAZ2β.11 | 1500-1970 | 84 | 85 |

INDUSTRIAL APPLICABILITY

The present invention provides a novel transcriptional regulator having a bromodomain, DNA coding said transcriptional regulator, a vector containing said DNA, a transformant expressively retaining said DNA, an antibody binding to said transcriptional regulator, and the method of screening a compound binding to said transcriptional regulator. A transcriptional regulator and DNA of the present invention are expected to be used as indices to diagnose and treat cancer and proliferative diseases, and to screen a drug with a new action mechanism. A compound binding to a transcriptional regulator of the present invention could also be used as a pharmaceutical to treat the diseases described above.

What is claimed is:

1. An isolated nucleic acid comprising:
   a) a nucleotide sequence that encodes a polypeptide comprising the amino acid sequence as set forth in SEQ ID NO: 13, or
   b) the complement of the nucleotide sequence of a).

2. A vector comprising the nucleic acid of claim 1.

3. A cultured host cell comprising the nucleic acid of claim 1.

4. A method of preparing a polypeptide, the method comprising culturing the host cell of claim 3, wherein the host cell expresses the polypeptide, and isolating the polypeptide from the host cell.

5. An isolated nucleic acid comprising:
   a) a nucleic acid strand that hybridizes under high stringency conditions (65° C., 2×SSC, 0.1% SDS) to a probe, wherein the nucleotide sequence of the probe consists of the complement of SEQ ID NO: 14, and wherein the nucleic acid strand encodes a polypeptide comprising the amino acid sequence of SEQ ID NO: 13; or b) the complement of the nucleic acid strand of a).

6. A vector comprising the nucleic acid of claim 5.

7. A cultured host cell comprising the nucleic acid of claim 5.

8. A method of preparing a polypeptide, the method comprising culturing the host cell of claim 7, wherein the host cell expresses the polypeptide, and isolating the polypeptide from the host cell.

9. The isolated nucleic acid of claim 5, wherein the isolated nucleic acid is labeled.

10. The isolated nucleic acid of claim 9, wherein the isolated nucleic acid is radioactively labeled.

11. A method of detecting the presence of a bromodomain adjacent to zinc finger (BAZ) nucleic acid in a sample, the method comprising:
   contacting the isolated nucleic acid of claim 5 with a nucleic acid sample, wherein the isolated nucleic acid consists of the complement specified in claim 12 (b); and
   determining whether the isolated nucleic acid hybridizes with the nucleic acid sample; wherein hybridization of the isolated nucleic acid with the nucleic acid sample indicates the presence of the BAZ nucleic acid in the sample.

12. The method of claim 11, wherein the BAZ nucleic acid comprises a BAZ2α sequence.

13. The method of claim 11, wherein the nucleic acid sample comprises genomic DNA.

14. The method of claim 11, wherein the nucleic acid sample comprises cDNA.

15. The method of claim 11, wherein the nucleic acid sample comprises mRNA.

16. An isolated nucleic acid comprising: a) a nucleotide sequence comprising SEQ ID NO: 14, or b) the complement of the nucleotide sequence of a).

17. A vector comprising the nucleic acid of claim 16.

18. A cultured host cell comprising the nucleic acid of claim 16.

19. A method of preparing a polypeptide, the method comprising culturing the host cell of claim 18, wherein the host cell expresses the polypeptide encoded by the isolated nucleic acid, and isolating the polypeptide from the host cell.

20. The isolated nucleic acid of claim 16, wherein the isolated nucleic acid is labeled.

21. The isolated nucleic acid of claim 20, wherein the isolated nucleic acid is radioactively labeled.

22. A method of detecting the presence of a BAZ nucleic acid, the method comprising:
   contacting the isolated nucleic acid of claim 16 with a nucleic acid sample, wherein the sequence of the isolated nucleic acid consists of the complement of SEQ ID NO:14; and
   determining whether the isolated nucleic acid hybridizes with the nucleic acid sample;
   wherein hybridization of the isolated nucleic acid with the nucleic acid sample indicates the presence of the BAZ nucleic acid in the sample.

23. The method of claim 22, wherein the BAZ nucleic acid comprises a BAZ2α sequence.

24. The method of claim 22, wherein the nucleic acid sample comprises genomic DNA.

25. The method of claim 22, wherein the nucleic acid sample comprises cDNA.

26. The method of claim 22, wherein the nucleic acid sample comprises mRNA.

27. An isolated nucleic acid comprising:
   a) a nucleotide sequence encoding a polypeptide consisting of the amino acid sequence of SEQ ID NO:13; or
   b) the complement of the nucleotide sequence.

28. A vector comprising the nucleic acid of claim 27.

29. A cultured host cell comprising the nucleic acid of claim 27.

30. A method of preparing a polypeptide, the method comprising culturing the host cell of claim 29, wherein the host cell expresses the polypeptide, and isolating the polypeptide from the host cell.

31. An isolated nucleic acid comprising
   (a) a nucleotide sequence encoding a polypeptide comprising the amino acid sequence of SEQ ID NO: 13 in which 30 or fewer amino acid residues are substituted, added, or deleted wherein the polypeptide comprises a C4HC3 zinc finger domain, a leucine zipper (LXXLL) domain, and a nuclear transport signal sequence; or
   (b) the complement of the nucleotide sequence of (a).

32. The isolated nucleic acid of claim 31, wherein the number of amino acid residues that are substituted, added, or deleted is 10 or fewer.

33. The isolated nucleic acid of claim 32, wherein the polypeptide further comprises a bromodomain.

34. The isolated nucleic acid of claim 31, wherein the number of amino acid residues that are substituted, added, or deleted is 3 or fewer.

35. The isolated nucleic acid of claim 34, wherein the polypeptide further comprises a bromodomain.

36. The isolated nucleic acid of claim 31, wherein the polypeptide further comprises a bromodomain.

* * * * *

SEQUENCE LISTING

<160> NUMBER OF SEQ ID NOS: 72

<210> SEQ ID NO 1
<211> LENGTH: 1674
<212> TYPE: PRT
<213> ORGANISM: Homo sapiens

<400> SEQUENCE: 1

```
Met Glu Asp Ala Ser Glu Ser Ser Arg Gly Val Ala Pro Leu Ile Asn
  1               5                  10                  15

Asn Val Val Leu Pro Gly Ser Pro Leu Ser Leu Pro Val Ser Val Thr
                 20                  25                  30

Gly Cys Lys Ser His Arg Val Ala Asn Lys Val Glu Ala Arg Ser
             35                  40                  45

Glu Lys Leu Leu Pro Thr Ala Leu Pro Pro Ser Glu Pro Lys Val Asp
         50                  55                  60

Gln Lys Leu Pro Arg Ser Ser Glu Arg Arg Gly Ser Gly Gly Gly Thr
 65                  70                  75                  80

Gln Phe Pro Ala Arg Ser Arg Ala Val Ala Gly Glu Ala Ala Ala
                 85                  90                  95

Arg Gly Ala Ala Gly Pro Glu Arg Gly Ser Pro Leu Gly Arg Arg Val
             100                 105                 110

Ser Pro Arg Cys Leu Cys Ser Gly Glu Gly Gly Gln Val Ala Val Gly
             115                 120                 125

Val Ile Ala Gly Lys Arg Gly Arg Arg Gly Arg Asp Gly Ser Arg Arg
         130                 135                 140

Ala Pro Gly Gly Arg Glu Met Pro Leu Leu His Arg Lys Pro Phe Val
145                 150                 155                 160

Arg Gln Lys Pro Pro Ala Asp Leu Arg Pro Asp Glu Val Phe Tyr
                 165                 170                 175

Cys Lys Val Thr Asn Glu Ile Phe Arg His Tyr Asp Asp Phe Phe Glu
             180                 185                 190

Arg Thr Ile Leu Cys Asn Ser Leu Val Trp Ser Cys Ala Val Thr Gly
         195                 200                 205

Arg Pro Gly Leu Thr Tyr Gln Glu Ala Leu Glu Ser Glu Lys Lys Ala
210                 215                 220

Arg Gln Asn Leu Gln Ser Phe Pro Glu Pro Leu Ile Ile Pro Val Leu
225                 230                 235                 240

Tyr Leu Thr Ser Leu Thr His Arg Ser Arg Leu His Glu Ile Cys Asp
                 245                 250                 255

Asp Ile Phe Ala Tyr Val Lys Asp Arg Tyr Phe Val Glu Glu Thr Val
             260                 265                 270

Glu Val Ile Arg Asn Asn Gly Ala Arg Leu Gln Cys Thr Ile Leu Glu
         275                 280                 285

Val Leu Pro Pro Ser His Gln Asn Gly Phe Ala Asn Gly His Val Asn
290                 295                 300

Ser Val Asp Gly Glu Thr Ile Ile Ile Ser Asp Ser Asp Ser Glu
305                 310                 315                 320

Thr Gln Ser Cys Ser Phe Gln Asn Gly Lys Lys Asp Ala Ile Asp
                 325                 330                 335

Pro Leu Leu Phe Lys Tyr Lys Val Gln Pro Thr Lys Leu Glu Leu His
             340                 345                 350

Glu Ser Ala Ile Val Lys Ala Thr Gln Ile Ser Arg Arg Lys His Leu
         355                 360                 365

Phe Ser Arg Asp Lys Leu Lys Leu Phe Leu Lys Gln His Cys Glu Pro
370                 375                 380

Gln Glu Gly Val Ile Lys Ile Lys Ala Ser Ser Leu Ser Thr Tyr Lys
385                 390                 395                 400

Ile Ala Glu Gln Asp Phe Ser Tyr Phe Pro Asp Asp Pro Thr
                 405                 410                 415

Phe Ile Phe Ser Pro Ala Asn Arg Arg Arg Gly Arg Pro Pro Lys Arg
```

-continued

```
                420                 425                 430
Ile His Ile Ser Gln Glu Asp Asn Val Ala Asn Lys Gln Thr Leu Ala
        435                 440                 445
Ser Tyr Arg Ser Lys Ala Thr Lys Glu Arg Asp Lys Leu Leu Lys Gln
        450                 455                 460
Glu Met Lys Ser Leu Ala Phe Glu Lys Ala Lys Leu Lys Arg Glu
465                 470                 475                 480
Lys Ala Asp Ala Leu Glu Ala Lys Lys Glu Lys Glu Asp Lys Glu
                485                 490                 495
Lys Lys Arg Glu Glu Leu Lys Lys Ile Val Glu Glu Arg Leu Lys
                500                 505                 510
Lys Lys Glu Glu Lys Glu Arg Leu Lys Val Glu Arg Glu Lys Glu Arg
                515                 520                 525
Glu Lys Leu Arg Glu Glu Lys Arg Lys Tyr Val Glu Tyr Leu Lys Gln
                530                 535                 540
Trp Ser Lys Pro Arg Glu Asp Met Glu Cys Asp Asp Leu Lys Glu Leu
545                 550                 555                 560
Pro Glu Pro Thr Pro Val Lys Thr Arg Leu Pro Pro Glu Ile Phe Gly
                565                 570                 575
Asp Ala Leu Met Val Leu Glu Phe Leu Asn Ala Phe Gly Glu Leu Phe
                580                 585                 590
Asp Leu Gln Asp Glu Phe Pro Asp Gly Val Thr Leu Glu Val Leu Glu
                595                 600                 605
Glu Ala Leu Val Gly Asn Asp Ser Glu Gly Pro Leu Cys Glu Leu Leu
                610                 615                 620
Phe Phe Phe Leu Thr Ala Ile Phe Gln Ala Ile Ala Glu Glu Glu Glu
625                 630                 635                 640
Glu Val Ala Lys Glu Gln Leu Thr Asp Ala Asp Thr Lys Gly Cys Ser
                645                 650                 655
Leu Lys Ser Leu Asp Leu Asp Ser Cys Thr Leu Ser Glu Ile Leu Arg
                660                 665                 670
Leu His Ile Leu Ala Ser Gly Ala Asp Val Thr Ser Ala Asn Ala Lys
                675                 680                 685
Tyr Arg Tyr Gln Lys Arg Gly Gly Phe Asp Ala Thr Asp Ala Cys
        690                 695                 700
Met Glu Leu Arg Leu Ser Asn Pro Ser Leu Val Lys Lys Leu Ser Ser
705                 710                 715                 720
Thr Ser Val Tyr Asp Leu Thr Pro Gly Glu Lys Met Lys Ile Leu His
                725                 730                 735
Ala Leu Cys Gly Lys Leu Leu Thr Leu Val Ser Thr Arg Asp Phe Ile
                740                 745                 750
Glu Asp Tyr Val Asp Ile Leu Arg Gln Ala Lys Gln Glu Phe Arg Glu
                755                 760                 765
Leu Lys Ala Glu Gln His Arg Lys Glu Arg Glu Ala Ala Ala Arg
        770                 775                 780
Ile Arg Lys Arg Lys Glu Glu Lys Leu Lys Glu Gln Glu Gln Lys Met
785                 790                 795                 800
Lys Glu Lys Gln Glu Lys Leu Lys Glu Asp Glu Gln Arg Asn Ser Thr
                805                 810                 815
Ala Asp Ile Ser Ile Gly Glu Glu Arg Glu Asp Phe Asp Thr Ser
        820                 825                 830
Ile Glu Ser Lys Asp Thr Glu Gln Lys Glu Leu Asp Gln Asp Met Phe
                835                 840                 845
```

-continued

```
Thr Glu Asp Glu Asp Pro Gly Ser His Lys Arg Gly Arg Arg Gly
    850                 855                 860
Lys Arg Gly Gln Asn Gly Phe Lys Glu Phe Thr Arg Gln Glu Gln Ile
865                 870                 875                 880
Asn Cys Val Thr Arg Glu Leu Leu Thr Ala Asp Glu Glu Ala Leu
                885                 890                 895
Lys Gln Glu His Gln Arg Lys Glu Lys Glu Leu Leu Lys Ile Gln
                900                 905                 910
Ser Ala Ile Ala Cys Thr Asn Ile Phe Pro Leu Gly Arg Asp Arg Met
                915                 920                 925
Tyr Arg Arg Tyr Trp Ile Phe Pro Ser Ile Pro Gly Leu Phe Ile Glu
    930                 935                 940
Glu Asp Tyr Ser Gly Leu Thr Glu Asp Met Leu Leu Pro Arg Pro Ser
945                 950                 955                 960
Ser Phe Gln Asn Val Gln Ser Gln Asp Pro Gln Val Ser Thr Lys
                965                 970                 975
Thr Gly Glu Pro Leu Met Ser Glu Ser Thr Ser Asn Ile Asp Gln Gly
                980                 985                 990
Pro Arg Asp His Ser Val Gln Leu Pro Lys Pro Val His Lys Pro Asn
                995                 1000                1005
Arg Trp Cys Phe Tyr Ser Ser Cys Glu Gln Leu Asp Gln Leu Ile Glu
                1010                1015                1020
Ala Leu Asn Ser Arg Gly His Arg Glu Ser Ala Leu Lys Glu Thr Leu
1025                1030                1035                1040
Leu Gln Glu Lys Ser Arg Ile Cys Ala Gln Leu Ala Arg Phe Ser Glu
                1045                1050                1055
Glu Lys Phe His Phe Ser Asp Lys Pro Gln Pro Asp Ser Lys Pro Thr
                1060                1065                1070
Tyr Ser Arg Gly Arg Ser Ser Asn Ala Tyr Asp Pro Ser Gln Met Cys
                1075                1080                1085
Ala Glu Lys Gln Leu Glu Leu Arg Leu Arg Asp Phe Leu Leu Asp Ile
                1090                1095                1100
Glu Asp Arg Ile Tyr Gln Gly Thr Leu Gly Ala Ile Lys Val Thr Asp
1105                1110                1115                1120
Arg His Ile Trp Arg Ser Ala Leu Glu Ser Gly Arg Tyr Glu Leu Leu
                1125                1130                1135
Ser Glu Glu Asn Lys Glu Asn Gly Ile Ile Lys Thr Val Asn Glu Asp
                1140                1145                1150
Val Glu Glu Met Glu Ile Asp Glu Gln Thr Lys Val Ile Val Lys Asp
                1155                1160                1165
Arg Leu Leu Gly Ile Lys Thr Glu Thr Pro Ser Thr Val Ser Thr Asn
                1170                1175                1180
Ala Ser Thr Pro Gln Ser Val Ser Ser Val His Tyr Leu Ala Met
1185                1190                1195                1200
Ala Leu Phe Gln Ile Glu Gln Gly Ile Glu Arg Arg Phe Leu Lys Ala
                1205                1210                1215
Pro Leu Asp Ala Ser Asp Ser Gly Arg Ser Tyr Lys Thr Val Leu Asp
                1220                1225                1230
Arg Trp Arg Glu Ser Leu Leu Ser Ser Ala Ser Leu Ser Gln Val Phe
                1235                1240                1245
Leu His Leu Ser Thr Leu Asp Arg Ser Val Ile Trp Ser Lys Ser Ile
                1250                1255                1260
```

-continued

```
Leu Asn Ala Arg Cys Lys Ile Cys Arg Lys Lys Gly Asp Ala Glu Asn
1265                1270                1275                1280

Met Val Leu Cys Asp Gly Cys Asp Arg Gly His His Thr Tyr Cys Val
            1285                1290                1295

Arg Pro Lys Leu Lys Thr Val Pro Glu Gly Asp Trp Phe Cys Pro Glu
        1300                1305                1310

Cys Arg Pro Lys Gln Arg Cys Arg Arg Leu Ser Phe Arg Gln Arg Pro
    1315                1320                1325

Ser Leu Glu Ser Asp Glu Asp Val Glu Asp Ser Met Gly Gly Glu Asp
1330                1335                1340

Asp Glu Val Asp Gly Asp Glu Glu Gly Gln Ser Glu Glu Glu Glu
1345                1350                1355                1360

Tyr Glu Val Glu Gln Asp Glu Asp Ser Gln Glu Glu Glu Glu Val
            1365                1370                1375

Ser Leu Pro Lys Arg Gly Arg Pro Gln Val Arg Leu Pro Val Lys Thr
        1380                1385                1390

Arg Gly Lys Leu Ser Ser Ser Phe Ser Ser Arg Gly Gln Gln Gln Glu
            1395                1400                1405

Pro Gly Arg Tyr Pro Ser Arg Ser Gln Gln Ser Thr Pro Lys Thr Thr
    1410                1415                1420

Val Ser Ser Lys Thr Gly Arg Ser Leu Arg Lys Ile Asn Ser Ala Pro
1425                1430                1435                1440

Pro Thr Glu Thr Lys Ser Leu Arg Ile Ala Ser Arg Ser Thr Arg His
            1445                1450                1455

Ser His Gly Pro Leu Gln Ala Asp Val Phe Val Glu Leu Leu Ser Pro
        1460                1465                1470

Arg Arg Lys Arg Gly Arg Lys Ser Ala Asn Asn Thr Pro Glu Asn
    1475                1480                1485

Ser Pro Asn Phe Pro Asn Phe Arg Val Ile Ala Thr Lys Ser Ser Glu
    1490                1495                1500

Gln Ser Arg Ser Val Asn Ile Ala Ser Lys Leu Ser Leu Gln Glu Ser
1505                1510                1515                1520

Glu Ser Lys Arg Arg Cys Arg Lys Arg Gln Ser Pro Glu Pro Ser Pro
            1525                1530                1535

Val Thr Leu Gly Arg Arg Ser Ser Gly Arg Gln Gly Gly Val His Glu
        1540                1545                1550

Leu Ser Ala Phe Glu Gln Leu Val Val Glu Leu Val Arg His Asp Asp
            1555                1560                1565

Ser Trp Pro Phe Leu Lys Leu Val Ser Lys Ile Gln Val Pro Asp Tyr
        1570                1575                1580

Tyr Asp Ile Ile Lys Lys Pro Ile Ala Leu Asn Ile Ile Arg Glu Lys
1585                1590                1595                1600

Val Asn Lys Cys Glu Tyr Lys Leu Ala Ser Glu Phe Ile Asp Asp Ile
            1605                1610                1615

Glu Leu Met Phe Ser Asn Cys Phe Glu Tyr Asn Pro Arg Asn Thr Ser
        1620                1625                1630

Glu Ala Lys Ala Gly Thr Arg Leu Gln Ala Phe Phe His Ile Gln Ala
    1635                1640                1645

Gln Lys Leu Gly Leu His Val Thr Pro Ser Asn Val Asp Gln Val Ser
    1650                1655                1660

Thr Pro Pro Ala Ala Lys Lys Ser Arg Ile
1665                1670
```

-continued

```
<210> SEQ ID NO 2
<211> LENGTH: 5934
<212> TYPE: DNA
<213> ORGANISM: Homo sapiens
<220> FEATURE:
<221> NAME/KEY: CDS
<222> LOCATION: (125)...(5146)
<220> FEATURE:
<221> NAME/KEY: misc_feature
<222> LOCATION: (1)...(5934)
<223> OTHER INFORMATION: n = A,T,C or G

<400> SEQUENCE: 2
gaattccggc ttttcccatc gtgtagtcaa gagtctgtgc cagacttgaa ggctttactt      60
tgttagccat gtgtttatga accccccagcg ctttccctag atcttttggc tgataatctc    120 aaac atg gag gat gct tct gaa tct tca cga ggg gtt gct cca tta att      169
     Met Glu Asp Ala Ser Glu Ser Ser Arg Gly Val Ala Pro Leu Ile
     1               5                   10                  15 aat aat gta gtt ctc cca ggc tct ccg ctg tct ctt cct gta tca gtg       217
Asn Asn Val Val Leu Pro Gly Ser Pro Leu Ser Leu Pro Val Ser Val
            20                  25                  30 aca ggc tgt aaa agt cat cga gta gcc aat aaa aag gta gaa gcg agg       265
Thr Gly Cys Lys Ser His Arg Val Ala Asn Lys Lys Val Glu Ala Arg
        35                  40                  45 agt gaa aag ctc ctc cca aca gct ctt cct cct tca gag ccg aaa gta       313
Ser Glu Lys Leu Leu Pro Thr Ala Leu Pro Pro Ser Glu Pro Lys Val
    50                  55                  60 gat cag aaa ctt ccc agg agc tcc gag agg cgg gga agt ggc ggt ggg       361
Asp Gln Lys Leu Pro Arg Ser Ser Glu Arg Arg Gly Ser Gly Gly Gly
65                  70                  75 acg caa ttc ccc gcg cgg agt cgg gca gtg gca gcg gga gaa gcg gca       409
Thr Gln Phe Pro Ala Arg Ser Arg Ala Val Ala Ala Gly Glu Ala Ala
            80                  85                  90                  95 gcc agg ggc gcg gcg ggg ccg gag aga ggc agt ccc ctg gga aga cgg       457
Ala Arg Gly Ala Ala Gly Pro Glu Arg Gly Ser Pro Leu Gly Arg Arg
                100                 105                 110 gtc tcc cct cgt tgc ctt tgt agt gga gaa ggt gga caa gtg gca gtc       505
Val Ser Pro Arg Cys Leu Cys Ser Gly Glu Gly Gly Gln Val Ala Val
            115                 120                 125 ggc gtg atc gca ggg aag cgg ggc cgg cgc ggg cgc gac ggg tcc agg       553
Gly Val Ile Ala Gly Lys Arg Gly Arg Arg Gly Arg Asp Gly Ser Arg
        130                 135                 140 cga gcc ccg ggc gga cgg gag atg ccg ctg cta cac cga aag ccg ttt       601
Arg Ala Pro Gly Gly Arg Glu Met Pro Leu Leu His Arg Lys Pro Phe
145                 150                 155 gtg aga cag aag ccg ccc gcg gac ctg cgg ccc gac gag gaa gtt ttc       649
Val Arg Gln Lys Pro Pro Ala Asp Leu Arg Pro Asp Glu Glu Val Phe
160                 165                 170                 175 tac tgt aaa gtc acc aac gag atc ttc cgc cac tac gat gac ttt ttt       697
Tyr Cys Lys Val Thr Asn Glu Ile Phe Arg His Tyr Asp Asp Phe Phe
            180                 185                 190 gaa cga acc att ctg tgc aac agc ctt gtg tgg agt tgt gct gtg acg       745
Glu Arg Thr Ile Leu Cys Asn Ser Leu Val Trp Ser Cys Ala Val Thr
        195                 200                 205 ggt aga cct gga ctg acg tat cag gaa gca ctt gag tca gaa aaa aaa       793
Gly Arg Pro Gly Leu Thr Tyr Gln Glu Ala Leu Glu Ser Glu Lys Lys
    210                 215                 220 gca aga cag aat ctt cag agt ttt cca gaa cca cta att att cca gtt       841
Ala Arg Gln Asn Leu Gln Ser Phe Pro Glu Pro Leu Ile Ile Pro Val
225                 230                 235 tta tac ttg acc agc ctt acc cat cgt tcg cgc tta cat gaa att tgt       889
```

```
                                                    -continued

Leu Tyr Leu Thr Ser Leu Thr His Arg Ser Arg Leu His Glu Ile Cys
240                 245                 250                 255 gat gat atc ttt gca tat gtc aag gat cga tat ttt gtc gaa gaa act       937
Asp Asp Ile Phe Ala Tyr Val Lys Asp Arg Tyr Phe Val Glu Glu Thr
                260                 265                 270 gtg gaa gtc att agg aac aat ggt gca agg ttg cag tgt acg att ttg       985
Val Glu Val Ile Arg Asn Asn Gly Ala Arg Leu Gln Cys Thr Ile Leu
                275                 280                 285 gaa gtc ctc cct cca tca cat caa aat ggt ttt gct aat gga cat gtt      1033
Glu Val Leu Pro Pro Ser His Gln Asn Gly Phe Ala Asn Gly His Val
                290                 295                 300 aac agt gtg gat gga gaa act att atc atc agt gat agt gat gat tca      1081
Asn Ser Val Asp Gly Glu Thr Ile Ile Ile Ser Asp Ser Asp Asp Ser
                305                 310                 315 gaa aca caa agc tgt tct ttt caa aat ggg aag aaa aaa gat gca att      1129
Glu Thr Gln Ser Cys Ser Phe Gln Asn Gly Lys Lys Lys Asp Ala Ile
320                 325                 330                 335 gat ccc tta cta ttc aag tat aaa gtg caa ccc act aaa aaa gaa tta      1177
Asp Pro Leu Leu Phe Lys Tyr Lys Val Gln Pro Thr Lys Lys Glu Leu
                340                 345                 350 cat gag tct gct att gtt aaa gca aca caa atc agc cgg aga aaa cac      1225
His Glu Ser Ala Ile Val Lys Ala Thr Gln Ile Ser Arg Arg Lys His
                355                 360                 365 cta ttt tct cgt gat aaa cta aag ctt ttt ctg aag caa cac tgt gaa      1273
Leu Phe Ser Arg Asp Lys Leu Lys Leu Phe Leu Lys Gln His Cys Glu
                370                 375                 380 cca caa gaa gga gtc att aaa ata aag gca tca tct ctt tca acg tat      1321
Pro Gln Glu Gly Val Ile Lys Ile Lys Ala Ser Ser Leu Ser Thr Tyr
385                 390                 395 aaa ata gca gaa caa gat ttt tct tat ttc ttc cct gat gat cca ccc      1369
Lys Ile Ala Glu Gln Asp Phe Ser Tyr Phe Phe Pro Asp Asp Pro Pro
400                 405                 410                 415 aca ttt atc ttc agt cct gct aac aga cga aga ggg aga cct ccc aaa      1417
Thr Phe Ile Phe Ser Pro Ala Asn Arg Arg Arg Gly Arg Pro Pro Lys
                420                 425                 430 cga ata cat att agt caa gag gac aat gtt gct aat aaa cag act ctt      1465
Arg Ile His Ile Ser Gln Glu Asp Asn Val Ala Asn Lys Gln Thr Leu
                435                 440                 445 gca agt tat agg agc aaa gct act aaa gaa aga gat aaa ctt ttg aaa      1513
Ala Ser Tyr Arg Ser Lys Ala Thr Lys Glu Arg Asp Lys Leu Leu Lys
                450                 455                 460 caa gaa gaa atg aag tca ctg gct ttt gaa aag gct aaa tta aaa aga      1561
Gln Glu Glu Met Lys Ser Leu Ala Phe Glu Lys Ala Lys Leu Lys Arg
465                 470                 475 gaa aaa gca gat gcc cta gaa gcg aag aaa aaa gaa aaa gaa gat aaa      1609
Glu Lys Ala Asp Ala Leu Glu Ala Lys Lys Lys Glu Lys Glu Asp Lys
480                 485                 490                 495 gag aaa aag agg gaa gaa ttg aaa aaa att gtt gaa gaa gag aga cta      1657
Glu Lys Lys Arg Glu Glu Leu Lys Lys Ile Val Glu Glu Glu Arg Leu
                500                 505                 510 aag aaa aaa gaa gaa aaa gag agg ctt aaa gta gaa aga gaa aag gaa      1705
Lys Lys Lys Glu Glu Lys Glu Arg Leu Lys Val Glu Arg Glu Lys Glu
                515                 520                 525 aga gag aag tta cgt gaa gaa aag cga aag tat gtg gaa tac tta aaa      1753
Arg Glu Lys Leu Arg Glu Glu Lys Arg Lys Tyr Val Glu Tyr Leu Lys
                530                 535                 540 cag tgg agt aaa cct aga gaa gat atg gaa tgt gat gac ctt aag gaa      1801
Gln Trp Ser Lys Pro Arg Glu Asp Met Glu Cys Asp Asp Leu Lys Glu
545                 550                 555
```

-continued

| | |
|---|---|
| ctt cca gaa cca aca cca gtg aaa act aga cta cct cct gaa atc ttt<br>Leu Pro Glu Pro Thr Pro Val Lys Thr Arg Leu Pro Pro Glu Ile Phe<br>560               565                 570               575 | 1849 |
| ggt gat gct ctg atg gtt ttg gag ttc ctt aat gca ttt ggg gaa ctt<br>Gly Asp Ala Leu Met Val Leu Glu Phe Leu Asn Ala Phe Gly Glu Leu<br>                     580                 585               590 | 1897 |
| ttt gat ctt caa gat gag ttt cct gat gga gta acc cta gaa gta tta<br>Phe Asp Leu Gln Asp Glu Phe Pro Asp Gly Val Thr Leu Glu Val Leu<br>           595                 600               605 | 1945 |
| gag gaa gct ctt gtt gga aat gac agt gaa ggc cca ctg tgt gaa ttg<br>Glu Glu Ala Leu Val Gly Asn Asp Ser Glu Gly Pro Leu Cys Glu Leu<br>610                     615               620 | 1993 |
| ctt ttt ttc ttc ctg act gca atc ttc cag gca ata gct gaa gaa gaa<br>Leu Phe Phe Phe Leu Thr Ala Ile Phe Gln Ala Ile Ala Glu Glu Glu<br>     625                 630               635 | 2041 |
| gag gaa gta gcc aaa gag caa cta act gat gct gac acc aaa ggc tgc<br>Glu Glu Val Ala Lys Glu Gln Leu Thr Asp Ala Asp Thr Lys Gly Cys<br>640                     645               650               655 | 2089 |
| agt ttg aaa agt ttg gat ctt gat agc tgc act ctt tca gaa atc ctc<br>Ser Leu Lys Ser Leu Asp Leu Asp Ser Cys Thr Leu Ser Glu Ile Leu<br>               660               665               670 | 2137 |
| aga ctg cac atc tta gct tca ggt gct gat gta aca tca gca aat gca<br>Arg Leu His Ile Leu Ala Ser Gly Ala Asp Val Thr Ser Ala Asn Ala<br>           675                 680               685 | 2185 |
| aag tat aga tat caa aaa cga gga gga ttt gat gct aca gat gat gct<br>Lys Tyr Arg Tyr Gln Lys Arg Gly Gly Phe Asp Ala Thr Asp Asp Ala<br>690                     695               700 | 2233 |
| tgt atg gag ctt cgt ttg agc aat ccc agt cta gtg aag aaa ctg tca<br>Cys Met Glu Leu Arg Leu Ser Asn Pro Ser Leu Val Lys Lys Leu Ser<br>705                     710               715 | 2281 |
| agc acc tca gtg tat gat ttg aca cca gga gaa aaa atg aag ata ctc<br>Ser Thr Ser Val Tyr Asp Leu Thr Pro Gly Glu Lys Met Lys Ile Leu<br>720                     725               730               735 | 2329 |
| cat gct ctc tgt gga aag cta ctg acc cta gtt tca act agg gat ttt<br>His Ala Leu Cys Gly Lys Leu Leu Thr Leu Val Ser Thr Arg Asp Phe<br>               740                 745               750 | 2377 |
| att gaa gat tat gtt gat ata tta cga cag gca aag cag gag ttc cgg<br>Ile Glu Asp Tyr Val Asp Ile Leu Arg Gln Ala Lys Gln Glu Phe Arg<br>           755                 760               765 | 2425 |
| gaa tta aaa gca gaa caa cat cga aaa gag agg gaa gaa gca gct gcc<br>Glu Leu Lys Ala Glu Gln His Arg Lys Glu Arg Glu Glu Ala Ala Ala<br>770                     775               780 | 2473 |
| aga att cgt aaa agg aag gaa aaa ctt aag gag caa gaa caa aaa<br>Arg Ile Arg Lys Arg Lys Glu Lys Leu Lys Glu Gln Glu Gln Lys<br>785                     790               795 | 2521 |
| atg aaa gag aaa caa gaa aaa ctg aaa gaa gat gag caa aga aat tca<br>Met Lys Glu Lys Gln Glu Lys Leu Lys Glu Asp Glu Gln Arg Asn Ser<br>800                     805               810               815 | 2569 |
| acg gca gat ata tct att ggg gag gaa gaa agg gaa gat ttt gat act<br>Thr Ala Asp Ile Ser Ile Gly Glu Glu Glu Arg Glu Asp Phe Asp Thr<br>               820                 825               830 | 2617 |
| agc att gag agc aaa gac aca gag caa aag gaa tta gat caa gat atg<br>Ser Ile Glu Ser Lys Asp Thr Glu Gln Lys Glu Leu Asp Gln Asp Met<br>           835                 840               845 | 2665 |
| ttc act gaa gat gaa gat gac cca gga tca cat aaa aga ggc aga agg<br>Phe Thr Glu Asp Glu Asp Asp Pro Gly Ser His Lys Arg Gly Arg Arg<br>850                     855               860 | 2713 |
| ggg aaa aga gga caa aat gga ttt aaa gaa ttt aca agg caa gaa cag<br>Gly Lys Arg Gly Gln Asn Gly Phe Lys Glu Phe Thr Arg Gln Glu Gln<br>           865                 870               875 | 2761 |

```
atc aac tgt gta aca aga gag ctt ctt act gct gat gag gaa gaa gca    2809
Ile Asn Cys Val Thr Arg Glu Leu Leu Thr Ala Asp Glu Glu Glu Ala
880             885                 890                 895 tta aaa cag gaa cac caa cga aaa gag aaa gag ctc tta gaa aaa atc    2857
Leu Lys Gln Glu His Gln Arg Lys Glu Lys Glu Leu Leu Glu Lys Ile
                900                 905                 910 caa agt gcc ata gcc tgt acc aat atc ttt ccc ttg ggt cgc gac cgc    2905
Gln Ser Ala Ile Ala Cys Thr Asn Ile Phe Pro Leu Gly Arg Asp Arg
            915                 920                 925 atg tat aga cga tac tgg att ttc cct tct att cct gga ctc ttt att    2953
Met Tyr Arg Arg Tyr Trp Ile Phe Pro Ser Ile Pro Gly Leu Phe Ile
        930                 935                 940 gaa gag gat tat tct ggt ctt act gaa gac atg ctg ttg cct aga cct    3001
Glu Glu Asp Tyr Ser Gly Leu Thr Glu Asp Met Leu Leu Pro Arg Pro
    945                 950                 955 tca tca ttt cag aat aat gta cag tct caa gat cct cag gta tcc act    3049
Ser Ser Phe Gln Asn Asn Val Gln Ser Gln Asp Pro Gln Val Ser Thr
960                 965                 970                 975 aaa act gga gag cct ttg atg tct gaa tct acc tcc aac att gac caa    3097
Lys Thr Gly Glu Pro Leu Met Ser Glu Ser Thr Ser Asn Ile Asp Gln
                980                 985                 990 ggt cca cgt gac cat tct gtg cag ctg cca aaa cca gtg cat aag cca    3145
Gly Pro Arg Asp His Ser Val Gln Leu Pro Lys Pro Val His Lys Pro
            995                 1000                1005 aat cgg tgg tgc ttt tac agt tct tgt gaa cag cta gac cag ctt att    3193
Asn Arg Trp Cys Phe Tyr Ser Ser Cys Glu Gln Leu Asp Gln Leu Ile
        1010                1015                1020 gaa gct ctt aat tct aga gga cat aga gaa agt gcc tta aaa gaa act    3241
Glu Ala Leu Asn Ser Arg Gly His Arg Glu Ser Ala Leu Lys Glu Thr
    1025                1030                1035 ttg tta caa gag aaa agc aga ata tgt gca cag cta gcc cgt ttt tct    3289
Leu Leu Gln Glu Lys Ser Arg Ile Cys Ala Gln Leu Ala Arg Phe Ser
1040                1045                1050                1055 gaa gag aaa ttt cat ttt tca gac aaa cct cag cct gat agc aaa cca    3337
Glu Glu Lys Phe His Phe Ser Asp Lys Pro Gln Pro Asp Ser Lys Pro
                1060                1065                1070 aca tat agt cgg gga aga tct tcc aat gca tat gat cca tct cag atg    3385
Thr Tyr Ser Arg Gly Arg Ser Ser Asn Ala Tyr Asp Pro Ser Gln Met
            1075                1080                1085 tgt gca gaa aag caa ctt gaa cta agg ctg aga gat ttt ctt tta gat    3433
Cys Ala Glu Lys Gln Leu Glu Leu Arg Leu Arg Asp Phe Leu Leu Asp
        1090                1095                1100 att gaa gat aga atc tac caa gga aca tta gga gcc atc aag gtt aca    3481
Ile Glu Asp Arg Ile Tyr Gln Gly Thr Leu Gly Ala Ile Lys Val Thr
    1105                1110                1115 gat cga cat atc tgg aga tca gca tta gaa agt gga cgg tat gag ctg    3529
Asp Arg His Ile Trp Arg Ser Ala Leu Glu Ser Gly Arg Tyr Glu Leu
1120                1125                1130                1135 tta agt gag gaa aac aag gaa aat ggg ata att aaa act gtg aat gaa    3577
Leu Ser Glu Glu Asn Lys Glu Asn Gly Ile Ile Lys Thr Val Asn Glu
                1140                1145                1150 gac gta gaa gag atg gaa att gat gaa caa aca aag gtc ata gta aaa    3625
Asp Val Glu Glu Met Glu Ile Asp Glu Gln Thr Lys Val Ile Val Lys
            1155                1160                1165 gac aga ctt ttg ggg ata aaa aca gaa act cca agt act gta tca aca    3673
Asp Arg Leu Leu Gly Ile Lys Thr Glu Thr Pro Ser Thr Val Ser Thr
        1170                1175                1180 aat gca agt aca cca caa tca gtg agc agt gtg gtt cat tat ctg gca    3721
Asn Ala Ser Thr Pro Gln Ser Val Ser Ser Val Val His Tyr Leu Ala
```

-continued

```
           1185                 1190                1195
atg gca ctc ttt caa ata gag cag ggc att gag cgg cgt ttt ctg aaa    3769
Met Ala Leu Phe Gln Ile Glu Gln Gly Ile Glu Arg Arg Phe Leu Lys
1200            1205                 1210                1215 gct cca ctt gat gcc agt gac agt ggg cgt tct tat aaa aca gtt ctg    3817
Ala Pro Leu Asp Ala Ser Asp Ser Gly Arg Ser Tyr Lys Thr Val Leu
            1220                 1225                1230 gac cgt tgg aga gag tct ctc ctt tct tct gct agt cta tcc caa gtt    3865
Asp Arg Trp Arg Glu Ser Leu Leu Ser Ser Ala Ser Leu Ser Gln Val
                1235                1240                1245 ttt ctt cac cta tcc acc ttg gat cgt agc gtg ata tgg tct aaa tct    3913
Phe Leu His Leu Ser Thr Leu Asp Arg Ser Val Ile Trp Ser Lys Ser
        1250                1255                1260 ata ctg aat gcg cgt tgc aag ata tgt cga aag aaa ggc gat gct gaa    3961
Ile Leu Asn Ala Arg Cys Lys Ile Cys Arg Lys Lys Gly Asp Ala Glu
    1265                1270                1275 aac atg gtt ctt tgt gat ggc tgt gat agg ggt cat cat acc tac tgt    4009
Asn Met Val Leu Cys Asp Gly Cys Asp Arg Gly His His Thr Tyr Cys
1280                1285                1290                1295 gtt cga cca aag ctc aag act gtg cct gaa gga gac tgg ttt tgt cca    4057
Val Arg Pro Lys Leu Lys Thr Val Pro Glu Gly Asp Trp Phe Cys Pro
                1300                1305                1310 gaa tgt cga cca aag caa cgt tgt aga aga ctg tcc ttt aga cag aga    4105
Glu Cys Arg Pro Lys Gln Arg Cys Arg Arg Leu Ser Phe Arg Gln Arg
            1315                1320                1325 cca tcc ttg gaa agt gat gaa gat gtg gaa gac agt atg gga ggt gag    4153
Pro Ser Leu Glu Ser Asp Glu Asp Val Glu Asp Ser Met Gly Gly Glu
        1330                1335                1340 gat gat gaa gtt gat ggc gat gaa gaa gaa ggt caa agt gag gag gaa    4201
Asp Asp Glu Val Asp Gly Asp Glu Glu Glu Gly Gln Ser Glu Glu Glu
    1345                1350                1355 gag tat gag gta gaa caa gat gaa gat gac tct caa gaa gag gaa gaa    4249
Glu Tyr Glu Val Glu Gln Asp Glu Asp Asp Ser Gln Glu Glu Glu Glu
1360                1365                1370                1375 gtc agc cta ccc aaa cga gga aga cca caa gtt aga ttg cca gtt aaa    4297
Val Ser Leu Pro Lys Arg Gly Arg Pro Gln Val Arg Leu Pro Val Lys
                1380                1385                1390 aca aga ggg aaa ctt agc tct tct ttc tca agt cgt ggc caa caa caa    4345
Thr Arg Gly Lys Leu Ser Ser Ser Phe Ser Ser Arg Gly Gln Gln Gln
            1395                1400                1405 gaa cct gga aga tac cct tcc agg agt cag cag agc aca ccc aaa aca    4393
Glu Pro Gly Arg Tyr Pro Ser Arg Ser Gln Gln Ser Thr Pro Lys Thr
        1410                1415                1420 act gtt tct tct aaa act ggt aga agc cta aga aag ata aac tct gct    4441
Thr Val Ser Ser Lys Thr Gly Arg Ser Leu Arg Lys Ile Asn Ser Ala
    1425                1430                1435 cct cct aca gaa aca aaa tct tta aga att gcc agt cgt tct act cgc    4489
Pro Pro Thr Glu Thr Lys Ser Leu Arg Ile Ala Ser Arg Ser Thr Arg
1440                1445                1450                1455 cac agt cat ggc cca ctg caa gca gat gta ttt gtg gaa ttg ctt agt    4537
His Ser His Gly Pro Leu Gln Ala Asp Val Phe Val Glu Leu Leu Ser
                1460                1465                1470 cct cgt aga aaa cgc aga ggc agg aaa agt gct aat aat aca cca gaa    4585
Pro Arg Arg Lys Arg Arg Gly Arg Lys Ser Ala Asn Asn Thr Pro Glu
            1475                1480                1485 aat agt ccc aac ttc cct aac ttc aga gtc att gcc aca aag tca agt    4633
Asn Ser Pro Asn Phe Pro Asn Phe Arg Val Ile Ala Thr Lys Ser Ser
        1490                1495                1500 gaa cag tca aga tct gta aat att gct tca aaa ctt tct ctc caa gag    4681
Glu Gln Ser Arg Ser Val Asn Ile Ala Ser Lys Leu Ser Leu Gln Glu
```

|   |   |   |   |   |   |   |   |   |   |   |   |   |   |   |
|---|---|---|---|---|---|---|---|---|---|---|---|---|---|---|
| Glu | Gln | Ser | Arg | Ser | Val | Asn | Ile | Ala | Ser | Lys | Leu | Ser | Leu | Gln Glu |
|  | 1505 |  |  |  | 1510 |  |  |  | 1515 |  |  |  |  |  |

```
agt gaa tcc aaa aga aga tgc aga aaa aga caa tct cca gag cca tcg       4729
Ser Glu Ser Lys Arg Arg Cys Arg Lys Arg Gln Ser Pro Glu Pro Ser
1520                1525                1530                1535 cct gtg aca ctg ggt cga agg agt tct ggc cga cag gga gga gtt cat       4777
Pro Val Thr Leu Gly Arg Arg Ser Ser Gly Arg Gln Gly Gly Val His
            1540                1545                1550 gaa ttg tct gct ttt gaa caa ctt gtt gta gaa ttg gta cga cat gat       4825
Glu Leu Ser Ala Phe Glu Gln Leu Val Val Glu Leu Val Arg His Asp
        1555                1560                1565 gac agc tgg cct ttt ttg aaa ctt gtt tct aaa atc cag gtc cca gac       4873
Asp Ser Trp Pro Phe Leu Lys Leu Val Ser Lys Ile Gln Val Pro Asp
    1570                1575                1580 tac tat gac atc atc aaa aag ccc att gcc tta aat ata att cgt gaa       4921
Tyr Tyr Asp Ile Ile Lys Lys Pro Ile Ala Leu Asn Ile Ile Arg Glu
1585                1590                1595 aaa gtg aat aag tgt gaa tat aaa tta gca tct gag ttt att gat gac       4969
Lys Val Asn Lys Cys Glu Tyr Lys Leu Ala Ser Glu Phe Ile Asp Asp
1600                1605                1610                1615 att gag tta atg ttt tcg aac tgc ttt gaa tac aac cct cgt aac aca       5017
Ile Glu Leu Met Phe Ser Asn Cys Phe Glu Tyr Asn Pro Arg Asn Thr
            1620                1625                1630 agt gaa gca aaa gct gga act agg ctt caa gca ttt ttt cat att cag       5065
Ser Glu Ala Lys Ala Gly Thr Arg Leu Gln Ala Phe Phe His Ile Gln
        1635                1640                1645 gct caa aag ctt gga ctc cac gtc aca ccc agt aat gtg gac caa gtt       5113
Ala Gln Lys Leu Gly Leu His Val Thr Pro Ser Asn Val Asp Gln Val
    1650                1655                1660 agc aca cca ccg gct gcg aaa aag tca cga atc tgactttgtc cttctaaagg     5166
Ser Thr Pro Pro Ala Ala Lys Lys Ser Arg Ile
1665                1670 atatatttga agaaaaacaa attgttcatg aaaatggaac attaaatcat gctgtataaa     5226
gcaataacaa acaattgatt gaccacatga aagtgtggcc tgcactatat tctcaatttt     5286
aatattaagc actcaggaga atgtaggaaa gatatccttt gctacagttt tgttcagtat     5346
ctaataagtt tgatagatgt attggataca gtactggttt acagaggttt tgtacatttt    5406
ttganatcat tcatgtgtcc agagatcttg gaaatatttt tttcacccac gatttatttt    5466
gttattgatg atttattttt aaagtggtgg tattaaggga gagttatcta catggatgag     5526
tcttccgcta tagcacagtt tagaaaaggt gtttatgtct taattaattg tttgagtaca     5586
ttctttcaac actacacatg aatgaatcca atcttataac cttgaagtgc tgtaccagtg     5646
ctggctgcag gtattaagtc caagtttatt aactagatat ttatttagta ttgagagtaa     5706
tttgtgaatt tgttttgtat ttataaaatt tatacctgga aaatgttcct taatgtttta    5766
aaccttttac tgtgttttta ttcctctaac ttccttaatg atcaatcaaa aaagtaaca     5826 ccctcccttt ttcctgacag ttcttcagc tttacagaac tgtattataa gttcgatgta      5886
taattttaac tgttcaaata aaatacattt ttccaataaa aaaaaaaa                  5934
```

<210> SEQ ID NO 3
<211> LENGTH: 140
<212> TYPE: DNA
<213> ORGANISM: Homo sapiens

<400> SEQUENCE: 3
gactaccacg acatcatcaa gaaaccaatg gatctgggca cagtcaagcg gaaaatggac     60

-continued

| aatcgcgagt acaagagcgc gccggaattt gccgccgacg tgcgattaat attcaccaac | 120 |
| tgctacaagt acaatccgcc | 140 |

<210> SEQ ID NO 4
<211> LENGTH: 23
<212> TYPE: DNA
<213> ORGANISM: Artificial Sequence
<220> FEATURE:
<223> OTHER INFORMATION: Synthetically generated primer

<400> SEQUENCE: 4

| agaaaaagac aatctccaga gca | 23 |

<210> SEQ ID NO 5
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 5

| gctgtcatca tgtcgtacca attc | 24 |

<210> SEQ ID NO 6
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 6

| aacacaagtg aagcaaaagc tgga | 24 |

<210> SEQ ID NO 7
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 7

| gtggtgtgct aacttggtcc acat | 24 |

<210> SEQ ID NO 8
<211> LENGTH: 25
<212> TYPE: DNA
<213> ORGANISM: Artificial Sequence
<220> FEATURE:
<223> OTHER INFORMATION: Synthetically generated primer

<400> SEQUENCE: 8

| cccatcgtga gtcaagagtg tctgt | 25 |

<210> SEQ ID NO 9
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 9

| ctcgcttcta ccttttatt ggct | 24 |

<210> SEQ ID NO 10
<211> LENGTH: 25

-continued

<210> SEQ ID NO 11
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 10
tcatcatctc tgccccctct gtctg                                              25

<210> SEQ ID NO 11
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 11
gacgcctgct tcaccacctt cttg                                               24

<210> SEQ ID NO 12
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 12
tcatgtggtc aatcaattgt ttgt                                               24

<210> SEQ ID NO 13
<211> LENGTH: 1878
<212> TYPE: PRT
<213> ORGANISM: Homo sapiens
<220> FEATURE:
<221> NAME/KEY: VARIANT
<222> LOCATION: (1)...(1878)
<223> OTHER INFORMATION: Xaa = Any Amino Acid

<400> SEQUENCE: 13

Met Glu Met Glu Ala Asn Glu Ala Asn Asp His Phe Asn Phe Thr Gly
 1               5                  10                  15

Leu Pro Pro Ala Pro Ala Ala Ser Gly Leu Lys Pro Ser Pro Ser Ser
            20                  25                  30

Gly Glu Gly Leu Tyr Thr Asn Gly Ser Pro Met Asn Phe Pro Gln Gln
         35                  40                  45

Gly Lys Ser Leu Asn Gly Asp Val Asn Val Asn Gly Leu Ser Thr Val
     50                  55                  60

Ser His Thr Thr Thr Ser Gly Ile Leu Asn Ser Ala Pro His Ser Ser
 65                  70                  75                  80

Ser Thr Ser His Leu His His Pro Ser Val Ala Tyr Asp Cys Leu Trp
                 85                  90                  95

Asn Tyr Ser Gln Tyr Pro Ser Ala Asn Pro Gly Ser Asn Leu Lys Asp
            100                 105                 110

Pro Pro Leu Leu Ser Gln Phe Ser Gly Gly Gln Tyr Pro Leu Asn Gly
        115                 120                 125

Ile Leu Gly Gly Ser Arg Gln Pro Ser Ser Pro Ser His Asn Thr Asn
    130                 135                 140

Leu Arg Ala Gly Ser Gln Lys Phe Trp Ala Asn Gly Thr His Ser Pro
145                 150                 155                 160

Met Gly Leu Asn Phe Asp Ser Gln Glu Leu Tyr Asp Ser Phe Pro Asp
                165                 170                 175

Gln Asn Phe Glu Glu Val Cys Ser Gly Ile His Pro Asp Glu Ala Ala

-continued

```
                180                 185                 190
Glu Lys Glu Met Thr Ser Val Val Ala Glu Asn Gly Thr Gly Leu Val
        195                 200                 205
Cys Ser Leu Glu Leu Glu Glu Xaa Gln Pro Glu Leu Lys Met Cys Gly
    210                 215                 220
Tyr Asn Gly Ser Val Pro Ser Val Glu Ser Leu His Gln Glu Val Ser
225                 230                 235                 240
Val Leu Val Pro Asp Pro Thr Val Ser Cys Leu Asp Asp Pro Ser His
                245                 250                 255
Leu Pro Asp Gln Leu Glu Asp Thr Pro Ile Leu Ser Glu Asp Ser Leu
            260                 265                 270
Glu Pro Phe Asn Ser Leu Ala Pro Glu Pro Val Ser Gly Gly Leu Tyr
        275                 280                 285
Gly Ile Asp Asp Thr Glu Leu Met Gly Ala Glu Asp Lys Leu Pro Leu
    290                 295                 300
Xaa Asp Ser Pro Val Ile Ser Ala Leu Asp Cys Pro Ser Leu Asn Asn
305                 310                 315                 320
Ala Thr Ala Phe Ser Leu Leu Ala Asp Asp Ser Gln Thr Ser Thr Ser
                325                 330                 335
Ile Phe Ala Ser Pro Thr Ser Pro Val Leu Gly Glu Ser Val Leu
            340                 345                 350
Gln Asp Asn Ser Phe Asp Leu Asn Asn Gly Ser Asp Ala Glu Gln Glu
        355                 360                 365
Glu Met Glu Thr Gln Ser Ser Asp Phe Pro Ser Leu Thr Gln Pro
    370                 375                 380
Ala Pro Asp Gln Ser Ser Thr Ile Gln Leu His Pro Ala Thr Ser Pro
385                 390                 395                 400
Ala Val Ser Pro Thr Thr Ser Pro Ala Val Ser Leu Val Ser Pro
                405                 410                 415
Ala Ala Ser Pro Glu Ile Ser Pro Glu Val Cys Pro Ala Ala Ser Thr
            420                 425                 430
Val Val Ser Pro Ala Val Phe Ser Val Val Ser Pro Ala Ser Ser Ala
        435                 440                 445
Val Leu Pro Ala Val Ser Leu Glu Val Pro Leu Thr Ala Ser Val Thr
    450                 455                 460
Ser Pro Lys Ala Ser Pro Val Thr Ser Pro Ala Ala Ala Phe Pro Thr
465                 470                 475                 480
Ala Ser Pro Ala Asn Lys Asp Val Ser Ser Phe Leu Glu Thr Thr Ala
                485                 490                 495
Asp Val Glu Glu Ile Thr Gly Glu Gly Leu Thr Ala Ser Gly Ser Gly
            500                 505                 510
Asp Val Met Arg Arg Ile Ala Thr Pro Glu Glu Val Arg Leu Pro
        515                 520                 525
Leu Gln His Gly Trp Arg Arg Glu Val Arg Ile Lys Lys Gly Ser His
    530                 535                 540
Arg Trp Gln Gly Glu Thr Trp Tyr Tyr Gly Pro Cys Gly Lys Arg Met
545                 550                 555                 560
Lys Gln Phe Pro Glu Val Ile Lys Tyr Leu Ser Arg Asn Leu Val His
                565                 570                 575
Ser Val Arg Arg Glu His Phe Ser Phe Ser Pro Arg Met Pro Val Gly
            580                 585                 590
Asp Phe Phe Glu Glu Arg Asp Thr Pro Glu Gly Leu Gln Trp Val Gln
        595                 600                 605
```

```
Leu Ser Ala Glu Glu Ile Pro Ser Arg Ile Gln Ala Ile Thr Gly Lys
    610                 615                 620

Arg Gly Arg Pro Arg Asn Thr Glu Lys Ala Lys Thr Lys Glu Val Pro
625                 630                 635                 640

Lys Val Lys Arg Gly Arg Gly Arg Pro Lys Val Lys Ile Thr Glu
                645                 650                 655

Leu Leu Asn Lys Thr Asp Asn Arg Pro Leu Lys Lys Leu Glu Ala Gln
            660                 665                 670

Glu Thr Leu Asn Glu Glu Asp Lys Ala Lys Ile Ala Lys Ser Lys Lys
        675                 680                 685

Lys Met Arg Gln Lys Val Gln Arg Gly Glu Cys Leu Thr Thr Ile Gln
    690                 695                 700

Gly Gln Ala Arg Asn Lys Arg Lys Gln Glu Thr Lys Ser Leu Lys His
705                 710                 715                 720

Lys Glu Ala Lys Lys Ser Xaa Ala Glu Lys Glu Lys Gly Lys Thr
                725                 730                 735

Lys Gln Glu Lys Leu Lys Glu Lys Val Lys Arg Glu Lys Lys Glu Lys
            740                 745                 750

Val Lys Met Lys Glu Lys Glu Val Thr Lys Ala Lys Pro Ala Cys
        755                 760                 765

Lys Ala Asp Lys Thr Leu Ala Thr Gln Arg Arg Leu Glu Glu Arg Gln
770                 775                 780

Lys Gln Gln Met Ile Leu Glu Glu Met Lys Lys Pro Thr Glu Asp Met
785                 790                 795                 800

Cys Leu Thr Asp His Gln Pro Leu Pro Asp Phe Ser Arg Val Pro Gly
                805                 810                 815

Leu Thr Leu Pro Ser Gly Ala Phe Ser Asp Cys Leu Thr Ile Val Glu
            820                 825                 830

Phe Leu His Ser Phe Gly Lys Val Leu Gly Phe Asp Pro Ala Lys Asp
        835                 840                 845

Val Pro Ser Leu Gly Val Leu Gln Glu Gly Leu Leu Cys Gln Gly Asp
    850                 855                 860

Ser Leu Gly Glu Val Gln Asp Leu Leu Val Arg Leu Leu Lys Ala Ala
865                 870                 875                 880

Leu His Asp Pro Gly Phe Pro Ser Tyr Cys Gln Ser Leu Lys Ile Leu
                885                 890                 895

Gly Glu Lys Val Ser Glu Ile Pro Leu Thr Arg Asp Asn Val Ser Glu
            900                 905                 910

Ile Leu Arg Cys Phe Leu Met Ala Tyr Gly Val Xaa Pro Ala Leu Cys
        915                 920                 925

Asp Arg Leu Arg Thr Gln Pro Phe Gln Ala Gln Pro Pro Gln Gln Lys
    930                 935                 940

Ala Ala Val Leu Ala Phe Pro Val His Glu Leu Asn Gly Ser Thr Leu
945                 950                 955                 960

Ile Ile Asn Glu Ile Asp Lys Thr Leu Glu Ser Met Ser Ser Tyr Arg
                965                 970                 975

Lys Asn Lys Trp Ile Val Glu Gly Arg Leu Arg Arg Leu Lys Thr Val
            980                 985                 990

Leu Ala Lys Arg Thr Gly Arg Ser Glu Val Glu Met Gly Arg Pro Glu
        995                 1000                1005

Glu Cys Leu Gly Arg Arg Ser Ser Arg Ile Met Glu Glu Thr Ser
    1010                1015                1020
```

```
Gly Met Glu Glu Glu Glu Glu Glu Ser Ile Ala Ala Val Pro Gly
1025                1030                1035                1040

Arg Arg Gly Arg Arg Asp Gly Glu Val Asp Ala Thr Ala Ser Ser Ile
        1045                1050                1055

Pro Glu Leu Glu Arg Gln Ile Glu Lys Leu Ser Lys Arg Gln Leu Phe
1060                1065                1070

Phe Arg Lys Lys Leu Leu His Ser Ser Gln Met Leu Arg Ala Val Ser
        1075                1080                1085

Leu Gly Gln Asp Arg Tyr Arg Arg Arg Tyr Trp Val Leu Pro Tyr Leu
        1090                1095                1100

Ala Gly Ile Phe Val Glu Gly Thr Glu Gly Asn Leu Val Pro Glu Glu
1105                1110                1115                1120

Val Ile Lys Lys Glu Thr Asp Ser Leu Lys Val Ala His Ala Ser
            1125                1130                1135

Leu Asn Pro Ala Leu Phe Ser Met Lys Met Glu Leu Ala Gly Ser Asn
            1140                1145                1150

Thr Thr Ala Ser Ser Pro Ala Arg Ala Arg Ser Arg Pro Leu Lys Thr
            1155                1160                1165

Lys Pro Gly Phe Met Gln Pro Arg His Phe Lys Ser Pro Val Arg Gly
1170                1175                1180

Gln Asp Ser Glu Gln Pro Gln Ala Gln Leu Gln Pro Glu Ala Gln Leu
1185                1190                1195                1200

His Val Pro Ala Gln Pro Gln Pro Gln Leu Gln Leu Gln Leu Gln Ser
            1205                1210                1215

His Lys Gly Phe Leu Gln Glu Gly Ser Pro Leu Ser Leu Gly Gln
        1220                1225                1230

Ser Gln His Asp Leu Ser Gln Ser Ala Phe Leu Ser Trp Leu Ser Gln
        1235                1240                1245

Thr Gln Ser His Ser Ser Leu Leu Ser Ser Val Leu Thr Pro Asp
        1250                1255                1260

Ser Ser Pro Gly Lys Leu Asp Pro Ala Pro Ser Gln Pro Pro Glu Glu
1265                1270                1275                1280

Pro Glu Pro Asp Glu Ala Glu Ser Ser Pro Asp Leu Gln Ala Phe Trp
            1285                1290                1295

Phe Asn Ile Ser Ala Gln Met Pro Cys Asn Ala Ala Pro Thr Pro Pro
            1300                1305                1310

Leu Ala Val Ser Glu Asp Gln Pro Thr Pro Ser Pro Gln Gln Leu Ala
        1315                1320                1325

Ser Ser Lys Pro Met Asn Arg Pro Ser Ala Ala Asn Pro Cys Ser Pro
        1330                1335                1340

Val Gln Phe Ser Ser Thr Pro Leu Ala Gly Leu Ala Pro Lys Arg Arg
1345                1350                1355                1360

Ala Gly Asp Pro Gly Glu Met Pro Gln Ser Pro Thr Gly Leu Gly Gln
            1365                1370                1375

Pro Lys Arg Arg Gly Arg Pro Pro Ser Lys Phe Phe Lys Gln Met Glu
        1380                1385                1390

Gln Arg Tyr Leu Thr Gln Leu Thr Ala Gln Pro Val Pro Pro Glu Met
        1395                1400                1405

Cys Ser Gly Trp Trp Trp Ile Pro Asp Pro Glu Met Leu Asp Ala Met
        1410                1415                1420

Leu Lys Ala Leu His Pro Arg Gly Ile Arg Glu Lys Ala Leu His Lys
1425                1430                1435                1440

His Leu Asn Lys His Arg Asp Phe Leu Gln Glu Val Cys Leu Arg Pro
```

-continued

```
              1445                1450                1455

Ser Ala Asp Pro Ile Phe Glu Pro Arg Gln Leu Pro Ala Phe Gln Glu
            1460                1465                1470

Gly Ile Met Ser Trp Ser Pro Lys Glu Lys Thr Tyr Glu Thr Asp Leu
        1475                1480                1485

Ala Val Leu Gln Trp Val Glu Leu Glu Gln Arg Val Ile Met Ser
    1490                1495                1500

Asp Leu Gln Ile Arg Gly Trp Thr Cys Pro Ser Pro Asp Ser Thr Arg
1505                1510                1515                1520

Glu Asp Leu Ala Tyr Cys Glu His Leu Ser Asp Ser Gln Glu Asp Ile
            1525                1530                1535

Thr Trp Arg Gly Pro Gly Arg Glu Gly Leu Ala Pro Gln Arg Lys Thr
        1540                1545                1550

Thr Asn Pro Leu Asp Leu Ala Val Met Arg Leu Ala Ala Leu Glu Gln
    1555                1560                1565

Asn Val Lys Arg Arg Tyr Leu Arg Glu Pro Leu Trp Pro Thr His Glu
    1570                1575                1580

Val Val Leu Glu Lys Ala Leu Leu Ser Thr Pro Asn Gly Ala Pro Glu
1585                1590                1595                1600

Gly Thr Thr Thr Glu Ile Ser Tyr Glu Ile Thr Pro Arg Ile Arg Ile
                1605                1610                1615

Trp Arg Gln Thr Leu Gln Arg Cys Arg Ser Ala Ala His Val Cys Leu
            1620                1625                1630

Cys Leu Gly His Leu Glu Arg Ser Ile Ala Trp Glu Lys Ser Val Asn
        1635                1640                1645

Lys Val Thr Cys Leu Val Cys Arg Lys Gly Asp Asn Asp Glu Phe Leu
    1650                1655                1660

Leu Leu Cys Asp Gly Cys Asp Arg Gly Cys His Ile Tyr Cys His Arg
1665                1670                1675                1680

Pro Lys Met Glu Ala Val Pro Glu Gly Asp Trp Phe Cys Thr Val Cys
                1685                1690                1695

Leu Ala Gln Gln Val Glu Gly Glu Phe Thr Gln Lys Pro Gly Phe Pro
            1700                1705                1710

Lys Arg Gly Gln Lys Arg Lys Ser Gly Tyr Ser Leu Asn Phe Ser Glu
        1715                1720                1725

Gly Asp Gly Arg Arg Arg Val Leu Leu Lys Gly Arg Glu Ser Pro
    1730                1735                1740

Ala Ala Gly Pro Arg Tyr Ser Glu Glu Arg Leu Ser Pro Ser Lys Arg
1745                1750                1755                1760

Arg Arg Leu Ser Met Arg Asn His His Ser Asp Leu Thr Phe Cys Glu
                1765                1770                1775

Ile Ile Leu Met Glu Met Glu Ser His Asp Ala Ala Trp Pro Phe Xaa
            1780                1785                1790

Glu Pro Val Asn Pro Arg Leu Val Ser Gly Tyr Arg Arg Ile Ile Lys
        1795                1800                1805

Asn Pro Met Asp Phe Ser Thr Met Arg Glu Arg Leu Leu Arg Gly Gly
    1810                1815                1820

Tyr Thr Ser Ser Glu Glu Phe Ala Ala Asp Ala Leu Leu Val Phe Asp
1825                1830                1835                1840

Asn Cys Gln Thr Phe Asn Glu Asp Asp Ser Glu Val Gly Lys Ala Gly
            1845                1850                1855

His Ile Met Arg Arg Phe Phe Glu Ser Arg Trp Glu Glu Phe Tyr Gln
        1860                1865                1870
```

Gly Lys Gln Ala Asn Leu
        1875

<210> SEQ ID NO 14
<211> LENGTH: 9408
<212> TYPE: DNA
<213> ORGANISM: Homo sapiens
<220> FEATURE:
<221> NAME/KEY: CDS
<222> LOCATION: (740)...(6373)
<220> FEATURE:
<221> NAME/KEY: misc_feature
<222> LOCATION: (1)...(9408)
<223> OTHER INFORMATION: n = A,T,C or G

<400> SEQUENCE: 14

```
gttccactca cagatttctt cttattgccc aggcttgagt gcaatgacct gttctcagct      60
tactcaacct ctgcctcttg ggtttcagtg attttttctgc ctcggcctcc tgagtagcta    120
agggaggagt cttgagatta tcatccacgg agggtggaag aggagagggt ggaaggggaa    180
taagaagaca ttcgggaggt gtcttgaggc tcagggagtt atcagttata gaatgttgtt    240
gagttggagg aagtggctgg cggcccatcc tgttttttaa agtttcacct gtgaagtagg    300
gccagtaggg caatcctgaa gaatgacgat gctccgctgc cgccattctg acctgtaagg    360
ccgaaagaaa gggaatgttt tcacacatat tcatttgatg acaaaatta ccgccaccaa     420 cacggtctgc accttctgtt gctggtgata aattttttgca cctttccatc ctccaggttt    480
caaaatagca gtatcagtgt cataatatca cccttccact gagtactgcc gacagctggg    540
gagtaaaaaa aagtcattgg gacatcaccc tacagcagtt caggctgtgt ggttcgcaag    600
aagcatacac tggcttttttg attcttgcta gttcccagct cacagtttgg gaggatccaa    660
caccaacctt tacgtgaagt ggaggcccaa ggacagtgag gagctgggtg gtcccagcct    720
ggagctgtgc cagcctgac atg gaa atg gag gca aac gag gca aac gac cat       772
               Met Glu Met Glu Ala Asn Glu Ala Asn Asp His
                 1               5                  10 ttt aac ttt act ggc ctt ccc cct gca cct gct gcc tca gga ctg aaa        820
Phe Asn Phe Thr Gly Leu Pro Pro Ala Pro Ala Ala Ser Gly Leu Lys
             15                  20                  25 ccc tct cct tcc tca ggg gag ggc ctc tac act aac ggg tct ccc atg        868
Pro Ser Pro Ser Ser Gly Glu Gly Leu Tyr Thr Asn Gly Ser Pro Met
         30                  35                  40 aac ttc ccc cag caa ggg aaa agt ttg aat ggg gat gtg aat gtt aat        916
Asn Phe Pro Gln Gln Gly Lys Ser Leu Asn Gly Asp Val Asn Val Asn
     45                  50                  55 ggc tta tct act gta tct cac act act act tca ggg att ttg aac tct       964
Gly Leu Ser Thr Val Ser His Thr Thr Thr Ser Gly Ile Leu Asn Ser
 60                  65                  70                  75 gct ccc cac tcc tcc agc acc tca cac ctc cat cac ccc agc gtg gcc      1012
Ala Pro His Ser Ser Ser Thr Ser His Leu His His Pro Ser Val Ala
                 80                  85                  90 tac gac tgt ctc tgg aac tac tca cag tac cca tct gcc aat cct ggc      1060
Tyr Asp Cys Leu Trp Asn Tyr Ser Gln Tyr Pro Ser Ala Asn Pro Gly
             95                  100                 105 agc aac ctc aag gac cca ccc ctt ctc tcc cag ttc tcg ggg gga caa      1108
Ser Asn Leu Lys Asp Pro Pro Leu Leu Ser Gln Phe Ser Gly Gly Gln
         110                 115                 120 tac cca ctc aac ggc atc ctt ggg ggc agc cgg caa cct tca tcc cca      1156
Tyr Pro Leu Asn Gly Ile Leu Gly Gly Ser Arg Gln Pro Ser Ser Pro
     125                 130                 135
```

```
agt cat aac act aac ctt cgg gct ggg agc caa aag ttc tgg gcc aac      1204
Ser His Asn Thr Asn Leu Arg Ala Gly Ser Gln Lys Phe Trp Ala Asn
140             145                 150                 155 ggt acc cat agt ccc atg ggg ctt aac ttt gat tca caa gaa ctg tat      1252
Gly Thr His Ser Pro Met Gly Leu Asn Phe Asp Ser Gln Glu Leu Tyr
                160                 165                 170 gat tcc ttt cct gac cag aat ttt gag gag gta tgc agt ggt atc cat      1300
Asp Ser Phe Pro Asp Gln Asn Phe Glu Glu Val Cys Ser Gly Ile His
            175                 180                 185 cct gat gag gca gca gaa aaa gag atg act tcc gtt gtg gca gaa aat      1348
Pro Asp Glu Ala Ala Glu Lys Glu Met Thr Ser Val Val Ala Glu Asn
        190                 195                 200 ggc act ggc ttg gta tgc agc ttg gag ctg gaa gaa naa cag cca gaa      1396
Gly Thr Gly Leu Val Cys Ser Leu Glu Leu Glu Glu Xaa Gln Pro Glu
    205                 210                 215 ctg aag atg tgt ggc tac aat ggc tct gtc cct tct gtg gaa tcg tta      1444
Leu Lys Met Cys Gly Tyr Asn Gly Ser Val Pro Ser Val Glu Ser Leu
220                 225                 230                 235 cac caa gag gtc tca gtc ctg gtc cct gac ccc aca gtg agc tgt tta      1492
His Gln Glu Val Ser Val Leu Val Pro Asp Pro Thr Val Ser Cys Leu
                240                 245                 250 gat gat cct tca cat ctt cct gat caa ctg gaa gac act cca atc ctc      1540
Asp Asp Pro Ser His Leu Pro Asp Gln Leu Glu Asp Thr Pro Ile Leu
            255                 260                 265 agt gaa gac tct ctg gag ccc ttc aac tct ctg gca cca gag cca gtg      1588
Ser Glu Asp Ser Leu Glu Pro Phe Asn Ser Leu Ala Pro Glu Pro Val
        270                 275                 280 agt gga gga cta tat ggt att gat gac acg gag ctg atg ggt gca gaa      1636
Ser Gly Gly Leu Tyr Gly Ile Asp Asp Thr Glu Leu Met Gly Ala Glu
    285                 290                 295 gac aag ctg cct ctt gan gac agc cct gtg att tct gcc ctt gat tgc      1684
Asp Lys Leu Pro Leu Xaa Asp Ser Pro Val Ile Ser Ala Leu Asp Cys
300                 305                 310                 315 cct tcc ctc aat aat gct act gcc ttc agt ctc ctg gca gat gat agt      1732
Pro Ser Leu Asn Asn Ala Thr Ala Phe Ser Leu Leu Ala Asp Asp Ser
                320                 325                 330 caa aca tca act tct atc ttt gcc agt ccc act tct cca cct gtc cta      1780
Gln Thr Ser Thr Ser Ile Phe Ala Ser Pro Thr Ser Pro Pro Val Leu
            335                 340                 345 ggg gag tct gtc ctg caa gat aac agc ttt gac ctg aat aat ggt agt      1828
Gly Glu Ser Val Leu Gln Asp Asn Ser Phe Asp Leu Asn Asn Gly Ser
        350                 355                 360 gac gct gaa cag gaa gaa atg gaa act caa tct tca gac ttc cca cca      1876
Asp Ala Glu Gln Glu Glu Met Glu Thr Gln Ser Ser Asp Phe Pro Pro
    365                 370                 375 tcc ctg acc cag cca gct cct gat cag tca tcc act att cag cta cat      1924
Ser Leu Thr Gln Pro Ala Pro Asp Gln Ser Ser Thr Ile Gln Leu His
380                 385                 390                 395 cca gca acc tca cca gca gtc tcg cca aca acc tcc cca gca gtc tcc      1972
Pro Ala Thr Ser Pro Ala Val Ser Pro Thr Thr Ser Pro Ala Val Ser
                400                 405                 410 cta gtg gtt tct cca gca gcc tcc cca gaa atc tct cca gaa gtt tgt      2020
Leu Val Val Ser Pro Ala Ala Ser Pro Glu Ile Ser Pro Glu Val Cys
            415                 420                 425 ccc gca gct tct aca gtt gtc tct cca gca gtc ttc agt gtc tct           2068
Pro Ala Ala Ser Thr Val Val Ser Pro Ala Val Phe Ser Val Ser
        430                 435                 440 cca gct tct tca gca gtc ctc cca gca gtc tcc tta gaa gtc ccg ttg      2116
Pro Ala Ser Ser Ala Val Leu Pro Ala Val Ser Leu Glu Val Pro Leu
    445                 450                 455
```

| | | | | | | | | | | | | | | | | |
|---|---|---|---|---|---|---|---|---|---|---|---|---|---|---|---|---|
| acg | gct | tca | gtg | aca | tcc | cca | aaa | gcc | tct | ccc | gta | act | tcc | cca | gca | 2164 |
| Thr | Ala | Ser | Val | Thr | Ser | Pro | Lys | Ala | Ser | Pro | Val | Thr | Ser | Pro | Ala | |
| 460 | | | | | 465 | | | | | 470 | | | | | 475 | | gct gcc ttt cca aca gcc tcc cca gca aat aag gat gtc agc agc ttt    2212
Ala Ala Phe Pro Thr Ala Ser Pro Ala Asn Lys Asp Val Ser Ser Phe
                480                 485                 490 cta gaa acc act gct gac gtg gaa gag atc act gga gaa gga ctc act    2260
Leu Glu Thr Thr Ala Asp Val Glu Glu Ile Thr Gly Glu Gly Leu Thr
        495                 500                 505 gct tct ggt agt ggt gat gtc atg agg aga cgt att gct acc cca gaa    2308
Ala Ser Gly Ser Gly Asp Val Met Arg Arg Arg Ile Ala Thr Pro Glu
    510                 515                 520 gaa gtt cgt ctt ccc ctc caa cat ggg tgg cgg aga gag gtg cgc atc    2356
Glu Val Arg Leu Pro Leu Gln His Gly Trp Arg Arg Glu Val Arg Ile
525                 530                 535 aag aag ggc agc cac cga tgg cag ggg gag acn tgg tat tat ggc ccc    2404
Lys Lys Gly Ser His Arg Trp Gln Gly Glu Thr Trp Tyr Tyr Gly Pro
540                 545                 550                 555 tgt ggg aag agg atg aag caa ttt cca gaa gtg atc aag tac ctg agc    2452
Cys Gly Lys Arg Met Lys Gln Phe Pro Glu Val Ile Lys Tyr Leu Ser
                560                 565                 570 cgc aac ctg gta cac agt gtc cgc cga gag cac ttc agc ttc agt ccc    2500
Arg Asn Leu Val His Ser Val Arg Arg Glu His Phe Ser Phe Ser Pro
            575                 580                 585 cgt atg cct gtt gga gat ttc ttt gaa gaa aga gac acg cca gag ggc    2548
Arg Met Pro Val Gly Asp Phe Phe Glu Glu Arg Asp Thr Pro Glu Gly
        590                 595                 600 ttg cag tgg gtg cag ctc tca gca gag gag atc ccg tcg agg att cag    2596
Leu Gln Trp Val Gln Leu Ser Ala Glu Glu Ile Pro Ser Arg Ile Gln
    605                 610                 615 gca att act ggc aaa cgg ggt cga cct cga aac act gag aag gct aag    2644
Ala Ile Thr Gly Lys Arg Gly Arg Pro Arg Asn Thr Glu Lys Ala Lys
620                 625                 630                 635 act aag gaa gtc ccc aag gtg aaa cgg ggt cga ggt cgg cca cct aag    2692
Thr Lys Glu Val Pro Lys Val Lys Arg Gly Arg Gly Arg Pro Pro Lys
                640                 645                 650 gtc aaa atc act gag cta ttg aac aag aca gac aac cgc ccc cta aag    2740
Val Lys Ile Thr Glu Leu Leu Asn Lys Thr Asp Asn Arg Pro Leu Lys
            655                 660                 665 aaa ctg gag gcc caa gaa aca ttg aat gag gag gat aaa gca aag att    2788
Lys Leu Glu Ala Gln Glu Thr Leu Asn Glu Glu Asp Lys Ala Lys Ile
        670                 675                 680 gct aaa agc aag aag aag atg agg cag aag gtt caa cgg gga gag tgt    2836
Ala Lys Ser Lys Lys Lys Met Arg Gln Lys Val Gln Arg Gly Glu Cys
    685                 690                 695 ctn act act atc caa ggg cag gcc aga aat aag cgg aaa caa gag acc    2884
Leu Thr Thr Ile Gln Gly Gln Ala Arg Asn Lys Arg Lys Gln Glu Thr
700                 705                 710                 715 aag agc tta aag cac aag gaa gct aag aag aaa tcc nag gct gag aaa    2932
Lys Ser Leu Lys His Lys Glu Ala Lys Lys Lys Ser Xaa Ala Glu Lys
                720                 725                 730 gaa aaa gga aag aca aag cag gaa aaa ctg aag gaa aaa gtc aag agg    2980
Glu Lys Gly Lys Thr Lys Gln Glu Lys Leu Lys Glu Lys Val Lys Arg
            735                 740                 745 gaa aag aag gag aag gtt aaa atg aag gaa aag gag gag gtg acc aaa    3028
Glu Lys Lys Glu Lys Val Lys Met Lys Glu Lys Glu Glu Val Thr Lys
        750                 755                 760 gcc aag cca gcc tgt aaa gca gat aag acc ctg gcc aca cag agg cgc    3076
Ala Lys Pro Ala Cys Lys Ala Asp Lys Thr Leu Ala Thr Gln Arg Arg -continued

```
                 765                 770                 775
ttg gag gaa cgg cag aag cag cag atg atc ttg gag gaa atg aag aag      3124
Leu Glu Glu Arg Gln Lys Gln Gln Met Ile Leu Glu Glu Met Lys Lys
780                 785                 790                 795 ccg aca gag gat atg tgt ctg act gac cac cag ccc ctg cct gac ttc      3172
Pro Thr Glu Asp Met Cys Leu Thr Asp His Gln Pro Leu Pro Asp Phe
                    800                 805                 810 tca cga gtc cct ggt ctg aca ttg ccc agt gga gcc ttc tca gac tgc      3220
Ser Arg Val Pro Gly Leu Thr Leu Pro Ser Gly Ala Phe Ser Asp Cys
            815                 820                 825 ttg acc att gtg gag ttc ctg cat agc ttt ggc aag gtg ctg ggc ttt      3268
Leu Thr Ile Val Glu Phe Leu His Ser Phe Gly Lys Val Leu Gly Phe
        830                 835                 840 gat cct gcc aaa gat gtg cct agc ctg ggg gtc ctg cag gag gga ctc      3316
Asp Pro Ala Lys Asp Val Pro Ser Leu Gly Val Leu Gln Glu Gly Leu
    845                 850                 855 ctg tgt caa ggt gac agc ttg ggt gag gtg caa gac ctg ctg gtc agg      3364
Leu Cys Gln Gly Asp Ser Leu Gly Glu Val Gln Asp Leu Leu Val Arg
860                 865                 870                 875 ctg ctg aag gct gca ctc cat gat cct ggc ttt ccc tcc tac tgt cag      3412
Leu Leu Lys Ala Ala Leu His Asp Pro Gly Phe Pro Ser Tyr Cys Gln
                    880                 885                 890 tcc cta aag atc ttg ggg gag aag gtg tct gaa atc cca ctg aca aga      3460
Ser Leu Lys Ile Leu Gly Glu Lys Val Ser Glu Ile Pro Leu Thr Arg
            895                 900                 905 gac aat gtg tca gag atc ctg cgc tgc ttc ctt atg gca tat gga gta      3508
Asp Asn Val Ser Glu Ile Leu Arg Cys Phe Leu Met Ala Tyr Gly Val
        910                 915                 920 nag cca gcc ctc tgt gac cgc ctg cgc acc cag cct ttt cag gcc cag      3556
Xaa Pro Ala Leu Cys Asp Arg Leu Arg Thr Gln Pro Phe Gln Ala Gln
    925                 930                 935 cca ccc cag cag aag gct gct gtc ctg gcc ttc cct gtg cat gag ctc      3604
Pro Pro Gln Gln Lys Ala Ala Val Leu Ala Phe Pro Val His Glu Leu
940                 945                 950                 955 aat ggc tcc acc ctc atc atc aat gag att gac aag act ctg gag agt      3652
Asn Gly Ser Thr Leu Ile Ile Asn Glu Ile Asp Lys Thr Leu Glu Ser
                    960                 965                 970 atg tcc agc tac agg aaa aac aag tgg att gtt gaa ggc cgg ctc cgg      3700
Met Ser Ser Tyr Arg Lys Asn Lys Trp Ile Val Glu Gly Arg Leu Arg
            975                 980                 985 agg ctg aaa act gtt ctg gcc aag cga act ggg cgg tct gaa gta gag      3748
Arg Leu Lys Thr Val Leu Ala Lys Arg Thr Gly Arg Ser Glu Val Glu
        990                 995                 1000 atg gga agg cca gag gaa tgc ctg gga cgg agg cgc agt tct cgg atc      3796
Met Gly Arg Pro Glu Glu Cys Leu Gly Arg Arg Arg Ser Ser Arg Ile
    1005                1010                1015 atg gag gag acc agt ggc atg gaa gaa gag gaa gaa gag gag tct ata      3844
Met Glu Glu Thr Ser Gly Met Glu Glu Glu Glu Glu Glu Glu Ser Ile
1020                1025                1030                1035 gca gct gtc cct ggc cgc agg ggt cga aga gat gga gag gtt gat gcc      3892
Ala Ala Val Pro Gly Arg Arg Gly Arg Arg Asp Gly Glu Val Asp Ala
                    1040                1045                1050 aca gca tct agc atc cca gag cta gag cgc cag ata gaa aaa ctc agc      3940
Thr Ala Ser Ser Ile Pro Glu Leu Glu Arg Gln Ile Glu Lys Leu Ser
            1055                1060                1065 aag cgt cag ctt ttc ttt cgc aaa aag ctg ctt cac tca tcc cag atg      3988
Lys Arg Gln Leu Phe Phe Arg Lys Lys Leu Leu His Ser Ser Gln Met
        1070                1075                1080 ctt cgg gcg gtc tcc ctg ggt cag gac cgc tac aga cgt cgc tac tgg      4036
Leu Arg Ala Val Ser Leu Gly Gln Asp Arg Tyr Arg Arg Arg Tyr Trp
```

```
Leu Arg Ala Val Ser Leu Gly Gln Asp Arg Tyr Arg Arg Tyr Trp
    1085                1090                1095 gta ttg ccg tat ttg gct ggt atc ttt gta gaa gga aca gag ggg aac      4084
Val Leu Pro Tyr Leu Ala Gly Ile Phe Val Glu Gly Thr Glu Gly Asn
1100                1105                1110                1115 tta gtt cct gag gag gtg ata aag aag gaa act gac tcc tta aaa gtg      4132
Leu Val Pro Glu Glu Val Ile Lys Lys Glu Thr Asp Ser Leu Lys Val
            1120                1125                1130 gca gcc cat gcg tca ctc aac cct gcc ctc ttc tct atg aag atg gag      4180
Ala Ala His Ala Ser Leu Asn Pro Ala Leu Phe Ser Met Lys Met Glu
                1135                1140                1145 tta gct ggc tcc aac acc act gcc agt tct cct gcc cgg gcc cga agc      4228
Leu Ala Gly Ser Asn Thr Thr Ala Ser Ser Pro Ala Arg Ala Arg Ser
            1150                1155                1160 cga cct cta aaa act aag ccc ggg ttt atg caa cct agg cat ttt aag      4276
Arg Pro Leu Lys Thr Lys Pro Gly Phe Met Gln Pro Arg His Phe Lys
        1165                1170                1175 tcc cct gtc agg ggt cag gat tca gaa cag ccc cag gcc cag ctt cag      4324
Ser Pro Val Arg Gly Gln Asp Ser Glu Gln Pro Gln Ala Gln Leu Gln
1180                1185                1190                1195 cct gag gct cag ctt cat gtt cct gcc cag ccc cag cct cag ctt cag      4372
Pro Glu Ala Gln Leu His Val Pro Ala Gln Pro Gln Pro Gln Leu Gln
            1200                1205                1210 ctt cag ctt cag tcc cat aag ggg ttc ctg gag caa gaa ggc tcc cct      4420
Leu Gln Leu Gln Ser His Lys Gly Phe Leu Glu Gln Glu Gly Ser Pro
                1215                1220                1225 ttg tca ctg ggt cag agc cag cat gac ctc agc cag tca gcc ttc ctg      4468
Leu Ser Leu Gly Gln Ser Gln His Asp Leu Ser Gln Ser Ala Phe Leu
            1230                1235                1240 tct tgg ctg agc cag act cag agc cat agc tcc ctg ttg agc agc tca      4516
Ser Trp Leu Ser Gln Thr Gln Ser His Ser Ser Leu Leu Ser Ser Ser
        1245                1250                1255 gtc ctc aca cct gat agc agt ccg gga aaa cta gac cca gct cca tca      4564
Val Leu Thr Pro Asp Ser Ser Pro Gly Lys Leu Asp Pro Ala Pro Ser
1260                1265                1270                1275 caa ccc ccg gag gag cca gag cct gat gag gca gaa tcc agc cct gat      4612
Gln Pro Pro Glu Glu Pro Glu Pro Asp Glu Ala Glu Ser Ser Pro Asp
            1280                1285                1290 ctt caa gca ttc tgg ttt aac atc tca gcc cag atg ccc tgc aat gct      4660
Leu Gln Ala Phe Trp Phe Asn Ile Ser Ala Gln Met Pro Cys Asn Ala
                1295                1300                1305 gcc ccc aca ccg ccc ctt gca gtt tct gag gac caa ccc act ccc tcc      4708
Ala Pro Thr Pro Pro Leu Ala Val Ser Glu Asp Gln Pro Thr Pro Ser
            1310                1315                1320 cct cag cag ctt gcc tcc tcc aag cca atg aat aga cct agt gct gcc      4756
Pro Gln Gln Leu Ala Ser Ser Lys Pro Met Asn Arg Pro Ser Ala Ala
        1325                1330                1335 aac cct tgt tct cca gtg cag ttc tct tcc acg ccc ttg gct ggg ttg      4804
Asn Pro Cys Ser Pro Val Gln Phe Ser Ser Thr Pro Leu Ala Gly Leu
1340                1345                1350                1355 gcc cct aag agg cga gca gga gac cct gga gaa atg cca cag agt ccc      4852
Ala Pro Lys Arg Arg Ala Gly Asp Pro Gly Glu Met Pro Gln Ser Pro
            1360                1365                1370 aca ggg ctg gga cag ccc aaa cgg aga ggg aga cct ccc agt aag ttc      4900
Thr Gly Leu Gly Gln Pro Lys Arg Arg Gly Arg Pro Pro Ser Lys Phe
                1375                1380                1385 ttc aaa cag atg gaa cag cgt tac cta acc cag ctg aca gcc cag cct      4948
Phe Lys Gln Met Glu Gln Arg Tyr Leu Thr Gln Leu Thr Ala Gln Pro
            1390                1395                1400
```

```
gtc cca cct gag atg tgc tca ggc tgg tgg tgg ata cca gat cct gag    4996
Val Pro Pro Glu Met Cys Ser Gly Trp Trp Trp Ile Pro Asp Pro Glu
         1405                1410                1415 atg ttg gat gcc atg ctc aag gcc cta cac ccc cga ggt atc cgg gag    5044
Met Leu Asp Ala Met Leu Lys Ala Leu His Pro Arg Gly Ile Arg Glu
1420                1425                1430                1435 aag gca ctt cac aaa cac ctt aac aag cac agg gac ttc ttg cag gaa    5092
Lys Ala Leu His Lys His Leu Asn Lys His Arg Asp Phe Leu Gln Glu
                1440                1445                1450 gtc tgc ctg cgg ccc tca gct gac ccc atc ttt gag ccc agg caa cta    5140
Val Cys Leu Arg Pro Ser Ala Asp Pro Ile Phe Glu Pro Arg Gln Leu
         1455                1460                1465 cct gcc ttt caa gaa ggg att atg agc tgg tcc ccc aaa gag aag aca    5188
Pro Ala Phe Gln Glu Gly Ile Met Ser Trp Ser Pro Lys Glu Lys Thr
    1470                1475                1480 tac gag aca gac cta gca gtg ctt caa tgg gta gag gag ctg gag cag    5236
Tyr Glu Thr Asp Leu Ala Val Leu Gln Trp Val Glu Glu Leu Glu Gln
1485                1490                1495 cgg gtt atc atg tct gat ctg cag att cgg ggc tgg aca tgt cct agc    5284
Arg Val Ile Met Ser Asp Leu Gln Ile Arg Gly Trp Thr Cys Pro Ser
1500                1505                1510                1515 cca gac tct acc cgt gaa gac ttg gcc tac tgt gag cac ctc tcc gac    5332
Pro Asp Ser Thr Arg Glu Asp Leu Ala Tyr Cys Glu His Leu Ser Asp
                1520                1525                1530 tcc cag gag gat atc acc tgg cga ggt ccg ggc agg gag gga ctg gca    5380
Ser Gln Glu Asp Ile Thr Trp Arg Gly Pro Gly Arg Glu Gly Leu Ala
         1535                1540                1545 cct caa cgt aaa act acc aac cct ttg gac ctg gct gtg atg cgg ctg    5428
Pro Gln Arg Lys Thr Thr Asn Pro Leu Asp Leu Ala Val Met Arg Leu
    1550                1555                1560 gct gcc ctg gaa caa aat gta aaa cgg cgg tac ctg cgg gag ccc ctc    5476
Ala Ala Leu Glu Gln Asn Val Lys Arg Arg Tyr Leu Arg Glu Pro Leu
1565                1570                1575 tgg cca act cat gag gtt gtg ctg gag aaa gcc ctg ctt agc aca cct    5524
Trp Pro Thr His Glu Val Val Leu Glu Lys Ala Leu Leu Ser Thr Pro
1580                1585                1590                1595 aat ggt gcc cct gag ggc acc act aca gag ata tca tat gag atc acc    5572
Asn Gly Ala Pro Glu Gly Thr Thr Thr Glu Ile Ser Tyr Glu Ile Thr
                1600                1605                1610 cct cgc att cgt atc tgg cgc cag acc ctc cag cgg tgc cgg agc gca    5620
Pro Arg Ile Arg Ile Trp Arg Gln Thr Leu Gln Arg Cys Arg Ser Ala
         1615                1620                1625 gcc cat gtg tgc ttg tgc ctg ggc cat ctg gag agg tcc att gcc tgg    5668
Ala His Val Cys Leu Cys Leu Gly His Leu Glu Arg Ser Ile Ala Trp
    1630                1635                1640 gag aag tct gtc aac aaa gtg aca tgt cta gtc tgc cgg aag ggt gac    5716
Glu Lys Ser Val Asn Lys Val Thr Cys Leu Val Cys Arg Lys Gly Asp
1645                1650                1655 aat gat gag ttt ctt ctg ctt tgt gat ggg tgt gac cgt ggc tgc cac    5764
Asn Asp Glu Phe Leu Leu Leu Cys Asp Gly Cys Asp Arg Gly Cys His
1660                1665                1670                1675 att tac tgc cat cgt ccc aag atg gag gct gtc cca gaa gga gat tgg    5812
Ile Tyr Cys His Arg Pro Lys Met Glu Ala Val Pro Glu Gly Asp Trp
                1680                1685                1690 ttc tgt act gtc tgt ttg gct cag cag gtg gag gga gaa ttc act cag    5860
Phe Cys Thr Val Cys Leu Ala Gln Gln Val Glu Gly Glu Phe Thr Gln
         1695                1700                1705 aag cct ggt ttc cca aag cgt ggc cag aag cgg aaa agt ggt tat tcg    5908
Lys Pro Gly Phe Pro Lys Arg Gly Gln Lys Arg Lys Ser Gly Tyr Ser
    1710                1715                1720
```

```
ctg aac ttc tca gaa ggt gat ggc cgc cga cgc cgg gta ctg ttg aag      5956
Leu Asn Phe Ser Glu Gly Asp Gly Arg Arg Arg Arg Val Leu Leu Lys
        1725                1730                1735 ggc cga gaa agc cca gca gca ggg cct cgg tac tcg gaa gaa agg ctc      6004
Gly Arg Glu Ser Pro Ala Ala Gly Pro Arg Tyr Ser Glu Glu Arg Leu
1740                1745                1750                1755 tcc ccc tcc aag cgg cgg cga ctc tct atg cgg aac cac cac agt gat      6052
Ser Pro Ser Lys Arg Arg Arg Leu Ser Met Arg Asn His His Ser Asp
                1760                1765                1770 ctc aca ttt tgc gag att atc ctg atg gag atg gaa tcc cat gat gca      6100
Leu Thr Phe Cys Glu Ile Ile Leu Met Glu Met Glu Ser His Asp Ala
        1775                1780                1785 gcc tgg cct ttc nta gag cct gtg aac cca cgt ttg gtg agt ggg tac      6148
Ala Trp Pro Phe Xaa Glu Pro Val Asn Pro Arg Leu Val Ser Gly Tyr
        1790                1795                1800 cgg cgc atc atc aaa aat cct atg gat ttt tcc acc atg cgg gag cgg      6196
Arg Arg Ile Ile Lys Asn Pro Met Asp Phe Ser Thr Met Arg Glu Arg
        1805                1810                1815 ctg ctc agg gga ggg tac acc agc tca gag gag ttt gcg gct gat gcc      6244
Leu Leu Arg Gly Gly Tyr Thr Ser Ser Glu Glu Phe Ala Ala Asp Ala
1820                1825                1830                1835 ctc ctg gta ttt gac aac tgc cag act ttc aac gag gat gac tct gaa      6292
Leu Leu Val Phe Asp Asn Cys Gln Thr Phe Asn Glu Asp Asp Ser Glu
                1840                1845                1850 gta ggc aag gct ggg cac atc atg cgc cgc ttc ttc gag agc cgc tgg      6340
Val Gly Lys Ala Gly His Ile Met Arg Arg Phe Phe Glu Ser Arg Trp
        1855                1860                1865 gag gag ttt tat cag gga aaa cag gcc aat ctg tgaggcaagg gaggtgggga   6393
Glu Glu Phe Tyr Gln Gly Lys Gln Ala Asn Leu
        1870                1875 gtcaccttgt ggcatctccc cccaccttcc aaacaaaaac ctgccatttt cacctgctga    6453
tgctgccctg gtccagact caagtcagat acaaccctga tttttgacct tgcccttggc    6513
agtgccccac atcctcttat tcctacatcc ctttctccct tcctcctct tgctcctcaa    6573
gtaagaggtg cagagaggag tccttctgga ctaaaagcca aaaaagaaa gaaaaaaata    6633
atttttcttt tctgttttat ttgctaatta aaaatgggga gggggaaagt cgtccctact    6693
tcctcctccg tgcttcctct cctcccctgt acgtgcccca gcattctggg gttatttaac    6753
aatagcaata gttctagtga atgtgtgaaa ccaagaaaca ctctgtactg tgtgcggacc    6813
cgcagtgacg gccagtaaag tggacttaac tcccaagtgt gtcgcggccg acaccgggc    6873
cctggacatg ctgcttccat gttcagtccc ttccctgctt ctcgctgtct ttcttttccc    6933
acctcccacc cccagttttt cagattttct ctcatccaat aatgtaaaac tatcgtgtac    6993
gggttcctcc ctccttttct cttctcccaa atcttttccc ttcaaaggaa aaaaaatgt    7053
tcagaggtcc ctgtcttctg tccccatctt cctgccgata gctatcccct gtatgatgtt    7113
ggatgctcct cacatgctga gtttccagcc ttttctgaaa ctcattagct ggggagaggg    7173
cagggaggct tcctgggcct tccaacctcc ttccccacct ccttcccaaa ccctcttggg    7233
aactcctcag ggacaactac tgctgagttt gggtgcaccc aaagatggag gccaagtagc    7293
aatgggggccg gcctcacaga gagcgccgtg tgtgtgtgtg tgtgtgtgtg tgtgtgtgtg    7353
tccgccacac aacgcgctgt gtgtgtgtgt gtgtgtctca cacacacagc gcgcagtgtg    7413
tgtgtgtgtg tgtgtgtgta tgtgtgtgtg tgtgtgaccc tgtattgttt gataggatcc    7473
attcagtttc cccaagtacc tgttttcatt cccattttt ccattgttta aaaccatcac    7533
```

```
tttttttgtct tgggaaacc acaggaacaa tttctctgga gacaaggctg tgtctctctc      7593
ctggtcattt ttgttccagc ctcttcagac tgtgcatctt ttcagcagga actccctctc      7653
ttctcggtag ctttgaatct taagcttcta cgggagagtg gtagaactgg atcatttcat      7713
aatcccattt agttgtgctt ttcttcatat acttcatacc ccaggacccc ttccccagca      7773
gcagagaccc tggagcacag gagagtaggg aggaggggtt ctgggtccat cactgcctta      7833
catgtgacta tgtccaagtt aagcccccaa cacgagagga aagctgctga ctcccagcta      7893
tagccatggg cacttggccc cctgcttttc ctgctcagca gagcccctcc cttcagagat      7953
tacgggtact tgcactgggg aggtggctgc tggctggccc aagcagagag ctgaggcatc      8013
caagaaatgt tccattgggg ggtgggggtg ccaggtgagg tggagcattc cttgtattct      8073
ggcagcactg aagagccact gaaggggta ggggcagtgt aggtcctggg gcagcccctt      8133 tattcccttta tgccccttct ccctcatagc ctatttctaa agtcgccttt tctgtcagat      8193
aaacctcaaa acttttaatt ttatttgaga ttttttttttg cttttaagag gtggattgaa      8253
gaatatttga attgacttta tattatgcat aaatatttat attttatcta ataactgcg      8313 ctgtaacaaa cttttgtgtta gacagttgaa actgttagag ttggggcta tgcttttcc     8373 ccctggcaat tttcccttgg tataagatgt gctagattaa tttcattgtg aggtggatgg      8433
gggagtgaaa ttgtgaggtg gatggggggag tgaaatctcc atggttcctg ctttgtgttc      8493
ctctcccagc tccatctctt tccctaggga ccaggcactc atatggcggg gtggggtcct      8553
agcctcagtt tgaagaagtg ggggctggag cggggttggg ggtggtaggg atagggcatg      8613
atcaaagggg ccatttcttg cttttctttc ctcatcttca ctgcccccctt gagctaggtg      8673 gattttctct tcatgacaag agtatttggt agggaaagca ggtttaaaat aaaaagacaa      8733 cccacccccct gccctttttgc ttccctccca tcagtctggt tgacaggaag aaaccacacc     8793
atcaacacca acaagtttnt gtgttccttt tacagcaaaa gggactttttt atataaccaa      8853 atgtggtgtt ttagtgactt tttgataatg tacagttttt tgtgaattta aatttatttc      8913
tttctatatt tttaggacca atttcatttt taataaggtt aaaaagaaaa aaaaagtcta      8973
gcgaaaaaac tcctgttttt gccatgtgat gttccacaag tgcagctgta gaaaagtgct      9033
tgtcagttgt tgaataaaaa aaccacattt gatagagatt caaagactc tgtgtattca     9093 tcttcccttc tacacacctg aggggggagac ggcgttggga taggtatgac tggcttaaga      9153
gaccacaggc aagggaacaa caggggctcc tgttccatac cctctgtgtg ggatggaaag      9213
ggtcattagt gctcccgcct aaatgtctgg ctgagttgct ggaagcaaag gggggattca      9273
gtgcatccag gtcctgcctt gtgagatgtg gccccagctt cctaagctgc cacctctgtg     9333
ttcctgtcat agcaaatatg ggaccatcac cagcttacca cttcccactc acggataaga      9393
caccaagacg tagac                                                      9408
```

<210> SEQ ID NO 15
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 15
tgactctgaa gtaggcaagg ctgg                                             24

<210> SEQ ID NO 16
<211> LENGTH: 22

-continued

```
<212> TYPE: DNA
<213> ORGANISM: Artificial Sequence
<220> FEATURE:
<223> OTHER INFORMATION: Synthetically generated primer

<400> SEQUENCE: 16
cttgcctcac agattggcct gt                                              22

<210> SEQ ID NO 17
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 17
ttgccgtatt tggctggtat c                                               21

<210> SEQ ID NO 18
<211> LENGTH: 23
<212> TYPE: DNA
<213> ORGANISM: Artificial Sequence
<220> FEATURE:
<223> OTHER INFORMATION: Synthetically generated primer

<400> SEQUENCE: 18
catagagaag agggcagggt tga                                             23

<210> SEQ ID NO 19
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 19
cttttgagca agttcagcct                                                 20

<210> SEQ ID NO 20
<211> LENGTH: 22
<212> TYPE: DNA
<213> ORGANISM: Artificial Sequence
<220> FEATURE:
<223> OTHER INFORMATION: Synthetically generated primer

<400> SEQUENCE: 20
gtcggcttct tcatttcctc ca                                              22

<210> SEQ ID NO 21
<211> LENGTH: 1972
<212> TYPE: PRT
<213> ORGANISM: Homo sapiens

<400> SEQUENCE: 21

Met Gly Gln Thr Lys Ser Thr Ser Ser Gly Gly Gly Asn Arg Lys Cys
 1               5                  10                  15

Asn Gln Glu Gln Ser Lys Asn Gln Pro Leu Asp Ala Arg Val Asp Lys
            20                  25                  30

Ile Lys Asp Lys Lys Pro Arg Lys Lys Ala Met Glu Ser Ser Ser Asn
        35                  40                  45

Ser Asp Ser Asp Ser Gly Thr Ser Ser Asp Thr Ser Ser Glu Gly Ile
    50                  55                  60

Ser Ser Ser Asp Ser Asp Asp Leu Glu Glu Asp Glu Glu Glu Glu Asp
65                  70                  75                  80
```

```
Gln Ser Ile Glu Glu Ser Glu Asp Asp Ser Asp Ser Glu
             85                  90                  95

Ala Gln His Lys Ser Asn Asn Gln Val Leu Leu His Gly Ile Ser Asp
                100                 105                 110

Pro Lys Ala Asp Gly Gln Lys Ala Thr Glu Lys Ala Gln Glu Lys Arg
            115                 120                 125

Ile His Gln Pro Leu Pro Leu Ala Phe Glu Ser Gln Thr His Ser Phe
            130                 135                 140

Gln Ser Gln Gln Lys Gln Pro Gln Val Leu Ser Gln Leu Pro Phe
145                 150                 155                 160

Ile Phe Gln Ser Ser Gln Ala Lys Glu Glu Ser Val Asn Lys His Thr
                165                 170                 175

Ser Val Ile Gln Ser Thr Gly Leu Val Ser Asn Val Lys Pro Leu Ser
            180                 185                 190

Leu Val Asn Gln Ala Lys Lys Glu Thr Tyr Met Lys Leu Ile Val Pro
            195                 200                 205

Ser Pro Asp Val Leu Lys Ala Gly Asn Lys Asn Thr Ser Glu Glu Ser
            210                 215                 220

Ser Leu Leu Thr Ser Glu Leu Arg Ser Lys Arg Glu Gln Tyr Lys Gln
225                 230                 235                 240

Ala Phe Pro Ser Gln Leu Lys Lys Gln Glu Ser Ser Lys Ser Leu Lys
                245                 250                 255

Lys Val Ile Ala Ala Leu Ser Asn Pro Lys Ala Thr Ser Ser Ser Pro
            260                 265                 270

Ala His Pro Lys Gln Thr Leu Glu Asn Asn His Pro Asn Pro Phe Leu
            275                 280                 285

Thr Asn Ala Leu Leu Gly Asn His Gln Pro Asn Gly Val Ile Gln Ser
            290                 295                 300

Val Ile Gln Glu Ala Pro Leu Ala Leu Thr Thr Lys Thr Lys Met Gln
305                 310                 315                 320

Ser Lys Ile Asn Glu Asn Ile Ala Ala Ala Ser Ser Thr Pro Phe Ser
                325                 330                 335

Ser Pro Val Asn Leu Ser Thr Ser Gly Arg Arg Thr Pro Gly Asn Gln
            340                 345                 350

Thr Pro Val Met Pro Ser Ala Ser Pro Ile Leu His Ser Gln Gly Lys
            355                 360                 365

Glu Lys Ala Val Ser Asn Asn Val Asn Pro Val Lys Thr Gln His His
            370                 375                 380

Ser His Pro Ala Lys Ser Leu Val Glu Gln Phe Arg Gly Thr Asp Ser
385                 390                 395                 400

Asp Ile Pro Ser Ser Lys Asp Ser Glu Asp Ser Asn Glu Asp Glu Glu
                405                 410                 415

Glu Asp Asp Glu Glu Asp Glu Glu Asp Asp Glu Asp Asp Glu Ser
            420                 425                 430

Asp Asp Ser Gln Ser Glu Ser Asp Ser Asn Ser Glu Ser Asp Thr Glu
            435                 440                 445

Gly Ser Glu Glu Glu Asp Asp Asp Lys Asp Gln Asp Glu Ser Asp
            450                 455                 460

Ser Asp Thr Glu Gly Glu Lys Thr Ser Met Lys Leu Asn Lys Thr Thr
465                 470                 475                 480

Ser Ser Val Lys Ser Pro Ser Met Ser Leu Thr Gly His Ser Thr Pro
                485                 490                 495
```

```
Arg Asn Leu His Ile Ala Lys Ala Pro Gly Ser Ala Pro Ala Ala Leu
            500                 505                 510
Cys Ser Glu Ser Gln Ser Pro Ala Phe Leu Gly Thr Ser Ser Ser Thr
        515                 520                 525
Leu Thr Ser Ser Pro His Ser Gly Thr Ser Lys Arg Arg Arg Val Thr
    530                 535                 540
Asp Glu Arg Glu Leu Arg Ile Pro Leu Glu Tyr Gly Trp Gln Arg Glu
545                 550                 555                 560
Thr Arg Ile Arg Asn Phe Gly Gly Arg Leu Gln Gly Glu Val Ala Tyr
                565                 570                 575
Tyr Ala Pro Cys Gly Lys Lys Leu Arg Gln Tyr Pro Glu Val Ile Lys
            580                 585                 590
Tyr Leu Ser Arg Asn Gly Ile Met Asp Ile Ser Arg Asp Asn Phe Ser
        595                 600                 605
Phe Ser Ala Lys Ile Arg Val Gly Asp Phe Tyr Glu Ala Arg Asp Gly
    610                 615                 620
Pro Gln Glu Met Gln Trp Cys Leu Leu Lys Glu Glu Asp Val Ile Pro
625                 630                 635                 640
Arg Ile Arg Ala Met Glu Gly Arg Arg Gly Arg Pro Pro Asn Pro Asp
                645                 650                 655
Arg Gln Arg Ala Arg Glu Glu Ser Arg Met Arg Arg Lys Gly Arg
            660                 665                 670
Pro Pro Asn Val Gly Asn Ala Glu Phe Leu Asp Asn Ala Asp Ala Lys
        675                 680                 685
Leu Leu Arg Lys Leu Gln Ala Gln Glu Ile Ala Arg Gln Ala Ala Gln
    690                 695                 700
Ile Lys Leu Leu Arg Lys Leu Gln Lys Gln Glu Gln Ala Arg Val Ala
705                 710                 715                 720
Lys Glu Ala Lys Lys Gln Gln Ala Ile Met Ala Ala Glu Glu Lys Arg
                725                 730                 735
Lys Gln Lys Glu Gln Ile Lys Ile Met Lys Gln Gln Glu Lys Ile Lys
            740                 745                 750
Arg Ile Gln Gln Ile Arg Met Glu Lys Glu Leu Arg Ala Gln Gln Ile
        755                 760                 765
Leu Glu Ala Lys Lys Lys Lys Glu Glu Ala Ala Asn Ala Lys Leu
    770                 775                 780
Leu Glu Ala Glu Lys Arg Ile Lys Glu Lys Glu Met Arg Arg Gln Gln
785                 790                 795                 800
Ala Val Leu Leu Lys His Gln Glu Arg Glu Arg Arg Gln His Met
                805                 810                 815
Met Leu Met Lys Ala Met Glu Ala Arg Lys Lys Ala Glu Glu Lys Glu
            820                 825                 830
Arg Leu Lys Gln Glu Lys Arg Asp Glu Lys Arg Leu Asn Lys Glu Arg
        835                 840                 845
Lys Leu Glu Gln Arg Arg Leu Glu Leu Glu Met Ala Lys Glu Leu Lys
    850                 855                 860
Lys Pro Asn Glu Asp Met Cys Leu Ala Asp Gln Lys Pro Leu Pro Glu
865                 870                 875                 880
Leu Pro Arg Ile Pro Gly Leu Val Leu Ser Gly Ser Thr Phe Ser Asp
                885                 890                 895
Cys Leu Met Val Val Gln Phe Leu Arg Asn Phe Gly Lys Val Leu Gly
            900                 905                 910
Phe Asp Val Asn Ile Asp Val Pro Asn Leu Ser Val Leu Gln Glu Gly
```

-continued

```
                915                 920                 925
Leu Leu Asn Ile Gly Asp Ser Met Gly Glu Val Gln Asp Leu Leu Val
        930                 935                 940
Arg Leu Leu Ser Ala Ala Val Cys Asp Pro Gly Leu Ile Thr Gly Tyr
945                 950                 955                 960
Lys Ala Lys Thr Ala Leu Gly Glu His Leu Leu Asn Val Gly Val Asn
                965                 970                 975
Arg Asp Asn Val Ser Glu Ile Leu Gln Ile Phe Met Glu Ala His Cys
            980                 985                 990
Gly Gln Thr Glu Leu Thr Glu Ser Leu Lys Thr Lys Ala Phe Gln Ala
        995                 1000                1005
His Thr Pro Ala Gln Lys Ala Ser Val Leu Ala Phe Leu Ile Asn Glu
        1010                1015                1020
Leu Ala Cys Ser Lys Ser Val Ser Glu Ile Asp Lys Asn Ile Asp
1025                1030                1035                1040
Tyr Met Ser Asn Leu Arg Arg Asp Lys Trp Val Val Glu Gly Lys Leu
                1045                1050                1055
Arg Lys Leu Arg Ile Ile His Ala Lys Lys Thr Gly Lys Arg Asp Thr
            1060                1065                1070
Ser Gly Gly Ile Asp Leu Gly Glu Glu Gln His Pro Leu Gly Thr Pro
        1075                1080                1085
Thr Pro Gly Arg Lys Arg Arg Arg Lys Gly Gly Asp Ser Asp Tyr Asp
        1090                1095                1100
Asp Asp Asp Asp Asp Ser Asp Asp Gln Gly Asp Glu Asp Glu
1105                1110                1115                1120
Asp Glu Glu Asp Lys Glu Asp Gln Lys Gly Lys Lys Thr Asp Ile Cys
                1125                1130                1135
Glu Asp Glu Asp Glu Gly Asp Gln Ala Ala Ser Val Glu Glu Leu Glu
            1140                1145                1150
Lys Gln Ile Glu Lys Leu Ser Lys Gln Gln Ser Gln Tyr Arg Arg Lys
        1155                1160                1165
Leu Phe Asp Ala Ser His Ser Leu Arg Ser Val Met Phe Gly Pro Asp
        1170                1175                1180
Arg Tyr Arg Arg Arg Tyr Trp Ile Leu Pro Arg Cys Gly Gly Ile Phe
1185                1190                1195                1200
Val Glu Gly Met Glu Ser Gly Glu Gly Leu Glu Glu Ile Ala Lys Glu
                1205                1210                1215
Arg Glu Lys Leu Lys Lys Ala Glu Ser Val Gln Ile Lys Glu Glu Met
            1220                1225                1230
Phe Glu Thr Ser Gly Asp Ser Leu Asn Cys Ser Asn Thr Asp His Cys
        1235                1240                1245
Glu Gln Lys Glu Asp Leu Lys Glu Lys Asp Asn Thr Asn Leu Phe Leu
        1250                1255                1260
Gln Lys Pro Gly Ser Phe Ser Lys Leu Ser Lys Leu Leu Glu Val Ala
1265                1270                1275                1280
Lys Met Pro Pro Glu Ser Glu Val Met Thr Pro Lys Pro Asn Ala Gly
                1285                1290                1295
Ala Asn Gly Cys Thr Leu Ser Tyr Gln Asn Ser Gly Lys His Ser Leu
            1300                1305                1310
Gly Ser Val Gln Ser Thr Ala Thr Gln Ser Asn Val Glu Lys Ala Asp
        1315                1320                1325
Ser Asn Asn Leu Phe Asn Thr Gly Ser Ser Gly Pro Gly Lys Phe Tyr
        1330                1335                1340
```

```
Ser Pro Leu Pro Asn Asp Gln Leu Leu Lys Thr Leu Thr Glu Lys Asn
1345                1350                1355                1360

Arg Gln Trp Phe Ser Leu Leu Pro Arg Thr Pro Cys Asp Asp Thr Ser
                1365                1370                1375

Leu Thr His Ala Asp Met Ser Thr Ala Ser Leu Val Thr Pro Gln Ser
            1380                1385                1390

Gln Pro Pro Ser Lys Ser Pro Ser Pro Thr Pro Ala Pro Leu Gly Ser
        1395                1400                1405

Ser Ala Gln Asn Pro Val Gly Leu Asn Pro Phe Ala Leu Ser Pro Leu
    1410                1415                1420

Gln Val Lys Gly Gly Val Ser Met Met Gly Leu Gln Phe Cys Gly Trp
1425                1430                1435                1440

Pro Thr Gly Val Val Thr Ser Asn Ile Pro Phe Thr Leu Ser Val Pro
                1445                1450                1455

Ser Leu Gly Ser Gly Leu Gly Leu Ser Glu Gly Asn Gly Asn Ser Phe
            1460                1465                1470

Leu Thr Ser Asn Val Ala Ser Ser Lys Ser Glu Ser Pro Val Pro Gln
        1475                1480                1485

Asn Glu Lys Ala Thr Ser Ala Gln Pro Ala Ala Val Glu Val Ala Lys
    1490                1495                1500

Pro Val Asp Phe Pro Ser Pro Lys Pro Ile Pro Glu Glu Met Gln Phe
1505                1510                1515                1520

Gly Trp Trp Arg Ile Ile Asp Pro Glu Asp Leu Lys Ala Leu Leu Lys
                1525                1530                1535

Val Leu His Leu Arg Gly Ile Arg Glu Lys Ala Leu Gln Lys Gln Ile
            1540                1545                1550

Gln Lys His Leu Asp Tyr Ile Thr Gln Ala Cys Leu Lys Asn Lys Asp
        1555                1560                1565

Val Ala Ile Ile Glu Leu Asn Glu Asn Glu Asn Gln Val Thr Arg
    1570                1575                1580

Asp Ile Val Glu Asn Trp Ser Val Glu Glu Gln Ala Met Glu Met Asp
1585                1590                1595                1600

Leu Ser Val Leu Gln Gln Val Glu Asp Leu Glu Arg Arg Val Ala Ser
                1605                1610                1615

Ala Ser Leu Gln Val Lys Gly Trp Met Cys Pro Glu Pro Ala Ser Glu
            1620                1625                1630

Arg Glu Asp Leu Val Tyr Phe Glu His Lys Ser Phe Thr Lys Leu Cys
        1635                1640                1645

Lys Glu His Asp Gly Glu Phe Thr Gly Glu Asp Glu Ser Ser Ala His
    1650                1655                1660

Ala Leu Glu Arg Lys Ser Asp Asn Pro Leu Asp Ile Ala Val Thr Arg
1665                1670                1675                1680

Leu Ala Asp Leu Glu Arg Asn Ile Glu Arg Ile Glu Glu Asp Ile
                1685                1690                1695

Ala Pro Gly Leu Arg Val Trp Arg Arg Ala Leu Ser Glu Ala Arg Ser
            1700                1705                1710

Ala Ala Gln Val Ala Leu Cys Ile Gln Gln Leu Gln Lys Ser Ile Ala
        1715                1720                1725

Trp Glu Lys Ser Ile Met Lys Val Tyr Cys Gln Ile Cys Arg Lys Gly
    1730                1735                1740

Asp Asn Glu Glu Leu Leu Leu Leu Cys Asp Gly Cys Asp Lys Gly Cys
1745                1750                1755                1760
```

```
His Thr Tyr Cys His Arg Pro Lys Ile Thr Thr Ile Pro Asp Gly Asp
            1765                1770                1775

Trp Phe Cys Pro Ala Cys Ile Ala Lys Ala Ser Gly Gln Thr Leu Lys
        1780                1785                1790

Ile Lys Lys Leu His Val Lys Gly Lys Lys Thr Asn Glu Ser Lys Lys
    1795                1800                1805

Gly Lys Lys Val Thr Leu Thr Gly Asp Thr Glu Asp Glu Asp Ser Ala
1810                1815                1820

Ser Thr Ser Ser Ser Leu Lys Arg Gly Asn Lys Asp Leu Gln Lys Arg
1825                1830                1835                1840

Lys Met Glu Glu Asn Thr Ser Ile Asn Leu Ser Lys Gln Glu Ser Phe
                1845                1850                1855

Thr Ser Val Lys Lys Pro Lys Arg Asp Asp Ser Lys Asp Leu Ala Leu
            1860                1865                1870

Cys Ser Met Ile Leu Thr Glu Met Glu Thr His Glu Asp Ala Trp Pro
        1875                1880                1885

Phe Leu Leu Pro Val Asn Leu Lys Leu Val Pro Gly Tyr Lys Lys Val
    1890                1895                1900

Ile Lys Lys Pro Met Asp Phe Ser Thr Ile Arg Glu Lys Leu Ser Ser
1905                1910                1915                1920

Gly Gln Tyr Pro Asn Leu Glu Thr Phe Ala Leu Asp Val Arg Leu Val
                1925                1930                1935

Phe Asp Asn Cys Glu Thr Phe Asn Glu Asp Asp Ser Asp Ile Gly Arg
            1940                1945                1950

Ala Gly His Asn Met Arg Lys Tyr Phe Glu Lys Lys Trp Thr Asp Thr
        1955                1960                1965

Phe Lys Val Ser
    1970

<210> SEQ ID NO 22
<211> LENGTH: 7585
<212> TYPE: DNA
<213> ORGANISM: Homo sapiens
<220> FEATURE:
<221> NAME/KEY: CDS
<222> LOCATION: (367)...(6282)

<400> SEQUENCE: 22
ggtctcgatc tcctgacctt gtgatccacc tcctcggcct cccaaagtgc tgggattaca      60
ggcatgagcc acggcaccca gcctcatttg ctgttaaact catttattga gtcacctttt     120
tcttcctcac acttttagt  cttagaattt ttgtgtgttt ttatttaccc taacctgtca     180
atttcatagt ttccactttc ttgttgaagt ttccaaactt gacctcatgc ctttgaatat     240
actaattcta ttgctttgac acatttttt  cccgaaaaag gtgtaaatgg gtcaataaat     300
ggaagtaata catcatctgt aattggtatc aacacatctg tactatccac tactgcttca     360 agttcc atg gga caa act aaa agt aca agc tca ggt gga gga aat cga        408
       Met Gly Gln Thr Lys Ser Thr Ser Ser Gly Gly Gly Asn Arg
           1               5                   10 aaa tgt aat cag gaa caa agc aaa aac cag cct ttg gat gct aga gtt       456
Lys Cys Asn Gln Glu Gln Ser Lys Asn Gln Pro Leu Asp Ala Arg Val
 15              20                  25                  30 gac aaa atc aaa gat aag aaa cca agg aag aaa gca atg gaa agt tct       504
Asp Lys Ile Lys Asp Lys Lys Pro Arg Lys Lys Ala Met Glu Ser Ser
                 35                  40                  45 agc aac agt gat agt gat tca ggc aca tca tca gac acc tca agt gaa       552
Ser Asn Ser Asp Ser Asp Ser Gly Thr Ser Ser Asp Thr Ser Ser Glu
```

-continued

```
                50                  55                  60
ggc att agt agc agt gat tca gat gat cta gaa gaa gat gaa gaa gaa        600
Gly Ile Ser Ser Ser Asp Ser Asp Asp Leu Glu Glu Asp Glu Glu Glu
        65                  70                  75 gaa gat caa agt att gaa gaa agt gaa gat gat gat tct gat tca gag        648
Glu Asp Gln Ser Ile Glu Glu Ser Glu Asp Asp Asp Ser Asp Ser Glu
    80                  85                  90 agt gaa gca caa cat aaa agt aac aac cag gtg cta tta cat ggt att        696
Ser Glu Ala Gln His Lys Ser Asn Asn Gln Val Leu Leu His Gly Ile
95                  100                 105                 110 tca gac cca aaa gca gat gga cag aaa gca act gaa aaa gcc cag gaa        744
Ser Asp Pro Lys Ala Asp Gly Gln Lys Ala Thr Glu Lys Ala Gln Glu
                115                 120                 125 aaa aga ata cac cag cca tta cct ctt gcg ttt gaa tcc cag act cac        792
Lys Arg Ile His Gln Pro Leu Pro Leu Ala Phe Glu Ser Gln Thr His
            130                 135                 140 tca ttc caa tcc cag cag aag cag cct cag gtt ttg tca cag cag ctt        840
Ser Phe Gln Ser Gln Gln Lys Gln Pro Gln Val Leu Ser Gln Gln Leu
        145                 150                 155 cca ttt att ttc caa agc tct cag gca aag gag gaa tct gtg aac aaa        888
Pro Phe Ile Phe Gln Ser Ser Gln Ala Lys Glu Glu Ser Val Asn Lys
    160                 165                 170 cac acc agt gta ata cag tct acg gga ttg gtg tcc aat gtg aaa cct        936
His Thr Ser Val Ile Gln Ser Thr Gly Leu Val Ser Asn Val Lys Pro
175                 180                 185                 190 tta tct ttg gta aat caa gcc aaa aag gaa act tac atg aaa ctc ata        984
Leu Ser Leu Val Asn Gln Ala Lys Lys Glu Thr Tyr Met Lys Leu Ile
                195                 200                 205 gtt cct tct cct gat gtt ctt aaa gca ggg aat aaa aat acc tct gaa       1032
Val Pro Ser Pro Asp Val Leu Lys Ala Gly Asn Lys Asn Thr Ser Glu
            210                 215                 220 gaa tct agt tta ttg acc agt gaa ttg aga tcc aaa cgg gaa caa tat       1080
Glu Ser Ser Leu Leu Thr Ser Glu Leu Arg Ser Lys Arg Glu Gln Tyr
        225                 230                 235 aaa cag gca ttc cca tca cag tta aag aaa caa gag tca tcg aag agc       1128
Lys Gln Ala Phe Pro Ser Gln Leu Lys Lys Gln Glu Ser Ser Lys Ser
    240                 245                 250 ctg aag aag gtt att gca gct ttg tca aat cca aaa gca acc tct agt       1176
Leu Lys Lys Val Ile Ala Ala Leu Ser Asn Pro Lys Ala Thr Ser Ser
255                 260                 265                 270 tca cca gca cat cca aaa caa aca tta gaa aac aac cac cca aat cca       1224
Ser Pro Ala His Pro Lys Gln Thr Leu Glu Asn Asn His Pro Asn Pro
                275                 280                 285 ttc ttg aca aat gca ctt tta ggt aat cac caa cca aat gga gtt att       1272
Phe Leu Thr Asn Ala Leu Leu Gly Asn His Gln Pro Asn Gly Val Ile
            290                 295                 300 caa agt gtc att caa gaa gct cct cta gca ctt act acc aaa act aaa       1320
Gln Ser Val Ile Gln Glu Ala Pro Leu Ala Leu Thr Thr Lys Thr Lys
        305                 310                 315 atg cag agc aag att aat gaa aac att gct gct gca agt agc acc cct       1368
Met Gln Ser Lys Ile Asn Glu Asn Ile Ala Ala Ala Ser Ser Thr Pro
    320                 325                 330 ttt tcc tca cct gta aat ctg agt aca agt ggg aga aga acc cct ggc       1416
Phe Ser Ser Pro Val Asn Leu Ser Thr Ser Gly Arg Arg Thr Pro Gly
335                 340                 345                 350 aat cag aca cct gta atg cct tct gcc tct ccc atc ctg cat agt caa       1464
Asn Gln Thr Pro Val Met Pro Ser Ala Ser Pro Ile Leu His Ser Gln
                355                 360                 365 ggg aag gaa aaa gca gtt agc aat aat gta aac cca gta aaa aca cag       1512
```

```
                Gly Lys Glu Lys Ala Val Ser Asn Asn Val Asn Pro Val Lys Thr Gln
                                370                 375                 380 cat cac tcc cat cct gca aaa tct tta gtg gaa caa ttc aga gga aca              1560
His His Ser His Pro Ala Lys Ser Leu Val Glu Gln Phe Arg Gly Thr
            385                 390                 395 gat tca gac att ccc agt agt aaa gat tct gaa gat tca aat gag gat              1608
Asp Ser Asp Ile Pro Ser Ser Lys Asp Ser Glu Asp Ser Asn Glu Asp
400                 405                 410 gaa gag gaa gat gat gaa gaa gaa gat gag gaa gat gat gaa gat gat              1656
Glu Glu Glu Asp Asp Glu Glu Glu Asp Glu Glu Asp Asp Glu Asp Asp
415                 420                 425                 430 gaa tct gat gac agc caa tca gaa tca gat agt aat tca gaa tca gat              1704
Glu Ser Asp Asp Ser Gln Ser Glu Ser Asp Ser Asn Ser Glu Ser Asp
                435                 440                 445 aca gaa gga tca gaa gaa gaa gat gat gat gat aaa gac caa gat gaa              1752
Thr Glu Gly Ser Glu Glu Glu Asp Asp Asp Asp Lys Asp Gln Asp Glu
            450                 455                 460 tca gat agt gat act gaa gga gag aaa act tca atg aaa ctg aat aaa              1800
Ser Asp Ser Asp Thr Glu Gly Glu Lys Thr Ser Met Lys Leu Asn Lys
465                 470                 475 aca act tcc tct gtc aaa agc cct tcc atg agt ctc aca ggt cac tca              1848
Thr Thr Ser Ser Val Lys Ser Pro Ser Met Ser Leu Thr Gly His Ser
480                 485                 490 aca cct cgt aac ctc cac ata gca aaa gcc cca ggc tct gct cct gct              1896
Thr Pro Arg Asn Leu His Ile Ala Lys Ala Pro Gly Ser Ala Pro Ala
495                 500                 505                 510 gcc tta tgt tct gaa tcc cag tca cct gct ttt ctt ggt aca tct tct              1944
Ala Leu Cys Ser Glu Ser Gln Ser Pro Ala Phe Leu Gly Thr Ser Ser
                515                 520                 525 tcc aca ctt act tca agc cca cac tct ggc act tcc aaa aga aga aga              1992
Ser Thr Leu Thr Ser Ser Pro His Ser Gly Thr Ser Lys Arg Arg Arg
            530                 535                 540 gta aca gat gaa cgt gaa ctg cgt att cca ttg gaa tat ggc tgg cag              2040
Val Thr Asp Glu Arg Glu Leu Arg Ile Pro Leu Glu Tyr Gly Trp Gln
545                 550                 555 aga gag aca aga ata aga aac ttt gga ggg cgc ctt caa gga gaa gta              2088
Arg Glu Thr Arg Ile Arg Asn Phe Gly Gly Arg Leu Gln Gly Glu Val
560                 565                 570 gca tat tat gct cca tgt gga aag aaa ctt agg cag tac cct gaa gta              2136
Ala Tyr Tyr Ala Pro Cys Gly Lys Lys Leu Arg Gln Tyr Pro Glu Val
575                 580                 585                 590 ata aag tat ctc agc aga aat gga ata atg gat atc tca agg gac aat              2184
Ile Lys Tyr Leu Ser Arg Asn Gly Ile Met Asp Ile Ser Arg Asp Asn
                595                 600                 605 ttc agc ttc agt gca aaa ata aga gtg ggt gac ttc tat gaa gcc aga              2232
Phe Ser Phe Ser Ala Lys Ile Arg Val Gly Asp Phe Tyr Glu Ala Arg
            610                 615                 620 gat gga ccg cag gaa atg cag tgg tgt ctt ttg aaa gaa gag gat gtc              2280
Asp Gly Pro Gln Glu Met Gln Trp Cys Leu Leu Lys Glu Glu Asp Val
625                 630                 635 att cct cgt atc agg gca atg gaa ggt cgt aga gga aga cca cca aat              2328
Ile Pro Arg Ile Arg Ala Met Glu Gly Arg Arg Gly Arg Pro Pro Asn
640                 645                 650 cca gat aga caa cga gca aga gag gaa tcc agg atg aga cgt cgg aaa              2376
Pro Asp Arg Gln Arg Ala Arg Glu Glu Ser Arg Met Arg Arg Arg Lys
655                 660                 665                 670 ggt cga cct cca aat gtt ggc aat gct gaa ttc cta gat aac gca gat              2424
Gly Arg Pro Pro Asn Val Gly Asn Ala Glu Phe Leu Asp Asn Ala Asp
                675                 680                 685
```

```
gca aag ttg cta aga aaa ctg caa gct caa gaa ata gcc agg caa gca    2472
Ala Lys Leu Leu Arg Lys Leu Gln Ala Gln Glu Ile Ala Arg Gln Ala
            690                 695                 700 gca caa ata aag ctt ttg aga aaa ctt caa aag cag gaa cag gct cgg    2520
Ala Gln Ile Lys Leu Leu Arg Lys Leu Gln Lys Gln Glu Gln Ala Arg
        705                 710                 715 gtt gct aaa gaa gcc aaa aaa caa caa gca ata atg gct gct gag gag    2568
Val Ala Lys Glu Ala Lys Lys Gln Gln Ala Ile Met Ala Ala Glu Glu
    720                 725                 730 aag cgg aag caa aaa gaa cag ata aag att atg aaa cag cag gaa aaa    2616
Lys Arg Lys Gln Lys Glu Gln Ile Lys Ile Met Lys Gln Gln Glu Lys
735                 740                 745                 750 att aag aga ata cag caa atc aga atg gaa aaa gaa ctt cga gct cag    2664
Ile Lys Arg Ile Gln Gln Ile Arg Met Glu Lys Glu Leu Arg Ala Gln
                755                 760                 765 caa att cta gag gct aaa aag aaa aag aag gaa gaa gcg gca aat gcc    2712
Gln Ile Leu Glu Ala Lys Lys Lys Lys Glu Glu Ala Ala Asn Ala
            770                 775                 780 aaa tta ttg gag gcc gag aaa cga ata aag gaa aaa gaa atg aga aga    2760
Lys Leu Leu Glu Ala Glu Lys Arg Ile Lys Glu Lys Glu Met Arg Arg
        785                 790                 795 caa caa gct gtt ctt ctg aaa cat cag gaa cga gag cga agg cga caa    2808
Gln Gln Ala Val Leu Leu Lys His Gln Glu Arg Glu Arg Arg Arg Gln
    800                 805                 810 cac atg atg ctt atg aaa gct atg gaa gct cgt aaa aaa gca gaa gaa    2856
His Met Met Leu Met Lys Ala Met Glu Ala Arg Lys Lys Ala Glu Glu
815                 820                 825                 830 aaa gag cgg ttg aaa caa gaa aaa cgt gat gag aaa aga tta aat aaa    2904
Lys Glu Arg Leu Lys Gln Glu Lys Arg Asp Glu Lys Arg Leu Asn Lys
                835                 840                 845 gag cgt aaa cta gag cag cga aga tta gaa tta gaa atg gca aag gaa    2952
Glu Arg Lys Leu Glu Gln Arg Arg Leu Glu Leu Glu Met Ala Lys Glu
            850                 855                 860 cta aag aag cct aat gaa gac atg tgc tta gca gac caa aag cct ttg    3000
Leu Lys Lys Pro Asn Glu Asp Met Cys Leu Ala Asp Gln Lys Pro Leu
        865                 870                 875 cca gag ttg cct cgt att cca gga ctt gtt ctc tct gga agt aca ttt    3048
Pro Glu Leu Pro Arg Ile Pro Gly Leu Val Leu Ser Gly Ser Thr Phe
    880                 885                 890 tca gac tgt ctc atg gtg gtg cag ttc tta cga aac ttt ggt aaa gtt    3096
Ser Asp Cys Leu Met Val Val Gln Phe Leu Arg Asn Phe Gly Lys Val
895                 900                 905                 910 ttg ggc ttt gat gtg aat att gat gtt cca aac ctg agt gtt ctt caa    3144
Leu Gly Phe Asp Val Asn Ile Asp Val Pro Asn Leu Ser Val Leu Gln
                915                 920                 925 gag gga ttg cta aat ata ggg gac agc atg ggt gaa gta caa gac ttg    3192
Glu Gly Leu Leu Asn Ile Gly Asp Ser Met Gly Glu Val Gln Asp Leu
            930                 935                 940 ctt gtg agg ctc ctc tca gct gct gta tgt gat cca ggt cta ata aca    3240
Leu Val Arg Leu Leu Ser Ala Ala Val Cys Asp Pro Gly Leu Ile Thr
        945                 950                 955 gga tac aag gct aaa aca gct ctt gga gaa cat ttg ctg aat gtt ggt    3288
Gly Tyr Lys Ala Lys Thr Ala Leu Gly Glu His Leu Leu Asn Val Gly
    960                 965                 970 gtg aat cga gac aat gtt tcc gag att tta cag ata ttt atg gaa gcc    3336
Val Asn Arg Asp Asn Val Ser Glu Ile Leu Gln Ile Phe Met Glu Ala
975                 980                 985                 990 cac tgt gga caa act gag ctt act gaa agt ctg aag acc aaa gct ttt    3384
His Cys Gly Gln Thr Glu Leu Thr Glu Ser Leu Lys Thr Lys Ala Phe
                995                 1000                1005
```

```
                                                                       -continued cag gct cac act cca gca cag aaa gct tca gtc ctg gct ttc ctg atc         3432
Gln Ala His Thr Pro Ala Gln Lys Ala Ser Val Leu Ala Phe Leu Ile
        1010                1015                1020 aat gaa ctg gca tgc agc aag agt gtg gtc agt gaa atc gac aag aac         3480
Asn Glu Leu Ala Cys Ser Lys Ser Val Val Ser Glu Ile Asp Lys Asn
    1025                1030                1035 att gat tat atg tca aac ttg agg aga gat aaa tgg gtg gta gaa ggt         3528
Ile Asp Tyr Met Ser Asn Leu Arg Arg Asp Lys Trp Val Val Glu Gly
        1040                1045                1050 aaa ctc cgc aag ctc aga atc att cat gct aag aaa aca ggc aaa aga         3576
Lys Leu Arg Lys Leu Arg Ile Ile His Ala Lys Lys Thr Gly Lys Arg
1055                1060                1065                1070 gac act tca ggt ggc att gat ctg gga gaa gag cag cat ccc ttg ggc         3624
Asp Thr Ser Gly Gly Ile Asp Leu Gly Glu Glu Gln His Pro Leu Gly
            1075                1080                1085 aca ccc act cca gga cgc aag cga aga agg aag gga gga gac agt gat         3672
Thr Pro Thr Pro Gly Arg Lys Arg Arg Arg Lys Gly Gly Asp Ser Asp
        1090                1095                1100 tat gac gat gat gat gac gat gac agt gat gac caa ggg gat gaa gat         3720
Tyr Asp Asp Asp Asp Asp Asp Asp Ser Asp Asp Gln Gly Asp Glu Asp
        1105                1110                1115 gat gag gat gaa gaa gat aag gaa gac caa aaa gga aaa aag act gat         3768
Asp Glu Asp Glu Glu Asp Lys Glu Asp Gln Lys Gly Lys Lys Thr Asp
        1120                1125                1130 atc tgt gaa gat gag gat gaa ggt gac caa gca gca agt gtt gaa gag         3816
Ile Cys Glu Asp Glu Asp Glu Gly Asp Gln Ala Ala Ser Val Glu Glu
1135                1140                1145                1150 ctg gaa aaa cag att gaa aaa ctg agt aaa caa cag agt cag tac aga         3864
Leu Glu Lys Gln Ile Glu Lys Leu Ser Lys Gln Gln Ser Gln Tyr Arg
            1155                1160                1165 agg aag ctc ttt gat gcg tct cac tca ttg cgt tca gtg atg ttt ggc         3912
Arg Lys Leu Phe Asp Ala Ser His Ser Leu Arg Ser Val Met Phe Gly
        1170                1175                1180 cca gat cgt tac aga cgc cgg tac tgg att ctt ccc cga tgt ggg ggg         3960
Pro Asp Arg Tyr Arg Arg Arg Tyr Trp Ile Leu Pro Arg Cys Gly Gly
        1185                1190                1195 att ttt gta gaa ggc atg gag agt ggt gaa gga cta gaa gaa att gca         4008
Ile Phe Val Glu Gly Met Glu Ser Gly Glu Gly Leu Glu Glu Ile Ala
        1200                1205                1210 aaa gaa aga gaa aaa ctg aaa aag gca gaa agt gtc cag atc aaa gaa         4056
Lys Glu Arg Glu Lys Leu Lys Lys Ala Glu Ser Val Gln Ile Lys Glu
1215                1220                1225                1230 gaa atg ttt gag act tct ggg gac agt tta aat tgt tca aat aca gat         4104
Glu Met Phe Glu Thr Ser Gly Asp Ser Leu Asn Cys Ser Asn Thr Asp
            1235                1240                1245 cac tgt gaa caa aag gaa gat ctt aaa gaa aaa gat aac aca aat cta         4152
His Cys Glu Gln Lys Glu Asp Leu Lys Glu Lys Asp Asn Thr Asn Leu
        1250                1255                1260 ttc ctt cag aaa cct ggc tct ttt tcc aaa tta agc aag ctt ttg gaa         4200
Phe Leu Gln Lys Pro Gly Ser Phe Ser Lys Leu Ser Lys Leu Leu Glu
        1265                1270                1275 gta gct aag atg cct cct gag tca gag gtt atg acc ccc aaa cca aat         4248
Val Ala Lys Met Pro Pro Glu Ser Glu Val Met Thr Pro Lys Pro Asn
    1280                1285                1290 gct ggt gca aat ggg tgc acg ttg tct tat cag aac agt gga aaa cat         4296
Ala Gly Ala Asn Gly Cys Thr Leu Ser Tyr Gln Asn Ser Gly Lys His
    1295                1300                1305                1310 tca ctg ggc agc gtt cag tca aca gca acg caa agc aat gtg gaa aag         4344
Ser Leu Gly Ser Val Gln Ser Thr Ala Thr Gln Ser Asn Val Glu Lys
```

-continued

```
                  1315                1320                1325
gca gac tct aat aat ctg ttt aat act ggt tca agt ggt cca ggg aag      4392
Ala Asp Ser Asn Asn Leu Phe Asn Thr Gly Ser Ser Gly Pro Gly Lys
        1330                1335                1340 ttc tac agt cct ctc ccc aat gac cag tta cta aaa acg ctg act gaa      4440
Phe Tyr Ser Pro Leu Pro Asn Asp Gln Leu Leu Lys Thr Leu Thr Glu
    1345                1350                1355 aag aat aga caa tgg ttt agt ctt ttg cca cga aca ccc tgt gat gac      4488
Lys Asn Arg Gln Trp Phe Ser Leu Leu Pro Arg Thr Pro Cys Asp Asp
1360                1365                1370 act tca ctt act cat gcc gat atg tca act gct tct ttg gtg act cct      4536
Thr Ser Leu Thr His Ala Asp Met Ser Thr Ala Ser Leu Val Thr Pro
1375                1380                1385                1390 cag tct cag cca cca tct aag tca cct tca cct acc cca gct cct ctt      4584
Gln Ser Gln Pro Pro Ser Lys Ser Pro Ser Pro Thr Pro Ala Pro Leu
        1395                1400                1405 gga tct tct gct cag aat cct gtt ggc tta aat cca ttt gct tta tca      4632
Gly Ser Ser Ala Gln Asn Pro Val Gly Leu Asn Pro Phe Ala Leu Ser
    1410                1415                1420 cct ctt cag gtg aaa ggt gga gta tct atg atg gga ctt cag ttt tgt      4680
Pro Leu Gln Val Lys Gly Gly Val Ser Met Met Gly Leu Gln Phe Cys
1425                1430                1435 gga tgg ccc act ggt gtg gtt act tct aat att cca ttt aca tta tct      4728
Gly Trp Pro Thr Gly Val Val Thr Ser Asn Ile Pro Phe Thr Leu Ser
1440                1445                1450 gta cct agt cta gga tcg ggg tta ggg tta tca gaa gga aat ggt aat      4776
Val Pro Ser Leu Gly Ser Gly Leu Gly Leu Ser Glu Gly Asn Gly Asn
1455                1460                1465                1470 tca ttc ttg act tcc aat gtt gct tca agt aaa agt gaa tct cca gta      4824
Ser Phe Leu Thr Ser Asn Val Ala Ser Ser Lys Ser Glu Ser Pro Val
        1475                1480                1485 cca cag aat gaa aag gcc act tca gct caa cct gca gct gtt gaa gta      4872
Pro Gln Asn Glu Lys Ala Thr Ser Ala Gln Pro Ala Ala Val Glu Val
    1490                1495                1500 gca aaa cca gta gat ttt cct agt cca aaa cct att cca gaa gaa atg      4920
Ala Lys Pro Val Asp Phe Pro Ser Pro Lys Pro Ile Pro Glu Glu Met
1505                1510                1515 cag ttt ggt tgg tgg aga att att gac cca gag gac cta aaa gct ttg      4968
Gln Phe Gly Trp Trp Arg Ile Ile Asp Pro Glu Asp Leu Lys Ala Leu
1520                1525                1530 ctc aaa gtg ctg cat ctc aga gga ata aga gaa aag gca tta caa aaa      5016
Leu Lys Val Leu His Leu Arg Gly Ile Arg Glu Lys Ala Leu Gln Lys
1535                1540                1545                1550 caa att cag aaa cat ttg gat tat att act caa gcc tgc ctc aag aat      5064
Gln Ile Gln Lys His Leu Asp Tyr Ile Thr Gln Ala Cys Leu Lys Asn
        1555                1560                1565 aag gat gtt gct att att gaa ctg aat gaa aat gaa gaa aac caa gta      5112
Lys Asp Val Ala Ile Ile Glu Leu Asn Glu Asn Glu Glu Asn Gln Val
    1570                1575                1580 act cga gat att gtg gag aac tgg tca gta gaa gaa caa gca atg gaa      5160
Thr Arg Asp Ile Val Glu Asn Trp Ser Val Glu Glu Gln Ala Met Glu
1585                1590                1595 atg gat ttg agt gtc ctt caa cag gta gaa gat cta gaa agg aga gtt      5208
Met Asp Leu Ser Val Leu Gln Gln Val Glu Asp Leu Glu Arg Arg Val
1600                1605                1610 gca tcc gca agt ttg caa gtg aag ggt tgg atg tgt cca gag cct gca      5256
Ala Ser Ala Ser Leu Gln Val Lys Gly Trp Met Cys Pro Glu Pro Ala
1615                1620                1625                1630 tca gaa agg gag gac ttg gta tat ttt gaa cat aaa tca ttt act aaa      5304
```

```
Ser Glu Arg Glu Asp Leu Val Tyr Phe Glu His Lys Ser Phe Thr Lys
            1635                1640                1645 ttg tgc aag gag cat gat gga gaa ttt act ggc gaa gac gaa agc agt    5352
Leu Cys Lys Glu His Asp Gly Glu Phe Thr Gly Glu Asp Glu Ser Ser
            1650                1655                1660 gca cat gca cta gaa cgg aag agt gac aac ccc cta gat ata gct gtt    5400
Ala His Ala Leu Glu Arg Lys Ser Asp Asn Pro Leu Asp Ile Ala Val
            1665                1670                1675 acc agg ctg gct gat ttg gag cgg aac att gaa aga aga att gag gaa    5448
Thr Arg Leu Ala Asp Leu Glu Arg Asn Ile Glu Arg Arg Ile Glu Glu
            1680                1685                1690 gat att gct cca ggg ctc agg gtg tgg aga agg gca tta tca gaa gct    5496
Asp Ile Ala Pro Gly Leu Arg Val Trp Arg Arg Ala Leu Ser Glu Ala
1695                1700                1705                1710 cgc agt gct gca cag gta gct ctg tgc att cag caa tta cag aaa tca    5544
Arg Ser Ala Ala Gln Val Ala Leu Cys Ile Gln Gln Leu Gln Lys Ser
            1715                1720                1725 ata gca tgg gaa aaa tca att atg aaa gtt tac tgc caa atc tgt cga    5592
Ile Ala Trp Glu Lys Ser Ile Met Lys Val Tyr Cys Gln Ile Cys Arg
            1730                1735                1740 aag gga gat aat gaa gaa ctg ctt ctt ctt tgt gat ggc tgt gac aaa    5640
Lys Gly Asp Asn Glu Glu Leu Leu Leu Leu Cys Asp Gly Cys Asp Lys
            1745                1750                1755 ggc tgt cat acc tac tgc cat aga ccc aag att aca aca atc cca gat    5688
Gly Cys His Thr Tyr Cys His Arg Pro Lys Ile Thr Thr Ile Pro Asp
            1760                1765                1770 gga gac tgg ttt tgt cca gct tgc att gct aag gca agt ggt caa act    5736
Gly Asp Trp Phe Cys Pro Ala Cys Ile Ala Lys Ala Ser Gly Gln Thr
1775                1780                1785                1790 cta aaa atc aaa aaa ctt cat gtc aaa gga aaa aag act aat gag tct    5784
Leu Lys Ile Lys Lys Leu His Val Lys Gly Lys Lys Thr Asn Glu Ser
            1795                1800                1805 aag aaa ggc aag aag gta act tta aca gga gat act gaa gat gaa gac    5832
Lys Lys Gly Lys Lys Val Thr Leu Thr Gly Asp Thr Glu Asp Glu Asp
            1810                1815                1820 tct gca tct aca agt agt tca cta aaa aga gga aac aaa gac ctc cag    5880
Ser Ala Ser Thr Ser Ser Ser Leu Lys Arg Gly Asn Lys Asp Leu Gln
            1825                1830                1835 aaa aga aaa atg gag gaa aac act tct att aac ttg tca aaa caa gaa    5928
Lys Arg Lys Met Glu Glu Asn Thr Ser Ile Asn Leu Ser Lys Gln Glu
            1840                1845                1850 agt ttt act tca gtt aag aaa cct aaa aga gat gac tcc aag gac cta    5976
Ser Phe Thr Ser Val Lys Lys Pro Lys Arg Asp Asp Ser Lys Asp Leu
1855                1860                1865                1870 gct ctt tgc agt atg att ctg act gaa atg gaa act cat gag gat gca    6024
Ala Leu Cys Ser Met Ile Leu Thr Glu Met Glu Thr His Glu Asp Ala
            1875                1880                1885 tgg cct ttt cta ctt cct gta aac ttg aaa ctt gtt cct ggt tat aag    6072
Trp Pro Phe Leu Leu Pro Val Asn Leu Lys Leu Val Pro Gly Tyr Lys
            1890                1895                1900 aaa gtt att aag aag cct atg gat ttt tcc aca att aga gag aaa cta    6120
Lys Val Ile Lys Lys Pro Met Asp Phe Ser Thr Ile Arg Glu Lys Leu
            1905                1910                1915 agt agt gga cag tat cca aac ctt gaa acc ttt gct cta gat gtc agg    6168
Ser Ser Gly Gln Tyr Pro Asn Leu Glu Thr Phe Ala Leu Asp Val Arg
            1920                1925                1930 ctt gtt ttt gac aac tgt gaa aca ttt aat gaa gat gat tct gat ata    6216
Leu Val Phe Asp Asn Cys Glu Thr Phe Asn Glu Asp Asp Ser Asp Ile
1935                1940                1945                1950
```

-continued

```
ggc aga gct ggc cac aat atg agg aag tat ttt gaa aaa aag tgg aca      6264
Gly Arg Ala Gly His Asn Met Arg Lys Tyr Phe Glu Lys Lys Trp Thr
            1955                1960                1965 gat act ttc aaa gtg agc tgaagttata ataatctctt tattttttc              6312
Asp Thr Phe Lys Val Ser
        1970 cttctaaaca aggacaaatg agaccagcaa tgtgaactgt atttacataa acgtgcaagg     6372 cacatacata atgactttct ttttccttaa gtataaaaaa aaagtatcag aagaatgata     6432 ccatttttaa aggcttcatt cctacaacaa ccaaggccct cggttattgg tttgtgtgat     6492 ttatcagcta atttaggtag aacagggaag cacacccaaa gaattttcaa aggaaagggt     6552 gttatagtgc aatagcaatt aaaatatatc aaatcgcact gaatactcaa caccagagct     6612 ctaatgtggg aaatggttct cctttccctc tcaataaata tctattttc atttttttac      6672 tttgtagttt attttttagt gaatgtattt aatttatga attatttatg attaaaccac      6732 atccagaatc ttcgttttct gtgaaaagga agaactagaa aattgcttta aatcttgaaa     6792 atacaaggaa tgttttaaaa tataaaacaa agccaagtta aactgtttac actgatgtgc     6852 tataaaagca ccaaaaagaa actttactgt agagttacaa gtacatttat atatatatgt     6912 tgctgcatca cttgtgtagt taaattgtat ttcaaaacag tgaaaaaatt gacatgtata     6972 tactgttcat tcttgtttat attaagtctt gttttaaata tgtattatgt gtatatattg     7032 tttgcagaca ttattgttca tgccttagag gattgtagca ttttattttc gtctgaaggt     7092 aatgatagct atacagtctg tacagtaatt atcctctacc aacactgtgg cgtctccttta    7152 atcttggtag tgcctgcctt tgaaacaggg tgtaggggat attagttttc cattttcta      7212 ttttgttata aattttaag ccaccagggc ctaaattaaa gtataatcat ttgtatccat      7272 gtggaataaa attgtgacaa tttcctacgc acacagtatt ttttcataga acatttccc      7332 tcccatttgc cttgcctcag aaataaattt aaaagacgtt tgtaaccact gtgttttatc     7392 tactgtgtgt tgtggtggcc tgttggaggc aaatagatca gatttttttt gtacctacgt     7452 aagagtactt gaagttttat ttaaaataaa atgttgtgga aaaggtagca ttctttttt      7512 aggagtgtta ttttcacta tgtgtggcac ggatacaata aaagactttt acaaactaaa      7572 aaaaaaaaaa aaa                                                        7585
```

<210> SEQ ID NO 23
<211> LENGTH: 25
<212> TYPE: DNA
<213> ORGANISM: Artificial Sequence
<220> FEATURE:
<223> OTHER INFORMATION: Synthetically generated primer

<400> SEQUENCE: 23
ctgactgaaa tggaaactca tgagg          25

<210> SEQ ID NO 24
<211> LENGTH: 25
<212> TYPE: DNA
<213> ORGANISM: Artificial Sequence
<220> FEATURE:
<223> OTHER INFORMATION: Synthetically generated primer

<400> SEQUENCE: 24
ctagagcaaa ggtttcaagg tttgg          25

<210> SEQ ID NO 25
<211> LENGTH: 24

```
<212> TYPE: DNA
<213> ORGANISM: Artificial Sequence
<220> FEATURE:
<223> OTHER INFORMATION: Synthetically generated primer

<400> SEQUENCE: 25
tgttgctgca tcacttgtgt agtt                                              24

<210> SEQ ID NO 26
<211> LENGTH: 23
<212> TYPE: DNA
<213> ORGANISM: Artificial Sequence
<220> FEATURE:
<223> OTHER INFORMATION: Synthetically generated primer

<400> SEQUENCE: 26
ggcatgacaa taatgtctgc aaa                                               23

<210> SEQ ID NO 27
<211> LENGTH: 1527
<212> TYPE: PRT
<213> ORGANISM: Homo sapiens

<400> SEQUENCE: 27
```

Met Ala Pro Leu Leu Gly Arg Lys Pro Phe Pro Leu Val Asn Pro Leu
 1               5                  10                  15

Pro Gly Glu Glu Pro Phe Phe Thr Ile Pro His Thr Gln Glu Ala Phe
             20                  25                  30

Arg Thr Arg Glu Glu Tyr Glu Ala Arg Leu Glu Arg Tyr Ser Glu Arg
         35                  40                  45

Ile Trp Thr Cys Lys Ser Thr Gly Ser Ser Gln Leu Thr His Lys Glu
     50                  55                  60

Ala Trp Glu Glu Glu Gln Glu Val Ala Glu Leu Leu Lys Glu Glu Phe
 65                  70                  75                  80

Pro Ala Trp Tyr Glu Lys Leu Val Leu Glu Met Val His His Asn Thr
                 85                  90                  95

Ala Ser Leu Glu Lys Leu Val Asp Thr Ala Trp Leu Glu Ile Met Thr
            100                 105                 110

Lys Tyr Ala Val Gly Glu Glu Cys Asp Phe Glu Val Gly Lys Glu Lys
        115                 120                 125

Met Leu Lys Val Lys Ile Val Lys Ile His Pro Leu Glu Lys Val Asp
    130                 135                 140

Glu Glu Ala Thr Glu Lys Lys Ser Asp Gly Ala Cys Asp Ser Pro Ser
145                 150                 155                 160

Ser Asp Lys Glu Asn Ser Ser Gln Ile Ala Gln Asp His Gln Lys Lys
                165                 170                 175

Glu Thr Val Val Lys Glu Asp Glu Gly Arg Arg Glu Ser Ile Asn Asp
            180                 185                 190

Arg Ala Arg Arg Ser Pro Arg Lys Leu Pro Thr Ser Leu Lys Lys Gly
        195                 200                 205

Glu Arg Lys Trp Ala Pro Pro Lys Phe Leu Pro His Lys Tyr Asp Val
    210                 215                 220

Lys Leu Gln Asn Glu Asp Lys Ile Ile Ser Asn Val Pro Ala Asp Ser
225                 230                 235                 240

Leu Ile Arg Thr Glu Arg Pro Asn Lys Glu Ile Val Arg Tyr Phe
                245                 250                 255

Ile Arg His Asn Ala Leu Arg Ala Gly Thr Gly Glu Asn Ala Pro Trp
            260                 265                 270

```
Val Val Glu Asp Glu Leu Val Lys Lys Tyr Ser Leu Pro Ser Lys Phe
            275                 280                 285

Ser Asp Phe Leu Leu Asp Pro Tyr Lys Tyr Met Thr Leu Asn Pro Ser
    290                 295                 300

Thr Lys Arg Lys Asn Thr Gly Ser Pro Asp Arg Lys Pro Ser Lys Lys
305                 310                 315                 320

Ser Lys Thr Asp Asn Ser Ser Leu Ser Ser Pro Leu Asn Pro Lys Leu
                325                 330                 335

Trp Cys His Val His Leu Lys Lys Ser Leu Ser Gly Ser Pro Leu Lys
            340                 345                 350

Val Lys Asn Ser Lys Asn Ser Lys Ser Pro Glu Glu His Leu Glu Glu
    355                 360                 365

Met Met Lys Met Met Ser Pro Asn Lys Leu His Thr Asn Phe His Ile
        370                 375                 380

Pro Lys Lys Gly Pro Pro Ala Lys Lys Pro Gly Lys His Ser Asp Lys
385                 390                 395                 400

Pro Leu Lys Ala Lys Gly Arg Ser Lys Gly Ile Leu Asn Gly Gln Lys
                405                 410                 415

Ser Thr Gly Asn Ser Lys Ser Pro Lys Lys Gly Leu Lys Thr Pro Lys
            420                 425                 430

Thr Lys Met Lys Gln Met Thr Leu Leu Asp Met Ala Lys Gly Thr Gln
        435                 440                 445

Lys Met Thr Arg Ala Pro Arg Asn Ser Gly Gly Thr Pro Arg Thr Ser
    450                 455                 460

Ser Lys Pro His Lys His Leu Pro Pro Ala Ala Leu His Leu Ile Ala
465                 470                 475                 480

Tyr Tyr Lys Glu Asn Lys Asp Arg Glu Asp Lys Arg Ser Ala Leu Ser
                485                 490                 495

Cys Val Ile Ser Lys Thr Ala Arg Leu Leu Ser Ser Glu Asp Arg Ala
            500                 505                 510

Arg Leu Pro Glu Glu Leu Arg Ser Leu Val Gln Lys Arg Tyr Glu Leu
        515                 520                 525

Leu Glu His Lys Lys Arg Trp Ala Ser Met Ser Glu Glu Gln Arg Lys
    530                 535                 540

Glu Tyr Leu Lys Lys Arg Glu Glu Leu Lys Lys Lys Leu Lys Glu
545                 550                 555                 560

Lys Ala Lys Glu Arg Arg Glu Lys Glu Met Leu Glu Arg Leu Glu Lys
                565                 570                 575

Gln Lys Arg Tyr Glu Asp Gln Glu Leu Thr Gly Lys Asn Leu Pro Ala
            580                 585                 590

Phe Arg Leu Val Asp Thr Pro Glu Gly Leu Pro Asn Thr Leu Phe Gly
        595                 600                 605

Asp Val Ala Met Val Val Glu Phe Leu Ser Cys Tyr Ser Gly Leu Leu
    610                 615                 620

Leu Pro Asp Ala Gln Tyr Pro Ile Thr Ala Val Ser Leu Met Glu Ala
625                 630                 635                 640

Leu Ser Ala Asp Lys Gly Gly Phe Leu Tyr Leu Asn Arg Val Leu Val
                645                 650                 655

Ile Leu Leu Gln Thr Leu Leu Gln Asp Glu Ile Ala Glu Asp Tyr Gly
            660                 665                 670

Glu Leu Gly Met Lys Leu Ser Glu Ile Pro Leu Thr Leu His Ser Val
        675                 680                 685
```

-continued

```
Ser Glu Leu Val Arg Leu Cys Leu Arg Arg Ser Asp Val Gln Glu Glu
    690                 695                 700
Ser Glu Gly Ser Asp Thr Asp Asp Asn Lys Asp Ser Ala Ala Phe Glu
705                 710                 715                 720
Asp Asn Glu Val Gln Asp Glu Phe Leu Glu Lys Leu Glu Thr Ser Glu
                725                 730                 735
Phe Phe Glu Leu Thr Ser Glu Glu Lys Leu Gln Ile Leu Thr Ala Leu
            740                 745                 750
Cys His Arg Ile Leu Met Thr Tyr Ser Val Gln Asp His Met Glu Thr
        755                 760                 765
Arg Gln Gln Met Ser Ala Glu Leu Trp Lys Glu Arg Leu Ala Val Leu
    770                 775                 780
Lys Glu Glu Asn Asp Lys Lys Arg Ala Glu Lys Gln Lys Arg Lys Glu
785                 790                 795                 800
Met Glu Ala Lys Asn Lys Glu Asn Gly Lys Val Glu Asn Gly Leu Gly
                805                 810                 815
Lys Thr Asp Arg Lys Lys Arg Ile Val Lys Phe Glu Pro Gln Val Asp
            820                 825                 830
Thr Glu Ala Glu Asp Met Ile Ser Ala Val Lys Ser Arg Arg Leu Leu
        835                 840                 845
Ala Ile Gln Ala Lys Lys Glu Arg Glu Ile Gln Glu Arg Glu Met Lys
    850                 855                 860
Val Lys Leu Glu Arg Gln Ala Glu Glu Glu Arg Ile Arg Lys His Lys
865                 870                 875                 880
Ala Ala Ala Glu Lys Ala Phe Gln Glu Gly Ile Ala Lys Ala Lys Leu
                885                 890                 895
Val Met Arg Arg Thr Pro Ile Gly Thr Asp Arg Asn His Asn Arg Tyr
            900                 905                 910
Trp Leu Phe Ser Asp Glu Val Pro Gly Leu Phe Ile Glu Lys Gly Trp
        915                 920                 925
Val His Asp Ser Ile Asp Tyr Arg Phe Asn His His Cys Lys Asp His
    930                 935                 940
Thr Val Ser Gly Asp Glu Asp Tyr Cys Pro Arg Ser Lys Lys Ala Asn
945                 950                 955                 960
Leu Gly Lys Asn Ala Ser Met Asn Thr Gln His Gly Thr Ala Thr Glu
                965                 970                 975
Val Ala Val Glu Thr Thr Thr Pro Lys Gln Gly Gln Asn Leu Trp Phe
            980                 985                 990
Leu Cys Asp Ser Gln Lys Glu Leu Asp Glu Leu Leu Asn Cys Leu His
        995                 1000                1005
Pro Gln Gly Ile Arg Glu Ser Gln Leu Lys Glu Arg Leu Glu Lys Arg
    1010                1015                1020
Tyr Gln Asp Ile Ile His Ser Ile His Leu Ala Arg Lys Pro Asn Leu
1025                1030                1035                1040
Gly Leu Lys Ser Cys Asp Gly Asn Gln Glu Leu Leu Asn Phe Leu Arg
                1045                1050                1055
Ser Asp Leu Ile Glu Val Ala Thr Arg Leu Gln Lys Gly Gly Leu Gly
            1060                1065                1070
Tyr Val Glu Glu Thr Ser Glu Phe Glu Ala Arg Val Ile Ser Leu Glu
        1075                1080                1085
Lys Leu Lys Asp Phe Gly Glu Cys Val Ile Ala Leu Gln Ala Ser Val
    1090                1095                1100
Ile Lys Lys Phe Leu Gln Gly Phe Met Ala Pro Lys Gln Lys Arg Arg
```

-continued

```
            1105                1110                1115                1120
Lys Leu Gln Ser Glu Asp Ser Ala Lys Thr Glu Glu Val Asp Glu Glu
                1125                1130                1135
Lys Lys Met Val Glu Ala Lys Val Ala Ser Ala Leu Glu Lys Trp
            1140                1145                1150
Lys Thr Ala Ile Arg Glu Ala Gln Thr Phe Ser Arg Met His Val Leu
            1155                1160                1165
Leu Gly Met Leu Asp Ala Cys Ile Lys Trp Asp Met Ser Ala Glu Asn
            1170                1175                1180
Ala Arg Cys Lys Val Cys Pro Lys Lys Gly Glu Asp Lys Leu Ile
1185                1190                1195                1200
Leu Cys Asp Glu Cys Asn Lys Ala Phe His Leu Phe Cys Leu Arg Pro
            1205                1210                1215
Ala Leu Tyr Glu Val Pro Asp Gly Glu Trp Gln Cys Pro Ala Cys Gln
            1220                1225                1230
Pro Ala Thr Ala Arg Arg Asn Ser Arg Gly Arg Asn Tyr Thr Glu Glu
            1235                1240                1245
Ser Ala Ser Glu Asp Ser Glu Asp Asp Glu Ser Asp Glu Glu Glu
            1250                1255                1260
Glu Glu Glu Glu Glu Glu Glu Glu Asp Tyr Glu Val Ala Gly Leu
1265                1270                1275                1280
Arg Leu Arg Pro Arg Lys Thr Ile Arg Gly Lys His Ser Val Ile Pro
            1285                1290                1295
Pro Ala Ala Arg Ser Gly Arg Arg Pro Gly Lys Lys Pro His Ser Thr
            1300                1305                1310
Arg Arg Ser Gln Pro Lys Ala Pro Pro Val Asp Asp Ala Glu Val Asp
            1315                1320                1325
Glu Leu Val Leu Gln Thr Lys Arg Ser Ser Arg Arg Gln Ser Leu Glu
            1330                1335                1340
Leu Gln Lys Cys Glu Glu Ile Leu His Lys Ile Val Lys Tyr Arg Phe
1345                1350                1355                1360
Ser Trp Pro Phe Arg Glu Pro Val Thr Arg Asp Glu Ala Glu Asp Tyr
            1365                1370                1375
Tyr Asp Val Ile Thr His Pro Met Asp Phe Gln Thr Val Gln Asn Lys
            1380                1385                1390
Cys Ser Cys Gly Ser Tyr Arg Ser Val Gln Glu Phe Leu Thr Asp Met
            1395                1400                1405
Lys Gln Val Phe Thr Asn Ala Glu Val Tyr Asn Cys Arg Gly Ser His
            1410                1415                1420
Val Leu Ser Cys Met Val Lys Thr Glu Gln Cys Leu Val Val Leu Leu
1425                1430                1435                1440
His Lys His Leu Pro Gly His Pro Tyr Val Arg Arg Lys Arg Lys Lys
            1445                1450                1455
Phe Pro Asp Arg Leu Ala Glu Asp Glu Gly Asp Ser Glu Pro Glu Ala
            1460                1465                1470
Val Gly Gln Ser Arg Asp Glu Asp Arg Arg Ser Arg Glu Ala Glu Ile
            1475                1480                1485
Gln Glu Trp Leu Gln Asp Thr Ser Leu Tyr Ser Ala Lys Ile Asn Ser
            1490                1495                1500
Lys Asp His Asn Cys Phe Met Met Leu Val Asn Thr Gln Phe Cys Met
1505                1510                1515                1520
Ala Leu Thr Asp Thr Val Thr
            1525
```

<210> SEQ ID NO 28
<211> LENGTH: 5561
<212> TYPE: DNA
<213> ORGANISM: Homo sapiens
<220> FEATURE:
<221> NAME/KEY: CDS
<222> LOCATION: (346)...(4926)

<400> SEQUENCE: 28

```
cgggcccggg ggaggagggg aatctcccgc cattttttcaa taatttcctc cggtgctgct    60
gaggaggagt cgtgactgcc ggccgccggg acccgaagcg gaggtcggcg gggggctgct   120
gggaggcgcg gcggtgtgcg cgggagctct gcgccgtggc gttccgctcc atgactgtcg   180 gcgcggccgcg ccggcggtga gggagccgga gttcgcgccg ccctctcacc cctcccttcc   240
cccaccccac ccccgggcgc ctggcgctcg ctccgggccg cggggcctag tgctgcgccg   300
cggggccggc cccagcagcc gccagtcccc accgccgccg ccgcg atg gcg ccg ctc    357
                                                Met Ala Pro Leu
                                                  1
```

| | | | | | | | | | | | | | | | | |
|---|---|---|---|---|---|---|---|---|---|---|---|---|---|---|---|---|
| ctg | ggc | cgc | aag | ccc | ttc | ccg | ctg | gtg | aat | ccg | ttg | ccc | gga | gag | gag | 405 |
| Leu | Gly | Arg | Lys | Pro | Phe | Pro | Leu | Val | Asn | Pro | Leu | Pro | Gly | Glu | Glu | |
| 5 | | | | 10 | | | | | 15 | | | | | 20 | | |

| | | | | | | | | | | | | | | | | |
|---|---|---|---|---|---|---|---|---|---|---|---|---|---|---|---|---|
| ccg | ttc | ttc | acc | atc | ccg | cac | act | cag | gag | gcc | ttc | cgc | acc | cgg | gaa | 453 |
| Pro | Phe | Phe | Thr | Ile | Pro | His | Thr | Gln | Glu | Ala | Phe | Arg | Thr | Arg | Glu | |
| | | 25 | | | | | 30 | | | | | 35 | | | | |

| | | | | | | | | | | | | | | | | |
|---|---|---|---|---|---|---|---|---|---|---|---|---|---|---|---|---|
| gag | tat | gaa | gcc | cgc | ttg | gaa | agg | tac | agt | gag | cgc | att | tgg | acg | tgc | 501 |
| Glu | Tyr | Glu | Ala | Arg | Leu | Glu | Arg | Tyr | Ser | Glu | Arg | Ile | Trp | Thr | Cys | |
| | | | 40 | | | | | 45 | | | | | 50 | | | |

| | | | | | | | | | | | | | | | | |
|---|---|---|---|---|---|---|---|---|---|---|---|---|---|---|---|---|
| aag | agt | act | gga | agc | agt | cag | cta | aca | cac | aag | gaa | gcc | tgg | gag | gaa | 549 |
| Lys | Ser | Thr | Gly | Ser | Ser | Gln | Leu | Thr | His | Lys | Glu | Ala | Trp | Glu | Glu | |
| | 55 | | | | | 60 | | | | | 65 | | | | | |

| | | | | | | | | | | | | | | | | |
|---|---|---|---|---|---|---|---|---|---|---|---|---|---|---|---|---|
| gaa | cag | gaa | gtt | gct | gag | ctt | ttg | aag | gag | gag | ttt | cct | gcc | tgg | tat | 597 |
| Glu | Gln | Glu | Val | Ala | Glu | Leu | Leu | Lys | Glu | Glu | Phe | Pro | Ala | Trp | Tyr | |
| | | 70 | | | | | 75 | | | | | 80 | | | | |

| | | | | | | | | | | | | | | | | |
|---|---|---|---|---|---|---|---|---|---|---|---|---|---|---|---|---|
| gag | aag | ctt | gtt | ctg | gaa | atg | gtt | cac | cat | aac | aca | gcc | tcc | tta | gag | 645 |
| Glu | Lys | Leu | Val | Leu | Glu | Met | Val | His | His | Asn | Thr | Ala | Ser | Leu | Glu | |
| 85 | | | | | 90 | | | | | 95 | | | | | 100 | |

| | | | | | | | | | | | | | | | | |
|---|---|---|---|---|---|---|---|---|---|---|---|---|---|---|---|---|
| aag | tta | gta | gat | act | gct | tgg | ttg | gag | atc | atg | acc | aaa | tat | gct | gtg | 693 |
| Lys | Leu | Val | Asp | Thr | Ala | Trp | Leu | Glu | Ile | Met | Thr | Lys | Tyr | Ala | Val | |
| | | | | 105 | | | | | 110 | | | | | 115 | | |

| | | | | | | | | | | | | | | | | |
|---|---|---|---|---|---|---|---|---|---|---|---|---|---|---|---|---|
| gga | gaa | gag | tgt | gac | ttc | gag | gtt | ggg | aag | gag | aaa | atg | ctc | aag | gtg | 741 |
| Gly | Glu | Glu | Cys | Asp | Phe | Glu | Val | Gly | Lys | Glu | Lys | Met | Leu | Lys | Val | |
| | | | 120 | | | | | 125 | | | | | 130 | | | |

| | | | | | | | | | | | | | | | | |
|---|---|---|---|---|---|---|---|---|---|---|---|---|---|---|---|---|
| aag | att | gtg | aag | att | cat | cct | ttg | gag | aaa | gtg | gat | gaa | gag | gcc | act | 789 |
| Lys | Ile | Val | Lys | Ile | His | Pro | Leu | Glu | Lys | Val | Asp | Glu | Glu | Ala | Thr | |
| | | 135 | | | | | 140 | | | | | 145 | | | | |

| | | | | | | | | | | | | | | | | |
|---|---|---|---|---|---|---|---|---|---|---|---|---|---|---|---|---|
| gag | aag | aaa | tct | gat | ggt | gcc | tgt | gat | tct | cca | tca | agt | gac | aaa | gag | 837 |
| Glu | Lys | Lys | Ser | Asp | Gly | Ala | Cys | Asp | Ser | Pro | Ser | Ser | Asp | Lys | Glu | |
| | 150 | | | | | 155 | | | | | 160 | | | | | |

| | | | | | | | | | | | | | | | | |
|---|---|---|---|---|---|---|---|---|---|---|---|---|---|---|---|---|
| aac | tcc | agt | cag | att | gct | cag | gac | cat | cag | aag | aag | gag | aca | gtt | gtg | 885 |
| Asn | Ser | Ser | Gln | Ile | Ala | Gln | Asp | His | Gln | Lys | Lys | Glu | Thr | Val | Val | |
| 165 | | | | | 170 | | | | | 175 | | | | | 180 | |

| | | | | | | | | | | | | | | | | |
|---|---|---|---|---|---|---|---|---|---|---|---|---|---|---|---|---|
| aaa | gag | gat | gaa | gga | agg | aga | gag | agt | att | aat | gac | aga | gca | cgt | aga | 933 |
| Lys | Glu | Asp | Glu | Gly | Arg | Arg | Glu | Ser | Ile | Asn | Asp | Arg | Ala | Arg | Arg | |
| | | | | 185 | | | | | 190 | | | | | 195 | | |

| | | | | | | | | | | | | | | | | |
|---|---|---|---|---|---|---|---|---|---|---|---|---|---|---|---|---|
| tcg | cca | cga | aaa | ctt | cct | act | tca | tta | aaa | aaa | gga | gaa | agg | aaa | tgg | 981 |
| Ser | Pro | Arg | Lys | Leu | Pro | Thr | Ser | Leu | Lys | Lys | Gly | Glu | Arg | Lys | Trp | |
| | | | 200 | | | | | 205 | | | | | 210 | | | |

| | | | | | | | | | | | | | | | | |
|---|---|---|---|---|---|---|---|---|---|---|---|---|---|---|---|---|
| gct | cct | cca | aaa | ttt | ctg | cct | cac | aaa | tat | gat | gtg | aaa | cta | caa | aat | 1029 |

```
                Ala Pro Pro Lys Phe Leu Pro His Lys Tyr Asp Val Lys Leu Gln Asn
                        215                 220                 225 gaa gat aag atc atc agt aac gtg cca gca gac agc ttg att cgt aca       1077
Glu Asp Lys Ile Ile Ser Asn Val Pro Ala Asp Ser Leu Ile Arg Thr
        230                 235                 240 gag cgc cca cca aat aag gag ata gtt cga tac ttt ata cgg cat aat       1125
Glu Arg Pro Pro Asn Lys Glu Ile Val Arg Tyr Phe Ile Arg His Asn
245                 250                 255                 260 gca tta cga gct ggt act ggt gaa aat gca cct tgg gtc gta gaa gat       1173
Ala Leu Arg Ala Gly Thr Gly Glu Asn Ala Pro Trp Val Val Glu Asp
                265                 270                 275 gaa ttg gtg aag aaa tac tct ctg ccc agc aag ttc agt gac ttt tta       1221
Glu Leu Val Lys Lys Tyr Ser Leu Pro Ser Lys Phe Ser Asp Phe Leu
        280                 285                 290 ctt gat cca tac aag tat atg act ctc aac cct tct act aag agg aag       1269
Leu Asp Pro Tyr Lys Tyr Met Thr Leu Asn Pro Ser Thr Lys Arg Lys
                295                 300                 305 aat act gga tcc cca gac agg aag ccc tca aag aaa tcc aag aca gac       1317
Asn Thr Gly Ser Pro Asp Arg Lys Pro Ser Lys Lys Ser Lys Thr Asp
        310                 315                 320 aac tct tct ctt agt tca cca cta aat cct aag tta tgg tgt cac gta       1365
Asn Ser Ser Leu Ser Ser Pro Leu Asn Pro Lys Leu Trp Cys His Val
325                 330                 335                 340 cac ttg aag aag tca ttg agt ggc tcg cca ctc aaa gtg aag aac tca       1413
His Leu Lys Lys Ser Leu Ser Gly Ser Pro Leu Lys Val Lys Asn Ser
                345                 350                 355 aag aat tcc aaa tct cct gaa gaa cat cta gaa gaa atg atg aag atg       1461
Lys Asn Ser Lys Ser Pro Glu Glu His Leu Glu Glu Met Met Lys Met
        360                 365                 370 atg tcg ccc aat aag ttg cac act aac ttt cac att cct aaa aaa ggc       1509
Met Ser Pro Asn Lys Leu His Thr Asn Phe His Ile Pro Lys Lys Gly
                375                 380                 385 cca cct gcc aag aaa cca ggg aag cac agt gac aag cct ttg aag gca       1557
Pro Pro Ala Lys Lys Pro Gly Lys His Ser Asp Lys Pro Leu Lys Ala
        390                 395                 400 aag ggc aga agc aaa ggc atc ctg aat gga cag aaa tcc aca ggg aat       1605
Lys Gly Arg Ser Lys Gly Ile Leu Asn Gly Gln Lys Ser Thr Gly Asn
405                 410                 415                 420 tcc aaa tct ccc aaa aaa gga ctg aag act cct aaa acc aaa atg aag       1653
Ser Lys Ser Pro Lys Lys Gly Leu Lys Thr Pro Lys Thr Lys Met Lys
                425                 430                 435 cag atg act ttg ttg gat atg gcc aaa ggc acg cag aag atg aca cga       1701
Gln Met Thr Leu Leu Asp Met Ala Lys Gly Thr Gln Lys Met Thr Arg
        440                 445                 450 gcc cca cgg aat tct ggg ggt aca cct agg acc tct agt aaa cct cat       1749
Ala Pro Arg Asn Ser Gly Gly Thr Pro Arg Thr Ser Ser Lys Pro His
                455                 460                 465 aaa cat ctg cct cct gca gcc cta cac ctc att gca tac tac aaa gaa       1797
Lys His Leu Pro Pro Ala Ala Leu His Leu Ile Ala Tyr Tyr Lys Glu
        470                 475                 480 aac aaa gac agg gag gac aag agg agc gcc ctg tcc tgt gtt atc tcc       1845
Asn Lys Asp Arg Glu Asp Lys Arg Ser Ala Leu Ser Cys Val Ile Ser
485                 490                 495                 500 aaa aca gct cgt ctt ctc tct agt gaa gat aga gct cgt ctc cca gaa       1893
Lys Thr Ala Arg Leu Leu Ser Ser Glu Asp Arg Ala Arg Leu Pro Glu
                505                 510                 515 gaa ttg cga agt ctt gtt caa aaa cgc tat gaa ctt cta gag cac aaa       1941
Glu Leu Arg Ser Leu Val Gln Lys Arg Tyr Glu Leu Leu Glu His Lys
        520                 525                 530
```

```
aag agg tgg gct tct atg tct gaa gaa caa cgg aaa gaa tat ttg aaa    1989
Lys Arg Trp Ala Ser Met Ser Glu Glu Gln Arg Lys Glu Tyr Leu Lys
        535                 540                 545 aag aaa cgg gag gag ctg aaa aag aag ttg aag gaa aaa gcc aaa gaa    2037
Lys Lys Arg Glu Glu Leu Lys Lys Lys Leu Lys Glu Lys Ala Lys Glu
    550                 555                 560 cga aga gag aaa gaa atg ctt gag aga tta gaa aaa cag aag cgg tat    2085
Arg Arg Glu Lys Glu Met Leu Glu Arg Leu Glu Lys Gln Lys Arg Tyr
565                 570                 575                 580 gag gac caa gag tta act ggc aaa aac ctt cca gca ttc aga ttg gtg    2133
Glu Asp Gln Glu Leu Thr Gly Lys Asn Leu Pro Ala Phe Arg Leu Val
                585                 590                 595 gat acc cct gaa ggg ctg ccc aac acg ctg ttt ggg gat gtg gcc atg    2181
Asp Thr Pro Glu Gly Leu Pro Asn Thr Leu Phe Gly Asp Val Ala Met
            600                 605                 610 gtg gtg gaa ttc ttg agc tgt tat tct ggg cta ctt tta cca gat gct    2229
Val Val Glu Phe Leu Ser Cys Tyr Ser Gly Leu Leu Leu Pro Asp Ala
        615                 620                 625 cag tat cct att act gct gtg tcc ctt atg gaa gcc ttg agt gca gat    2277
Gln Tyr Pro Ile Thr Ala Val Ser Leu Met Glu Ala Leu Ser Ala Asp
    630                 635                 640 aag ggt ggc ttt tta tac ctt aac agg gtg ttg gtc atc ctc tta cag    2325
Lys Gly Gly Phe Leu Tyr Leu Asn Arg Val Leu Val Ile Leu Leu Gln
645                 650                 655                 660 acc ctc cta caa gat gag ata gcc gaa gac tat ggt gaa ttg gga atg    2373
Thr Leu Leu Gln Asp Glu Ile Ala Glu Asp Tyr Gly Glu Leu Gly Met
                665                 670                 675 aag ctg tca gaa atc ccc ttg act ctg cat tct gtt tca gag ctg gtg    2421
Lys Leu Ser Glu Ile Pro Leu Thr Leu His Ser Val Ser Glu Leu Val
            680                 685                 690 cgg ctc tgc ttg cgc aga tct gat gtt cag gag gaa agc gag ggc tca    2469
Arg Leu Cys Leu Arg Arg Ser Asp Val Gln Glu Glu Ser Glu Gly Ser
        695                 700                 705 gac aca gat gac aat aaa gat tca gct gca ttt gag gat aat gag gta    2517
Asp Thr Asp Asp Asn Lys Asp Ser Ala Ala Phe Glu Asp Asn Glu Val
    710                 715                 720 caa gat gag ttc cta gaa aag ctg gag acc tct gaa ttt ttt gag ctg    2565
Gln Asp Glu Phe Leu Glu Lys Leu Glu Thr Ser Glu Phe Phe Glu Leu
725                 730                 735                 740 acg tca gag gag aag cta cag att ttg aca gca ctg tgc cac cgg atc    2613
Thr Ser Glu Glu Lys Leu Gln Ile Leu Thr Ala Leu Cys His Arg Ile
                745                 750                 755 ctc atg aca tac tca gtg caa gac cac atg gag acc aga cag cag atg    2661
Leu Met Thr Tyr Ser Val Gln Asp His Met Glu Thr Arg Gln Gln Met
            760                 765                 770 tct gca gag ttg tgg aag gaa cgg ctt gct gtg ttg aag gaa gaa aat    2709
Ser Ala Glu Leu Trp Lys Glu Arg Leu Ala Val Leu Lys Glu Glu Asn
        775                 780                 785 gat aag aag aga gca gag aaa cag aaa cgg aaa gaa atg gaa gcc aaa    2757
Asp Lys Lys Arg Ala Glu Lys Gln Lys Arg Lys Glu Met Glu Ala Lys
    790                 795                 800 aat aaa gaa aat gga aaa gtt gag aat ggg tta ggc aaa act gat agg    2805
Asn Lys Glu Asn Gly Lys Val Glu Asn Gly Leu Gly Lys Thr Asp Arg
805                 810                 815                 820 aaa aaa aga att gtg aag ttt gag ccc caa gta gat aca gaa gct gaa    2853
Lys Lys Arg Ile Val Lys Phe Glu Pro Gln Val Asp Thr Glu Ala Glu
                825                 830                 835 gac atg att agt gct gtg aag agc aga agg ttg ctt gcc att caa gct    2901
Asp Met Ile Ser Ala Val Lys Ser Arg Arg Leu Leu Ala Ile Gln Ala
            840                 845                 850
```

```
aag aag gaa cgg gaa atc cag gaa aga gaa atg aaa gtg aaa ctg gaa        2949
Lys Lys Glu Arg Glu Ile Gln Glu Arg Glu Met Lys Val Lys Leu Glu
        855                 860                 865 cgc caa gct gaa gaa gaa cga ata cgg aag cac aaa gca gct gct gag        2997
Arg Gln Ala Glu Glu Glu Arg Ile Arg Lys His Lys Ala Ala Ala Glu
    870                 875                 880 aaa gct ttc cag gaa ggg att gcc aag gcc aaa cta gtc atg cgc agg        3045
Lys Ala Phe Gln Glu Gly Ile Ala Lys Ala Lys Leu Val Met Arg Arg
885                 890                 895                 900 act cct att ggc aca gat cga aac cat aat aga tac tgg ctc ttc tca        3093
Thr Pro Ile Gly Thr Asp Arg Asn His Asn Arg Tyr Trp Leu Phe Ser
                905                 910                 915 gat gaa gtt cca gga tta ttc att gaa aaa ggc tgg gta cat gac agc        3141
Asp Glu Val Pro Gly Leu Phe Ile Glu Lys Gly Trp Val His Asp Ser
            920                 925                 930 att gac tac cga ttc aac cat cac tgc aaa gac cac aca gtc tct ggt        3189
Ile Asp Tyr Arg Phe Asn His His Cys Lys Asp His Thr Val Ser Gly
        935                 940                 945 gat gag gat tac tgt cct cgc agt aag aaa gca aac tta ggt aaa aat        3237
Asp Glu Asp Tyr Cys Pro Arg Ser Lys Lys Ala Asn Leu Gly Lys Asn
    950                 955                 960 gca agc atg aac aca caa cat gga aca gca aca gaa gtt gct gta gag        3285
Ala Ser Met Asn Thr Gln His Gly Thr Ala Thr Glu Val Ala Val Glu
965                 970                 975                 980 aca acc aca ccc aaa caa gga cag aac cta tgg ttt tta tgt gat agt        3333
Thr Thr Thr Pro Lys Gln Gly Gln Asn Leu Trp Phe Leu Cys Asp Ser
                985                 990                 995 caa aag gag ctg gat gag ttg cta aac tgt ctt cac cct cag gga ata        3381
Gln Lys Glu Leu Asp Glu Leu Leu Asn Cys Leu His Pro Gln Gly Ile
            1000                1005                1010 aga gaa agt caa ctt aaa gag aga cta gag aag agg tac cag gac att        3429
Arg Glu Ser Gln Leu Lys Glu Arg Leu Glu Lys Arg Tyr Gln Asp Ile
        1015                1020                1025 att cac tct att cat cta gca cgg aag cca aat ttg ggt cta aaa tct        3477
Ile His Ser Ile His Leu Ala Arg Lys Pro Asn Leu Gly Leu Lys Ser
    1030                1035                1040 tgt gat ggc aac cag gag ctt tta aac ttc ctt cgt agt gat ctc att        3525
Cys Asp Gly Asn Gln Glu Leu Leu Asn Phe Leu Arg Ser Asp Leu Ile
1045                1050                1055                1060 gaa gtt gca aca agg tta caa aaa gga gga ctt gga tat gtg gaa gaa        3573
Glu Val Ala Thr Arg Leu Gln Lys Gly Gly Leu Gly Tyr Val Glu Glu
                1065                1070                1075 aca tca gaa ttt gaa gcc cgg gtc att tca tta gag aaa ttg aag gat        3621
Thr Ser Glu Phe Glu Ala Arg Val Ile Ser Leu Glu Lys Leu Lys Asp
            1080                1085                1090 ttt ggt gag tgt gtg att gcc ctt cag gcc agt gtc ata aag aaa ttt        3669
Phe Gly Glu Cys Val Ile Ala Leu Gln Ala Ser Val Ile Lys Lys Phe
        1095                1100                1105 ctc caa ggc ttc atg gct ccc aag caa aag aga aga aaa ctc caa agt        3717
Leu Gln Gly Phe Met Ala Pro Lys Gln Lys Arg Arg Lys Leu Gln Ser
    1110                1115                1120 gaa gat tca gca aaa act gag gaa gtg gat gaa gag aag aaa atg gta        3765
Glu Asp Ser Ala Lys Thr Glu Glu Val Asp Glu Glu Lys Lys Met Val
1125                1130                1135                1140 gag gaa gca aag gtt gca tct gca ctg gag aaa tgg aag aca gca atc        3813
Glu Glu Ala Lys Val Ala Ser Ala Leu Glu Lys Trp Lys Thr Ala Ile
                1145                1150                1155 cgg gaa gct cag act ttc tcc agg atg cac gtg ctg ctt ggg atg ctt        3861
Arg Glu Ala Gln Thr Phe Ser Arg Met His Val Leu Leu Gly Met Leu
```

-continued

```
                1160                1165                1170
gat gcc tgt atc aag tgg gat atg tcc gca gaa aat gct agg tgc aaa    3909
Asp Ala Cys Ile Lys Trp Asp Met Ser Ala Glu Asn Ala Arg Cys Lys
            1175                1180                1185 gtt tgt cca aag aaa ggt gag gat gac aaa ttg atc ttg tgt gat gag    3957
Val Cys Pro Lys Lys Gly Glu Asp Asp Lys Leu Ile Leu Cys Asp Glu
    1190                1195                1200 tgt aat aaa gcc ttc cac ctg ttt tgt ctg agg ccg gcc ctc tat gaa    4005
Cys Asn Lys Ala Phe His Leu Phe Cys Leu Arg Pro Ala Leu Tyr Glu
1205                1210                1215                1220 gta cca gat ggt gag tgg cag tgc cca gct tgc cag ccc gct act gcc    4053
Val Pro Asp Gly Glu Trp Gln Cys Pro Ala Cys Gln Pro Ala Thr Ala
                1225                1230                1235 agg cgc aac tcc cgt ggc agg aac tat act gaa gag tct gct tct gag    4101
Arg Arg Asn Ser Arg Gly Arg Asn Tyr Thr Glu Glu Ser Ala Ser Glu
        1240                1245                1250 gac agt gaa gat gat gag agt gat gaa gag gag gag gag gaa gaa gag    4149
Asp Ser Glu Asp Asp Glu Ser Asp Glu Glu Glu Glu Glu Glu Glu Glu
    1255                1260                1265 gag gag gag gaa gaa gat tat gag gtg gct ggt ttg cga ttg aga cct    4197
Glu Glu Glu Glu Glu Asp Tyr Glu Val Ala Gly Leu Arg Leu Arg Pro
1270                1275                1280 cga aag acc atc cgg ggc aag cac agc gtc atc ccc cct gca gca agg    4245
Arg Lys Thr Ile Arg Gly Lys His Ser Val Ile Pro Pro Ala Ala Arg
1285                1290                1295                1300 tca ggc cgg cgc ccg ggt aag aag cca cac tct acc agg agg tct cag    4293
Ser Gly Arg Arg Pro Gly Lys Lys Pro His Ser Thr Arg Arg Ser Gln
                1305                1310                1315 ccc aag gca cca cct gtg gat gat gct gag gtg gat gag ctg gtg ctt    4341
Pro Lys Ala Pro Pro Val Asp Asp Ala Glu Val Asp Glu Leu Val Leu
        1320                1325                1330 cag acc aag cgg agc tcc cgg agg caa agc ctg gag ctg cag aag tgt    4389
Gln Thr Lys Arg Ser Ser Arg Arg Gln Ser Leu Glu Leu Gln Lys Cys
    1335                1340                1345 gaa gag atc ctc cac aag atc gtg aag tac cgc ttc agc tgg ccc ttc    4437
Glu Glu Ile Leu His Lys Ile Val Lys Tyr Arg Phe Ser Trp Pro Phe
1350                1355                1360 agg gag cct gtg acc aga gat gag gcc gag gac tac tat gat gtg atc    4485
Arg Glu Pro Val Thr Arg Asp Glu Ala Glu Asp Tyr Tyr Asp Val Ile
1365                1370                1375                1380 acg cac ccc atg gac ttt cag aca gtg cag aac aaa tgt tcc tgt ggg    4533
Thr His Pro Met Asp Phe Gln Thr Val Gln Asn Lys Cys Ser Cys Gly
                1385                1390                1395 agc tac cgc tct gtg cag gag ttt ctt act gac atg aag caa gtg ttt    4581
Ser Tyr Arg Ser Val Gln Glu Phe Leu Thr Asp Met Lys Gln Val Phe
        1400                1405                1410 acc aat gct gag gtt tac aac tgc cgt ggc agc cat gtg cta agc tgc    4629
Thr Asn Ala Glu Val Tyr Asn Cys Arg Gly Ser His Val Leu Ser Cys
    1415                1420                1425 atg gtg aag aca gaa cag tgt cta gtg gtt ctg ttg cat aaa cac ctt    4677
Met Val Lys Thr Glu Gln Cys Leu Val Val Leu Leu His Lys His Leu
1430                1435                1440 cct ggc cac cca tat gtc cgc agg aag cgc aag aag ttt cct gat agg    4725
Pro Gly His Pro Tyr Val Arg Arg Lys Arg Lys Lys Phe Pro Asp Arg
1445                1450                1455                1460 ctt gct gaa gat gaa ggg gac agt gag cca gag gcc gtt gga cag tcc    4773
Leu Ala Glu Asp Glu Gly Asp Ser Glu Pro Glu Ala Val Gly Gln Ser
                1465                1470                1475 agg gac gaa gac aga aga agt aga gag gcg gag att cag gaa tgg ctc    4821
```

-continued

```
Arg Asp Glu Asp Arg Arg Ser Arg Glu Ala Glu Ile Gln Glu Trp Leu
            1480                1485                1490 cag gac acg tcc ctt tac tct gcc aag atc aac tca aaa gac cac aac    4869
Gln Asp Thr Ser Leu Tyr Ser Ala Lys Ile Asn Ser Lys Asp His Asn
        1495                1500                1505 tgt ttc atg atg ctg gtg aat aca caa ttc tgt atg gca ctc act gat    4917
Cys Phe Met Met Leu Val Asn Thr Gln Phe Cys Met Ala Leu Thr Asp
    1510                1515                1520 act gtc acc tgagaggaag acggggaag agacagagta tgggcttaaa              4966
Thr Val Thr
1525 gaaacaagac tgtataataa atacagatta aaaagaaaa atcgccacca tctcccctgt    5026 tggcctgatt accccgatcc tgctatgtaa cacagcaatc cctcccctgg agaccagagg    5086 ggcttggcac tgtggtggaa gccagaacga gcaggccctt aggaaagaag caggaacag    5146 gaactggctt caccagaaaa gctagaccct cggactcctc ctggaaactc tcagaaggga    5206 gggttatggc cctctttgtc ccttcatatt tctggacaaa gaccaccaac ccaatatcaa    5266 gccccataaa gagcttttag aaaaacagca taagcttggg atgacaggcg tttctggact    5326 ccctgtgatc tcttccaggt tcttggtctt cctcgctcgc ctccctccca ccctccctag    5386 ctgtccccc acctcagctc ccttaccacg gccctgcctc tctacttctt ctgtcttcgt     5446 cccctggact gtccaacggc ctctggctca ctgtcccttc atcttcagca acctatcagg    5506 aaacttcttg cgcttcctgc ggacatatgg gtggccagga agtgtttatg caaca          5561
```

<210> SEQ ID NO 29
<211> LENGTH: 1531
<212> TYPE: PRT
<213> ORGANISM: Homo sapiens

<400> SEQUENCE: 29

```
Met Ala Pro Leu Leu Gly Arg Lys Pro Phe Pro Leu Val Asn Pro Leu
  1               5                  10                  15

Pro Gly Glu Glu Pro Phe Phe Thr Ile Pro His Thr Gln Glu Ala Phe
             20                  25                  30

Arg Thr Arg Glu Glu Tyr Glu Ala Arg Leu Glu Arg Tyr Ser Glu Arg
         35                  40                  45

Ile Trp Thr Cys Lys Ser Thr Gly Ser Ser Gln Leu Thr His Lys Glu
     50                  55                  60

Ala Trp Glu Glu Glu Gln Glu Val Ala Glu Leu Leu Lys Glu Glu Phe
 65                  70                  75                  80

Pro Ala Trp Tyr Glu Lys Leu Val Leu Glu Met Val His His Asn Thr
                 85                  90                  95

Ala Ser Leu Glu Lys Leu Val Asp Thr Ala Trp Leu Glu Ile Met Thr
            100                 105                 110

Lys Tyr Ala Val Gly Glu Glu Cys Asp Phe Val Gly Lys Glu Lys
        115                 120                 125

Met Leu Lys Val Lys Ile Val Lys Ile His Pro Leu Glu Lys Val Asp
    130                 135                 140

Glu Glu Ala Thr Glu Lys Lys Ser Asp Gly Ala Cys Asp Ser Pro Ser
145                 150                 155                 160

Ser Asp Lys Glu Asn Ser Ser Gln Ile Ala Gln Asp His Gln Lys Lys
                165                 170                 175

Glu Thr Val Val Lys Glu Asp Glu Gly Arg Arg Glu Ser Ile Asn Asp
            180                 185                 190
```

-continued

```
Arg Ala Arg Arg Ser Pro Arg Lys Leu Pro Thr Ser Leu Lys Lys Gly
            195                 200                 205

Glu Arg Lys Trp Ala Pro Pro Lys Phe Leu Pro His Lys Tyr Asp Val
        210                 215                 220

Lys Leu Gln Asn Glu Asp Lys Ile Ile Ser Asn Val Pro Ala Asp Ser
225                 230                 235                 240

Leu Ile Arg Thr Glu Arg Pro Pro Asn Lys Glu Ile Val Arg Tyr Phe
                245                 250                 255

Ile Arg His Asn Ala Leu Arg Ala Gly Thr Gly Glu Asn Ala Pro Trp
            260                 265                 270

Val Val Glu Asp Glu Leu Val Lys Lys Tyr Ser Leu Pro Ser Lys Phe
        275                 280                 285

Ser Asp Phe Leu Leu Asp Pro Tyr Lys Tyr Met Thr Leu Asn Pro Ser
    290                 295                 300

Thr Lys Arg Lys Asn Thr Gly Ser Pro Asp Arg Lys Pro Ser Lys Lys
305                 310                 315                 320

Ser Lys Thr Asp Asn Ser Ser Leu Ser Ser Pro Leu Asn Pro Lys Leu
                325                 330                 335

Trp Cys His Val His Leu Lys Lys Ser Leu Ser Gly Ser Pro Leu Lys
            340                 345                 350

Val Lys Asn Ser Lys Asn Ser Lys Ser Pro Glu Glu His Leu Glu Glu
        355                 360                 365

Met Met Lys Met Met Ser Pro Asn Lys Leu His Thr Asn Phe His Ile
    370                 375                 380

Pro Lys Lys Gly Pro Pro Ala Lys Lys Pro Gly Lys His Ser Asp Lys
385                 390                 395                 400

Pro Leu Lys Ala Lys Gly Arg Ser Lys Gly Ile Leu Asn Gly Gln Lys
                405                 410                 415

Ser Thr Gly Asn Ser Lys Ser Pro Lys Lys Gly Leu Lys Thr Pro Lys
            420                 425                 430

Thr Lys Met Lys Gln Met Thr Leu Leu Asp Met Ala Lys Gly Thr Gln
        435                 440                 445

Lys Met Thr Arg Ala Pro Arg Asn Ser Gly Gly Thr Pro Arg Thr Ser
    450                 455                 460

Ser Lys Pro His Lys His Leu Pro Pro Ala Ala Leu His Leu Ile Ala
465                 470                 475                 480

Tyr Tyr Lys Glu Asn Lys Asp Arg Glu Asp Lys Arg Ser Ala Leu Ser
                485                 490                 495

Cys Val Ile Ser Lys Thr Ala Arg Leu Leu Ser Ser Glu Asp Arg Ala
            500                 505                 510

Arg Leu Pro Glu Glu Leu Arg Ser Leu Val Gln Lys Arg Tyr Glu Leu
        515                 520                 525

Leu Glu His Lys Lys Arg Trp Ala Ser Met Ser Glu Glu Gln Arg Lys
    530                 535                 540

Glu Tyr Leu Lys Lys Arg Glu Glu Leu Lys Lys Lys Leu Lys Glu
545                 550                 555                 560

Lys Ala Lys Glu Arg Arg Glu Lys Glu Met Leu Glu Arg Leu Glu Lys
                565                 570                 575

Gln Lys Arg Tyr Glu Asp Gln Glu Leu Thr Gly Lys Asn Leu Pro Ala
            580                 585                 590

Phe Arg Leu Val Asp Thr Pro Glu Gly Leu Pro Asn Thr Leu Phe Gly
        595                 600                 605

Asp Val Ala Met Val Val Glu Phe Leu Ser Cys Tyr Ser Gly Leu Leu
```

```
              610                 615                 620
Leu Pro Asp Ala Gln Tyr Pro Ile Thr Ala Val Ser Leu Met Glu Ala
625                 630                 635                 640

Leu Ser Ala Asp Lys Gly Gly Phe Leu Tyr Leu Asn Arg Val Leu Val
                    645                 650                 655

Ile Leu Leu Gln Thr Leu Leu Gln Thr Leu Leu Gln Asp Glu Ile Ala
                660                 665                 670

Glu Asp Tyr Gly Glu Leu Gly Met Lys Leu Ser Glu Ile Pro Leu Thr
            675                 680                 685

Leu His Ser Val Ser Glu Leu Val Arg Leu Cys Leu Arg Arg Ser Asp
690                 695                 700

Val Gln Glu Glu Ser Glu Gly Ser Asp Thr Asp Asn Lys Asp Ser
705                 710                 715                 720

Ala Ala Phe Glu Asp Asn Glu Val Gln Asp Glu Phe Leu Glu Lys Leu
                    725                 730                 735

Glu Thr Ser Glu Phe Phe Glu Leu Thr Ser Glu Glu Lys Leu Gln Ile
                740                 745                 750

Leu Thr Ala Leu Cys His Arg Ile Leu Met Thr Tyr Ser Val Gln Asp
            755                 760                 765

His Met Glu Thr Arg Gln Gln Met Ser Ala Glu Leu Trp Lys Glu Arg
770                 775                 780

Leu Ala Val Leu Lys Glu Asn Asp Lys Lys Arg Ala Glu Lys Gln
785                 790                 795                 800

Lys Arg Lys Glu Met Glu Ala Lys Asn Lys Glu Asn Gly Lys Val Glu
                    805                 810                 815

Asn Gly Leu Gly Lys Thr Asp Arg Lys Lys Arg Ile Val Lys Phe Glu
                820                 825                 830

Pro Gln Val Asp Thr Glu Ala Glu Asp Met Ile Ser Ala Val Lys Ser
            835                 840                 845

Arg Arg Leu Leu Ala Ile Gln Ala Lys Lys Glu Arg Glu Ile Gln Glu
850                 855                 860

Arg Glu Met Lys Val Lys Leu Glu Arg Gln Ala Glu Glu Glu Arg Ile
865                 870                 875                 880

Arg Lys His Lys Ala Ala Ala Glu Lys Ala Phe Gln Glu Gly Ile Ala
                    885                 890                 895

Lys Ala Lys Leu Val Met Arg Arg Thr Pro Ile Gly Thr Asp Arg Asn
                900                 905                 910

His Asn Arg Tyr Trp Leu Phe Ser Asp Glu Val Pro Gly Leu Phe Ile
            915                 920                 925

Glu Lys Gly Trp Val His Asp Ser Ile Asp Tyr Arg Phe Asn His His
930                 935                 940

Cys Lys Asp His Thr Val Ser Gly Asp Glu Asp Tyr Cys Pro Arg Ser
945                 950                 955                 960

Lys Lys Ala Asn Leu Gly Lys Asn Ala Ser Met Asn Thr Gln His Gly
                    965                 970                 975

Thr Ala Thr Glu Val Ala Val Glu Thr Thr Thr Pro Lys Gln Gly Gln
                980                 985                 990

Asn Leu Trp Phe Leu Cys Asp Ser Gln Lys Glu Leu Asp Glu Leu Leu
            995                 1000                1005

Asn Cys Leu His Pro Gln Gly Ile Arg Glu Ser Gln Leu Lys Glu Arg
            1010                1015                1020

Leu Glu Lys Arg Tyr Gln Asp Ile Ile His Ser Ile His Leu Ala Arg
1025                1030                1035                1040
```

-continued

```
Lys Pro Asn Leu Gly Leu Lys Ser Cys Asp Gly Asn Gln Glu Leu Leu
            1045                1050                1055

Asn Phe Leu Arg Ser Asp Leu Ile Glu Val Ala Thr Arg Leu Gln Lys
            1060                1065                1070

Gly Gly Leu Gly Tyr Val Glu Glu Thr Ser Glu Phe Glu Ala Arg Val
            1075                1080                1085

Ile Ser Leu Glu Lys Leu Lys Asp Phe Gly Glu Cys Val Ile Ala Leu
            1090                1095                1100

Gln Ala Ser Val Ile Lys Lys Phe Leu Gln Gly Phe Met Ala Pro Lys
1105                1110                1115                1120

Gln Lys Arg Arg Lys Leu Gln Ser Glu Asp Ser Ala Lys Thr Glu Glu
            1125                1130                1135

Val Asp Glu Glu Lys Lys Met Val Glu Glu Ala Lys Val Ala Ser Ala
            1140                1145                1150

Leu Glu Lys Trp Lys Thr Ala Ile Arg Glu Ala Gln Thr Phe Ser Arg
            1155                1160                1165

Met His Val Leu Leu Gly Met Leu Asp Ala Cys Ile Lys Trp Asp Met
            1170                1175                1180

Ser Ala Glu Asn Ala Arg Cys Lys Val Cys Pro Lys Lys Gly Glu Asp
1185                1190                1195                1200

Asp Lys Leu Ile Leu Cys Asp Glu Cys Asn Lys Ala Phe His Leu Phe
            1205                1210                1215

Cys Leu Arg Pro Ala Leu Tyr Glu Val Pro Asp Gly Glu Trp Gln Cys
            1220                1225                1230

Pro Ala Cys Gln Pro Ala Thr Ala Arg Arg Asn Ser Arg Gly Arg Asn
            1235                1240                1245

Tyr Thr Glu Glu Ser Ala Ser Glu Asp Ser Glu Asp Asp Glu Ser Asp
            1250                1255                1260

Glu Glu Glu Glu Glu Glu Glu Glu Glu Glu Glu Glu Asp Tyr Glu
1265                1270                1275                1280

Val Ala Gly Leu Arg Leu Arg Pro Arg Lys Thr Ile Arg Gly Lys His
            1285                1290                1295

Ser Val Ile Pro Pro Ala Ala Arg Ser Gly Arg Arg Pro Gly Lys Lys
            1300                1305                1310

Pro His Ser Thr Arg Arg Ser Gln Pro Lys Ala Pro Pro Val Asp Asp
            1315                1320                1325

Ala Glu Val Asp Glu Leu Val Leu Gln Thr Lys Arg Ser Ser Arg Arg
1330                1335                1340

Gln Ser Leu Glu Leu Gln Lys Cys Glu Glu Ile Leu His Lys Ile Val
1345                1350                1355                1360

Lys Tyr Arg Phe Ser Trp Pro Phe Arg Glu Pro Val Thr Arg Asp Glu
            1365                1370                1375

Ala Glu Asp Tyr Tyr Asp Val Ile Thr His Pro Met Asp Phe Gln Thr
            1380                1385                1390

Val Gln Asn Lys Cys Ser Cys Gly Ser Tyr Arg Ser Val Gln Glu Phe
            1395                1400                1405

Leu Thr Asp Met Lys Gln Val Phe Thr Asn Ala Glu Val Tyr Asn Cys
            1410                1415                1420

Arg Gly Ser His Val Leu Ser Cys Met Val Lys Thr Glu Gln Cys Leu
1425                1430                1435                1440

Val Val Leu Leu His Lys His Leu Pro Gly His Pro Tyr Val Arg Arg
            1445                1450                1455
```

-continued

```
Lys Arg Lys Lys Phe Pro Asp Arg Leu Ala Glu Asp Glu Gly Asp Ser
            1460                1465                1470

Glu Pro Glu Ala Val Gly Gln Ser Arg Asp Glu Asp Arg Arg Ser Arg
        1475                1480                1485

Glu Ala Glu Ile Gln Glu Trp Leu Gln Asp Thr Ser Leu Tyr Ser Ala
    1490                1495                1500

Lys Ile Asn Ser Lys Asp His Asn Cys Phe Met Met Leu Val Asn Thr
1505                1510                1515                1520

Gln Phe Cys Met Ala Leu Thr Asp Thr Val Thr
                1525                1530

<210> SEQ ID NO 30
<211> LENGTH: 5573
<212> TYPE: DNA
<213> ORGANISM: Homo sapiens
<220> FEATURE:
<221> NAME/KEY: CDS
<222> LOCATION: (346)...(4938)

<400> SEQUENCE: 30
cgggcccggg ggaggagggg aatctcccgc cattttcaa taatttcctc cggtgctgct      60
gaggaggagt cgtgactgcc ggccgccggg acccgaagcg gaggtcggcg ggggctgct    120 gggaggcgcg gcgtgtgcg cgggagctct gcgccgtggc gttccgctcc atgactgtcg    180
cgcggccgcg ccggcggtga gggagccgga gttcgcgccg ccctctcacc cctcccttcc    240
cccaccccac ccccgggcgc ctggcgctcg ctccgggccg cggggcctag tgctgcgccg    300
cggggccggc cccagcagcc gccagtcccc accgccgccg ccgcg atg gcg ccg ctc    357
                                                Met Ala Pro Leu
                                                  1 ctg ggc cgc aag ccc ttc ccg ctg gtg aat ccg ttg ccc gga gag gag      405
Leu Gly Arg Lys Pro Phe Pro Leu Val Asn Pro Leu Pro Gly Glu Glu
  5                  10                  15                  20 ccg ttc ttc acc atc ccg cac act cag gag gcc ttc cgc acc cgg gaa      453
Pro Phe Phe Thr Ile Pro His Thr Gln Glu Ala Phe Arg Thr Arg Glu
             25                  30                  35 gag tat gaa gcc cgc ttg gaa agg tac agt gag cgc att tgg acg tgc      501
Glu Tyr Glu Ala Arg Leu Glu Arg Tyr Ser Glu Arg Ile Trp Thr Cys
         40                  45                  50 aag agt act gga agc agt cag cta aca cac aag gaa gcc tgg gag gaa      549
Lys Ser Thr Gly Ser Ser Gln Leu Thr His Lys Glu Ala Trp Glu Glu
     55                  60                  65 gaa cag gaa gtt gct gag ctt ttg aag gag gag ttt cct gcc tgg tat      597
Glu Gln Glu Val Ala Glu Leu Leu Lys Glu Glu Phe Pro Ala Trp Tyr
 70                  75                  80 gag aag ctt gtt ctg gaa atg gtt cac cat aac aca gcc tcc tta gag      645
Glu Lys Leu Val Leu Glu Met Val His His Asn Thr Ala Ser Leu Glu
 85                  90                  95                 100 aag tta gta gat act gct tgg ttg gag atc atg acc aaa tat gct gtg      693
Lys Leu Val Asp Thr Ala Trp Leu Glu Ile Met Thr Lys Tyr Ala Val
                105                 110                 115 gga gaa gag tgt gac ttc gag gtt ggg aag gag aaa atg ctc aag gtg      741
Gly Glu Glu Cys Asp Phe Glu Val Gly Lys Glu Lys Met Leu Lys Val
            120                 125                 130 aag att gtg aag att cat cct ttg gag aaa gtg gat gaa gag gcc act      789
Lys Ile Val Lys Ile His Pro Leu Glu Lys Val Asp Glu Glu Ala Thr
        135                 140                 145 gag aag aaa tct gat ggt gcc tgt gat tct cca tca agt gac aaa gag      837
Glu Lys Lys Ser Asp Gly Ala Cys Asp Ser Pro Ser Ser Asp Lys Glu
    150                 155                 160
```

```
aac tcc agt cag att gct cag gac cat cag aag aag gag aca gtt gtg        885
Asn Ser Ser Gln Ile Ala Gln Asp His Gln Lys Lys Glu Thr Val Val
165                 170                 175                 180 aaa gag gat gaa gga agg aga gag agt att aat gac aga gca cgt aga        933
Lys Glu Asp Glu Gly Arg Arg Glu Ser Ile Asn Asp Arg Ala Arg Arg
                    185                 190                 195 tcg cca cga aaa ctt cct act tca tta aaa aaa gga gaa agg aaa tgg        981
Ser Pro Arg Lys Leu Pro Thr Ser Leu Lys Lys Gly Glu Arg Lys Trp
                200                 205                 210 gct cct cca aaa ttt ctg cct cac aaa tat gat gtg aaa cta caa aat       1029
Ala Pro Pro Lys Phe Leu Pro His Lys Tyr Asp Val Lys Leu Gln Asn
            215                 220                 225 gaa gat aag atc atc agt aac gtg cca gca gac agc ttg att cgt aca       1077
Glu Asp Lys Ile Ile Ser Asn Val Pro Ala Asp Ser Leu Ile Arg Thr
230                 235                 240 gag cgc cca cca aat aag gag ata gtt cga tac ttt ata cgg cat aat       1125
Glu Arg Pro Pro Asn Lys Glu Ile Val Arg Tyr Phe Ile Arg His Asn
245                 250                 255                 260 gca tta cga gct ggt act ggt gaa aat gca cct tgg gtc gta gaa gat       1173
Ala Leu Arg Ala Gly Thr Gly Glu Asn Ala Pro Trp Val Val Glu Asp
                    265                 270                 275 gaa ttg gtg aag aaa tac tct ctg ccc agc aag ttc agt gac ttt tta       1221
Glu Leu Val Lys Lys Tyr Ser Leu Pro Ser Lys Phe Ser Asp Phe Leu
                280                 285                 290 ctt gat cca tac aag tat atg act ctc aac cct tct act aag agg aag       1269
Leu Asp Pro Tyr Lys Tyr Met Thr Leu Asn Pro Ser Thr Lys Arg Lys
            295                 300                 305 aat act gga tcc cca gac agg aag ccc tca aag aaa tcc aag aca gac       1317
Asn Thr Gly Ser Pro Asp Arg Lys Pro Ser Lys Lys Ser Lys Thr Asp
310                 315                 320 aac tct tct ctt agt tca cca cta aat cct aag tta tgg tgt cac gta       1365
Asn Ser Ser Leu Ser Ser Pro Leu Asn Pro Lys Leu Trp Cys His Val
325                 330                 335                 340 cac ttg aag aag tca ttg agt ggc tcg cca ctc aaa gtg aag aac tca       1413
His Leu Lys Lys Ser Leu Ser Gly Ser Pro Leu Lys Val Lys Asn Ser
                    345                 350                 355 aag aat tcc aaa tct cct gaa gaa cat cta gaa gaa atg atg aag atg       1461
Lys Asn Ser Lys Ser Pro Glu Glu His Leu Glu Glu Met Met Lys Met
                360                 365                 370 atg tcg ccc aat aag ttg cac act aac ttt cac att cct aaa aaa ggc       1509
Met Ser Pro Asn Lys Leu His Thr Asn Phe His Ile Pro Lys Lys Gly
            375                 380                 385 cca cct gcc aag aaa cca ggg aag cac agt gac aag cct ttg aag gca       1557
Pro Pro Ala Lys Lys Pro Gly Lys His Ser Asp Lys Pro Leu Lys Ala
390                 395                 400 aag ggc aga agc aaa ggc atc ctg aat gga cag aaa tcc aca ggg aat       1605
Lys Gly Arg Ser Lys Gly Ile Leu Asn Gly Gln Lys Ser Thr Gly Asn
405                 410                 415                 420 tcc aaa tct ccc aaa aaa gga ctg aag act cct aaa acc aaa atg aag       1653
Ser Lys Ser Pro Lys Lys Gly Leu Lys Thr Pro Lys Thr Lys Met Lys
                425                 430                 435 cag atg act ttg ttg gat atg gcc aaa ggc acg cag aag atg aca cga       1701
Gln Met Thr Leu Leu Asp Met Ala Lys Gly Thr Gln Lys Met Thr Arg
                440                 445                 450 gcc cca cgg aat tct ggg ggt aca cct agg acc tct agt aaa cct cat       1749
Ala Pro Arg Asn Ser Gly Gly Thr Pro Arg Thr Ser Ser Lys Pro His
            455                 460                 465 aaa cat ctg cct cct gca gcc cta cac ctc att gca tac tac aaa gaa       1797
Lys His Leu Pro Pro Ala Ala Leu His Leu Ile Ala Tyr Tyr Lys Glu
```

```
              470                 475                 480
aac aaa gac agg gag gac aag agg agc gcc ctg tcc tgt gtt atc tcc    1845
Asn Lys Asp Arg Glu Asp Lys Arg Ser Ala Leu Ser Cys Val Ile Ser
485                 490                 495                 500 aaa aca gct cgt ctt ctc tct agt gaa gat aga gct cgt ctc cca gaa    1893
Lys Thr Ala Arg Leu Leu Ser Ser Glu Asp Arg Ala Arg Leu Pro Glu
                505                 510                 515 gaa ttg cga agt ctt gtt caa aaa cgc tat gaa ctt cta gag cac aaa    1941
Glu Leu Arg Ser Leu Val Gln Lys Arg Tyr Glu Leu Leu Glu His Lys
            520                 525                 530 aag agg tgg gct tct atg tct gaa gaa caa cgg aaa gaa tat ttg aaa    1989
Lys Arg Trp Ala Ser Met Ser Glu Glu Gln Arg Lys Glu Tyr Leu Lys
        535                 540                 545 aag aaa cgg gag gag ctg aaa aag aag ttg aag gaa aaa gcc aaa gaa    2037
Lys Lys Arg Glu Glu Leu Lys Lys Lys Leu Lys Glu Lys Ala Lys Glu
550                 555                 560 cga aga gag aaa gaa atg ctt gag aga tta gaa aaa cag aag cgg tat    2085
Arg Arg Glu Lys Glu Met Leu Glu Arg Leu Glu Lys Gln Lys Arg Tyr
565                 570                 575                 580 gag gac caa gag tta act ggc aaa aac ctt cca gca ttc aga ttg gtg    2133
Glu Asp Gln Glu Leu Thr Gly Lys Asn Leu Pro Ala Phe Arg Leu Val
                585                 590                 595 gat acc cct gaa ggg ctg ccc aac acg ctg ttt ggg gat gtg gcc atg    2181
Asp Thr Pro Glu Gly Leu Pro Asn Thr Leu Phe Gly Asp Val Ala Met
            600                 605                 610 gtg gtg gaa ttc ttg agc tgt tat tct ggg cta ctt tta cca gat gct    2229
Val Val Glu Phe Leu Ser Cys Tyr Ser Gly Leu Leu Leu Pro Asp Ala
        615                 620                 625 cag tat cct att act gct gtg tcc ctt atg gaa gcc ttg agt gca gat    2277
Gln Tyr Pro Ile Thr Ala Val Ser Leu Met Glu Ala Leu Ser Ala Asp
630                 635                 640 aag ggt ggc ttt tta tac ctt aac agg gtg ttg gtc atc ctc tta cag    2325
Lys Gly Gly Phe Leu Tyr Leu Asn Arg Val Leu Val Ile Leu Leu Gln
645                 650                 655                 660 acc ctc cta cag acc ctc cta caa gat gag ata gcc gaa gac tat ggt    2373
Thr Leu Leu Gln Thr Leu Leu Gln Asp Glu Ile Ala Glu Asp Tyr Gly
                665                 670                 675 gaa ttg gga atg aag ctg tca gaa atc ccc ttg act ctg cat tct gtt    2421
Glu Leu Gly Met Lys Leu Ser Glu Ile Pro Leu Thr Leu His Ser Val
            680                 685                 690 tca gag ctg gtg cgg ctc tgc ttg cgc aga tct gat gtt cag gag gaa    2469
Ser Glu Leu Val Arg Leu Cys Leu Arg Arg Ser Asp Val Gln Glu Glu
        695                 700                 705 agc gag ggc tca gac aca gat gac aat aaa gat tca gct gca ttt gag    2517
Ser Glu Gly Ser Asp Thr Asp Asp Asn Lys Asp Ser Ala Ala Phe Glu
710                 715                 720 gat aat gag gta caa gat gag ttc cta gaa aag ctg gag acc tct gaa    2565
Asp Asn Glu Val Gln Asp Glu Phe Leu Glu Lys Leu Glu Thr Ser Glu
725                 730                 735                 740 ttt ttt gag ctg acg tca gag gag aag cta cag att ttg aca gca ctg    2613
Phe Phe Glu Leu Thr Ser Glu Glu Lys Leu Gln Ile Leu Thr Ala Leu
                745                 750                 755 tgc cac cgg atc ctc atg aca tac tca gtg caa gac cac atg gag acc    2661
Cys His Arg Ile Leu Met Thr Tyr Ser Val Gln Asp His Met Glu Thr
            760                 765                 770 aga cag cag atg tct gca gag ttg tgg aag gaa cgg ctt gct gtg ttg    2709
Arg Gln Gln Met Ser Ala Glu Leu Trp Lys Glu Arg Leu Ala Val Leu
        775                 780                 785 aag gaa gaa aat gat aag aag aga gca gag aaa cag aaa cgg aaa gaa    2757
```

```
Lys Glu Glu Asn Asp Lys Lys Arg Ala Glu Lys Gln Lys Arg Lys Glu
    790                 795                 800 atg gaa gcc aaa aat aaa gaa aat gga aaa gtt gag aat ggg tta ggc      2805
Met Glu Ala Lys Asn Lys Glu Asn Gly Lys Val Glu Asn Gly Leu Gly
805                 810                 815                 820 aaa act gat agg aaa aaa aga att gtg aag ttt gag ccc caa gta gat      2853
Lys Thr Asp Arg Lys Lys Arg Ile Val Lys Phe Glu Pro Gln Val Asp
                825                 830                 835 aca gaa gct gaa gac atg att agt gct gtg aag agc aga agg ttg ctt      2901
Thr Glu Ala Glu Asp Met Ile Ser Ala Val Lys Ser Arg Arg Leu Leu
            840                 845                 850 gcc att caa gct aag aag gaa cgg gaa atc cag gaa aga gaa atg aaa      2949
Ala Ile Gln Ala Lys Lys Glu Arg Glu Ile Gln Glu Arg Glu Met Lys
        855                 860                 865 gtg aaa ctg gaa cgc caa gct gaa gaa gaa cga ata cgg aag cac aaa      2997
Val Lys Leu Glu Arg Gln Ala Glu Glu Glu Arg Ile Arg Lys His Lys
870                 875                 880 gca gct gct gag aaa gct ttc cag gaa ggg att gcc aag gcc aaa cta      3045
Ala Ala Ala Glu Lys Ala Phe Gln Glu Gly Ile Ala Lys Ala Lys Leu
885                 890                 895                 900 gtc atg cgc agg act cct att ggc aca gat cga aac cat aat aga tac      3093
Val Met Arg Arg Thr Pro Ile Gly Thr Asp Arg Asn His Asn Arg Tyr
                905                 910                 915 tgg ctc ttc tca gat gaa gtt cca gga tta ttc att gaa aaa ggc tgg      3141
Trp Leu Phe Ser Asp Glu Val Pro Gly Leu Phe Ile Glu Lys Gly Trp
            920                 925                 930 gta cat gac agc att gac tac cga ttc aac cat cac tgc aaa gac cac      3189
Val His Asp Ser Ile Asp Tyr Arg Phe Asn His His Cys Lys Asp His
        935                 940                 945 aca gtc tct ggt gat gag gat tac tgt cct cgc agt aag aaa gca aac      3237
Thr Val Ser Gly Asp Glu Asp Tyr Cys Pro Arg Ser Lys Lys Ala Asn
    950                 955                 960 tta ggt aaa aat gca agc atg aac aca caa cat gga aca gca aca gaa      3285
Leu Gly Lys Asn Ala Ser Met Asn Thr Gln His Gly Thr Ala Thr Glu
965                 970                 975                 980 gtt gct gta gag aca acc aca ccc aaa caa gga cag aac cta tgg ttt      3333
Val Ala Val Glu Thr Thr Thr Pro Lys Gln Gly Gln Asn Leu Trp Phe
                985                 990                 995 tta tgt gat agt caa aag gag ctg gat gag ttg cta aac tgt ctt cac      3381
Leu Cys Asp Ser Gln Lys Glu Leu Asp Glu Leu Leu Asn Cys Leu His
            1000                1005                1010 cct cag gga ata aga gaa agt caa ctt aaa gag aga cta gag aag agg      3429
Pro Gln Gly Ile Arg Glu Ser Gln Leu Lys Glu Arg Leu Glu Lys Arg
        1015                1020                1025 tac cag gac att att cac tct att cat cta gca cgg aag cca aat ttg      3477
Tyr Gln Asp Ile Ile His Ser Ile His Leu Ala Arg Lys Pro Asn Leu
    1030                1035                1040 ggt cta aaa tct tgt gat ggc aac cag gag ctt tta aac ttc ctt cgt      3525
Gly Leu Lys Ser Cys Asp Gly Asn Gln Glu Leu Leu Asn Phe Leu Arg
1045                1050                1055                1060 agt gat ctc att gaa gtt gca aca agg tta caa aaa gga gga ctt gga      3573
Ser Asp Leu Ile Glu Val Ala Thr Arg Leu Gln Lys Gly Gly Leu Gly
                1065                1070                1075 tat gtg gaa gaa aca tca gaa ttt gaa gcc cgg gtc att tca tta gag      3621
Tyr Val Glu Glu Thr Ser Glu Phe Glu Ala Arg Val Ile Ser Leu Glu
            1080                1085                1090 aaa ttg aag gat ttt ggt gag tgt gtg att gcc ctt cag gcc agt gtc      3669
Lys Leu Lys Asp Phe Gly Glu Cys Val Ile Ala Leu Gln Ala Ser Val
        1095                1100                1105
```

```
ata aag aaa ttt ctc caa ggc ttc atg gct ccc aag caa aag aga aga    3717
Ile Lys Lys Phe Leu Gln Gly Phe Met Ala Pro Lys Gln Lys Arg Arg
    1110                1115                1120 aaa ctc caa agt gaa gat tca gca aaa act gag gaa gtg gat gaa gag    3765
Lys Leu Gln Ser Glu Asp Ser Ala Lys Thr Glu Glu Val Asp Glu Glu
1125                1130                1135                1140 aag aaa atg gta gag gaa gca aag gtt gca tct gca ctg gag aaa tgg    3813
Lys Lys Met Val Glu Glu Ala Lys Val Ala Ser Ala Leu Glu Lys Trp
            1145                1150                1155 aag aca gca atc cgg gaa gct cag act ttc tcc agg atg cac gtg ctg    3861
Lys Thr Ala Ile Arg Glu Ala Gln Thr Phe Ser Arg Met His Val Leu
        1160                1165                1170 ctt ggg atg ctt gat gcc tgt atc aag tgg gat atg tcc gca gaa aat    3909
Leu Gly Met Leu Asp Ala Cys Ile Lys Trp Asp Met Ser Ala Glu Asn
    1175                1180                1185 gct agg tgc aaa gtt tgt cca aag aaa ggt gag gat gac aaa ttg atc    3957
Ala Arg Cys Lys Val Cys Pro Lys Lys Gly Glu Asp Asp Lys Leu Ile
1190                1195                1200 ttg tgt gat gag tgt aat aaa gcc ttc cac ctg ttt tgt ctg agg ccg    4005
Leu Cys Asp Glu Cys Asn Lys Ala Phe His Leu Phe Cys Leu Arg Pro
1205                1210                1215                1220 gcc ctc tat gaa gta cca gat ggt gag tgg cag tgc cca gct tgc cag    4053
Ala Leu Tyr Glu Val Pro Asp Gly Glu Trp Gln Cys Pro Ala Cys Gln
            1225                1230                1235 ccc gct act gcc agg cgc aac tcc cgt ggc agg aac tat act gaa gag    4101
Pro Ala Thr Ala Arg Arg Asn Ser Arg Gly Arg Asn Tyr Thr Glu Glu
        1240                1245                1250 tct gct tct gag gac agt gaa gat gat gag agt gat gaa gag gag gag    4149
Ser Ala Ser Glu Asp Ser Glu Asp Asp Glu Ser Asp Glu Glu Glu Glu
    1255                1260                1265 gag gaa gaa gag gag gag gag gaa gaa gat tat gag gtg gct ggt ttg    4197
Glu Glu Glu Glu Glu Glu Glu Glu Glu Asp Tyr Glu Val Ala Gly Leu
1270                1275                1280 cga ttg aga cct cga aag acc atc cgg ggc aag cac agc gtc atc ccc    4245
Arg Leu Arg Pro Arg Lys Thr Ile Arg Gly Lys His Ser Val Ile Pro
1285                1290                1295                1300 cct gca gca agg tca ggc cgg cgc ccg ggt aag aag cca cac tct acc    4293
Pro Ala Ala Arg Ser Gly Arg Arg Pro Gly Lys Lys Pro His Ser Thr
            1305                1310                1315 agg agg tct cag ccc aag gca cca cct gtg gat gat gct gag gtg gat    4341
Arg Arg Ser Gln Pro Lys Ala Pro Pro Val Asp Asp Ala Glu Val Asp
        1320                1325                1330 gag ctg gtg ctt cag acc aag cgg agc tcc cgg agg caa agc ctg gag    4389
Glu Leu Val Leu Gln Thr Lys Arg Ser Ser Arg Arg Gln Ser Leu Glu
    1335                1340                1345 ctg cag aag tgt gaa gag atc ctc cac aag atc gtg aag tac cgc ttc    4437
Leu Gln Lys Cys Glu Glu Ile Leu His Lys Ile Val Lys Tyr Arg Phe
1350                1355                1360 agc tgg ccc ttc agg gag cct gtg acc aga gat gag gcc gag gac tac    4485
Ser Trp Pro Phe Arg Glu Pro Val Thr Arg Asp Glu Ala Glu Asp Tyr
1365                1370                1375                1380 tat gat gtg atc acg cac ccc atg gac ttt cag aca gtg cag aac aaa    4533
Tyr Asp Val Ile Thr His Pro Met Asp Phe Gln Thr Val Gln Asn Lys
            1385                1390                1395 tgt tcc tgt ggg agc tac cgc tct gtg cag gag ttt ctt act gac atg    4581
Cys Ser Cys Gly Ser Tyr Arg Ser Val Gln Glu Phe Leu Thr Asp Met
        1400                1405                1410 aag caa gtg ttt acc aat gct gag gtt tac aac tgc cgt ggc agc cat    4629
Lys Gln Val Phe Thr Asn Ala Glu Val Tyr Asn Cys Arg Gly Ser His
    1415                1420                1425
```

```
gtg cta agc tgc atg gtg aag aca gaa cag tgt cta gtg gtt ctg ttg    4677
Val Leu Ser Cys Met Val Lys Thr Glu Gln Cys Leu Val Val Leu Leu
        1430                1435                1440 cat aaa cac ctt cct ggc cac cca tat gtc cgc agg aag cgc aag aag    4725
His Lys His Leu Pro Gly His Pro Tyr Val Arg Arg Lys Arg Lys Lys
1445                1450                1455                1460 ttt cct gat agg ctt gct gaa gat gaa ggg gac agt gag cca gag gcc    4773
Phe Pro Asp Arg Leu Ala Glu Asp Glu Gly Asp Ser Glu Pro Glu Ala
                1465                1470                1475 gtt gga cag tcc agg gac gaa gac aga aga agt aga gag gcg gag att    4821
Val Gly Gln Ser Arg Asp Glu Asp Arg Arg Ser Arg Glu Ala Glu Ile
        1480                1485                1490 cag gaa tgg ctc cag gac acg tcc ctt tac tct gcc aag atc aac tca    4869
Gln Glu Trp Leu Gln Asp Thr Ser Leu Tyr Ser Ala Lys Ile Asn Ser
                1495                1500                1505 aaa gac cac aac tgt ttc atg atg ctg gtg aat aca caa ttc tgt atg    4917
Lys Asp His Asn Cys Phe Met Met Leu Val Asn Thr Gln Phe Cys Met
1510                1515                1520 gca ctc act gat act gtc acc tgagaggaag acgggggaag agacagagta       4968
Ala Leu Thr Asp Thr Val Thr
1525                1530 tgggcttaaa gaaacaagac tgtataataa atacagatta aaaaagaaaa atcgccacca    5028
tctcccctgt tggcctgatt accccgatcc tgctatgtaa cacagcaatc cctcccctgg    5088
agaccagagg ggcttggcac tgtggtggaa gccagaacga gcaggccctt aggaaagaag    5148
gcaggaacag gaactggctt caccagaaaa gctagaccct cggactcctc ctggaaactc    5208
tcagaaggga gggttatggc cctctttgtc ccttcatatt tctggacaaa gaccaccaac    5268
ccaatatcaa gccccataaa gagcttttag aaaaacagca taagctttggg atgacaggcg   5328 tttctggact ccctgtgatc tcttccaggt tcttggtctt cctcgctcgc ctccctccca    5388
ccctccctag ctgtcccccc acctcagctc ccttaccacg gccctgcctc tctacttctt    5448
ctgtcttcgt ccctggact gtccaacggc ctctggctca ctgtcccttc atcttcagca    5508
acctatcagg aaacttcttg cgcttcctgc ggacatatgg gtggccagga agtgtttatg    5568
caaca                                                                5573

<210> SEQ ID NO 31
<211> LENGTH: 22
<212> TYPE: DNA
<213> ORGANISM: Artificial Sequence
<220> FEATURE:
<223> OTHER INFORMATION: Synthetically generated primer

<400> SEQUENCE: 31
tggatgatgc tgaggtggat ga                                              22

<210> SEQ ID NO 32
<211> LENGTH: 22
<212> TYPE: DNA
<213> ORGANISM: Artificial Sequence
<220> FEATURE:
<223> OTHER INFORMATION: Synthetically generated primer

<400> SEQUENCE: 32
ggggtgcgtg atgacatcat ag                                              22

<210> SEQ ID NO 33
<211> LENGTH: 24
<212> TYPE: DNA
```

```
<213> ORGANISM: Artificial Sequence
<220> FEATURE:
<223> OTHER INFORMATION: Synthetically generated primer

<400> SEQUENCE: 33
gagtgcagat aagggtggct tttt                                          24

<210> SEQ ID NO 34
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 34
ccaattcacc atagtcttcg gcta                                          24

<210> SEQ ID NO 35
<211> LENGTH: 22
<212> TYPE: DNA
<213> ORGANISM: Artificial Sequence
<220> FEATURE:
<223> OTHER INFORMATION: Synthetically generated primer

<400> SEQUENCE: 35
gaaacgggag gagctgaaaa ag                                            22

<210> SEQ ID NO 36
<211> LENGTH: 22
<212> TYPE: DNA
<213> ORGANISM: Artificial Sequence
<220> FEATURE:
<223> OTHER INFORMATION: Synthetically generated primer

<400> SEQUENCE: 36
ccttcagggg tatccaccaa tc                                            22

<210> SEQ ID NO 37
<211> LENGTH: 59
<212> TYPE: PRT
<213> ORGANISM: Homo sapiens

<400> SEQUENCE: 37

Ser Trp Pro Phe Leu Lys Leu Val Ser Lys Ile Gln Val Pro Asp Tyr
  1               5                  10                  15

Tyr Asp Ile Ile Lys Lys Pro Ile Ala Leu Asn Ile Ile Arg Glu Lys
             20                  25                  30

Val Asn Lys Cys Glu Tyr Lys Leu Ala Ser Glu Phe Ile Asp Asp Ile
         35                  40                  45

Glu Leu Met Phe Ser Asn Cys Phe Glu Tyr Asn
     50                  55

<210> SEQ ID NO 38
<211> LENGTH: 59
<212> TYPE: PRT
<213> ORGANISM: Saccharomyces cerevisiae

<400> SEQUENCE: 38

Ser Trp Pro Phe Leu Lys Pro Val Asn Lys Lys Gln Val Lys Asp Tyr
  1               5                  10                  15

Tyr Thr Val Ile Lys Arg Pro Met Asp Ile Glu Ile Ile Gly Lys Asn
             20                  25                  30

Ile Glu Ala His Arg Tyr His Ser Arg Ala Glu Tyr Leu Ala Asp Ile
```

```
                 35                  40                  45

Glu Leu Ile Ala Thr Asn Cys Glu Gln Tyr Asn
         50                  55

<210> SEQ ID NO 39
<211> LENGTH: 59
<212> TYPE: PRT
<213> ORGANISM: Homo sapiens

<400> SEQUENCE: 39

Thr Tyr Pro Phe His Thr Pro Val Asn Ala Lys Val Val Lys Asp Tyr
 1               5                  10                  15

Tyr Lys Ile Ile Thr Arg Pro Met Asp Leu Gln Ile Leu Arg Glu Asn
             20                  25                  30

Val Arg Lys Arg Leu Tyr Pro Ser Arg Glu Glu Phe Arg Glu His Leu
         35                  40                  45

Glu Leu Ile Val Lys Asn Ser Ala Thr Tyr Asn
         50                  55

<210> SEQ ID NO 40
<211> LENGTH: 59
<212> TYPE: PRT
<213> ORGANISM: Homo sapiens

<400> SEQUENCE: 40

Ala Trp Pro Phe Met Glu Pro Val Lys Arg Thr Glu Ala Pro Gly Tyr
 1               5                  10                  15

Tyr Glu Val Ile Arg Ser Pro Met Asp Leu Lys Ile Met Ser Glu Arg
             20                  25                  30

Leu Lys Asn Arg Tyr Tyr Val Ser Lys Lys Leu Phe Met Ala Asp Leu
         35                  40                  45

Gln Arg Val Phe Thr Asn Cys Lys Glu Tyr Asn
         50                  55

<210> SEQ ID NO 41
<211> LENGTH: 61
<212> TYPE: PRT
<213> ORGANISM: Homo sapiens

<400> SEQUENCE: 41

Ser Leu Pro Phe Arg Gln Pro Val Asp Pro Gln Leu Leu Gly Ile Pro
 1               5                  10                  15

Asp Tyr Glu Asp Ile Val Lys Asn Pro Met Asp Leu Ser Ile Ile Lys
             20                  25                  30

Arg Lys Leu Asp Thr Gly Gln Tyr Gln Glu Pro Trp Gln Tyr Val Asp
         35                  40                  45

Asp Val Trp Leu Met Phe Asn Asn Ala Trp Leu Tyr Asn
         50                  55                  60

<210> SEQ ID NO 42
<211> LENGTH: 45
<212> TYPE: PRT
<213> ORGANISM: Homo sapiens

<400> SEQUENCE: 42

Cys Lys Ile Cys Arg Lys Lys Gly Asp Ala Glu Asn Met Val Leu Cys
 1               5                  10                  15

Asp Gly Cys Asp Arg Gly His His Thr Tyr Cys Val Arg Pro Lys Leu
             20                  25                  30
```

```
Lys Thr Val Pro Glu Gly Asp Trp Phe Cys Pro Glu Cys
        35                  40                  45

<210> SEQ ID NO 43
<211> LENGTH: 44
<212> TYPE: PRT
<213> ORGANISM: Caenorhabditis elegans

<400> SEQUENCE: 43

Cys Gln Ile Cys Lys Ser Met Asp Gly Asp Glu Met Leu Val Cys Asp
  1               5                  10                  15

Gly Cys Glu Ser Gly Cys His Met Glu Cys Phe Arg Pro Arg Met Thr
             20                  25                  30

Lys Val Pro Glu Gly Asp Trp Phe Cys Gln Arg Cys
        35                  40

<210> SEQ ID NO 44
<211> LENGTH: 45
<212> TYPE: PRT
<213> ORGANISM: Homo sapiens

<400> SEQUENCE: 44

Cys Met Phe Cys Gly Arg Gly Asn Asn Glu Asp Lys Leu Leu Leu Cys
  1               5                  10                  15

Asp Gly Cys Asp Asp Ser Tyr His Thr Phe Cys Leu Ile Pro Pro Leu
             20                  25                  30

Pro Asp Val Pro Lys Gly Asp Trp Arg Cys Pro Lys Cys
        35                  40                  45

<210> SEQ ID NO 45
<211> LENGTH: 54
<212> TYPE: PRT
<213> ORGANISM: Homo sapiens

<400> SEQUENCE: 45

Cys Ser Phe Cys Leu Gly Thr Lys Glu Gln Asn Arg Glu Lys Lys Pro
  1               5                  10                  15

Glu Glu Leu Ile Ser Cys Ala Asp Cys Gly Asn Ser Gly His Pro Ser
             20                  25                  30

Cys Leu Lys Phe Ser Pro Glu Leu Thr Val Arg Val Lys Ala Leu Arg
        35                  40                  45

Trp Gln Cys Ile Glu Cys
         50

<210> SEQ ID NO 46
<211> LENGTH: 46
<212> TYPE: PRT
<213> ORGANISM: Homo sapiens

<400> SEQUENCE: 46

Cys Ser Ser Cys Arg Asp Gln Gly Lys Asn Ala Asp Asn Met Leu Phe
  1               5                  10                  15

Cys Asp Ser Cys Asp Arg Gly Phe His Met Glu Cys Cys Asp Pro Pro
             20                  25                  30

Leu Thr Arg Met Pro Lys Gly Met Trp Ile Cys Gln Ile Cys
        35                  40                  45

<210> SEQ ID NO 47
<211> LENGTH: 75
<212> TYPE: PRT
<213> ORGANISM: Homo sapiens
```

```
<400> SEQUENCE: 47

Cys Glu Lys Cys Phe Asn Glu Ile Gln Gly Glu Ser Val Ser Leu Gly
1               5                   10                  15

Asp Asp Pro Ser Gln Pro Gln Thr Thr Ile Asn Asn Glu Gln Phe Ser
            20                  25                  30

Lys Arg Lys Asn Asp Thr Leu Asp Pro Glu Leu Phe Val Glu Cys Thr
        35                  40                  45

Glu Cys Gly Arg Lys Met His Gln Ile Cys Val Leu His His Glu Ile
    50                  55                  60

Ile Trp Pro Ala Gly Phe Val Cys Asp Gly Cys
65                  70                  75

<210> SEQ ID NO 48
<211> LENGTH: 75
<212> TYPE: PRT
<213> ORGANISM: Homo sapiens

<400> SEQUENCE: 48

Cys Glu Lys Cys Phe Thr Glu Ile Gln Gly Glu Asn Val Thr Leu Gly
1               5                   10                  15

Asp Asp Pro Ser Gln Pro Gln Thr Thr Ile Ser Lys Asp Gln Phe Glu
            20                  25                  30

Lys Lys Lys Asn Asp Thr Leu Asp Pro Glu Pro Phe Val Asp Cys Lys
        35                  40                  45

Glu Cys Gly Arg Lys Met His Gln Ile Cys Val Leu His Tyr Asp Ile
    50                  55                  60

Ile Trp Pro Ser Gly Phe Val Cys Asp Asn Cys
65                  70                  75

<210> SEQ ID NO 49
<211> LENGTH: 59
<212> TYPE: PRT
<213> ORGANISM: Homo sapiens

<400> SEQUENCE: 49

Ser Trp Pro Phe Leu Lys Leu Val Ser Lys Ile Gln Val Pro Asp Tyr
1               5                   10                  15

Tyr Asp Ile Ile Lys Lys Pro Ile Ala Leu Asn Ile Ile Arg Glu Lys
            20                  25                  30

Val Asn Lys Cys Glu Tyr Lys Leu Ala Ser Glu Phe Ile Asp Asp Ile
        35                  40                  45

Glu Leu Met Phe Ser Asn Cys Phe Glu Tyr Asn
    50                  55

<210> SEQ ID NO 50
<211> LENGTH: 59
<212> TYPE: PRT
<213> ORGANISM: Homo sapiens

<400> SEQUENCE: 50

Ser Trp Pro Phe His His Pro Val Asn Lys Lys Phe Val Pro Asp Tyr
1               5                   10                  15

Tyr Lys Val Ile Val Asn Pro Met Asp Ile Glu Thr Ile Arg Lys Asn
            20                  25                  30

Ile Ser Lys His Lys Tyr Gln Ser Arg Glu Ser Phe Leu Asp Asp Val
        35                  40                  45

Asn Leu Ile Leu Ala Asn Ser Val Lys Tyr Asn
```

```
                50                  55

<210> SEQ ID NO 51
<211> LENGTH: 59
<212> TYPE: PRT
<213> ORGANISM: Homo sapiens

<400> SEQUENCE: 51

Ala Trp Pro Phe Leu Glu Pro Val Asn Pro Arg Leu Val Ser Gly Tyr
 1               5                  10                  15

Arg Arg Ile Ile Lys Asn Pro Met Asp Phe Ser Thr Met Arg Glu Arg
            20                  25                  30

Leu Leu Arg Gly Gly Tyr Thr Ser Ser Glu Glu Phe Ala Ala Asp Ala
        35                  40                  45

Leu Leu Val Phe Asp Asn Cys Gln Thr Phe Asn
    50                  55

<210> SEQ ID NO 52
<211> LENGTH: 59
<212> TYPE: PRT
<213> ORGANISM: Homo sapiens

<400> SEQUENCE: 52

Ala Trp Pro Phe Met Glu Pro Val Lys Arg Thr Glu Ala Pro Gly Tyr
 1               5                  10                  15

Tyr Glu Val Ile Arg Ser Pro Met Asp Leu Lys Thr Met Ser Glu Arg
            20                  25                  30

Leu Lys Asn Arg Tyr Tyr Val Ser Lys Lys Leu Phe Met Ala Asp Leu
        35                  40                  45

Gln Arg Val Phe Thr Asn Cys Lys Glu Tyr Asn
    50                  55

<210> SEQ ID NO 53
<211> LENGTH: 82
<212> TYPE: PRT
<213> ORGANISM: Caenorhabditis elegans

<400> SEQUENCE: 53

Ala Leu Pro Phe Leu Glu Pro Val Asn Pro Lys Leu Val Pro Gly Tyr
 1               5                  10                  15

Lys Met Ile Ile Ser Lys Pro Met Asp Leu Lys Thr Ile Arg Gln Lys
            20                  25                  30

Asn Glu Lys Leu Ile Val Ser Glu Thr Tyr Gln Phe Cys Phe Phe Ala
        35                  40                  45

Ile Phe Asp Leu Lys Leu Lys Met Lys Ile Thr Gln Tyr Glu Thr Pro
    50                  55                  60

Glu Asp Phe Ala Glu Asp Ile Glu Leu Met Phe Ala Asn Cys Arg Gln
65                  70                  75                  80

Phe Asn

<210> SEQ ID NO 54
<211> LENGTH: 61
<212> TYPE: PRT
<213> ORGANISM: Homo sapiens

<400> SEQUENCE: 54

Ser Leu Pro Phe Arg Gln Pro Val Asp Pro Gln Leu Leu Gly Ile Pro
 1               5                  10                  15

Asp Tyr Phe Asp Ile Val Lys Met Pro Met Asp Leu Ser Thr Ile Lys
```

```
                    20                  25                  30

Arg Lys Leu Asp Thr Gly Gln Tyr Gln Glu Pro Trp Gln Tyr Val Asp
        35                  40                  45

Asp Val Trp Leu Met Phe Asn Asn Ala Trp Leu Tyr Asn
    50                  55                  60

<210> SEQ ID NO 55
<211> LENGTH: 45
<212> TYPE: PRT
<213> ORGANISM: Homo sapiens

<400> SEQUENCE: 55

Cys Lys Ile Cys Arg Lys Lys Gly Asp Ala Glu Asn Met Val Leu Cys
1               5                   10                  15

Asp Gly Cys Asp Arg Gly His His Thr Tyr Cys Val Arg Pro Lys Leu
                20                  25                  30

Lys Thr Val Pro Glu Gly Asp Trp Phe Cys Pro Glu Cys
        35                  40                  45

<210> SEQ ID NO 56
<211> LENGTH: 44
<212> TYPE: PRT
<213> ORGANISM: Caenorhabditis elegans

<400> SEQUENCE: 56

Cys Gln Ile Cys Lys Ser Met Asp Gly Asp Glu Met Leu Val Cys Asp
1               5                   10                  15

Gly Cys Glu Ser Gly Cys His Met Glu Cys Phe Arg Pro Arg Met Thr
                20                  25                  30

Lys Val Pro Glu Gly Asp Trp Phe Cys Gln Arg Cys
        35                  40

<210> SEQ ID NO 57
<211> LENGTH: 44
<212> TYPE: PRT
<213> ORGANISM: Homo sapiens

<400> SEQUENCE: 57

Cys Met Phe Cys Gly Arg Gly Asn Asn Glu Asp Lys Leu Leu Leu Cys
1               5                   10                  15

Asp Gly Cys Asp Ser Tyr His Thr Phe Cys Leu Ile Pro Pro Leu Pro
                20                  25                  30

Asp Val Pro Lys Gly Asp Trp Arg Cys Pro Lys Cys
        35                  40

<210> SEQ ID NO 58
<211> LENGTH: 54
<212> TYPE: PRT
<213> ORGANISM: Homo sapiens

<400> SEQUENCE: 58

Cys Ser Phe Cys Leu Gly Thr Lys Glu Gln Asn Arg Glu Lys Lys Pro
1               5                   10                  15

Glu Glu Leu Ile Ser Cys Ala Asp Cys Gly Asn Ser Gly His Pro Ser
                20                  25                  30

Cys Leu Lys Phe Ser Pro Glu Leu Thr Val Arg Val Lys Ala Leu Arg
        35                  40                  45

Trp Gln Cys Ile Glu Cys
    50
```

<210> SEQ ID NO 59
<211> LENGTH: 46
<212> TYPE: PRT
<213> ORGANISM: Homo sapiens

<400> SEQUENCE: 59

Cys Ser Ser Cys Arg Asp Gln Gly Lys Asn Ala Asp Asn Met Leu Phe
1               5                   10                  15

Cys Asp Ser Cys Asp Arg Gly Phe His Met Glu Cys Cys Asp Pro Pro
            20                  25                  30

Leu Thr Arg Met Pro Lys Gly Met Trp Ile Cys Gln Ile Cys
        35                  40                  45

<210> SEQ ID NO 60
<211> LENGTH: 75
<212> TYPE: PRT
<213> ORGANISM: Homo sapiens

<400> SEQUENCE: 60

Cys Glu Lys Cys Phe Asn Glu Ile Gln Gly Glu Ser Val Ser Leu Gly
1               5                   10                  15

Asp Asp Pro Ser Gln Pro Gln Thr Thr Ile Asn Lys Glu Gln Phe Ser
            20                  25                  30

Lys Arg Lys Asn Asp Thr Leu Asp Pro Glu Leu Phe Val Glu Cys Thr
        35                  40                  45

Glu Cys Gly Arg Lys Met His Gln Ile Cys Val Leu His His Glu Ile
    50                  55                  60

Ile Trp Pro Ala Gly Phe Val Cys Asp Gly Cys
65                  70                  75

<210> SEQ ID NO 61
<211> LENGTH: 45
<212> TYPE: PRT
<213> ORGANISM: Homo sapiens

<400> SEQUENCE: 61

Cys Leu Val Cys Arg Lys Gly Asp Asn Asp Arg Phe Leu Leu Leu Cys
1               5                   10                  15

Asp Gly Cys Asp Arg Gly Cys His Ile Tyr Cys His Arg Pro Lys Met
            20                  25                  30

Glu Ala Val Pro Glu Gly Asp Trp Phe Cys Thr Val Cys
        35                  40                  45

<210> SEQ ID NO 62
<211> LENGTH: 211
<212> TYPE: PRT
<213> ORGANISM: Homo sapiens

<400> SEQUENCE: 62

Arg Glu Glu Lys Arg Lys Tyr Val Glu Tyr Leu Lys Gln Trp Ser Lys
1               5                   10                  15

Pro Arg Glu Asp Met Glu Cys Asp Asp Leu Lys Glu Leu Pro Glu Pro
            20                  25                  30

Thr Pro Val Lys Thr Arg Leu Pro Pro Glu Ile Phe Gly Asp Ala Leu
        35                  40                  45

Met Val Leu Glu Phe Leu Asn Ala Phe Gly Glu Leu Phe Asp Leu Gln
    50                  55                  60

Asp Glu Phe Pro Asp Gly Val Thr Leu Glu Val Leu Glu Glu Ala Leu
65                  70                  75                  80

```
Val Gly Asn Asp Ser Glu Gly Pro Leu Cys Glu Leu Phe Phe Phe
                85                  90                  95

Leu Thr Ala Ile Phe Gln Ala Ile Ala Glu Glu Glu Glu Val Ala
            100                 105                 110

Lys Glu Gln Leu Thr Asp Ala Asp Thr Lys Gly Cys Ser Leu Lys Ser
        115                 120                 125

Leu Asp Leu Asp Ser Cys Thr Leu Ser Glu Ile Leu Arg Leu His Ile
    130                 135                 140

Leu Ala Ser Gly Ala Asp Val Thr Ser Ala Asn Ala Lys Tyr Arg Tyr
145                 150                 155                 160

Gln Lys Arg Gly Gly Phe Asp Ala Thr Asp Asp Ala Cys Met Glu Leu
                165                 170                 175

Arg Leu Ser Asn Pro Ser Leu Val Lys Lys Leu Ser Ser Thr Ser Val
                180                 185                 190

Tyr Asp Leu Thr Pro Gly Glu Lys Met Lys Ile Leu His Ala Leu Cys
            195                 200                 205

Gly Lys Leu
    210

<210> SEQ ID NO 63
<211> LENGTH: 185
<212> TYPE: PRT
<213> ORGANISM: Caenorhabditis elegans

<400> SEQUENCE: 63

Leu Asn Asp Glu Phe Thr Glu Glu Leu Val His Ser Gln Ile Met Ser
  1               5                  10                  15

Asn Gly Val Asp Glu Cys Lys Ile Arg Glu Arg Glu Ala Asp Asp Leu
             20                  25                  30

Leu Val Asn Ile Asn Asp Val Arg His Leu Pro Asp Phe Ser Arg Ile
         35                  40                  45

Gly Asn Gln Cys Leu Ser Ser Gln Gly Phe Ala Asp Ala Leu Met Val
     50                  55                  60

His Glu Phe Val Gln Asn Phe Gly His Val Leu Gly Ile Asp Leu Glu
 65                  70                  75                  80

Ile Ala Pro Lys Leu Glu Ser Leu Cys Ala Gly Leu Asp Gly Asp Ala
                 85                  90                  95

Asn His Ala Glu Gln Thr Leu Gln Leu Thr Arg Gln Leu Leu Arg Leu
            100                 105                 110

Ala Leu Glu Phe Pro Gly Met Gly Asn Glu Lys Arg Phe Gly Gln Gly
        115                 120                 125

Gly Gly Glu Met Gly Leu Asp Arg Glu Asn Phe Ser Glu Val Met Arg
    130                 135                 140

Leu Phe Leu Ile Asp Lys Gly Lys Arg Gly Glu Glu Leu Ser Gln Pro
145                 150                 155                 160

Leu Leu Thr Cys Asn Phe Leu Ser Ile Ser Pro Glu Gln Lys Ala Ser
                165                 170                 175

Ile Leu Ala Phe Leu Cys Asp Glu Leu
            180                 185

<210> SEQ ID NO 64
<211> LENGTH: 175
<212> TYPE: PRT
<213> ORGANISM: Homo sapiens

<400> SEQUENCE: 64
```

Leu Glu Glu Arg Gln Lys Gln Met Ile Leu Glu Met Lys Lys
 1               5                  10                  15

Pro Thr Glu Asp Met Cys Leu Thr Asp His Gln Pro Leu Pro Asp Phe
                20                  25                  30

Ser Arg Val Pro Gly Leu Thr Leu Pro Ser Gly Ala Phe Ser Asp Cys
            35                  40                  45

Leu Thr Ile Val Glu Phe Leu His Ser Phe Gly Lys Val Leu Gly Phe
        50                  55                  60

Asp Pro Ala Lys Asp Val Pro Ser Leu Gly Val Leu Gln Glu Gly Leu
 65                  70                  75                  80

Leu Cys Gln Gly Asp Ser Leu Gly Glu Val Gln Asp Leu Leu Val Arg
                85                  90                  95

Leu Leu Lys Ala Ala Leu His Asp Pro Gly Phe Pro Ser Tyr Cys Gln
                100                 105                 110

Ser Leu Lys Ile Leu Gly Glu Lys Val Ser Glu Ile Pro Leu Thr Arg
                115                 120                 125

Asp Asn Val Ser Glu Ile Leu Arg Cys Pro Leu Met Ala Tyr Gly Val
 130                 135                 140

Glu Pro Ala Leu Cys Asp Arg Leu Arg Thr Gln Pro Pro Gln Ala Gln
145                 150                 155                 160

Pro Pro Gln Lys Ala Ala Val Leu Ala Phe Pro Val His Glu Leu
                165                 170                 175

<210> SEQ ID NO 65
<211> LENGTH: 176
<212> TYPE: PRT
<213> ORGANISM: Homo sapiens

<400> SEQUENCE: 65

Leu Glu Gln Arg Arg Leu Glu Leu Glu Met Ala Lys Glu Leu Lys Lys
 1               5                  10                  15

Pro Asn Glu Asp Met Cys Leu Ala Asp Gln Lys Pro Leu Pro Glu Leu
                20                  25                  30

Pro Arg Ile Pro Gly Leu Val Leu Ser Gly Ser Thr Phe Ser Asp Cys
            35                  40                  45

Leu Met Val Val Gln Phe Leu Arg Asn Phe Gly Lys Val Leu Gly Phe
        50                  55                  60

Asp Val Asn Ile Asp Val Pro Asn Leu Ser Val Leu Gln Glu Gly Leu
 65                  70                  75                  80

Leu Asn Ile Gly Asp Ser Met Gly Glu Val Gln Asp Leu Leu Val Arg
                85                  90                  95

Leu Leu Ser Ala Ala Val Cys Asp Pro Gly Leu Ile Thr Gly Tyr Lys
                100                 105                 110

Ala Lys Thr Ala Leu Gly Glu His Leu Leu Asn Val Gly Val Asn Arg
                115                 120                 125

Asp Asn Val Ser Glu Ile Leu Gln Ile Phe Met Glu Ala His Cys Gly
 130                 135                 140

Gln Thr Glu Leu Thr Glu Ser Leu Lys Thr Lys Ala Phe Gln Ala His
145                 150                 155                 160

Thr Pro Ala Gln Lys Ala Ser Val Leu Ala Phe Leu Ile Asn Glu Leu
                165                 170                 175

<210> SEQ ID NO 66
<211> LENGTH: 59
<212> TYPE: PRT

<213> ORGANISM: Homo sapiens

<400> SEQUENCE: 66

Tyr Pro Ile Thr Ala Val Ser Leu Met Glu Ala Leu Ser Ala Asp Lys
1               5                   10                  15

Gly Gly Phe Leu Tyr Leu Asn Arg Val Leu Val Ile Leu Leu Gln Thr
            20                  25                  30

Leu Leu Gln Asp Glu Ile Ala Glu Asp Tyr Gly Glu Leu Gly Met Lys
        35                  40                  45

Leu Ser Glu Ile Pro Leu His Ser Val Ser Glu
    50                  55

<210> SEQ ID NO 67
<211> LENGTH: 65
<212> TYPE: PRT
<213> ORGANISM: Homo sapiens

<400> SEQUENCE: 67

Tyr Pro Ile Thr Ala Val Ser Leu Met Glu Ala Leu Ser Ala Asp Lys
1               5                   10                  15

Gly Gly Phe Leu Tyr Leu Asn Arg Val Leu Val Ile Leu Leu Gln Thr
            20                  25                  30

Leu Leu Gln Thr Leu Leu Gln Asp Glu Ile Ala Glu Asp Tyr Gly Glu
        35                  40                  45

Leu Gly Met Lys Leu Ser Lys Ile Pro Leu Thr Leu His Ser Val Ser
    50                  55                  60

Glu
 65

<210> SEQ ID NO 68
<211> LENGTH: 1525
<212> TYPE: PRT
<213> ORGANISM: Homo sapiens

<400> SEQUENCE: 68

Met Ala Pro Leu Leu Gly Arg Lys Pro Phe Pro Leu Val Asn Pro Leu
1               5                   10                  15

Pro Gly Glu Glu Pro Phe Phe Thr Ile Pro His Thr Gln Glu Ala Phe
            20                  25                  30

Arg Thr Arg Glu Glu Tyr Glu Ala Arg Leu Glu Arg Tyr Ser Glu Arg
        35                  40                  45

Ile Trp Thr Cys Lys Ser Thr Gly Ser Ser Gln Leu Thr His Lys Glu
    50                  55                  60

Ala Trp Glu Glu Gln Glu Val Ala Glu Leu Leu Lys Glu Phe
65                  70                  75                  80

Pro Ala Trp Tyr Glu Lys Leu Val Leu Glu Met Val His His Asn Thr
                85                  90                  95

Ala Ser Leu Glu Lys Leu Val Asp Thr Ala Trp Leu Glu Ile Met Thr
            100                 105                 110

Lys Tyr Ala Val Gly Glu Glu Cys Asp Phe Glu Val Gly Lys Glu Lys
        115                 120                 125

Met Leu Lys Val Lys Ile Val Lys Ile His Pro Leu Glu Lys Val Asp
    130                 135                 140

Glu Glu Ala Thr Glu Lys Lys Ser Asp Gly Ala Cys Asp Ser Pro Ser
145                 150                 155                 160

Ser Asp Lys Glu Asn Ser Ser Gln Ile Ala Gln Asp His Gln Lys Lys
                165                 170                 175

-continued

```
Glu Thr Val Val Lys Glu Asp Glu Gly Arg Arg Glu Ser Ile Asn Asp
            180                 185                 190

Arg Ala Arg Arg Ser Pro Arg Lys Leu Pro Thr Ser Leu Lys Lys Gly
        195                 200                 205

Glu Arg Lys Trp Ala Pro Pro Lys Phe Leu Pro His Lys Tyr Asp Val
    210                 215                 220

Lys Leu Gln Asn Glu Asp Lys Ile Ile Ser Asn Val Pro Ala Asp Ser
225                 230                 235                 240

Leu Ile Arg Thr Glu Arg Pro Pro Asn Lys Glu Ile Val Arg Tyr Phe
                245                 250                 255

Ile Arg His Asn Ala Leu Arg Ala Gly Thr Gly Glu Asn Ala Pro Trp
            260                 265                 270

Val Val Glu Asp Glu Leu Val Lys Tyr Ser Leu Pro Ser Lys Phe
        275                 280                 285

Ser Asp Phe Leu Leu Asp Pro Tyr Lys Tyr Met Thr Leu Asn Pro Ser
    290                 295                 300

Thr Lys Arg Lys Asn Thr Gly Ser Pro Asp Arg Lys Pro Ser Lys Lys
305                 310                 315                 320

Ser Lys Thr Asp Asn Ser Ser Leu Ser Ser Pro Leu Asn Pro Lys Leu
                325                 330                 335

Trp Cys His Val His Leu Lys Lys Ser Leu Ser Gly Ser Pro Leu Lys
            340                 345                 350

Val Lys Asn Ser Lys Asn Ser Lys Ser Pro Glu Glu His Leu Glu Glu
        355                 360                 365

Met Met Lys Met Met Ser Pro Asn Lys Leu His Thr Asn Pro His Ile
    370                 375                 380

Pro Lys Lys Gly Pro Pro Ala Lys Pro Gly Lys His Ser Asp Lys
385                 390                 395                 400

Pro Leu Lys Ala Lys Gly Arg Ser Lys Gly Ile Leu Asn Gly Gln Lys
                405                 410                 415

Ser Thr Gly Asn Ser Lys Ser Pro Lys Lys Gly Leu Lys Thr Pro Lys
            420                 425                 430

Thr Lys Met Lys Gln Met Thr Leu Leu Asp Met Ala Lys Gly Thr Gln
        435                 440                 445

Lys Met Thr Arg Ala Pro Arg Asn Ser Gly Gly Thr Pro Arg Thr Ser
    450                 455                 460

Ser Lys Pro His Lys His Leu Pro Pro Ala Ala Leu His Leu Ile Ala
465                 470                 475                 480

Tyr Tyr Lys Glu Asn Lys Asp Arg Glu Asp Lys Arg Ser Ala Leu Ser
                485                 490                 495

Cys Val Ile Ser Lys Thr Ala Arg Leu Leu Ser Ser Glu Asp Arg Ala
            500                 505                 510

Arg Leu Pro Glu Glu Leu Arg Ser Leu Val Gln Lys Arg Tyr Glu Leu
        515                 520                 525

Leu Glu His Lys Lys Arg Trp Ala Ser Met Ser Glu Glu Gln Arg Lys
    530                 535                 540

Glu Tyr Leu Lys Lys Arg Glu Glu Leu Lys Lys Leu Lys Glu
545                 550                 555                 560

Lys Ala Lys Glu Arg Arg Glu Lys Glu Met Leu Glu Arg Leu Glu Lys
                565                 570                 575

Gln Lys Arg Tyr Glu Asp Gln Glu Leu Thr Gly Lys Asn Leu Pro Ala
            580                 585                 590
```

```
Phe Arg Leu Val Asp Thr Pro Glu Gly Leu Pro Asn Thr Leu Phe Gly
        595                 600                 605

Asp Val Ala Met Val Val Glu Phe Leu Ser Cys Tyr Ser Gly Leu Leu
        610                 615                 620

Leu Pro Asp Ala Gln Tyr Pro Ile Thr Ala Val Ser Leu Met Glu Ala
625                 630                 635                 640

Leu Ala Asp Lys Gly Gly Phe Leu Tyr Leu Asn Arg Val Leu Val Ile
                645                 650                 655

Leu Leu Gln Thr Leu Leu Gln Asp Glu Ile Ala Glu Asp Tyr Gly Glu
            660                 665                 670

Leu Gly Met Lys Leu Ser Glu Ile Pro Leu Thr Leu His Ser Val Ser
        675                 680                 685

Glu Leu Val Arg Leu Cys Leu Arg Arg Ser Asp Val Gln Glu Glu Ser
        690                 695                 700

Glu Gly Ser Asp Thr Asp Asn Lys Asp Ser Ala Ala Phe Glu Asp
705                 710                 715                 720

Asn Glu Val Gln Asp Glu Phe Leu Glu Lys Leu Glu Thr Ser Glu Phe
                725                 730                 735

Phe Glu Leu Thr Ser Glu Glu Lys Gln Ile Leu Thr Ala Leu Cys
            740                 745                 750

His Arg Ile Leu Met Thr Tyr Ser Val Gln Asp His Met Glu Thr Arg
        755                 760                 765

Gln Gln Met Ser Ala Glu Leu Trp Lys Glu Arg Leu Ala Val Leu Lys
        770                 775                 780

Glu Glu Asn Asp Lys Lys Arg Ala Glu Lys Gln Lys Arg Lys Glu Met
785                 790                 795                 800

Glu Ala Lys Asn Lys Glu Asn Gly Lys Val Glu Asn Gly Leu Gly Lys
                805                 810                 815

Thr Asp Arg Lys Lys Arg Ile Val Lys Phe Glu Pro Gln Val Asp Thr
            820                 825                 830

Glu Ala Glu Asp Met Ile Ser Ala Val Lys Ser Arg Arg Leu Leu Ala
        835                 840                 845

Ile Gln Ala Lys Lys Glu Arg Glu Ile Gln Glu Arg Glu Met Lys Val
        850                 855                 860

Lys Leu Glu Arg Gln Ala Glu Glu Glu Arg Ile Arg Lys His Lys Ala
865                 870                 875                 880

Ala Ala Glu Lys Ala Phe Gln Glu Gly Ile Ala Lys Ala Lys Leu Val
                885                 890                 895

Met Arg Arg Thr Pro Ile Gly Thr Asp Arg Asn His Asn Arg Tyr Trp
            900                 905                 910

Leu Phe Ser Asp Glu Val Pro Gly Leu Phe Ile Glu Lys Gly Trp Val
        915                 920                 925

His Asp Ser Ile Asp Tyr Arg Phe Asn His His Cys Lys Asp His Thr
        930                 935                 940

Val Ser Gly Cys Glu Asp Tyr Cys Pro Arg Ser Lys Lys Ala Asn Leu
945                 950                 955                 960

Gly Lys Asn Ala Ser Met Asn Thr Gln His Gly Thr Ala Thr Glu Val
                965                 970                 975

Ala Val Glu Thr Thr Thr Pro Lys Gln Gly Gln Asn Leu Trp Phe Leu
            980                 985                 990

Cys Asp Ser Gln Lys Glu Leu Asp Glu Leu Leu Asn Cys Leu His Pro
        995                 1000                1005

Gln Gly Ile Arg Glu Ser Gln Leu Lys Glu Arg Leu Glu Lys Arg Tyr
```

```
                1010                1015                1020
Gln Asp Ile Ile His Ser Leu His Leu Ala Arg Lys Pro Asn Leu Gly
1025                1030                1035                1040

Leu Lys Ser Cys Asp Gly Asn Gln Glu Leu Leu Asn Phe Leu Arg Ser
                1045                1050                1055

Asp Leu Ile Glu Val Ala Thr Arg Leu Gln Lys Gly Gly Leu Gly Tyr
                1060                1065                1070

Val Glu Glu Thr Ser Glu Phe Glu Ala Arg Val Ile Ser Leu Glu Lys
                1075                1080                1085

Leu Lys Asp Phe Gly Cys Val Ile Ala Leu Gln Ala Ser Val Ile
1090                1095                1100

Lys Lys Phe Leu Gln Gly Phe Met Ala Pro Lys Gln Lys Arg Arg Lys
1105                1110                1115                1120

Leu Gln Ser Glu Asp Ser Ala Lys Thr Glu Glu Val Asp Glu Glu Lys
                1125                1130                1135

Lys Met Val Glu Ala Lys Val Ala Ser Ala Leu Glu Lys Trp Lys
                1140                1145                1150

Thr Ala Ile Arg Glu Ala Gln Thr Phe Ser Arg Met His Val Leu Leu
                1155                1160                1165

Gly Met Leu Asp Ala Cys Ile Lys Trp Asp Met Ser Ala Glu Asn Ala
                1170                1175                1180

Arg Cys Lys Val Cys Pro Lys Lys Gly Glu Asp Asp Lys Leu Ile Leu
1185                1190                1195                1200

Cys Asp Glu Cys Asn Lys Ala Phe His Leu Phe Cys Leu Arg Pro Ala
                1205                1210                1215

Leu Tyr Glu Val Pro Asp Gly Glu Trp Gln Cys Pro Ala Cys Gln Pro
                1220                1225                1230

Ala Thr Ala Arg Arg Asn Ser Arg Gly Arg Asn Tyr Thr Glu Glu Ser
                1235                1240                1245

Ala Ser Glu Asp Ser Glu Asp Glu Ser Asp Glu Glu Glu Glu Glu
                1250                1255                1260

Glu Glu Glu Glu Glu Glu Glu Asp Tyr Glu Val Ala Gly Leu Arg Leu
1265                1270                1275                1280

Arg Pro Arg Lys Thr Ile Arg Gly Lys His Ser Val Ile Pro Pro Ala
                1285                1290                1295

Ala Arg Ser Gly Arg Arg Pro Gly Lys Lys Pro His Ser Thr Arg Arg
                1300                1305                1310

Ser Gln Pro Lys Ala Pro Pro Val Asp Ala Glu Val Asp Glu Leu Val
                1315                1320                1325

Leu Gln Thr Lys Arg Ser Ser Arg Arg Gln Ser Leu Glu Leu Gln Lys
                1330                1335                1340

Cys Glu Glu Ile Leu His Lys Ile Val Lys Tyr Arg Phe Ser Trp Pro
1345                1350                1355                1360

Phe Arg Glu Pro Val Thr Arg Asp Glu Ala Glu Asp Tyr Tyr Asp Val
                1365                1370                1375

Ile Thr His Pro Met Asp Phe Gln Thr Val Gln Asn Lys Cys Ser Cys
                1380                1385                1390

Gly Ser Tyr Arg Ser Val Gln Glu Phe Leu Thr Asp Met Lys Gln Val
                1395                1400                1405

Phe Thr Asn Ala Glu Val Tyr Asn Cys Arg Gly Ser His Val Leu Ser
                1410                1415                1420

Cys Met Val Lys Thr Glu Gln Cys Leu Val Val Leu Leu His Lys His
1425                1430                1435                1440
```

```
Leu Pro Gly His Pro Tyr Val Arg Arg Lys Arg Lys Phe Pro Asp
            1445                1450                1455

Arg Leu Ala Glu Asp Glu Gly Asp Ser Glu Pro Glu Ala Val Gly Gln
        1460                1465                1470

Ser Arg Asp Glu Asp Arg Arg Ser Arg Glu Ala Glu Ile Gln Glu Trp
    1475                1480                1485

Leu Gln Asp Thr Ser Leu Tyr Ala Ser Ala Lys Ile Asn Ser Lys Asp
        1490                1495                1500

His Asn Cys Phe Met Met Leu Val Asn Thr Gln Phe Cys Met Ala Leu
1505                1510                1515                1520

Thr Asp Thr Val Thr
            1525

<210> SEQ ID NO 69
<211> LENGTH: 1673
<212> TYPE: PRT
<213> ORGANISM: Homo sapiens

<400> SEQUENCE: 69

Met Glu Asp Ala Ser Glu Ser Ser Arg Gly Val Ala Pro Leu Ile Asn
 1               5                  10                  15

Asn Val Val Leu Pro Gly Ser Pro Leu Ser Leu Pro Val Ser Val Thr
                20                  25                  30

Gly Cys Lys Ser His Arg Val Ala Asn Lys Lys Val Glu Ala Arg Ser
            35                  40                  45

Glu Lys Leu Leu Pro Thr Ala Leu Pro Pro Ser Glu Pro Lys Val Asp
        50                  55                  60

Gln Lys Leu Pro Arg Ser Ser Glu Arg Arg Gly Ser Gly Gly Gly Thr
65                  70                  75                  80

Gln Phe Pro Ala Arg Ser Arg Ala Val Ala Ala Gly Glu Ala Ala Ala
                85                  90                  95

Arg Gly Ala Ala Gly Pro Glu Arg Gly Ser Pro Leu Gly Arg Arg Val
            100                 105                 110

Ser Pro Arg Cys Leu Cys Ser Gly Glu Gly Gln Val Ala Val Ala Gly
        115                 120                 125

Val Ile Ala Gly Lys Arg Gly Arg Arg Gly Arg Asp Gly Ser Arg Arg
130                 135                 140

Ala Pro Gly Gly Arg Glu Met Pro Leu Leu His Arg Lys Pro Phe Val
145                 150                 155                 160

Arg Gln Lys Pro Pro Ala Asp Leu Arg Pro Asp Glu Val Phe Tyr
                165                 170                 175

Cys Lys Val Thr Asn Glu Ile Phe Arg His Tyr Asp Asp Phe Phe Glu
            180                 185                 190

Arg Thr Ile Leu Cys Asn Ser Leu Val Trp Ser Cys Ala Val Thr Gly
        195                 200                 205

Arg Pro Gly Leu Thr Tyr Gln Glu Ala Leu Glu Ser Glu Lys Lys Ala
    210                 215                 220

Arg Gln Asn Leu Gln Ser Phe Pro Glu Pro Leu Ile Ile Pro Val Leu
225                 230                 235                 240

Tyr Leu Thr Ser Leu Thr His Arg Ser Arg Leu His Glu Ile Cys Asp
                245                 250                 255

Asp Ile Phe Ala Tyr Val Lys Asp Arg Tyr Phe Val Glu Glu Thr Val
            260                 265                 270

Glu Val Ile Arg Asn Asn Gly Ala Arg Leu Gln Cys Thr Ile Leu Glu
```

-continued

```
                275                 280                 285
Val Leu Pro Pro Ser His Gln Asn Gly Phe Ala Asn Gly His Val Asn
290                 295                 300
Ser Val Asp Gly Glu Thr Ile Ile Ile Ser Asp Ser Asp Ser Glu
305                 310                 315                 320
Thr Gln Ser Cys Ser Phe Gln Asn Gly Lys Lys Asp Ala Ile Asp
            325                 330                 335
Pro Leu Leu Phe Lys Tyr Lys Val Gln Pro Thr Lys Lys Glu Leu His
                340                 345                 350
Glu Ser Ala Ile Val Lys Ala Thr Gln Ile Ser Arg Arg Lys His Leu
        355                 360                 365
Phe Ser Arg Asp Lys Leu Lys Leu Phe Leu Lys Gln His Cys Glu Pro
370                 375                 380
Gln Glu Gly Val Ile Lys Ile Lys Ala Ser Ser Leu Ser Thr Tyr Lys
385                 390                 395                 400
Ile Ala Glu Gln Asp Phe Ser Tyr Phe Phe Pro Asp Asp Pro Pro Thr
                405                 410                 415
Phe Ile Phe Ser Pro Ala Asn Arg Arg Arg Gly Arg Pro Pro Lys Arg
            420                 425                 430
Ile His Ile Ser Gln Glu Asp Asn Val Ala Asn Lys Gln Thr Leu Ala
        435                 440                 445
Ser Tyr Arg Ser Lys Ala Thr Lys Glu Arg Asp Lys Leu Leu Lys Gln
    450                 455                 460
Glu Glu Met Lys Ser Leu Ala Phe Glu Lys Ala Lys Leu Lys Arg Glu
465                 470                 475                 480
Lys Ala Asp Ala Leu Glu Ala Lys Lys Glu Lys Glu Asp Lys Glu
                485                 490                 495
Lys Lys Arg Glu Glu Leu Lys Lys Ile Val Glu Glu Arg Leu Lys
            500                 505                 510
Lys Lys Glu Glu Lys Glu Arg Leu Lys Val Glu Arg Glu Lys Glu Arg
        515                 520                 525
Glu Lys Leu Arg Glu Glu Lys Arg Lys Tyr Val Glu Tyr Lys Gln Trp
    530                 535                 540
Ser Lys Pro Arg Glu Asp Met Glu Cys Asp Asp Leu Lys Glu Leu Pro
545                 550                 555                 560
Glu Pro Thr Pro Val Lys Thr Arg Leu Pro Pro Glu Ile Phe Gly Asp
                565                 570                 575
Ala Leu Met Val Leu Glu Phe Leu Asn Ala Phe Gly Glu Leu Phe Asp
            580                 585                 590
Leu Gln Asp Glu Phe Pro Asp Gly Val Thr Leu Glu Val Leu Glu Glu
        595                 600                 605
Ala Leu Val Gly Asn Asp Ser Glu Gly Pro Leu Cys Glu Leu Leu Phe
    610                 615                 620
Phe Phe Leu Thr Ala Ile Phe Gln Ala Ile Ala Glu Glu Glu Glu
625                 630                 635                 640
Val Ala Lys Glu Gln Leu Thr Asp Ala Asp Thr Lys Gly Cys Ser Leu
                645                 650                 655
Lys Ser Leu Asp Leu Asp Ser Cys Thr Leu Ser Glu Ile Leu Arg Leu
            660                 665                 670
His Ile Leu Ala Ser Gly Ala Asp Val Thr Ser Ala Asn Ala Lys Tyr
        675                 680                 685
Arg Tyr Gln Lys Arg Gly Gly Phe Asp Ala Thr Asp Asp Ala Cys Met
    690                 695                 700
```

-continued

```
Glu Leu Arg Leu Ser Asn Pro Ser Leu Val Lys Lys Leu Ser Ser Thr
705                 710                 715                 720

Ser Val Tyr Asp Leu Thr Pro Gly Glu Lys Met Lys Ile Leu His Ala
            725                 730                 735

Leu Cys Gly Lys Leu Leu Thr Leu Val Ser Thr Arg Asp Phe Ile Glu
            740                 745                 750

Asp Tyr Val Asp Ile Leu Arg Gln Ala Lys Gln Glu Phe Arg Glu Leu
            755                 760                 765

Lys Ala Glu Gln His Arg Lys Glu Arg Glu Ala Ala Ala Arg Ile
770                 775                 780

Arg Lys Arg Lys Glu Glu Lys Leu Lys Glu Gln Glu Gln Lys Met Lys
785                 790                 795                 800

Glu Lys Gln Glu Lys Leu Lys Glu Asp Glu Gln Arg Asn Ser Thr Ala
                805                 810                 815

Asp Ile Ser Ile Gly Glu Glu Arg Glu Asp Phe Asp Thr Ser Ile
            820                 825                 830

Glu Ser Lys Asp Thr Glu Gln Lys Glu Leu Asp Gln Asp Met Phe Thr
            835                 840                 845

Glu Asp Glu Asp Pro Gly Ser His Lys Arg Gly Arg Gly Lys
850                 855                 860

Arg Gly Gln Asn Gly Phe Lys Glu Phe Thr Arg Gln Glu Gln Ile Asn
865                 870                 875                 880

Cys Val Thr Arg Glu Leu Leu Thr Ala Asp Glu Glu Glu Ala Leu Lys
            885                 890                 895

Gln Glu His Gln Arg Lys Glu Lys Glu Leu Leu Glu Lys Leu Gln Ser
            900                 905                 910

Ala Ile Ala Cys Thr Asn Ile Phe Pro Leu Gly Arg Asp Arg Met Tyr
            915                 920                 925

Arg Arg Tyr Trp Ile Phe Pro Ser Leu Pro Gly Leu Phe Ile Glu Glu
930                 935                 940

Asp Tyr Ser Gly Leu Thr Glu Asp His Leu Leu Pro Arg Pro Ser Ser
945                 950                 955                 960

Phe Gln Asn Asn Val Gln Ser Gln Asp Pro Gln Val Ser Thr Lys Thr
                965                 970                 975

Gly Glu Pro Leu Met Ser Glu Ser Thr Ser Asn Ile Asp Gln Gly Pro
            980                 985                 990

Arg Asp His Ser Val Gln Leu Pro Lys Pro Val His Lys Pro Asn Arg
            995                 1000                1005

Trp Cys Phe Tyr Ser Ser Cys Glu Gln Leu Asp Gln Leu Ile Glu Ala
    1010                1015                1020

Leu Asn Ser Arg Gly His Arg Glu Ser Ala Leu Lys Glu Thr Leu Leu
1025                1030                1035                1040

Gln Glu Lys Ser Arg Ile Cys Ala Gln Leu Ala Arg Phe Ser Glu Glu
                1045                1050                1055

Lys Phe His Phe Ser Asp Lys Arg Gln Pro Asp Ser Lys Pro Thr Tyr
        1060                1065                1070

Ser Arg Gly Arg Ser Ser Asn Ala Tyr Asp Pro Ser Gln Met Cys Ala
    1075                1080                1085

Glu Lys Gln Leu Glu Leu Arg Leu Arg Asp Phe Leu Leu Asp Ile Glu
        1090                1095                1100

Asp Arg Ile Tyr Gln Gly Thr Leu Gly Ala Ile Lys Val Thr Asp Arg
1105                1110                1115                1120
```

-continued

```
His Ile Trp Arg Ser Ala Leu Glu Ser Gly Arg Tyr Glu Leu Leu Ser
            1125                1130                1135

Glu Glu Asn Lys Glu Asn Gly Ile Ile Lys Thr Val Asn Glu Asp Val
        1140                1145                1150

Glu Glu Met Glu Ile Asp Glu Gln Thr Lys Val Ile Val Lys Asp Arg
    1155                1160                1165

Leu Leu Gly Ile Lys Thr Glu Thr Pro Ser Thr Val Ser Thr Asn Ala
1170                1175                1180

Ser Thr Pro Gln Ser Val Ser Val Val His Tyr Leu Ala Met Ala
1185                1190                1195                1200

Leu Phe Gln Ile Glu Gln Gly Leu Glu Arg Arg Phe Leu Lys Ala Pro
            1205                1210                1215

Leu Asp Ala Ser Asp Ser Gly Arg Ser Tyr Lys Thr Val Leu Asp Arg
        1220                1225                1230

Trp Arg Glu Ser Leu Leu Ser Ser Ala Ser Leu Ser Gln Val Phe Leu
    1235                1240                1245

His Leu Ser Thr Leu Asp Arg Ser Val Ile Trp Ser Lys Ser Ile Leu
1250                1255                1260

Asn Ala Arg Cys Lys Ile Cys Arg Lys Lys Gly Asp Ala Glu Asn Met
1265                1270                1275                1280

Val Leu Cys Asp Gly Cys Asp Arg Gly His His Thr Tyr Cys Val Arg
            1285                1290                1295

Pro Lys Leu Lys Ile Val Pro Glu Gly Asp Trp Phe Cys Pro Glu Cys
        1300                1305                1310

Arg Pro Lys Gln Arg Cys Arg Arg Leu Ser Phe Arg Gln Arg Pro Ser
    1315                1320                1325

Leu Glu Ser Asp Glu Asp Val Glu Asp Ser Met Gly Gly Glu Asp Asp
1330                1335                1340

Glu Val Asp Gly Asp Glu Glu Glu Gly Gln Ser Glu Glu Glu Tyr
1345                1350                1355                1360

Glu Val Glu Gln Asp Glu Asp Ser Gln Glu Glu Glu Val Ser
            1365                1370                1375

Leu Pro Lys Arg Gly Arg Pro Gln Val Arg Leu Pro Val Lys Thr Arg
        1380                1385                1390

Gly Lys Leu Ser Ser Ser Phe Ser Ser Arg Gly Gln Gln Gln Glu Pro
    1395                1400                1405

Gly Arg Tyr Pro Ser Arg Ser Gln Gln Ser Thr Pro Lys Thr Thr Val
    1410                1415                1420

Ser Ser Lys Thr Gly Arg Ser Leu Arg Lys Ile Asn Ser Ala Pro Pro
1425                1430                1435                1440

Thr Glu Thr Lys Ser Leu Arg Ile Ala Ser Arg Ser Thr Arg His Ser
            1445                1450                1455

His Gly Pro Leu Gln Ala Asp Val Phe Val Glu Leu Leu Ser Pro Arg
        1460                1465                1470

Arg Lys Arg Arg Gly Arg Lys Ser Ala Asn Asn Thr Pro Glu Asn Ser
    1475                1480                1485

Pro Asn Phe Pro Asn Phe Arg Val Ile Ala Thr Lys Ser Ser Glu Gln
        1490                1495                1500

Ser Arg Ser Val Asn Ile Ala Ser Lys Leu Ser Leu Gln Glu Ser Glu
1505                1510                1515                1520

Ser Lys Arg Arg Cys Arg Lys Arg Gln Ser Pro Glu Pro Ser Pro Val
            1525                1530                1535

Thr Leu Gly Arg Arg Ser Ser Gly Arg Gln Gly Gly Val His Glu Leu
```

```
                    1540            1545            1550
Ser Ala Phe Glu Gln Leu Val Val Glu Leu Val Arg His Asp Asp Ser
    1555                1560                1565

Trp Pro Phe Leu Lys Leu Val Ser Lys Ile Gln Val Pro Asp Tyr Tyr
    1570                1575                1580

Asp Ile Ile Lys Lys Pro Ile Ala Leu Asn Ile Ile Arg Glu Lys Val
1585                1590                1595                1600

Asn Lys Cys Glu Tyr Lys Leu Ala Ser Glu Phe Ile Asp Asp Ile Glu
                1605                1610                1615

Leu Met Phe Ser Asn Cys Phe Glu Tyr Asn Pro Arg Asn Thr Ser Glu
            1620                1625                1630

Ala Lys Ala Gly Thr Arg Leu Gln Ala Phe Phe His Ile Gln Ala Gln
        1635                1640                1645

Lys Leu Gly Leu His Val Thr Pro Ser Asn Val Asp Gln Val Ser Thr
    1650                1655                1660

Pro Pro Ala Ala Lys Lys Ser Arg Ile
1665                1670

<210> SEQ ID NO 70
<211> LENGTH: 1876
<212> TYPE: PRT
<213> ORGANISM: Homo sapiens

<400> SEQUENCE: 70

Met Glu Met Glu Ala Asn Glu Ala Asn Asp His Phe Asn Phe Thr Gly
1               5                   10                  15

Leu Pro Pro Ala Pro Ala Ala Ser Gly Leu Lys Pro Ser Pro Ser Ser
                20                  25                  30

Gly Glu Gly Leu Tyr Thr Asn Gly Ser Pro His Asn Phe Pro Gln Gln
            35                  40                  45

Gly Lys Ser Leu Asn Gly Asp Val Asn Val Asn Gly Leu Ser Thr Val
        50                  55                  60

Ser His Thr Thr Thr Ser Gly Ile Leu Asn Ser Ala Pro His Ser Ser
65                  70                  75                  80

Ser Thr Ser His Leu His His Pro Ser Val Ala Tyr Asp Cys Leu Trp
                85                  90                  95

Asn Tyr Ser Gln Tyr Pro Ser Ala Asn Pro Gly Ser Asn Leu Lys Asp
                100                 105                 110

Pro Pro Leu Leu Ser Gln Phe Ser Gly Gly Gln Tyr Pro Leu Asn Gly
            115                 120                 125

Ile Leu Gly Gly Ser Arg Gln Pro Ser Ser Pro Ser His Asn Thr Asn
        130                 135                 140

Leu Arg Ala Gly Ser Gln Lys Phe Trp Ala Asn Gly Thr His Ser Pro
145                 150                 155                 160

Met Gly Leu Asn Phe Asp Ser Gln Glu Leu Tyr Asp Ser Phe Pro Asp
                165                 170                 175

Gln Asn Phe Glu Glu Val Cys Ser Gly Ile His Pro Asp Glu Ala Ala
            180                 185                 190

Glu Lys Glu Met Thr Ser Val Val Ala Glu Asn Gly Thr Gly Leu Val
        195                 200                 205

Cys Ser Leu Glu Leu Glu Glu Gln Pro Glu Leu Lys Met Cys Gly
        210                 215                 220

Tyr Asn Gly Ser Val Pro Ser Val Glu Ser Leu His Gln Glu Val Ser
225                 230                 235                 240
```

-continued

```
Val Leu Val Pro Asp Pro Thr Val Ser Cys Leu Asp Pro Ser His
            245                 250                 255

Leu Pro Asp Gln Leu Glu Asp Thr Pro Ile Leu Ser Glu Asp Ser Leu
            260                 265                 270

Glu Pro Phe Asn Ser Leu Ala Pro Glu Pro Val Ser Gly Gly Leu Tyr
            275                 280                 285

Gly Ile Asp Asp Thr Glu Leu Met Gly Ala Glu Asp Lys Leu Pro Leu
    290                 295                 300

Glu Asp Ser Pro Val Ile Ser Ala Leu Asp Cys Pro Ser Leu Asn Asn
305                 310                 315                 320

Ala Thr Ala Phe Ser Leu Leu Ala Asp Asp Ser Gln Thr Ser Thr Ser
                325                 330                 335

Ile Phe Ala Ser Pro Thr Ser Pro Pro Val Leu Gly Glu Ser Val Leu
                340                 345                 350

Gln Asp Asn Ser Phe Asp Leu Asn Asn Gly Ser Asp Ala Glu Gln Glu
            355                 360                 365

Glu Met Glu Thr Gln Ser Ser Asp Phe Pro Pro Ser Leu Thr Gln Pro
    370                 375                 380

Ala Pro Asp Gln Ser Ser Thr Ile Gln Leu His Pro Ala Thr Ser Pro
385                 390                 395                 400

Ala Val Ser Pro Thr Thr Ser Pro Ala Val Ser Leu Val Val Ser Pro
                405                 410                 415

Ala Ala Ser Pro Glu Ile Ser Pro Glu Val Cys Pro Ala Ala Ser Thr
                420                 425                 430

Val Val Ser Pro Ala Val Phe Ser Val Val Ser Pro Ala Ser Ser Ala
            435                 440                 445

Val Leu Pro Ala Val Ser Leu Glu Val Pro Leu Thr Ala Ser Val Thr
    450                 455                 460

Ser Pro Lys Ala Ser Pro Val Thr Ser Pro Ala Ala Ala Phe Pro Thr
465                 470                 475                 480

Ala Ser Pro Ala Asn Lys Asp Val Ser Ser Phe Leu Glu Thr Thr Ala
                485                 490                 495

Asp Val Glu Glu Ile Thr Gly Glu Gly Leu Thr Ala Ser Gly Ser Gly
                500                 505                 510

Asp Val Met Arg Arg Arg Ile Ala Thr Pro Glu Glu Val Arg Leu Pro
            515                 520                 525

Leu Gln His Gly Trp Arg Arg Glu Val Arg Ile Lys Lys Gly Ser His
    530                 535                 540

Arg Trp Gln Gly Glu Thr Trp Tyr Tyr Gly Pro Cys Gly Lys Arg Met
545                 550                 555                 560

Lys Gln Phe Pro Glu Val Ile Lys Tyr Leu Ser Arg Asn Leu Val His
                565                 570                 575

Ser Val Arg Arg Glu His Phe Ser Phe Ser Pro Arg Met Pro Val Gly
            580                 585                 590

Asp Phe Phe Glu Glu Arg Asp Thr Pro Glu Gly Leu Gln Trp Val Gln
            595                 600                 605

Leu Ser Ala Glu Glu Ile Pro Ser Arg Ile Gln Ala Ile Thr Gly Lys
    610                 615                 620

Arg Gly Arg Pro Arg Asn Thr Glu Lys Ala Lys Thr Lys Glu Val Pro
625                 630                 635                 640

Lys Val Lys Arg Gly Arg Gly Arg Pro Lys Val Lys Ile Thr Glu
                645                 650                 655

Leu Leu Asn Lys Thr Asp Asn Arg Pro Leu Lys Lys Leu Glu Ala Gln
```

```
                    660                 665                 670
Glu Thr Leu Asn Glu Glu Asp Lys Ala Lys Ile Ala Lys Ser Lys Lys
            675                 680                 685
Lys Met Arg Gln Lys Val Gln Arg Gly Glu Cys Leu Thr Thr Ile Gln
            690                 695                 700
Gly Gln Ala Arg Asn Lys Phe Lys Gln Glu Thr Lys Ser Leu Lys His
705                 710                 715                 720
Lys Glu Ala Lys Lys Ser Lys Ala Glu Lys Arg Gly Lys Thr
            725                 730                 735
Lys Gln Glu Lys Leu Lys Glu Lys Val Lys Arg Glu Lys Lys Glu Lys
            740                 745                 750
Val Lys Lys Glu Lys Glu Glu Val Thr Lys Ala Lys Pro Ala Cys Lys
            755                 760                 765
Ala Asp Lys Thr Leu Ala Thr Gln Arg Arg Leu Glu Arg Gln Lys
            770                 775             780
Gln Gln Met Ile Leu Glu Met Lys Lys Pro Thr Glu Asp Met Cys
785                 790                 795                 800
Leu Thr Asp His Gln Pro Leu Pro Asp Phe Ser Arg Val Pro Gly Leu
                805                 810                 815
Thr Leu Pro Ser Gly Ala Phe Ser Asp Cys Leu Thr Ile Val Glu Phe
            820                 825                 830
Leu His Ser Pro Gly Lys Val Leu Gly Phe Asp Pro Ala Lys Asp Val
            835                 840                 845
Pro Ser Leu Gly Val Leu Gln Glu Gly Leu Leu Cys Gln Gly Asp Ser
850                 855                 860
Leu Gly Glu Val Gln Asp Leu Leu Val Arg Leu Leu Lys Ala Ala Leu
865                 870                 875                 880
His Asp Pro Gly Phe Pro Ser Tyr Cys Gln Ser Lys Lys Ile Leu Gly
                885                 890                 895
Glu Lys Val Ser Glu Ile Pro Leu Thr Arg Asp Asn Val Ser Glu Ile
                900                 905                 910
Leu Arg Cys Phe Leu Met Ala Tyr Gly Val Glu Pro Ala Leu Cys Asp
            915                 920                 925
Arg Leu Arg Thr Gln Pro Phe Gln Ala Gln Pro Pro Gln Gln Lys Ala
930                 935                 940
Ala Val Leu Ala Phe Pro Val His Glu Leu Asn Gly Ser Thr Leu Ile
945                 950                 955                 960
Ile Asn Glu Ile Asp Lys Thr Leu Glu Ser Met Ser Ser Tyr Arg Lys
                965                 970                 975
Asn Lys Trp Ile Val Glu Gly Arg Leu Arg Arg Leu Lys Thr Val Leu
            980                 985                 990
Ala Lys Arg Thr Gly Arg Ser Glu Val Glu Met Gly Arg Pro Glu Glu
            995                 1000                1005
Cys Leu Gly Arg Arg Arg Ser Arg Ile Met Glu Glu Thr Ser Gly
            1010                1015                1020
Met Glu Glu Glu Glu Glu Glu Ser Ile Ala Ala Val Pro Gly Arg
1025                1030                1035                1040
Arg Gly Arg Arg Asp Gly Glu Val Asp Ala Thr Ala Ser Ser Ile Pro
                1045                1050                1055
Glu Leu Glu Arg Gln Ile Glu Lys Leu Ser Lys Arg Gln Leu Phe Phe
                1060                1065                1070
Arg Lys Lys Leu Leu His Ser Ser Gln Met Leu Arg Ala Val Ser Leu
            1075                1080                1085
```

-continued

```
Gly Gln Asp Arg Tyr Arg Arg Arg Tyr Trp Val Leu Pro Tyr Leu Ala
    1090                1095                1100
Gly Ile Phe Val Glu Gly Thr Glu Gly Asn Leu Val Pro Glu Glu Val
1105                1110                1115                1120
Ile Lys Lys Glu Thr Asp Ser Leu Lys Val Ala Ala His Ala Ser Leu
                1125                1130                1135
Asn Pro Ala Leu Phe Ser Met Lys Met Glu Leu Ala Gly Ser Asn Thr
            1140                1145                1150
Thr Ala Ser Ser Pro Ala Arg Ala Arg Ser Arg Pro Leu Lys Thr Lys
        1155                1160                1165
Pro Gly Phe Met Gln Pro Arg Glu Phe Lys Ser Pro Val Arg Gly Gln
    1170                1175                1180
Asp Ser Glu Gln Pro Gln Ala Gln Leu Gln Pro Glu Ala Gln Leu His
1185                1190                1195                1200
Val Pro Ala Gln Pro Gln Pro Gln Leu Gln Leu Gln Leu Gln Ser His
                1205                1210                1215
Lys Gly Phe Leu Glu Gln Glu Gly Ser Pro Leu Ser Leu Gly Gln Ser
            1220                1225                1230
Gln His Asp Leu Ser Gln Ser Ala Phe Leu Ser Trp Leu Ser Gln Thr
        1235                1240                1245
Gln His Ser Ser Leu Leu Ser Ser Ser Val Leu Thr Pro Asp Ser Ser
    1250                1255                1260
Pro Gly Lys Leu Asp Pro Ala Pro Ser Gln Pro Pro Glu Glu Pro Glu
1265                1270                1275                1280
Pro Asp Glu Ala Glu Ser Ser Pro Asp Leu Gln Ala Phe Trp Phe Asn
                1285                1290                1295
Ile Ser Ala Gln Met Pro Cys Asn Ala Ala Pro Thr Pro Pro Leu Ala
            1300                1305                1310
Val Ser Glu Asp Gln Pro Thr Pro Ser Pro Gln Gln Leu Ala Ser Ser
        1315                1320                1325
Lys Pro Met Asn Arg Pro Ser Ala Ala Asn Pro Cys Ser Pro Val Gln
    1330                1335                1340
Phe Ser Ser Thr Pro Leu Ala Gly Leu Ala Pro Lys Arg Arg Ala Gly
1345                1350                1355                1360
Asp Pro Gly Glu Met Pro Gln Ser Pro Thr Gly Leu Gly Gln Pro Lys
                1365                1370                1375
Arg Arg Gly Arg Pro Pro Ser Lys Phe Phe Lys Gln Met Glu Gln Arg
            1380                1385                1390
Val Leu Thr Gln Leu Thr Ala Gln Pro Val Pro Pro Glu Met Cys Ser
        1395                1400                1405
Gly Trp Trp Trp Ile Pro Asp Pro Glu Met Leu Asp Ala Met Leu Lys
    1410                1415                1420
Ala Leu His Pro Arg Gly Ile Arg Glu Lys Ala Leu His Lys His Leu
1425                1430                1435                1440
Asn Lys His Arg Asp Phe Leu Gln Glu Val Cys Leu Arg Pro Ser Ala
                1445                1450                1455
Asp Pro Ile Pro Glu Pro Arg Gln Leu Pro Ala Phe Gln Glu Gly Ile
            1460                1465                1470
Met Ser Trp Ser Pro Lys Glu Lys Thr Tyr Glu Thr Asp Leu Ala Val
        1475                1480                1485
Leu Gln Trp Val Glu Glu Leu Glu Gln Arg Val Ile Met Ser Asp Leu
    1490                1495                1500
```

-continued

```
Gln Ile Arg Gly Trp Thr Cys Pro Ser Pro Asp Ser Thr Arg Glu Asp
1505                1510                1515                1520

Leu Ala Tyr Cys Glu His Leu Ser Asp Ser Gln Glu Asp Ile Thr Trp
            1525                1530                1535

Arg Gly Pro Gly Arg Glu Gly Leu Ala Pro Gln Arg Lys Thr Thr Asn
        1540                1545                1550

Pro Leu Asp Leu Ala Val Met Arg Leu Ala Ala Leu Glu Gln Asn Val
    1555                1560                1565

Lys Arg Arg Tyr Leu Arg Glu Pro Leu Trp Pro Thr His Glu Trp Val
1570                1575                1580

Leu Glu Lys Ala Leu Leu Ser Thr Pro Asn Gly Ala Pro Glu Gly Thr
1585                1590                1595                1600

Thr Thr Glu Ile Ser Tyr Glu Ile Thr Pro Arg Ile Arg Ile Trp Arg
                1605                1610                1615

Gln Thr Leu Gln Arg Cys Arg Ser Ala Ala His Val Cys Leu Cys Leu
            1620                1625                1630

Gly His Leu Glu Arg Ser Ile Ala Trp Glu Lys Ser Val Asn Lys Val
        1635                1640                1645

Thr Cys Leu Val Cys Arg Lys Gly Asp Asn Asp Glu Phe Leu Leu Leu
    1650                1655                1660

Cys Asp Gly Cys Asp Arg Gly Cys His Ile Tyr Cys His Arg Pro Lys
1665                1670                1675                1680

Met Glu Ala Val Pro Glu Gly Asp Trp Phe Cys Thr Val Cys Leu Ala
                1685                1690                1695

Gln Gln Val Glu Gly Glu Phe Thr Gln Lys Pro Gly Phe Pro Lys Arg
            1700                1705                1710

Gly Gln Lys Arg Lys Ser Gly Tyr Ser Leu Asn Phe Ser Glu Gly Asp
        1715                1720                1725

Gly Arg Arg Arg Arg Val Leu Leu Lys Gly Arg Glu Ser Pro Ala Ala
    1730                1735                1740

Gly Pro Arg Tyr Ser Glu Glu Arg Leu Ser Pro Ser Lys Arg Arg Pro
1745                1750                1755                1760

Leu Ser Met Arg Asn His His Ser Asp Leu Thr Phe Cys Glu Ile Ile
                1765                1770                1775

Leu Met Glu Met Glu Ser His Asp Ala Ala Trp Pro Phe Leu Glu Pro
            1780                1785                1790

Val Asn Pro Arg Leu Val Ser Gly Tyr Arg Arg Ile Ile Lys Asn Pro
        1795                1800                1805

Met Asp Phe Ser Thr Met Arg Glu Arg Leu Leu Arg Gly Gly Tyr Thr
    1810                1815                1820

Ser Ser Glu Glu Phe Ala Ala Asp Ala Leu Leu Val Phe Asp Asn Cys
1825                1830                1835                1840

Gln Thr Phe Asn Glu Asp Asp Ser Glu Val Gly Lys Ala Gly His Ile
                1845                1850                1855

Met Arg Arg Phe Phe Glu Ser Arg Trp Glu Glu Phe Tyr Gln Gly Lys
            1860                1865                1870

Gln Ala Asn Leu
        1875

<210> SEQ ID NO 71
<211> LENGTH: 1969
<212> TYPE: PRT
<213> ORGANISM: Homo sapiens

<400> SEQUENCE: 71
```

-continued

```
Met Gly Gln Thr Lys Ser Thr Ser Ser Gly Gly Asn Arg Lys Cys
  1               5                  10                  15

Asn Gln Glu Gln Ser Lys Asn Gln Pro Leu Asp Ala Arg Val Asp Lys
                 20                  25                  30

Ile Lys Asp Lys Lys Pro Arg Lys Lys Ala Met Glu Ser Ser Ser Asn
             35                  40                  45

Ser Asp Ser Asp Ser Gly Thr Ser Ser Asp Thr Ser Ser Glu Gly Ile
     50                  55                  60

Ser Ser Ser Asp Ser Asp Asp Leu Glu Glu Asp Glu Glu Glu Glu Asp
 65              70                  75                      80

Gln Ser Ile Glu Glu Ser Glu Asp Asp Ser Asp Ser Glu Ser Glu
                 85                  90                  95

Ala Gln His Lys Ser Asn Asn Gln Val Leu Leu His Gly Ile Ser Asp
             100                 105                 110

Pro Lys Ala Asp Gly Gln Lys Ala Thr Glu Lys Ala Gln Glu Lys Arg
             115                 120                 125

Ile His Gln Pro Leu Pro Leu Ala Phe Glu Ser Gln Thr His Ser Phe
 130                 135                 140

Gln Ser Gln Gln Lys Gln Pro Gln Val Leu Ser Gln Gln Leu Pro Phe
145                 150                 155                 160

Ile Phe Gln Ser Ser Gln Ala Lys Glu Glu Ser Val Asn Lys His Thr
                 165                 170                 175

Ser Val Ile Gln Ser Thr Gly Leu Val Ser Asn Val Lys Pro Leu Ser
                 180                 185                 190

Leu Val Asn Gln Ala Lys Lys Glu Thr Tyr Met Lys Leu Ile Val Pro
             195                 200                 205

Ser Pro Asp Val Leu Lys Ala Gly Asn Lys Asn Thr Ser Glu Glu Ser
     210                 215                 220

Ser Leu Leu Thr Ser Glu Leu Arg Ser Lys Arg Glu Gln Tyr Lys Gln
225                 230                 235                 240

Ala Phe Pro Ser Gln Leu Lys Lys Gln Glu Ser Ser Lys Ser Leu Lys
                 245                 250                 255

Lys Val Ile Ala Ala Leu Ser Asn Pro Lys Ala Thr Ser Ser Ser Pro
                 260                 265                 270

Ala His Pro Lys Gln Thr Leu Glu Asn Asn His Pro Asn Pro Phe Leu
             275                 280                 285

Thr Asn Ala Leu Leu Gly Asn His Gln Pro Asn Gly Val Ile Gln Ser
 290                 295                 300

Val Ile Gln Glu Ala Pro Leu Ala Leu Thr Thr Lys Thr Lys Met Gln
305                 310                 315                 320

Ser Lys Ile Asn Glu Asn Ile Ala Ala Ala Ser Ser Thr Pro Phe Ser
                 325                 330                 335

Ser Pro Val Asn Leu Ser Thr Ser Gly Arg Arg Thr Pro Gly Asn Gln
             340                 345                 350

Thr Pro Val Met Pro Ser Ala Ser Pro Ile Leu His Ser Gln Gly Lys
             355                 360                 365

Glu Lys Ala Val Ser Asn Asn Val Asn Pro Val Lys Thr Gln His His
 370                 375                 380

Ser His Pro Ala Lys Ser Leu Val Glu Gln Phe Arg Gly Thr Asp Ser
385                 390                 395                 400

Asp Ile Pro Ser Ser Lys Asp Ser Glu Asp Ser Asn Glu Asp Glu Glu
                 405                 410                 415
```

-continued

```
Glu Asp Asp Glu Glu Glu Asp Glu Glu Asp Glu Asp Asp Glu Ser Asp
            420                 425                 430

Asp Ser Gln Ser Glu Ser Asp Ser Asn Ser Glu Ser Asp Thr Glu Gly
        435                 440                 445

Ser Glu Glu Glu Asp Asp Asp Lys Asp Gln Asp Glu Ser Asp Ser
450                 455                 460

Asp Thr Glu Gly Glu Lys Thr Ser Met Lys Leu Asn Lys Thr Thr Ser
465                 470                 475                 480

Ser Lys Ser Pro Ser Met Ser Leu Thr Gly His Ser Thr Pro Arg Asn
                485                 490                 495

Leu His Ile Ala Lys Ala Pro Gly Ser Ala Pro Ala Ala Leu Cys Ser
            500                 505                 510

Glu Ser Gln Ser Pro Ala Phe Leu Gly Thr Ser Ser Thr Leu Thr
        515                 520                 525

Ser Ser Pro His Ser Gly Thr Ser Lys Arg Arg Arg Val Thr Asp Glu
530                 535                 540

Arg Glu Leu Arg Leu Pro Leu Glu Tyr Gly Trp Gln Arg Glu Thr Arg
545                 550                 555                 560

Ile Arg Asn Phe Gly Gly Arg Leu Gln Gly Glu Val Ala Tyr Tyr Ala
            565                 570                 575

Pro Cys Gly Lys Lys Leu Arg Gln Tyr Pro Glu Val Ile Lys Tyr Leu
        580                 585                 590

Ser Arg Asn Gly Ile Met Asp Ile Ser Arg Asp Asn Phe Ser Phe Ser
        595                 600                 605

Ala Lys Ile Arg Val Gly Asp Phe Tyr Glu Ala Arg Asp Gly Pro Gln
    610                 615                 620

Glu Met Gln Trp Cys Leu Leu Lys Glu Glu Asp Val Ile Pro Arg Ile
625                 630                 635                 640

Arg Ala Met Glu Gly Arg Arg Gly Arg Pro Pro Asn Pro Asp Arg Gln
            645                 650                 655

Arg Ala Arg Glu Glu Ser Arg Met Arg Arg Lys Gly Arg Pro Pro
        660                 665                 670

Asn Val Gly Asn Ala Glu Phe Leu Asp Asn Ala Asp Ala Lys Leu Leu
        675                 680                 685

Arg Lys Leu Gln Ala Gln Glu Ala Arg Gln Ala Ala Gln Ile Lys Leu
    690                 695                 700

Leu Arg Lys Leu Gln Lys Gln Glu Gln Ala Arg Val Ala Lys Glu Ala
705                 710                 715                 720

Lys Lys Gln Gln Ala Ile Met Ala Ala Glu Glu Lys Arg Lys Gln Lys
            725                 730                 735

Glu Gln Ile Lys Ile His Lys Gln Gln Glu Lys Ile Lys Arg Ile Gln
        740                 745                 750

Gln Ile Arg Met Glu Lys Glu Leu Arg Ala Gln Gln Ile Leu Glu Ala
        755                 760                 765

Lys Lys Lys Lys Lys Glu Glu Ala Ala Asn Ala Lys Leu Leu Glu Ala
    770                 775                 780

Glu Lys Arg Ile Lys Glu Arg Glu Met Arg Arg Gln Gln Ala Val Leu
785                 790                 795                 800

Leu Lys Arg Gln Glu Arg Glu Arg Arg Gln His Met Met Leu Met
            805                 810                 815

Lys Ala Met Glu Ala Arg Lys Lys Ala Glu Glu Lys Glu Arg Leu Lys
            820                 825                 830

Gln Glu Lys Arg Asp Glu Lys Arg Leu Asn Lys Glu Arg Lys Leu Glu
```

-continued

```
             835                 840                 845
Gln Arg Arg Leu Glu Leu Glu Met Ala Lys Glu Leu Lys Lys Pro Asn
    850                 855                 860
Glu Asp Met Cys Leu Ala Asp Gln Lys Pro Leu Pro Glu Leu Pro Arg
865                 870                 875                 880
Ile Pro Gly Leu Val Leu Ser Gly Ser Thr Phe Ser Asp Cys Leu Met
                885                 890                 895
Val Val Gln Phe Leu Arg Asn Phe Gly Lys Val Leu Gly Phe Asp Val
            900                 905                 910
Asn Ile Asp Val Pro Asn Leu Ser Val Leu Gln Glu Gly Ile Leu Leu
        915                 920                 925
Asn Ile Gly Asp Ser Met Gly Glu Val Gln Asp Leu Leu Val Arg Leu
    930                 935                 940
Leu Ser Ala Ala Val Cys Asp Pro Gly Leu Ile Thr Gly Tyr Lys Ala
945                 950                 955                 960
Lys Thr Ala Leu Gly Glu His Leu Leu Asn Val Gly Val Asn Arg Asp
                965                 970                 975
Asn Val Ser Glu Ile Leu Gln Ile Phe Met Glu Ala His Cys Gly Gln
            980                 985                 990
Thr Glu Leu Thr Glu Ser Leu Lys Thr Lys Ala Phe Gln Ala His Thr
        995                 1000                1005
Pro Ala Gln Lys Ala Val Leu Ala Phe Leu Ile Asn Glu Leu Ala Cys
    1010                1015                1020
Ser Lys Ser Val Val Ser Glu Ile Asp Lys Asn Ile Asp Tyr Met Ser
1025                1030                1035                1040
Asn Leu Arg Arg Asp Lys Asn Val Val Glu Gly Lys Leu Arg Lys Leu
                1045                1050                1055
Arg Ile Ile His Ala Lys Lys Thr Gly Lys Arg Asp Thr Ser Gly Gly
            1060                1065                1070
Ile Asp Leu Gly Glu Glu Gln His Pro Leu Gly Thr Pro Thr Pro Gly
        1075                1080                1085
Arg Lys Arg Arg Arg Lys Gly Gly Asp Ser Asp Tyr Asp Asp Asp Asp
    1090                1095                1100
Asp Asp Asp Ser Asp Asp Gln Gly Asp Glu Asp Asp Glu Asp Glu Glu
1105                1110                1115                1120
Asp Lys Glu Asp Gln Lys Gly Lys Lys Thr Asp Ile Cys Glu Asp Glu
                1125                1130                1135
Asp Glu Gly Asp Gln Ala Ala Ser Val Glu Glu Leu Glu Lys Gln Ile
            1140                1145                1150
Glu Lys Leu Ser Lys Gln Gln Ser Gln Tyr Arg Arg Lys Leu Phe Asp
        1155                1160                1165
Ala Ser His Ser Leu Arg Ser Val Met Phe Gly Pro Asp Arg Tyr Arg
    1170                1175                1180
Arg Arg Tyr Trp Ile Leu Pro Arg Cys Gly Gly Ile Phe Val Glu Gly
1185                1190                1195                1200
Met Glu Ser Gly Glu Gly Leu Glu Glu Ile Ala Lys Glu Arg Glu Lys
                1205                1210                1215
Leu Lys Lys Ala Glu Ser Val Gln Ile Lys Glu Glu Met Phe Glu Thr
            1220                1225                1230
Ser Gly Asp Ser Leu Asn Cys Ser Asn Thr Asp His Cys Glu Gln Lys
        1235                1240                1245
Glu Asp Leu Lys Glu Lys Asp Asn Thr Asn Leu Phe Leu Gln Lys Pro
    1250                1255                1260
```

```
Gly Ser Phe Ser Lys Leu Ser Lys Leu Leu Glu Val Ala Lys Met Pro
1265                1270                1275                1280

Pro Glu Ser Glu Val Met Thr Pro Lys Pro Asn Ala Gly Ala Asn Gly
                1285                1290                1295

Cys Thr Leu Ser Tyr Gln Asn Ser Gly Lys His Ser Leu Gly Ser Val
                1300                1305                1310

Gln Ser Thr Ala Thr Gln Ser Asn Val Glu Lys Ala Asp Ser Asn Asn
                1315                1320                1325

Leu Phe Asn Thr Gly Ser Ser Gly Pro Gly Lys Phe Tyr Ser Pro Leu
                1330                1335                1340

Pro Asn Asp Gln Leu Leu Lys Thr Leu Thr Glu Lys Asn Arg Gln Trp
1345                1350                1355                1360

Phe Ser Leu Leu Pro Arg Thr Pro Cys Asp Asp Thr Ser Leu Thr His
                1365                1370                1375

Ala Asp Met Ser Thr Ala Ser Leu Val Thr Pro Gln Ser Gln Pro Pro
                1380                1385                1390

Ser Lys Ser Pro Ser Pro Thr Pro Ala Pro Leu Gly Ser Ser Ala Gln
                1395                1400                1405

Asn Pro Val Gly Leu Asn Pro Phe Ala Leu Ser Pro Leu Gln Val Lys
                1410                1415                1420

Gly Gly Val Ser Met Met Gly Leu Gln Phe Cys Gly Trp Pro Thr Gly
1425                1430                1435                1440

Val Val Thr Ser Asn Ile Pro Phe Thr Leu Ser Val Pro Ser Leu Gly
                1445                1450                1455

Ser Gly Leu Gly Leu Ser Glu Gly Asn Gly Asn Ser Phe Leu Thr Ser
                1460                1465                1470

Asn Val Ala Ser Ser Lys Ser Glu Ser Pro Val Pro Gln Asn Glu Lys
                1475                1480                1485

Ala Thr Ser Ala Gln Pro Ala Ala Val Glu Val Ala Lys Pro Val Asp
                1490                1495                1500

Phe Pro Ser Pro Lys Pro Ile Pro Glu Glu Met Gln Phe Gly Trp Trp
1505                1510                1515                1520

Arg Ile Ile Asp Pro Glu Asp Leu Lys Ala Leu Leu Lys Val Leu His
                1525                1530                1535

Leu Arg Gly Ile Arg Glu Lys Ala Leu Gln Lys Gln Ile Gln Lys His
                1540                1545                1550

Leu Asp Tyr Ile Thr Gln Ala Cys Leu Lys Asn Lys Asp Val Ala Ile
                1555                1560                1565

Ile Glu Leu Asn Glu Asn Glu Asn Gln Val Thr Arg Asp Ile Val
                1570                1575                1580

Glu Asn Trp Ser Val Glu Glu Gln Ala Met Glu Met Asp Leu Ser Val
1585                1590                1595                1600

Leu Gln Gln Val Glu Asp Leu Glu Arg Arg Val Ala Ser Ala Ser Leu
                1605                1610                1615

Gln Val Lys Gly Trp Met Cys Pro Glu Pro Ala Ser Glu Arg Glu Asp
                1620                1625                1630

Leu Val Tyr Phe Glu His Lys Ser Phe Thr Lys Leu Cys Lys Glu His
                1635                1640                1645

Asp Gly Glu Phe Thr Gly Glu Asp Glu Ser Ser Ala His Ala Leu Glu
                1650                1655                1660

Arg Lys Ser Asp Asn Pro Leu Asp Ile Ala Val Thr Arg Leu Ala Asp
1665                1670                1675                1680
```

-continued

```
Leu Glu Arg Asn Ile Glu Arg Arg Ile Glu Glu Asp Ile Ala Pro Gly
            1685                1690                1695

Leu Arg Val Trp Arg Arg Ala Leu Ser Glu Ala Arg Ser Ala Ala Gln
            1700                1705                1710

Val Ala Leu Cys Ile Gln Gln Leu Gln Lys Ser Ile Ala Trp Glu Lys
        1715                1720                1725

Ser Ile Met Lys Val Tyr Cys Gln Ile Cys Arg Lys Gly Asp Asn Glu
        1730                1735                1740

Glu Leu Leu Leu Leu Cys Asp Gly Cys Asp Lys Gly Cys His Thr Tyr
1745                1750                1755                1760

Cys His Arg Pro Lys Ile Thr Thr Ile Pro Asp Gly Asp Trp Phe Cys
            1765                1770                1775

Pro Ala Cys Ile Ala Lys Ala Ser Gly Gln Thr Leu Lys Ile Lys Lys
            1780                1785                1790

Leu His Val Lys Gly Lys Lys Thr Asn Glu Ser Lys Lys Gly Lys Lys
            1795                1800                1805

Val Thr Leu Thr Gly Asp Thr Glu Asp Glu Asp Ser Ala Ser Thr Ser
        1810                1815                1820

Ser Ser Leu Lys Arg Gly Asn Lys Asp Leu Gln Lys Arg Lys Met Glu
1825                1830                1835                1840

Glu Asn Thr Ser Ile Asn Leu Ser Lys Gln Glu Ser Phe Thr Ser Val
            1845                1850                1855

Lys Lys Pro Lys Arg Asp Asp Ser Lys Asp Leu Ala Leu Cys Ser Met
            1860                1865                1870

Ile Leu Thr Glu Met Glu Thr His Glu Asp Ala Trp Pro Phe Leu Leu
            1875                1880                1885

Pro Val Asn Leu Lys Leu Val Pro Gly Tyr Lys Lys Val Ile Lys Lys
        1890                1895                1900

Pro Met Asp Phe Ser Thr Ile Arg Glu Lys Leu Ser Ser Gly Gln Tyr
1905                1910                1915                1920

Pro Asn Leu Glu Thr Phe Ala Leu Asp Val Arg Leu Val Phe Asp Asn
            1925                1930                1935

Cys Glu Thr Phe Trp Glu Asp Asp Ser Asp Ile Gly Arg Ala Gly His
            1940                1945                1950

Asn Met Arg Lys Tyr Phe Glu Lys Lys Trp Thr Asp Thr Phe Lys Val
            1955                1960                1965

Ser

<210> SEQ ID NO 72
<211> LENGTH: 12
<212> TYPE: DNA
<213> ORGANISM: Homo sapiens

<400> SEQUENCE: 72
tacagaccct cc                                                         12
```